United States Patent
Longshaw et al.

(10) Patent No.: US 10,294,216 B2
(45) Date of Patent: *May 21, 2019

(54) PYRAZOLYL UREAS AS KINASE INHIBITORS

(71) Applicant: RESPIVERT LIMITED, Buckinghamshire (GB)

(72) Inventors: Alistair Ian Longshaw, Nottingham (GB); Euan Alexander Fraser Fordyce, Nottingham (GB); Stuart Thomas Onions, Nottingham (GB); John King-Underwood, Worcestershire (GB); Jennifer Diane Venable, Solana Beach, CA (US); Iain Walters, Nottingham (GB)

(73) Assignee: RESPIVERT LIMITED, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,987

(22) Filed: Dec. 21, 2017

(65) Prior Publication Data

US 2018/0118719 A1    May 3, 2018

Related U.S. Application Data

(63) Continuation of application No. 15/118,708, filed as application No. PCT/GB2015/050401 on Feb. 13, 2015, now Pat. No. 9,884,845.

(60) Provisional application No. 61/941,064, filed on Feb. 18, 2014, provisional application No. 61/940,282, filed on Feb. 14, 2014.

(51) Int. Cl.

| A61K 31/4427 | (2006.01) |
| C07D 401/14 | (2006.01) |
| C07D 409/14 | (2006.01) |
| A61K 31/497 | (2006.01) |
| C07D 401/12 | (2006.01) |
| A61K 31/498 | (2006.01) |
| A61K 31/5377 | (2006.01) |
| A61K 31/541 | (2006.01) |
| A61K 31/551 | (2006.01) |
| C07D 413/14 | (2006.01) |
| C07D 487/04 | (2006.01) |
| A61K 9/00 | (2006.01) |
| A61K 47/26 | (2006.01) |

(52) U.S. Cl.
CPC .......... *C07D 401/14* (2013.01); *A61K 9/0075* (2013.01); *A61K 31/4427* (2013.01); *A61K 31/497* (2013.01); *A61K 31/498* (2013.01); *A61K 31/5377* (2013.01); *A61K 31/541* (2013.01); *A61K 31/551* (2013.01); *A61K 47/26* (2013.01); *C07D 401/12* (2013.01); *C07D 409/14* (2013.01); *C07D 413/14* (2013.01); *C07D 487/04* (2013.01)

(58) Field of Classification Search
CPC .................................................. C07D 401/14
See application file for complete search history.

(56) References Cited

U.S. PATENT DOCUMENTS

| 6,319,921 B1 | 11/2001 | Cirillo et al. |
| 6,492,393 B1 | 12/2002 | Breitfelder et al. |
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Sun et al. |
| 7,329,670 B1 | 2/2008 | Dumas et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 7,928,227 B2 | 4/2011 | Boyer et al. |
| 8,071,616 B2 | 12/2011 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |

(Continued)

FOREIGN PATENT DOCUMENTS

| EP | 2324825 A1 | 5/2011 |
| WO | 1999/32110 A1 | 7/1999 |

(Continued)

OTHER PUBLICATIONS

CAS Registry No. 1379397-83-7, Jun. 18, 2012; American Chemical Society.

(Continued)

*Primary Examiner* — Brian E McDowell
(74) *Attorney, Agent, or Firm* — McDermott Will & Emery LLP

(57) ABSTRACT

There are provided compounds of formula (I) shown below as defined in the specification which are p38 MAP kinase inhibitors for use as medicaments for the treatment inter alia of inflammatory diseases.

(I)

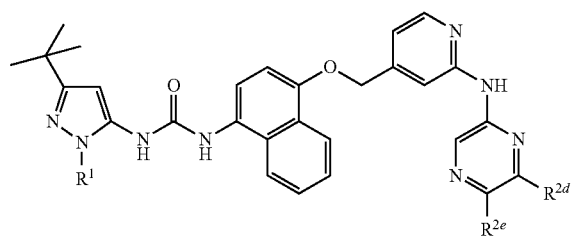

13 Claims, 1 Drawing Sheet

(56) References Cited

U.S. PATENT DOCUMENTS

| | | |
|---|---|---|
| 8,299,074 B2 | 10/2012 | Ito et al. |
| 8,455,471 B2 | 6/2013 | Wisdom et al. |
| 8,618,140 B2 | 12/2013 | Ito et al. |
| 8,642,773 B2 | 2/2014 | Ito et al. |
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood et al. |
| 9,108,950 B2 | 8/2015 | Ito et al. |
| 9,249,125 B2 | 2/2016 | Duffy et al. |
| 9,260,410 B2 | 2/2016 | King-Underwood et al. |
| 9,447,076 B2 | 9/2016 | Longshaw et al. |
| 9,475,796 B2 | 10/2016 | Ito et al. |
| 9,481,648 B2 | 11/2016 | Baker et al. |
| 9,499,486 B2 | 11/2016 | Fyfe |
| 9,624,196 B2 | 4/2017 | Longshaw et al. |
| 2004/0152725 A1 | 8/2004 | Moss et al. |
| 2008/0227828 A1 | 9/2008 | Dumas et al. |
| 2008/0300281 A1 | 12/2008 | Dumas et al. |
| 2009/0131437 A1 | 5/2009 | Furet et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2014/0057915 A1 | 2/2014 | Cariou et al. |
| 2014/0114061 A1 | 4/2014 | Kugimoto et al. |
| 2014/0114064 A1 | 4/2014 | Ito et al. |
| 2014/0249169 A1 | 9/2014 | Ito et al. |
| 2014/0296208 A1 | 10/2014 | Baker et al. |
| 2015/0166483 A1 | 6/2015 | Fyfe |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe |
| 2016/0039797 A1 | 2/2016 | Fyfe |
| 2016/0096805 A1 | 4/2016 | Fyfe |
| 2016/0102059 A1 | 4/2016 | Baker et al. |
| 2016/0318958 A1 | 11/2016 | Fyfe et al. |

FOREIGN PATENT DOCUMENTS

| | | |
|---|---|---|
| WO | 1999/32455 A1 | 7/1999 |
| WO | 2000/43384 A1 | 7/2000 |
| WO | 2001/04115 A1 | 1/2001 |
| WO | 2001/36403 A1 | 5/2001 |
| WO | 2001/64642 A1 | 9/2001 |
| WO | 2002/092576 A1 | 11/2002 |
| WO | 2003/005999 A1 | 1/2003 |
| WO | 2003/068228 A1 | 8/2003 |
| WO | 2003/072569 A1 | 8/2003 |
| WO | 2003/072569 A1 | 9/2003 |
| WO | 2004/002481 A1 | 1/2004 |
| WO | 2004/007472 A1 | 1/2004 |
| WO | 2004/078746 A1 | 9/2004 |
| WO | 2005/110994 A1 | 11/2005 |
| WO | 2006/072589 A1 | 7/2006 |
| WO | 2007/002635 A1 | 1/2007 |
| WO | 2008/067027 A1 | 6/2008 |
| WO | 2009/117080 A1 | 9/2009 |
| WO | 2010/038085 A1 | 4/2010 |
| WO | 2010/038086 A1 | 4/2010 |
| WO | 2010/067130 A1 | 6/2010 |
| WO | 2010/067131 A1 | 6/2010 |
| WO | 2010/112936 A1 | 10/2010 |
| WO | 2011/070368 A1 | 6/2011 |
| WO | 2011/070369 A1 | 6/2011 |
| WO | 2011/121366 A1 | 10/2011 |
| WO | 2011/124923 A1 | 10/2011 |
| WO | 2011/124930 A1 | 10/2011 |
| WO | 2011/158039 A1 | 12/2011 |
| WO | 2011/158042 A1 | 12/2011 |
| WO | 2011/158044 A1 | 12/2011 |
| WO | 2013/050756 A1 | 4/2013 |
| WO | 2013/050757 A1 | 4/2013 |
| WO | 2014/027209 A1 | 2/2014 |
| WO | 2014/033446 A1 | 3/2014 |
| WO | 2014/033447 A1 | 3/2014 |
| WO | 2014/033448 A1 | 3/2014 |
| WO | 2014/033449 A1 | 3/2014 |
| WO | 2014/076484 A1 | 5/2014 |
| WO | 2014/140582 A1 | 9/2014 |
| WO | 2014/162121 A1 | 10/2014 |
| WO | 2014/162122 A1 | 10/2014 |
| WO | 2014/162126 A1 | 10/2014 |
| WO | 2015/092423 A1 | 6/2015 |
| WO | 2015/121444 A1 | 8/2015 |
| WO | 2015/121660 A1 | 8/2015 |
| WO | 2016/051186 A1 | 4/2016 |

OTHER PUBLICATIONS

CAS Registry No. 1379457-84-7, Jun. 18, 2012; American Chemical Society.
CAS Registry No. 1384608-34-7, Jul. 27, 2012; American Chemical Society.
CAS Registry No. 1379462-36-8, Jun. 18, 2012; American Chemical Society.
CAS Registry No. 1384595-05-4, Jul. 27, 2012; American Chemical Society.
CAS Registry No. 1384611-77-1, Jul. 27, 2012; American Chemical Society.
CAS Registry No. 1384610-90-5, Jul. 27, 2012; American Chemical Society.
CAS Registry No. 1379401-24-7, Jun. 18, 2012; American Chemical Society.
CAS Registry No. 1379462-42-6, Jun. 18, 2012; American Chemical Society.
Onions, S et al. 2016 "The discovery of narrow spectrum kinase inhibitors: New therapeutic agents for the treatment of COPD and steroid-resistant asthma" Journal of Medicinal Chemistry; in 71 pages.
To, W.S. et al. 2015 "Potent anti-inflammatory effects of the narrow spectrum kinase inhibitor RV1088 on rheumatoid arthritis synovial membrane cells" British Journal of Pharmacology 172: 3805-3816.

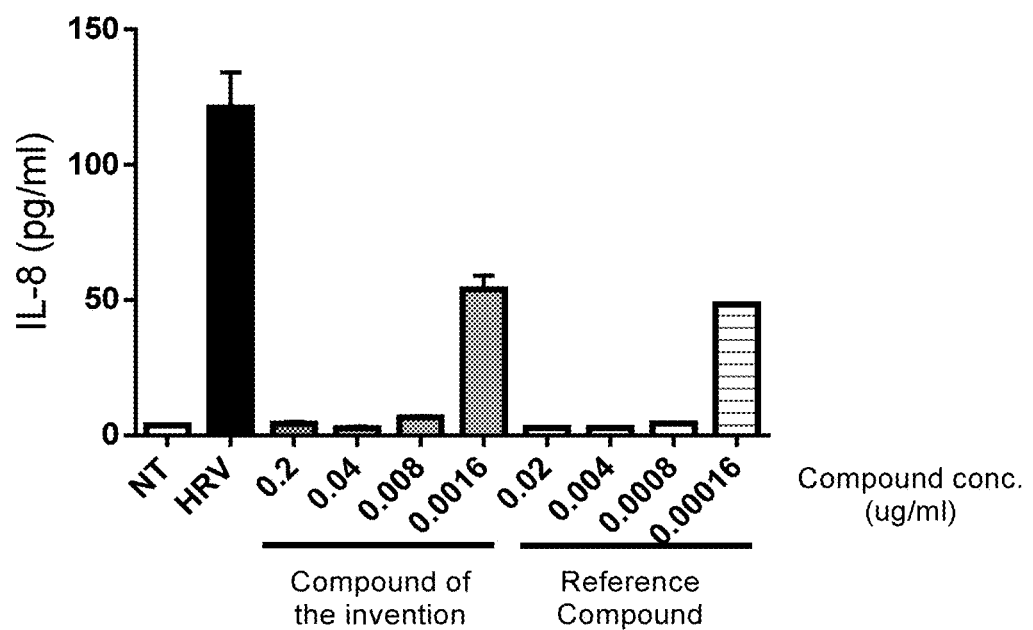

PYRAZOLYL UREAS AS KINASE INHIBITORS

RELATED APPLICATIONS

This application is a continuation of U.S. patent application Ser. No. 15/118,708, filed Aug. 12, 2016, which is the U.S. National Stage of International Application No. PCT/GB2015/050401, filed Feb. 13, 2015 and claims the benefit of U.S. Provisional Application No. 61/940,282, filed on Feb. 14, 2014 and claims the benefit of U.S. Provisional Application No. 61/941,064, filed on Feb. 18, 2014. The entire teachings of the foregoing applications are incorporated herein by reference.

FIELD OF THE INVENTION

The invention relates to compounds which are inhibitors of the family of p38 mitogen-activated protein kinase enzymes (referred to herein as p38 MAP kinase inhibitors), for example the alpha and gamma kinase sub-types thereof, and the Src family of tyrosine kinases, and to their use in therapy, including in pharmaceutical combinations, especially in the treatment of inflammatory diseases, in particular inflammatory diseases of the lung, such as asthma and COPD, as well as those of the gastrointestinal tract, such as ulcerative colitis, Irritable Bowel Disease (IBD) and Crohn's disease and of the eye, such as uveitis.

BACKGROUND OF THE INVENTION

Four p38 MAPK isoforms (alpha, beta, gamma and delta respectively), have been identified each displaying different patterns of tissue expression in man. The p38 MAPK alpha and beta isoforms are found ubiquitously in the body, being present in many different cell types.

The alpha isoform is well characterized in terms of its role in inflammation. Although studies using a chemical genetic approach in mice indicate that the p38 MAPK beta isoform does not play a role in inflammation (O' Keefe, S. J. et al., *J. Biol. Chem.*, 2007, 282(48):34663-71), it may be involved in pain mechanisms through the regulation of COX2 expression (Fitzsimmons, B. L. et al., *Neuroreport*, 2010, 21(4): 313-7). These isoforms are inhibited by a number of previously described small molecular weight compounds. Early classes of inhibitors were highly toxic due to the broad tissue distribution of these isoforms which resulted in multiple off-target effects of the compounds. Furthermore, development of a substantial number of inhibitors has been discontinued due to unacceptable safety profiles in clinical studies (Pettus, L. H. and Wurz, R. P., *Curr. Top. Med. Chem.*, 2008, 8(16):1452-67). As these adverse effects vary with chemotype, and the compounds have distinct kinase selectivity patterns, the observed toxicities may be structure-related rather than p38 mechanism-based. More recently, compounds with greater potency and specificity for p38α/β MAPK have been developed; however, levels of efficacy achieved in the treatment of chronic inflammatory diseases, including rheumatoid arthritis (SCIO-469, Genovese et al., *J. Rheumatol.*, 2011, 38:846-54; Pamapimod, Cohen et al., *Arthritis Rheum.*, 2009, 60:335-344; BMS-582949, Schieven et al., *Arthritis Rheum.*, 2010, 62:Suppl. 10:1513) and COPD (Losmapimod, Watz et al., *Lancet Resp. Med.*, 2014:63-72) have been disappointing. Furthermore, it is noteworthy that a p38 MAPK inhibitor was found to deliver benefit for patients with IBD after one week's treatment which was not sustained over a four week course of treatment (BIRB-796, Schreiber, S. et al., *Clin. Gastro. Hepatology*, 2006, 4:325-334).

An important conclusion drawn from these studies is that use of a target specific kinase inhibitor may not be sufficient to achieve and sustain therapeutic benefit in complex inflammatory diseases, where dysregulation of multiple immuno-inflammatory pathways and biological adaption can by-pass blockade of a single target mechanism, resulting in the loss of response. It can be argued that for complex inflammatory disease such as COPD, rheumatoid arthritis and IBD, inhibitors that target a set of kinases that are critical for regulation of the different immuno-inflammatory mechanisms linked to pathology will have greater potential to achieve efficacy and a sustained therapeutic response.

The role of p38 MAPK-alpha in the regulation of inflammatory pathways has been investigated extensively and is well established. Less is known about the p38 MAPK gamma and delta isoforms, which, unlike the alpha and beta isozymes are expressed in specific tissues and cells. The p38 MAPK-delta isoform is expressed more highly in the pancreas, testes, lung, small intestine and the kidney. It is also abundant in macrophages and detectable in neutrophils, CD4+ T cells and in endothelial cells (Shmueli, O. et al., *Comptes Rendus Biologies*, 2003, 326(10-11):1067-1072; Smith, S. *J. Br. J. Pharmacol.*, 2006, 149:393-404; Hale, K. K., *J. Immunol.*, 1999, 162(7):4246-52; Wang, X. S. et al., *J. Biol. Chem.*, 1997, 272(38):23668-23674.) Very little is known about the distribution of p38 MAPK gamma although it is expressed more highly in brain, skeletal muscle and heart, as well as in lymphocytes and macrophages (Shmueli, O. et al., *Comptes Rendus Biologies*, 2003, 326(10-11):1067-1072; Hale, K. K., *J. Immunol.*, 1999, 162(7):4246-52; Court, N. W. et al., *J. Mol. Cell. Cardiol.*, 2002, 34(4):413-26; Mertens, S. et al., *FEBS Lett.*, 1996, 383(3):273-6). Evidence that the p38 MAPK-gamma and p38 MAPK-delta kinases are expressed in immunologically important and pro-inflammatory cell types has raised interest in their functions relative to p38 MAPK-alpha. Selective small molecule inhibitors of p38 MAPK gamma and p38 MAPK delta are not currently available to assess the roles of these kinases pharmacologically, although one previously disclosed compound, BIRB-796, is known to possess pan-isoform inhibitory activity. The inhibition of p38 MAPK gamma and delta isoforms is observed at higher concentrations of the compound than those required to inhibit p38 MAPK alpha and p38 beta (Kuma, Y., *J. Biol. Chem.*, 2005, 280:19472-19479). In addition BIRB-796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, thereby impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and in COPD (Chung, F., *Chest*, 2011, 139(6):1470-1479). There is now an abundant literature which demonstrates that p38 MAP kinase is activated by a range of pro-inflammatory cytokines and that its activation results in the recruitment and release of additional pro-inflammatory cytokines. For instance Smith describes the inhibitory effect of p38 MAP kinase inhibitors on TNFα release from human PBMCs. However, the production of some cytokines (IL-8 and GM-CSF) by lung tissue macrophages isolated from smokers and ex-smokers was relatively insensitive to p38α/β MAPK inhibitors and Smith suggests that the abundance of p38 MAPK-delta expressed in these cells might account for the diminished effects of the compounds (Smith et al., *Br. J. Pharmacol.*, 2006, 149:393-404). Risco et al. (*Proc. Natl. Acad. Sci. U.S.A.,* 2012, 109:11200-11205) have used p38 MAPK-gamma and p38 MAPK-delta gene knockout mice to investigate the roles of these p38 isoforms in pathways regulating cytokine production by macrophages. These studies established that in mice both kinases are essential for innate immune inflammatory responses including proinflammatory cytokine production. More recently, Criado G. et al., (*Arthritis Rheum.*, 2014, 66(5):1208-17) have demonstrated that in a mouse model of inflammatory arthritis reduced disease severity in p38γ/δ−/− mice was associated with lower cytokine production and immunological activation than in normal control mice, indicating that p38 MAPK gamma and p38 MAPK delta are crucial regulators of inflammatory joint pathology. These findings suggest that in addition to p38 MAPK alpha, p38 MAPK gamma and p38 MAPK delta are potential therapeutic targets in complex diseases that involve innate and adaptive immune responses such as COPD.

The use of inhibitors of p38 MAP kinase in the treatment of chronic obstructive pulmonary disease (COPD) has also been investigated. Small molecule inhibitors targeted to p38 MAPK α/β have proved to be effective in reducing various parameters of inflammation in cells and in tissues obtained from patients with COPD, who are generally corticosteroid insensitive, (Smith, S. J., *Br. J. Pharmacol.*, 2006, 149:393-404) as well as in various in vivo animal models (Underwood, D. C. et al., *Am. J. Physiol.,* 2000, 279:L895-902; Nath, P. et al., *Eur. J. Pharmacol.,* 2006, 544:160-167). Irusen and colleagues have also suggested the possible involvement of p38 MAPK α/β with corticosteroid insensitivity via the reduction of binding affinity of the glucocorticoid receptor (GR) in nuclei (Irusen, E. et al., *J. Allergy Clin. Immunol.,* 2002, 109:649-657.). Clinical experience with a range of p38 MAP kinase inhibitors, including AMG548, BIRB-796, VX702, SC10469 and SC10323 has been described (Lee, M. R. and Dominguez, C., *Current Med. Chem.,* 2005, 12:2979-2994).

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. A recent publication of Mercado (Mercado, N., et al., *Mol. Pharmacol.,* 2011, 80(6):1128-1135) demonstrates that silencing p38 MAPK γ has the potential to restore sensitivity to corticosteroids. P38 MAPK alpha (Mercado, N. et al., *PLoS ONE,* 2012, 7(7):e41582) and JNK (Papi et al., *J. Allergy Clin. Immunol.,* 2013, 132:1075-1085) have also been reported to have roles in regulating corticosteroid insensitivity and Armstrong et al. (*JPET,* 2011, 338:732-740) have shown that the mixed p38 isoform inhibitor BIRB-796 and the corticosteroid dexamethasone have synergistic anti-inflammatory effects on COPD alveolar macrophages. Consequently there may be a benefit for patients in the use of a less p38 alpha-specific MAP kinase inhibitor for the treatment of COPD and severe asthma.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist.

Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

Epidemiological investigations have revealed a strong association between viral infections of the upper respiratory tract and a substantial percentage of the exacerbations suffered by patients already diagnosed with chronic respiratory diseases. Some of the most compelling data in this regard derives from longitudinal studies of children suffering from asthma (Papadopoulos, N. G., et al., *Paediatr. Respir. Rev.,* 2004, 5(3):255-260). A variety of additional studies support the conclusion that a viral infection can precipitate exacerbations and increase disease severity. For example, experimental clinical infections with rhinovirus have been reported to cause bronchial hyper-responsiveness to histamine in asthmatics that is unresponsive to treatment with corticosteroids (Grunberg, K., et al., *Am. J. Respir. Crit. Care Med.,* 2001, 164(10):1816-1822). Further evidence derives from the association observed between disease exacerbations in patients with cystic fibrosis and HRV infections (Wat, D., et al., *J. Cyst. Fibros.,* 2008, 7:320-328.). Also consistent with this body of data is the finding that respiratory viral infections, including rhinovirus, represent an independent risk factor that correlates negatively with the 12 month survival rate in paediatric, lung transplant recipients (Liu, M., et al., *Transpl. Infect. Dis.,* 2009, 11(4):304-312).

TLR3 is an endosomal pathogen pattern recognition receptor that senses viral dsRNA that is produced during viral infection. In human bronchial epithelial cells (BEAS2B) the TLR3 pathway is activated in response to rhinovirus infection (RV1B and RV39) (Wang et al., *J. Immunol.,* 2009, 183:6989-6997). Inhaled dsRNA and rhinovirus infection evoke neutrophilic exacerbation in allergic mice with established experimental asthma (Mahmutovic-Persson et al., *Allergy,* 2014, 69(3):348-358). In an allergic asthma model, rhinovirus-infected TLR3 knockout mice demonstrated reduced infiltration of neutrophils and macrophages into the lungs and significantly lower airways inflammation when compared with TLR3 positive controls (Wang Q. et al., *PLoS Pathog.,* 7(5):e1002070). Taken together these observations suggest that activation of the TLR3-pathway is likely to play an important role in the development of airways inflammation and exacerbations of respiratory disease in response to rhinovirus-mediated respiratory tract infections In human rhinovirus infected cells the activation of TLR3 has been shown to involve the receptor-recruitment and activation of c-Src kinase which mediates multiple downstream cellular effects. A small number of studies have appeared that link the activation of cellular Src (Src1 or p60-Src) or Src family kinases to specific responses following infection with viruses. These include a report that adenovirus elicits a PI3 kinase mediated activation of Akt through a c-Src dependent mechanism. Syk kinase activity is reported to be controlled by c-Src as an upstream kinase in HRV infection (Lau et al., *J. Immunol.*, 2008, 180:870-880). It has also been suggested that Rhinovirus-39 induced IL-8 production in epithelial cells depends upon Src kinase activation (Bentley, J. K., Newcomb, D. C., *J. Virol.*, 2007, 81:1186-1194). Finally, it has been proposed that activation of Src kinase is involved in the induction of mucin production by rhinovirus-14 in epithelial cells and sub-mucosal glands (Inoue, D. and Yamaya, M., *Respir. Physiol. Neurobiol.*, 2006, 154(3):484-499).

It has been disclosed previously that compounds that inhibit the activity of both c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Certain p38 MAPK inhibitors have also been described as inhibitors of the replication of respiratory syncitial virus (Cass, L. et al., WO 2011/158039).

For the reasons summarised above, compounds designed to treat chronic respiratory diseases that combine inhibition of c-Src and p59-HCK kinases with the inhibition of p38 MAPKs, are expected to be particularly efficacious.

In addition to playing key roles in cell signalling events which control the activity of pro-inflammatory pathways, kinase enzymes are now also recognised to regulate the activity of a range of cellular functions. Among those which have been discussed recently are the maintenance of DNA integrity (Shilo, Y., *Nature Reviews Cancer*, 2003, 3:155-168) and co-ordination of the complex processes of cell division. An illustration of recent findings is a publication describing the impact of a set of inhibitors acting upon the so-called "Olaharsky kinases" on the frequency of micronucleus formation in vitro (Olaharsky, A. J. et al., *PLoS Comput. Biol.*, 2009, 5(7):e1000446). Micronucleus formation is implicated in, or associated with, disruption of mitotic processes and is therefore an undesirable manifestation of potential toxicity. Inhibition of glycogen synthase kinase 3α (GSK3α) was found to be a particularly significant factor that increases the likelihood of a kinase inhibitor promoting micronucleus formation. Recently, inhibition of the kinase GSK3β with RNAi was also reported to promote micronucleus formation (Tighe, A. et al., *BMC Cell Biology*, 2007, 8:34).

It may be possible to attenuate the adverse effects arising from drug interactions with Olaharsky kinases, such as GSK3α, by optimisation of the dose and/or by changing the route of administration. However, it would be more advantageous to identify therapeutically useful molecules that demonstrate low or undetectable activity against these off-target enzymes and consequently elicit little or no disruption of mitotic processes, as measured in mitosis assays.

It is evident from consideration of the literature cited hereinabove that there remains a need to identify and develop new p38 MAP kinase inhibitors that have improved therapeutic potential over currently available treatments. Desirable compounds are those that exhibit a superior therapeutic index by exerting, at the least, an equally efficacious effect as previous agents but, in one or more respects, are less toxic at the relevant therapeutic dose. An objective of the present invention therefore, is to provide such novel compounds that inhibit the enzyme activity of p38 MAP kinase, for example with certain sub-type specificities (particularly alpha and gamma), together with tyrosine kinases within the Src family (particularly c-Src) thereby possessing good anti-inflammatory properties, and suitable for use in therapy. Preferred embodiments of the invention are compounds that exhibit weak or no inhibitory activity of Olaharsky kinases, such as GSK3α. Preferred embodiments of the invention are compounds that inhibit the enzyme activity of p59-HCK. Preferred embodiments of the invention are compounds that exhibit weak or no inhibitory activity of SYK kinase.

SUMMARY OF THE INVENTION

According to the invention, there is provided a compound of formula (I):

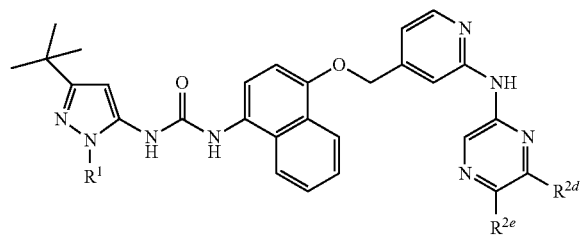

wherein:
$R^1$ represents

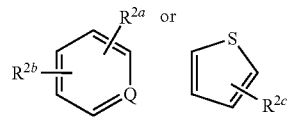

Q represents N or CH;
$R^{2a}$, $R^{2b}$ and $R^{2c}$ are independently selected from hydrogen, hydroxyl, halogen, —$C_{1-6}$alkyl, —$C_{1-6}$haloalkyl, $C_{3-5}$cycloalkyl; —$C_{1-3}$alkylene-OH, —$OC_{2-3}$alkylene-OH, —$C_{1-6}$ alkoxy, —$C_{1-3}$ alkylene-N—$(C_{1-3}$alky)$_2$, —N($C_{1-3}$alkyl)$_2$, —S$C_{1-3}$alkyl and —$C_{1-3}$ alkylene-S—$C_{1-3}$alkyl;
$R^{2d}$ and $R^{2e}$ are defined as follows: either
  (i) $R^{2d}$ represents hydrogen, —$C_{1-8}$ alkyl in which 1 to 3 carbon atoms are optionally substituted by halogen (e.g. F), —$C_{0-2}$alkylene-Cyc, —$C_{0-2}$alkylene-Het, —$CH_2$-J, —C≡C—$CH_2$-J, —$NR^3R^4$, —$OR^5$ or —CN; and $R^{2e}$ represents hydrogen or —$C_{1-6}$ alkyl (e.g. methyl); or
  (ii) $R^{2e}$ represents —$C_{0-2}$alkylene-Cyc, —$C_{0-2}$alkylene-Het, —CO—K-Cyc, —CO—K'-Het, —CO—K'-HetAr, —$CH_2$-J, —CO-J', or —$C_{1-8}$ alkyl in which 1 to 3 carbon atoms are optionally substituted by halogen (e.g. F); and $R^{2d}$ represents hydrogen or —$C_{1-6}$ alkyl (e.g. methyl); or
  (iii) $R^{2d}$ and $R^{2e}$ are joined and together represent a $C_{3-5}$alkylene chain in which one carbon atom of said alkylene chain, not being in a position adjacent to the pyrazine ring, is optionally replaced by O or $NR^{2f}$ wherein $R^{2f}$ represents H or $C_{1-3}$alkyl and wherein a carbon atom of said alkylene chain is optionally substituted by one or more groups selected from halogen (e.g. F), oxo and methyl;
J and J' independently represent a $C_{1-10}$ alkyl moiety in which 1, 2 or 3 carbon atoms are replaced by a heteroatom selected from O and N provided that any two heteroatoms if present are separated by at least two carbon atoms and wherein 1 or 2 carbon atoms are optionally substituted by oxo and which moiety is optionally substituted by 1 to 3 halogen (e.g. F) groups provided that J' does not represent OH;

K and K' independently represent a bond or a $C_{1-10}$ alkylene chain in which 1, 2 or 3 carbon atoms are optionally replaced by a heteroatom selected from O and N provided that any two heteroatoms if present are separated by at least two carbon atoms and provided that neither K nor K' represents O;

$R^3$ and $R^4$ independently represent H or —$C_{1-8}$ alkyl optionally substituted by 1 to 3 groups selected from hydroxyl, $C_{1-3}$alkoxy, hydroxy$C_{1-3}$alkyl and halogen (e.g. F) and wherein 1 or 2 carbon atoms of said alkyl are optionally substituted by oxo; or $R^3$ and $R^4$ are joined such that —$NR^3R^4$ together represents a 4-7 membered heterocyclic ring optionally substituted by one to three groups selected from $C_{1-3}$alkyl, hydroxyl, $C_{1-3}$alkoxy, hydroxy$C_{1-3}$alkyl and halogen (e.g. F) in which a carbon atom separated by at least two carbon atoms from the nitrogen atom is optionally replaced by a heteroatom selected from O and N; and wherein a methylene group is optionally substituted by oxo; or $R^3$ represents $C_{3-6}$cycloalkyl and $R^4$ represents hydrogen; $R^5$ represents —$C_{1-8}$ alkyl optionally substituted by 1 to 3 groups selected from hydroxyl, $C_{1-3}$alkoxy, hydroxy$C_{1-3}$alkyl and halogen (e.g. F) and wherein 1 to 3 carbon atoms are optionally substituted by halogen (e.g. F);

Het represents a 4 to 7 membered non-aromatic heterocyclic ring containing 1 or 2 heteroatoms selected from O, S and N or an 8 to 10 membered non-aromatic bicyclic heterocyclic ring containing 1, 2 or 3 heteroatoms selected from O, S and N in either case optionally substituted by one to three groups selected from $C_{1-3}$alkyl, hydroxyl, $C_{1-3}$alkoxy, hydroxy$C_{1-3}$alkyl-, $C_{1-3}$haloalkyl, halogen (e.g. F), oxo, —N($C_{1-3}$alkyl)$_2$, —C(=O)$C_{1-3}$alkyl, —C(=O)O$C_{1-3}$alkyl, —$C_{1-3}$ alkylene-N—($C_{1-3}$alkyl)$_2$, —$C_{1-3}$ alkylene-O—$C_{1-3}$ alkyl, $C_{3-6}$cycloalkyl and a 4-6 membered non-aromatic heterocyclic ring containing 1 or 2 heteroatoms selected from O, S and N optionally substituted by methyl, provided that Het is not directly attached to the pyrazine ring via a heteroatom and wherein a methylene group is optionally substituted by oxo;

Cyc represents a 3 to 7 membered non-aromatic carbocyclic ring optionally substituted by 1 to 3 groups selected from $C_{1-3}$alkyl, hydroxyl, $C_{1-3}$alkoxy, hydroxy$C_{1-3}$alkyl and halogen (e.g. F) and wherein a methylene group is optionally substituted by oxo; and HetAr represents a 5- or 6 membered heteroaromatic ring containing 1 to 3 heteroatoms selected from O, N and S and optionally substituted by one to three groups selected from $C_{1-3}$alkyl, hydroxyl, $C_{1-3}$alkoxy, hydroxy$C_{1-4}$alkyl-, halogen and $C_{1-3}$haloalkyl; or a pharmaceutically acceptable salt thereof.

Compounds of formula (I) together with their pharmaceutically acceptable salts are sometimes referred to herein as "compounds of the present invention" or similar.

BRIEF DESCRIPTION OF THE FIGURE

FIG. 1 shows the effect of test compounds (Example 2 as a compound of the invention, and Reference Compound) on rhinovirus-induced IL-8 Release in BEAS2B cells

DETAILED DESCRIPTION OF THE INVENTION

Alkyl groups may be branched or straight chain. $C_{1-8}$alkyl groups may for example represent $C_{1-6}$alkyl, $C_{1-4}$alkyl or $C_{1-3}$alkyl. Exemplary alkyl groups include methyl, ethyl, n-propyl, i-propyl, n-butyl, t-butyl and $CH_2CHMe_2$. In one embodiment alkyl refers to straight chain alkyl.

$C_{3-6}$cycloalkyl groups include cycloalkyl of 3-6 ring members which may optionally be substituted by methyl e.g. cyclopropyl, 1-Me-cyclopropyl, cyclobutyl, cyclopentyl and cyclohexyl.

Haloalkyl means an alkyl group substituted by one or more halogen atoms e.g. 1, 2 or 3 halogen atoms. Halogen atoms are suitably Cl, Br or F especially F. Examples of haloalkyl include —$CF_3$ and $CH_2CF_3$.

Alkoxy as used herein refers to straight or branched chain alkoxy, for example methoxy, ethoxy, propoxy, butoxy. Alkoxy as employed herein also extends to embodiments in which an oxygen atom (e.g. a single oxygen atom) is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule, for example —$C_{6-n}$alkyl-O—$C_{6-m}$alkyl in which n=1-5, m=1-5 and n+m=2-6. In one embodiment the alkoxy is linked through oxygen to the remainder of the molecule, for example —$OC_{1-6}$ alkyl. In one embodiment the disclosure relates to straight chain alkoxy. In one embodiment the alkoxy is linked through oxygen to the remainder of the molecule but the alkoxy group contains a further oxygen atom, for example —$OCH_2CH_2OCH_3$.

When alkyl groups may be substituted by halogen, they may suitably be substituted by Br, Cl or F, especially Cl or F, particularly F. Examples include $CF_3$ and $CH_2CF_3$.

Unless otherwise specified, alkylene as employed herein is a straight chain or branched chain carbon linking group, for example comprising methylenes, between two other moieties. In one embodiment alkylene moieties are straight chain alkylene moieties.

It will be clear to persons skilled in the art that where is carbon atom is said to be replaced by a heteroatom the heteroatom may replace a primary, secondary or tertiary carbon, that is a $CH_3$, —$CH_2$— or a —CH—, group, as technically appropriate and hydrogen or branching in the alkyl or alkylene chain will fill the valency of the heteroatom as appropriate to the location.

Thus, for example, where a terminal primary carbon is replaced by an oxygen heteroatom the terminal group will be an alcohol.

Cyc groups may be fully saturated or partially unsaturated e.g. they may contain one C=C bond. Suitably they are fully saturated.

Het groups may be fully saturated or partially unsaturated e.g. they may contain one C=C bond or C=N bond. Suitably they are fully saturated.

Examples of 4-7 membered non-aromatic heterocyclic rings containing 1 or 2 heteroatoms selected from O, S and N that Het may represent include azetidine, pyrrolidine, piperidine, piperazine, morpholine, dioxane, tetrahydrofuran and thiomorpholine.

Examples of 8-10 membered non-aromatic bicyclic heterocyclic rings containing 1 or 2 heteroatoms selected from O, S and N that Het may represent include octahydropyrrolo[1,2-a]pyrazine.

Het substituents may, for example, include methyl, hydroxyl, methoxy, hydroxymethyl and fluorine, especially methoxy. In an embodiment, Het does not bear a substituent. A further example of Het is thiomorpholine. Further exemplary Het substituents include oxo, —COOMe, —COMe, —$CH_2$OMe, NMe$_2$, and —$CH_2CH_2OH$. A further exemplary Het substituent is morpholinyl.

Examples of substituted Het moieties include 3-methoxy piperidin-1-yl, 4-methoxypiperidin-1-yl, 3-methoxypyrrolidin-1-yl, 3-hydroxypyrrolidin-1-yl, 1-methylpiperidin-3-yl, 1-methylpiperidin-4-yl, 1-methylpyrrolidin-3-yl, 4-hydroxypiperidin-1-yl, 3-hydroxypiperidin-1-yl, 3,4-dihydroxypyrrolidin-1-yl, 2,6-dimethylmorpholin-4-yl, 1-methyl-azetidin-3-yl, 4-methoxy-azetidin-1-yl, 3-methoxymethyl-azetidin-1-yl, 3-methoxy-azetidin-1-yl, 4-fluoro-azetidin-1-yl, 4-fluoropiperidin-1-yl, 4,4-difluoropiperidin-1-yl, 3-(morpholin-4-yl)-tetrahydrofuran-3-yl, 3-fluoropyrrolidin-1-yl, 3-fluoro-piperidin-1-yl, 1-(2-hydroxyethyl)-piperidin-4-yl, 4-acetylpiperazin-1-yl, 4-carboxymethyl-piperazin-1-yl, 4-methylpiperazin-1-yl, 5-oxo-1,4-diazepin-1-yl, 3-oxo-4-methyl-piperazin-1-yl, 3-oxo-piperazin-1-yl, 3-diaminomethyl-pyrrolidin-1-yl, 4-ethylpiperazin-1-yl, 4-dimethylamino-piperazin-1-yl, 4-(2-dimethylaminoethyl)-piperazin-1-yl, 4-methyl-1,4-diazepin-1-yl, 1-(2-methoxyethyl)piperidin-4-yl and 1,1-dioxothiomorpholin-1-yl.

Examples of moiety HetAr include 5 membered heteroaromatic rings such as thiophene, pyrrole, furan, imidazole, thiazole, thiadiazole, pyrazole and tetrazole and 6 membered heteroaromatic rings such as pyridine, pyrimidine and pyrazine. Exemplary substituents for HetAr include methyl, methoxy, halogen and trifluoromethyl. An example of a substituted HetAr is 1-methyl-imidazol-2-yl.

In one embodiment of the invention, the compound of formula (I) is a compound of formula (Ia):

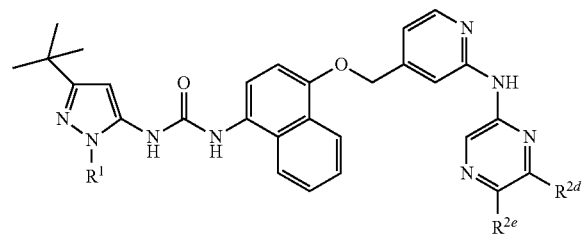

(Ia)

wherein:
$R^1$ represents

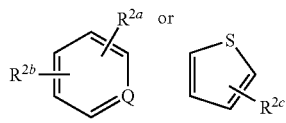

Q represents N or CH;
$R^{2a}$, $R^{2b}$ and $R^{2c}$ are independently selected from hydrogen, hydroxyl, halogen, —$C_{1-6}$alkyl, —$C_{1-6}$haloalkyl, $C_{3-5}$cycloalkyl; —$C_{1-3}$alkylene-OH, —$OC_{2-3}$alkylene-OH, and —$C_{1-6}$alkoxy; $R^{2d}$ and $R^{2e}$ are defined as follows: either (i) $R^{2d}$ represents hydrogen, —$C_{1-8}$ alkyl in which 1 to 3 carbon atoms are optionally substituted by halogen (e.g. F), —$C_{0-2}$alkylene-Cyc, —$C_{0-2}$alkylene-Het, —$CH_2$-J, —$NR^3R^4$, —$OR^5$ or —CN; and $R^{2e}$ represents hydrogen or —$C_{1-6}$ alkyl (e.g. methyl); or (ii) $R^{2e}$ represents —$C_{1-8}$ alkyl in which 1 to 3 carbon atoms are optionally substituted by halogen (e.g. F), —$C_{0-2}$alkylene-Cyc, —$C_{0-2}$alkylene-Het, —CO—K-Cyc, —CO—K'-Het, —$CH_2$-J, —CO-J'; and $R^{2d}$ represents hydrogen or —$C_{1-6}$ alkyl (e.g. methyl); or (iii) $R^{2d}$ and $R^{2e}$ are joined and together represent a $C_{3-5}$alkylene chain in which one carbon atom of said alkylene chain, not being in a position adjacent to the pyrazine ring, is optionally replaced by O or $NR^{2f}$ wherein $R^{2f}$ represents H or $C_{1-3}$alkyl and wherein a carbon atom of said alkylene chain is optionally substituted by one or more groups selected from halogen (e.g. F), oxo and methyl;

J and J' independently represent a $C_{1-7}$ alkyl moiety in which 1, 2 or 3 carbon atoms are replaced by a heteroatom selected from O and N provided that any two heteroatoms if present are separated by at least two carbon atoms and wherein 1 or 2 carbon atoms are optionally substituted by oxo and which moiety is optionally substituted by 1 to 3 halogen (e.g. F) groups provided that J' does not represent OH;

K and K' independently represent a bond or a $C_{1-7}$ alkylene chain in which 1, 2 or 3 carbon atoms are optionally replaced by a heteroatom selected from O and N provided that any two heteroatoms if present are separated by at least two carbon atoms and provided that neither K nor K' represents O;

$R^3$ and $R^4$ independently represent H or —$C_{1-8}$ alkyl optionally substituted by 1 to 3 groups selected from hydroxyl, $C_{1-3}$alkoxy, hydroxy$C_{1-3}$alkyl and halogen (e.g. F) and wherein 1 or 2 carbon atoms of said alkyl are optionally substituted by oxo; or $R^3$ and $R^4$ are joined such that —$NR^3R^4$ together represents a 4-7 membered heterocyclic ring optionally substituted by one to three groups selected from $C_{1-3}$alkyl, hydroxyl, $C_{1-3}$alkoxy, hydroxy$C_{1-3}$alkyl and halogen (e.g. F) in which a carbon atom separated by at least two carbon atoms from the nitrogen atom is optionally replaced by a heteroatom selected from O and N; and wherein a methylene group is optionally substituted by oxo;

$R^5$ represents —$C_{1-8}$ alkyl optionally substituted by 1 to 3 groups selected from hydroxyl, $C_{1-3}$alkoxy, hydroxy$C_{1-3}$alkyl and halogen (e.g. F) and wherein 1 to 3 carbon atoms are optionally substituted by halogen (e.g. F);

Het represents a 4-7 membered non-aromatic heterocyclic ring containing 1 or 2 heteroatoms selected from O, S and N optionally substituted by one to three groups selected from $C_{1-3}$alkyl, hydroxyl, $C_{1-3}$alkoxy, hydroxy$C_{1-3}$alkyl and halogen (e.g. F) provided that Het is not directly attached to the pyrazine ring via a heteroatom and wherein a methylene group is optionally substituted by oxo; and Cyc represents a 3-7 membered non-aromatic carbocyclic ring optionally substituted by 1 to 3 groups selected from $C_{1-3}$alkyl, hydroxyl, $C_{1-3}$alkoxy, hydroxy$C_{1-3}$alkyl and halogen (e.g. F) and wherein a methylene group is optionally substituted by oxo;

or a pharmaceutically acceptable salt thereof.

In relation to compounds of formula (I) and compounds of formula (Ia) (if appropriate):

Suitably Q represents CH.

When Q represents N, preferably it is in the meta position to the point of attachment to the pyrazole ring (i.e. Q represents optionally substituted pyridine-3-yl).

When $R^1$ represents substituted pyridin-3-yl, suitably $R^{2b}$ is hydrogen and $R^{2a}$ is a substituent in the 6 position.

When $R^1$ represents substituted thiophen-2-yl, suitably $R^{2c}$ is a substituent in the 5 position.

When $R^1$ represents substituted thiophen-3-yl, suitably $R^{2c}$ is a substituent in the 5 position.

When Q represents CH, suitably $R^{2b}$ is hydrogen and $R^{2a}$ is a substituent in the 4 position.

Suitably $R^{2a}$ is not hydrogen. Thus suitably $R^{2a}$ represents Cl, F, $CF_3$, —$CH_2OH$, —OH, —$C_{1-6}$ alkyl e.g. methyl, ethyl or isopropyl or $C_{1-6}$ alkoxy e.g. methoxy, more suitably —CH$_2$OH, —OH, —C$_{1-6}$ alkyl e.g. methyl or ethyl or C$_{1-6}$ alkoxy e.g. methoxy, most suitably R$^{2a}$ represents methyl or methoxy especially methyl. R$^{2a}$ may also, for example, represent —CH$_2$CH$_2$OH, methoxymethyl-, methoxyethyl- or methoxyethoxy-.

Suitably R$^{2b}$ represents hydrogen or methyl, especially hydrogen.

Suitably R$^{2c}$ represents —C$_{1-6}$ alkyl, e.g. methyl.

Suitably R$^1$ represents phenyl or pyridinyl substituted by R$^{2a}$ (and R$^{2b}$ represents hydrogen) especially phenyl substituted by R$^{2a}$.

Suitably R$^1$ represents 3-methyl-phenyl, 4-methyl-phenyl, 4-methoxyphenyl, 6-methoxy-pyridin-3-yl, 5-methyl-thiophen-2-yl, 5-methyl-thiophen-3-yl, 4-hydroxymethyl-phenyl, 4-hydroxyphenyl, 3-methyl-4-methoxyphenyl, 4-isopropyl-phenyl, 4-ethylphenyl, 4-chlorophenyl, 3-chloro-4-methoxyphenyl, 3-chlorophenyl, 3-fluorophenyl, 3,4-dimethylphenyl or 3-trifluoromethyl-4-methylphenyl, Further suitable R$^1$ moieties include 3-methoxyphenyl, 3-thiomethylphenyl, 4-thiomethylphenyl, 6-(dimethylamino)pyridine-3-yl, 6-methylpyridine-4-yl, 6-methoxypyridine-4-yl, 3-isopropylphenyl, 3-fluoro-4-methoxyphenyl, 3-fluoro-4-ethoxyphenyl, 3-fluoro-4-methylphenyl, 3-fluoro-5-methylphenyl, 3-methyl-4-(2-methoxyethoxy)phenyl, 3-ethylphenyl, 3-hydroxymethylphenyl, 3-(2-hydroxyethyl)phenyl, 3-methoxy-4-methylphenyl, 3-methoxy-5-methylphenyl, 6-methyl-pyridin-3-yl, 3-methoxy-5-fluorophenyl, 4-fluorophenyl, 3-methyl-4-ethoxyphenyl, 3-methyl-5-methoxyphenyl, 3-methyl-5-fluorophenyl, 3-methoxymethylphenyl, 4-methoxymethylphenyl, 3-(2-methoxyethoxy)phenyl, 3-dimethylaminomethylphenyl and 4-dimethylaminomethylphenyl.

More suitably, R$^1$ represents 3-methyl-phenyl, 4-methyl-phenyl, 4-methoxyphenyl, 6-methoxy-pyridin-3-yl, 5-methyl-thiophen-2-yl or 5-methyl-thiophen-3-yl, most suitably 3-methyl-phenyl or 4-methyl-phenyl, especially 4-methyl-phenyl.

Suitably J represents a C$_{1-7}$ alkyl moiety (e.g. a C$_{1-5}$ alkyl moiety) in which 1 or 2 (e.g. 1) carbon atoms are replaced by a heteroatom selected from O and N provided that any two heteroatoms if present are separated by at least two carbon atoms and wherein 1 carbon atom is optionally substituted by oxo.

In an embodiment, J represents NHCOMe, CONH$_2$, CONMe$_2$, CONHMe, OH or NH$_2$, especially CONHMe, OH or NH$_2$. Alternative examples of J include OMe, CH$_2$OMe, CH$_2$CH$_2$OMe, CH$_2$CH$_2$OH, CH$_2$OH and CONHCH$_2$CH$_2$OMe.

Suitably J' represents a C$_{1-7}$ alkyl moiety (e.g. a C$_{1-5}$ alkyl moiety) in which 1 or 2 (e.g. 1) carbon atoms are replaced by a heteroatom selected from O and N provided that any two heteroatoms if present are separated by at least two carbon atoms and wherein 1 carbon atom is optionally substituted by oxo provided that J' does not represent OH.

In an embodiment J' represents NMe$_2$, NHMe or NHCH$_2$CH$_2$OMe, especially NHMe or NHCH$_2$CH$_2$OMe. Alternative examples of J' include NHEt, NHCH$_2$CH$_2$OH, NMeCH$_2$CH$_2$CMe$_2$OH, N(CH$_2$CH$_2$OMe)$_2$, NHCH$_2$CMe$_2$OMe, NHCH$_2$CH$_2$OCHMe$_2$, NHCH$_2$CH$_2$OCMe$_3$, NHCH$_2$CH$_2$CH$_2$OH, NHCH$_2$CH$_2$CH$_2$OMe, NMeCH$_2$CH$_2$OH, NMeCH$_2$CH$_2$OMe and NHCH$_2$CH$_2$CH$_3$.

Suitably the first atom of J' is N.

Suitably K and K' independently represent a bond or a C$_{1-4}$ alkylene chain in which 1 or 2 (e.g. 1) carbon atoms are optionally replaced by a heteroatom selected from O and N provided that any two heteroatoms if present are separated by at least two carbon atoms and provided that neither K nor K' represents O;

In one embodiment K' represents a bond. In another embodiment, K' represents NCH$_2$CH$_2$. Alternative examples of K' include NH, NCH$_2$, NCH$_2$CH(OH)CH$_2$, NCH(Me)CH$_2$, NCH$_2$CH$_2$CH$_2$, NCH$_2$CMe$_2$ and NCMe$_2$CH$_2$.

K may, for example, represent the specific groups above mentioned for K'.

Suitably R$^3$ and R$^4$ independently represent H or —C$_{1-8}$ alkyl optionally substituted by 1 or 2 (e.g. 1) groups selected from hydroxyl, C$_{1-3}$alkoxy, hydroxyC$_{1-3}$alkyl and halogen (e.g. F) and wherein 1 carbon atom of said alkyl is optionally substituted by oxo; or R$^3$ and R$^4$ are joined such that —NR$^3$R$^4$ together represents a 4-7 membered heterocyclic ring optionally substituted by one to three groups selected from C$_{1-3}$alkyl, hydroxyl, C$_{1-3}$alkoxy, hydroxyC$_{1-3}$alkyl and halogen (e.g. F) in which a carbon atom separated by at least two carbon atoms from the nitrogen atom is optionally replaced by a heteroatom selected from O and N; and wherein a methylene group is optionally substituted by oxo.

Suitably R$^3$ and R$^4$ independently represent H or —C$_{1-8}$ alkyl e.g. independently represents C$_{1-4}$alkyl e.g. each represents methyl. Further examples of R$^3$ include ethyl and OCH$_2$OMe.

When R$^3$ and R$^4$ are joined, suitably —NR$^3$R$^4$ represents -azetidin-1-yl, -pyrrolidin-1-yl, piperidin-1-yl, —N-morpholinyl or 4-methyl-piperazin-1-yl and substituted derivatives thereof such as 3-hydroxy-azetidin-N-yl and 3-fluoro-azetidin-N-yl.

Suitably R$^5$ represents —C$_{1-8}$ alkyl optionally substituted by 1 or 2 (e.g. 1) groups selected from hydroxyl, C$_{1-3}$alkoxy, hydroxyC$_{1-3}$alkyl and halogen (e.g. F).

Suitably R$^5$ represents C$_{1-8}$alkyl e.g. C$_{1-4}$alkyl such as methyl. Further examples of R$^5$ include CH$_2$CH$_2$OH and CH$_2$CHMe$_2$.

Suitably Het represents a 5-7 (e.g. 5-6) membered non-aromatic heterocyclic ring containing 1 or 2 heteroatoms selected from O and N optionally substituted by 1 or 2 (e.g. 1) groups selected from C$_{1-3}$alkyl, hydroxyl, C$_{1-3}$alkoxy, hydroxyC$_{1-3}$alkyl and halogen (e.g. F) provided that Het is not directly attached to the pyrazine ring via a heteroatom and wherein a methylene group is optionally substituted by oxo.

Suitably Het represents pyrrolidinyl, piperidinyl, piperazinyl, N-methyl piperazinyl or morpholinyl, especially pyrrolidinyl, piperidinyl or morpholinyl.

Suitably Het is linked to —C$_{1-2}$alkylene in a —C$_{1-2}$alkyleneHet moiety via a nitrogen atom.

Suitably Het is linked to K' in a —CO—K'-Het moiety via a nitrogen atom.

Suitably Cyc represents a 3-6 (e.g. 3-5) membered non-aromatic carbocyclic ring (especially a fully saturated ring) optionally substituted by 1 or 2 (e.g. 1) groups selected from C$_{1-3}$alkyl, hydroxyl, C$_{1-3}$alkoxy, hydroxyC$_{1-3}$alkyl and halogen (e.g. F) and wherein a methylene group is optionally substituted by oxo.

Suitably Cyc represents cyclopropyl, cyclobutyl, cyclopentyl or cyclohexyl, especially cyclopropyl.

When R$^{2e}$ represents —CO—K'-Het, examples include —CO-Het wherein Het is selected from azetidine, pyrrolidine, piperidine, 4-methoxy piperidine and morpholinyl, in each case Het being attached to —CO— via a nitrogen atom.

When R$^{2d}$ represents —C≡C—CH$_2$-J, examples include —C≡C—CH$_2$—OMe.

When R$^{2d}$ and R$^{2e}$ are joined and together represent a C$_{3-5}$alkylene chain in which one carbon atom of said alkylene chain, not being in a position adjacent to the pyrazine ring, is optionally replaced by O or NR$^{2f}$ wherein R$^{2f}$ represents H or methyl and wherein a carbon atom on said alkylene chain is optionally substituted by one or more groups selected from F and methyl, examples include —CH$_2$CH$_2$OC(O)CH$_2$—, —(CH$_2$)$_3$—, CH$_2$OCH$_2$—, CH$_2$NHCH$_2$—, —CH$_2$)$_4$—, —CH$_2$CH$_2$OCH$_2$—, —CH$_2$CH$_2$NHCH$_2$—, —CH$_2$CH$_2$NMeCH$_2$—, —CH$_2$OCH$_2$CH$_2$—, CH$_2$NHCH$_2$CH$_2$—, —(CH$_2$)$_5$— —CH$_2$CHFCH$_2$CH$_2$— and —CH$_2$CHMeCH$_2$CH$_2$—. For example, R$^{2d}$ and R$^{2e}$ can be joined by a —(CH$_2$)$_3$— or a —(CH$_2$)$_4$— chain, Suitably (i) R$^{2d}$ represents —NMe$_2$, OMe, —OCH$_2$CH$_2$OH, 3-hydroxy-azetidin-N-yl, 3-fluoro-azetidin-N-yl, methyl, ethyl, cyclopropyl, —CN, CH$_2$OH, CH$_2$CONH$_2$, CH$_2$CONHMe or CH$_2$CONMe$_2$ (more suitably methyl, ethyl, cyclopropyl, —CN, CH$_2$OH, CH$_2$CONH$_2$, CH$_2$CONHMe or CH$_2$CONMe$_2$, most suitably methyl, ethyl, cyclopropyl or —CN) and R$^{2e}$ represents H; or (ii) R$^{2e}$ represents methyl, ethyl, cyclopropyl, —CH$_2$OH, —CONH(CH$_2$)$_2$—N-morpholinyl, —CO-pyrrolidin-N-yl, —CO-piperidin-N-yl, —CO-(4-methoxy)piperidin-N-yl, —CO-morpholin-N-yl, —CONMe$_2$, —CH$_2$NHCOMe —CH$_2$CONHMe, —CH$_2$CONMe$_2$, —CH$_2$CONH$_2$, —CONHMe, —CONH(CH$_2$)$_2$OMe or —CH$_2$NH$_2$ (more suitably methyl, ethyl, cyclopropyl, —CH$_2$OH, —CONH (CH$_2$)$_2$—N-morpholinyl, —CO-pyrrolidin-N-yl, —CO-(4-methoxy)piperidin-N-yl, —CH$_2$CONHMe, —CONHMe, —CONH(CH$_2$)$_2$OMe or —CH$_2$NH$_2$) and R$^{2d}$ represents H; or (iii) R$^{2d}$ and R$^{2e}$ each represent H; or (iv) R$^{2d}$ and R$^{2e}$ each represent methyl.

Alternatively, suitably (v) R$^{2d}$ represents cyclobutyl, cyclopentyl, pyrrolidin-1-yl, isopropyl, dimethylamino, amino, NHCOCH$_2$OMe, (CH$_2$)$_2$OMe, (CH$_2$)$_3$OMe, (CH$_2$)$_3$OH, 4-pyranyl, ethoxy, NHCHMe$_2$, morpholin-4-yl, NH-cyclopropyl, NHMe, OCH$_2$CH$_2$OH, OCH$_2$CHMe$_2$, 3-hydroxy-azetidin-1-yl, CH$_2$CH$_2$OH, n-propyl, CH$_2$CONHCH$_2$CH$_2$OMe, CH$_2$-morpholin-4-yl, C≡C—CH$_2$OMe, or 1-methyl-piperidin-4-yl and R$^{2e}$ represents hydrogen; or (vi) R$^{2e}$ represents CONH(CH$_2$)$_2$OH, CONH (CH$_2$)$_2$-(3-methoxy)piperidin-1-yl, CO-(4-methoxy)piperidin-1-yl, CONMeCH$_2$CH$_2$OMe, CO-(3-methoxy)-pyrrolidin-1-yl, CO-(3-hydroxy)-pyrrolidin-1-yl, CONHCH$_2$CH$_2$CMe$_2$OH, CON(CH$_2$CH$_2$OMe)$_2$, CONHCH$_2$CMe$_2$OMe, CONHCH$_2$CH$_2$(piperidin-1-yl), CONH(1-Me)-piperidin-4-yl, CONHCH$_2$(1-Me)-piperidin-4-yl, CONH-(1-Me)-pyrrolidin-3-yl, CONHCH$_2$CH$_2$-(4-OH)-piperidin-1-yl, CONHCH$_2$CH$_2$(2,6-dimethyl)-morpholin-4-yl, CONHCH$_2$CH$_2$pyrrolidin-1-yl, CONHCH$_2$CH(OH)CH$_2$morpholin-4-yl, CONH-(1-Me)-piperidin-3-yl, CONH-(1-Me)-azetidin-3-yl, CONHCH$_2$CH$_2$-(2-Me)-imidazol-1-yl, CONHCH$_2$CH$_2$-(4-COOMe)-piperazin-1-yl, CONHCH$_2$CH$_2$-(4-OMe)-piperidin-1-yl, CONH-(3-morpholin-4-yl)-tetrahydrofuran-3-yl, CONHCH$_2$CH$_2$-(4,4-difluoro)-piperidin-1-yl, CONHCH$_2$CH$_2$-(3-OH)-piperidin-1-yl, CONHCH$_2$CH$_2$-(4-F)-piperidin-1-yl, CONHCH$_2$CH$_2$-(3-OH)-pyrrolidin-1-yl, CONHCH$_2$CH$_2$-(3-OMe)-pyrrolidin-1-yl, CONHCH$_2$-(1-Me)-piperidin-4-yl, CONHCH$_2$CH$_2$-(3-F)-pyrrolidin-1-yl, CONHCH$_2$CH$_2$-(3-F)-piperidin-1-yl, CONHCH$_2$CH$_2$(4-acetyl)-piperazin-1-yl, CONH(1-CH$_2$CH$_2$OH)-piperidin-4-yl, OMe, CONHCH$_2$CH$_2$OMe, CO-(3-OH)-pyrrolidin-1-yl, CO-(4-OMe)-azetidin-1-yl, CONHCH$_2$CH$_2$OiPr, CONHCH$_2$CH$_2$Ot-Bu, CO-(3-OH)-pyrrolidin-1-yl, CO-(4-OH)-piperidin-1-yl, CONHCH$_2$CH$_2$OH, CO-azetidin-1-yl, CO-(4-Me)-piperazin-1-yl, CO-(4-F)-piperidin-1-yl, CO-(4-Me)-piperidin-1-yl, CONHCH$_2$CH$_2$OMe, CH$_2$CH$_2$CH$_2$OMe, CH$_2$OMe, CONHEt, CONHCH$_2$CH$_2$CH$_3$, CO-(4-F)-azetidin-1-yl, CH$_2$OMe, CO-(3-OMe)-pyrrolidin-1-yl, CONMeCH$_2$CH$_2$OMe, CO-(4-OMe)-piperidin-1-yl, CO-(2,6-di-Me)-morpholin-4-yl, CONMeCH$_2$CH$_2$CH$_2$OH, CO-(3-OMe)-azetidin-1-yl, CO-(3-CH$_2$OMe)-azetidin-1-yl, CONHCH$_2$CH$_2$CH$_2$OH, CO-(3-OH)-piperidin-1-yl, CO-(3-OMe)-piperidin-1-yl, CO-4-acetylpiperazine-1-yl, CO-(5-oxo)-1,4-diazepane-1-yl, CO-(3-F)-pyrrolidin-1-yl, CO-1,1-dioxothiomorpholin-4-yl, CO-3-oxo-4-methyl-piperazin-1-yl, CO-(4,4-difluoro)-piperidin-1-yl, CO-(3,4-dihydroxy)-pyrrolidin-1-yl, CO-3-oxopiperazin-1-yl, CO-(3-dimethylamino)-pyrrolidin-1-yl, CONHCH$_2$CH$_2$(4-Me-piperazin-1-yl), CH$_2$-morpholin-1-yl, CONHCH$_2$CH$_2$(1-Me-piperidin-4-yl), CONHCH$_2$CH$_2$NMe$_2$, CONHCH$_2$CH$_2$morpholin-1-yl, CO-(4-Et)-piperazin-1-yl, CO-4-dimethylamino-piperazin-1-yl, CO-(4-CH$_2$CH$_2$NMe$_2$)piperazin-1-yl, CO-(4-methyl)-1,4-diazepan-1-yl, CO-(octahydropyrrolo[1,2-a]pyrazin-2-yl), CH$_2$(4-Me-piperazin-1-yl), CONHCHMeCH$_2$morpholin-1-yl, CONHCH$_2$CH$_2$CH$_2$morpholin-1-yl, CONHCH$_2$CH$_2$CH$_2$(4-Me-piperazin-1-yl), CONHCH$_2$CMe$_2$-morpholin-1-yl, CONH—(N—CH$_2$CH$_2$OMe-piperidin-4-yl), CO-(4-dimethylamino-piperidin-1-yl), CONHCMe$_2$CH$_2$(N-morpholinyl) or CONHCH$_2$(1-Me-imidazol-2-yl) and R$^{2d}$ represents hydrogen; or (vii) R$^{2d}$ represents cyclopropyl or ethyl and R$^{2e}$ represents methyl; or (viii) R$^{2d}$ represents methyl or ethyl and R$^{2e}$ represents ethyl.

In one embodiment, R$^{2d}$ and R$^{2e}$ both represent hydrogen. In another embodiment, R$^{2d}$ and R$^{2e}$ both represent methyl. In one embodiment R$^{2e}$ represents ethyl and R$^{2d}$ represents hydrogen.

Suitably R$^{2d}$ and R$^{2e}$ moieties do not contain any F atoms attached to a carbon atom adjacent to the pyrazine ring.

Suitably R$^{2f}$ represents H or methyl, especially H.

Exemplary compounds of formula (I) include:

1-(3-(tert-butyl)-1-(p-tolyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl) ureido)naphthalen-1-yl)oxy)methyl)pyridin-2-yl)amino)-N-(2-methoxyethyl)pyrazine-2-carboxamide;

1-(3-(tert-butyl)-1-(p-tolyl)-1H-pyrazol-5-yl)-3-(4-((2-((5,6-dimethylpyrazin-2-yl)amino)pyridin-4-yl)methoxy) naphthalen-1-yl)urea;

1-(4-((2-((5-(aminomethyl)pyrazin-2-yl)amino)pyridin-4-yl)methoxy)naphthalen-1-yl)-3-(3-(tert-butyl)-1-(p-tolyl)-1H-pyrazol-5-yl)urea;

N-((5-((4-(((4-(3-(3-(tert-butyl)-1-(p-tolyl)-1H-pyrazol-5-yl)ureido)naphthalen-1-yl)oxy)methyl)pyridin-2-yl) amino)pyrazin-2-yl)methyl)acetamide;

5-((4-(((4-(3-(3-(tert-butyl)-1-(p-tolyl)-1H-pyrazol-5-yl) ureido)naphthalen-1-yl)oxy)methyl)pyridin-2-yl)amino)-N-methylpyrazine-2-carboxamide;

2-(6-((4-(((4-(3-(3-(tert-butyl)-1-(p-tolyl)-1H-pyrazol-5-yl) ureido)naphthalen-1-yl)oxy)methyl)pyridin-2-yl)amino) pyrazin-2-yl)-N,N-dimethylacetamide;

5-((4-(((4-(3-(3-(tert-butyl)-1-(p-tolyl)-1H-pyrazol-5-yl) ureido)naphthalen-1-yl)oxy)methyl)pyridin-2-yl)amino)-N,N-dimethylpyrazine-2-carboxamide;

1-(3-(tert-Butyl)-1-(p-tolyl)-1H-pyrazol-5-yl)-3-(4-((2-((5-(hydroxymethyl)pyrazin-2-yl)amino)pyridin-4-yl) methoxy)naphthalen-1-yl)urea;

1-(3-(tert-butyl)-1-(p-tolyl)-1H-pyrazol-5-yl)-3-(4-((2-((6-cyanopyrazin-2-yl)amino)pyridin-4-yl)methoxy)naphthalen-1-yl)urea;

1-(3-(tert-butyl)-1-(6-methoxypyridin-3-yl)-1H-pyrazol-5-yl)-3-(4-((2-(pyrazin-2-ylamino)pyridin-4-yl)methoxy)naphthalen-1-yl)urea;

1-(3-(tert-butyl)-1-(5-methylthiophen-2-yl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-cyclopropylpyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-morpholinoethyl)pyrazine-2-carboxamide;

1-(3-(tert-butyl)-1-(p-tolyl)-1H-pyrazol-5-yl)-3-(4-((2-((6-methoxypyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-methylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-methylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(hydroxymethyl)pyrazin-2-yl)amino)pyridin-4-yl)methoxy)naphthalen-1-yl)urea;

1-(3-(tert-butyl)-1-(4-methoxyphenyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(4-methoxyphenyl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(5-methylthiophen-2-yl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(4-(hydroxymethyl)phenyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(5-methylthiophen-2-yl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(5-methylthiophen-3-yl)-1H-pyrazol-5-yl)-3-(4-((2-((6-cyclopropylpyrazin-2-yl)amino)pyridin-4-yl)methoxy)naphthalen-1-yl)urea;

2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-methylacetamide;

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N,N-dimethylacetamide;

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)acetamide;

1-(3-(tert-butyl)-1-(5-methylthiophen-3-yl)-1H-pyrazol-5-yl)-3-(4-((2-(pyrazin-2-ylamino)pyridin-4-yl)methoxy)naphthalen-1-yl)urea;

2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)acetamide;

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-methylacetamide;

1-(3-(tert-butyl)-1-(4-hydroxyphenyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(morpholine-4-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-ethylpyrazin-2-yl)amino)pyridin-4-yl)methoxy)naphthalen-1-yl)urea;

1-(3-(tert-butyl)-1-(4-methoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(4-methoxy-3-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(m-tolyl)-1H-pyrazol-5-yl)-3-(4-((2-(pyrazin-2-ylamino)pyridin-4-yl)methoxy)naphthalen-1-yl)urea;

1-(3-(tert-butyl)-1-(4-isopropylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(4-ethylphenyl)-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(5-methylthiophen-2-yl)-1H-pyrazol-5-yl)ureido)naphthalen-1-yl)oxy)methyl)pyridin-2-yl)amino)-N-(2-methoxyethyl)pyrazine-2-carboxamide;

5-((4-(((4-(3-(3-(tert-butyl)-1-(5-methylthiophen-3-yl)-1H-pyrazol-5-yl)ureido)naphthalen-1-yl)oxy)methyl)pyridin-2-yl)amino)-N-(2-methoxyethyl)pyrazine-2-carboxamide;

1-(3-(tert-butyl)-1-(4-chlorophenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-chloro-4-methoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-cyclobutylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-cyclopentylpyrazin-2-yl)amino)pyridin-4-yl)methoxy)naphthalen-1-yl)urea;

1-(3-(tert-butyl)-1-(3-fluorophenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-chlorophenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3,4-dimethylphenyl)-1H-pyrazol-5-yl)-3-(4-((2-(pyrazin-2-ylamino)pyridin-4-yl)methoxy)naphthalen-1-yl)urea; and 1-(3-(tert-butyl)-1-(4-methyl-3-(trifluoromethyl)phenyl)-1H-pyrazol-5-yl)-3-(4-((2-(pyrazin-2-ylamino)pyridin-4-yl)methoxy)naphthalen-1-yl)urea;

and pharmaceutically acceptable salts of any one thereof.

Further exemplary compounds of formula (I) include:

5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-hydroxyethyl)pyrazine-2-carboxamide;

(S)-5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-(3-methoxypiperidin-1-yl)ethyl)pyrazine-2-carboxamide;

1-(3-(tert-butyl)-1-(p-tolyl)-1H-pyrazol-5-yl)-3-(4-((2-((6-(pyrrolidin-1-yl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-methoxypiperidine-1-carbonyl)pyrazin-2-yl)amino)pyridin-4-yl)methoxy)naphthalen-1-yl)urea;

1-(3-(tert-butyl)-1-(3-methoxy-4-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(m-tolyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(3-fluoro-4-methylphenyl)-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methoxyethyl)-N-methylpyrazine-2-carboxamide;

1-(3-(tert-butyl)-1-(m-tolyl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(3-fluorophenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(6-methoxypyridin-3-yl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(4-(methoxymethyl)phenyl)-1H-pyrazol-5-yl)-3-(4-((2-(pyrazin-2-ylamino)pyridin-4-yl)methoxy)naphthalen-1-yl)urea;

1-(3-(tert-butyl)-1-(m-tolyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

(R)-1-(3-(tert-butyl)-1-(p-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea;

(S)-1-(3-(tert-butyl)-1-(p-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-isopropylpyrazin-2-yl)amino)pyridin-4-yl)methoxy)naphthalen-1-yl)urea;

(R)-1-(3-(tert-butyl)-1-(m-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea;

1-(3-(tert-butyl)-1-(3-methoxy-4-methylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-(methoxymethyl)phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-hydroxy-3-methylbutyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N,N-bis(2-methoxyethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methoxy-2-methylpropyl)pyrazine-2-carboxamide;

1-(3-(tert-butyl)-1-phenyl-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(m-tolyl)-1H-pyrazol-5-yl)ureido)naphthalen-1-yl)oxy)methyl)pyridin-2-yl)amino)-N,N-bis(2-methoxyethyl)pyrazine-2-carboxamide;

1-(3-(tert-butyl)-1-(3-(methylthio)phenyl)-1H-pyrazol-5-yl)-3-(4-((2-(pyrazin-2-ylamino)pyridin-4-yl)methoxy)naphthalen-1-yl)urea;

1-(3-(tert-butyl)-1-(6-(dimethylamino)pyridin-3-yl)-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(piperidin-1-yl)ethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpiperidin-4-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-((1-methylpiperidin-4-yl)methyl)pyrazine-2-carboxamide;

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpyrrolidin-3-yl)pyrazine-2-carboxamide;

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpyrrolidin-3-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-hydroxypiperidin-1-yl)ethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-((2S,6R)-2,6-dimethylmorpholino)ethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(pyrrolidin-1-yl)ethyl)pyrazine-2-carboxamide;

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-hydroxy-3-morpholinopropyl)pyrazine-2-carboxamide;

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpiperidin-3-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylazetidin-3-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(2-methyl-1H-imidazol-1-yl)ethyl)pyrazine-2-carboxamide;

Methyl 4-(2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamido)ethyl)piperazine-1-carboxylate;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-methoxypiperidin-1-yl)ethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-((3R,4R)-4-morpholinotetrahydrofuran-3-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4,4-difluoropiperidin-1-yl)ethyl)pyrazine-2-carboxamide;

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-hydroxypiperidin-1-yl)ethyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-fluoropiperidin-1-yl)ethyl)pyrazine-2-carboxamide;

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-hydroxypyrrolidin-1-yl)ethyl)pyrazine-2-carboxamide;

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-methoxypyrrolidin-1-yl)ethyl)pyrazine-2-carboxamide;

5-((4-(((4-(3-(3-(tert-butyl)-1-(3-(methoxymethyl)phenyl)-1H-pyrazol-5-yl)ureido)naphthalen-1-yl)oxy)methyl)pyridin-2-yl)amino)-N-((1-methylpiperidin-4-yl)methyl)pyrazine-2-carboxamide;

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-fluoropyrrolidin-1-yl)ethyl)pyrazine-2-carboxamide;

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-fluoropiperidin-1-yl)ethyl)pyrazine-2-carboxamide;

N-(2-(4-acetylpiperazin-1-yl)ethyl)-5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-(2-hydroxyethyl)piperidin-4-yl)pyrazine-2-carboxamide;

1-(3-(tert-butyl)-1-(4-methoxyphenyl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-methoxypyrazin-2-yl)amino)pyridin-4-yl)methoxy)naphthalen-1-yl)urea;

1-(4-((2-((6-aminopyrazin-2-yl)amino)pyridin-4-yl)methoxy)naphthalen-1-yl)-3-(3-(tert-butyl)-1-(p-tolyl)-1H-pyrazol-5-yl)urea;

N-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-2-methoxyacetamide;

1-(3-(tert-butyl)-1-(4-methoxyphenyl)-1H-pyrazol-5-yl)-3-(4-((2-((6-methoxypyrazin-2-yl)amino)pyridin-4-yl)methoxy)naphthalen-1-yl)urea;

1-(3-(tert-butyl)-1-(5-methylthiophen-2-yl)-1H-pyrazol-5-yl)-3-(4-((2-((6-methoxypyrazin-2-yl)amino)pyridin-4-yl)methoxy)naphthalen-1-yl)urea;

1-(3-(tert-butyl)-1-(4-(hydroxymethyl)phenyl)-1H-pyrazol-5-yl)-3-(4-((2-((6-methoxypyrazin-2-yl)amino)pyridin-4-yl)methoxy)naphthalen-1-yl)urea;

1-(3-(tert-butyl)-1-(5-methylthiophen-2-yl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(5-methylthiophen-3-yl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(5-methylthiophen-3-yl)-1H-pyrazol-5-yl)-3-(4-((2-((6-methoxypyrazin-2-yl)amino)pyridin-4-yl)methoxy)naphthalen-1-yl)urea;

1-(3-(tert-butyl)-1-(4-(hydroxymethyl)phenyl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(4-hydroxyphenyl)-1H-pyrazol-5-yl)-3-(4-((2-((6-(dimethylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-ethoxypyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(isopropylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-morpholinopyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(cyclopropylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(methylamino)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(2-hydroxyethoxy)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-isobutoxypyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(3-hydroxyazetidin-1-yl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-isopropoxyethyl)pyrazine-2-carboxamide;

N-(2-(tert-butoxy)ethyl)-5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamide;

(S)-1-(3-(tert-butyl)-1-(p-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-hydroxypiperidine-1-carbonyl)pyrazin-2-yl)amino)pyridin-4-yl)methoxy)naphthalen-1-yl)urea;

1-(4-((2-((5-(azetidine-1-carbonyl)pyrazin-2-yl)amino)pyridin-4-yl)methoxy)naphthalen-1-yl)-3-(3-(tert-butyl)-1-(p-tolyl)-1H-pyrazol-5-yl)urea;

1-(3-(tert-butyl)-1-(p-tolyl)-1H-pyrazol-5-yl)-3-(4-((2-((5-ethyl-6-methylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6,7-dihydro-5H-cyclopenta[b]pyrazin-2-yl)amino)pyridin-4-yl)methoxy)naphthalen-1-yl)urea;

1-(3-(tert-butyl)-1-(3-isopropylphenyl)-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(4-methoxy-3-methylphenyl)-1H-pyrazol-5-yl)ureido)naphthalen-1-yl)oxy)methyl)pyridin-2-yl)amino)-N-(2-methoxyethyl)pyrazine-2-carboxamide;

1-(3-(tert-butyl)-1-(4-methoxy-3-methylphenyl)-1H-pyrazol-5-yl)-3-(4-((2-((5-(hydroxymethyl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-hydroxypropyl)pyrazine-2-carboxamide;

1-(3-(tert-butyl)-1-(4-methoxy-3-methylphenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-methylpiperazine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(piperidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5,6,7,8-tetrahydroquinoxalin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5,6-diethylpyrazin-2-yl)amino)pyridin-4-yl)methoxy)naphthalen-1-yl)urea;

1-(3-(tert-butyl)-1-(4-methoxy-3-methylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(m-tolyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-methoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-ethyl-5-methylpyrazin-2-yl)amino)pyridin-4-yl)methoxy)naphthalen-1-yl)urea;

1-(3-(tert-butyl)-1-(3,4-dimethylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3,4-dimethylphenyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(3,4-dimethylphenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(3,4-dimethylphenyl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(3-fluoro-4-methoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(4-(methylthio)phenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-cyclopropyl-5-methylpyrazin-2-yl)amino)pyridin-4-yl)methoxy)naphthalen-1-yl)urea;

1-(3-(tert-butyl)-1-(3,4-dimethylphenyl)-1H-pyrazol-5-yl)-3-(4-((2-((5-ethylpyrazin-2-yl)amino)pyridin-4-yl)methoxy)naphthalen-1-yl)urea;

5-((4-(((4-(3-(3-(tert-butyl)-1-(m-tolyl)-1H-pyrazol-5-yl)ureido)naphthalen-1-yl)oxy)methyl)pyridin-2-yl)amino)-N-(2-methoxyethyl)pyrazine-2-carboxamide;

1-(3-(tert-butyl)-1-(p-tolyl)-1H-pyrazol-5-yl)-3-(4-((2-((6-(3-methoxypropyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(2-methoxyethyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(3-hydroxypropyl)pyrazin-2-yl)amino)pyridin-4-yl)methoxy)naphthalen-1-yl)urea;

5-((4-(((4-(3-(3-(tert-butyl)-1-(3,4-dimethylphenyl)-1H-pyrazol-5-yl)ureido)naphthalen-1-yl)oxy)methyl)pyridin-2-yl)amino)-N-(2-methoxyethyl)pyrazine-2-carboxamide;

1-(3-(tert-butyl)-1-(4-(2-methoxyethoxy)-3-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((6-(3-methoxyprop-1-yn-1-yl)pyrazin-2-yl)amino)pyridin-4-yl)methoxy)naphthalen-1-yl)urea;

1-(3-(tert-butyl)-1-(m-tolyl)-1H-pyrazol-5-yl)-3-(4-((2-((5-ethylpyrazin-2-yl)amino)pyridin-4-yl)methoxy)naphthalen-1-yl)urea;

1-(3-(tert-butyl)-1-(m-tolyl)-1H-pyrazol-5-yl)-3-(4-((2-((6-cyclopropylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(tetrahydro-2H-pyran-4-yl)pyrazin-2-yl)amino)pyridin-4-yl)methoxy)naphthalen-1-yl)urea;

(R)-1-(3-(tert-butyl)-1-(p-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(3-methoxyazetidine-1-carbonyl)pyrazin-2-yl)amino)pyridin-4-yl)methoxy)naphthalen-1-yl)urea;

1-(3-(tert-butyl)-1-(4-ethylphenyl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(3-ethylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-(methoxymethyl)phenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-fluoro-4-methylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-fluoro-4-methoxyphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-fluorophenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(3-methoxyphenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(2-hydroxyethyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-propylpyrazin-2-yl)amino)pyridin-4-yl)methoxy)naphthalen-1-yl)urea;

1-(3-(tert-butyl)-1-(4-ethylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-(hydroxymethyl)phenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-chlorophenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-fluoropiperidine-1-carbonyl)pyrazin-2-yl)amino)pyridin-4-yl)methoxy)naphthalen-1-yl)urea;

1-(3-(tert-butyl)-1-(6-methoxypyridin-3-yl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(3-methoxyphenyl)-1H-pyrazol-5-yl)-3-(4-((2-((5-(hydroxymethyl)pyrazin-2-yl)amino)pyridin-4-yl)methoxy)naphthalen-1-yl)urea;

1-(3-(tert-butyl)-1-(3-chlorophenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(3,5-dimethylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-fluoro-5-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-fluoro-4-methylphenyl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(4-ethoxy-3-fluorophenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-ethoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((5-(4-methylpiperidine-1-carbonyl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-methoxypropyl)pyrazine-2-carboxamide;

1-(3-(tert-butyl)-1-(4-fluorophenyl)-1H-pyrazol-5-yl)-3-(4-((2-(pyrazin-2-ylamino)pyridin-4-yl)methoxy)naphthalen-1-yl)urea;

1-(3-(tert-butyl)-1-(p-tolyl)-1H-pyrazol-5-yl)-3-(4-((2-((5-(3-methoxypropyl)pyrazin-2-yl)amino)pyridin-4-yl)methoxy)naphthalen-1-yl)urea;

1-(3-(tert-butyl)-1-(3-methoxyphenyl)-1H-pyrazol-5-yl)-3-(4-((2-((6-propylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(methoxymethyl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-ethylpyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-propylpyrazine-2-carboxamide;

1-(3-(tert-butyl)-1-(p-tolyl)-1H-pyrazol-5-yl)-3-(4-((2-((5-(3-fluoroazetidine-1-carbonyl)pyrazin-2-yl)amino)pyridin-4-yl)methoxy)naphthalen-1-yl)urea;

1-(3-(tert-butyl)-1-(3-fluoro-4-methylphenyl)-1H-pyrazol-5-yl)-3-(4-((2-((6-propylpyrazin-2-yl)amino)pyridin-4-yl)methoxy)naphthalen-1-yl)urea;

1-(3-(tert-butyl)-1-(m-tolyl)-1H-pyrazol-5-yl)-3-(4-((2-((5-(methoxymethyl)pyrazin-2-yl)amino)pyridin-4-yl)methoxy)naphthalen-1-yl)urea;

1-(3-(tert-butyl)-1-(3-methoxy-5-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(4-ethoxy-3-methylphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(6-methylpyridin-3-yl)-1H-pyrazol-5-yl)-3-(4-((2-(pyrazin-2-ylamino)pyridin-4-yl)methoxy)naphthalen-1-yl)urea;

(R)-1-(3-(tert-butyl)-1-(m-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea;

(S)-1-(3-(tert-butyl)-1-(m-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea;

1-(3-(tert-butyl)-1-(m-tolyl)-1H-pyrazol-5-yl)-3-(4-((2-((6-propylpyrazin-2-yl)amino)pyridin-4-yl)methoxy)naphthalen-1-yl)urea;

1-(3-(tert-butyl)-1-(3-fluorophenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(3-fluorophenyl)-1H-pyrazol-5-yl)-3-(4-((2-((5-(methoxymethyl)pyrazin-2-yl)amino)pyridin-4-yl)methoxy)naphthalen-1-yl)urea;

5-((4-(((4-(3-(3-(tert-butyl)-1-(m-tolyl)-1H-pyrazol-5-yl)ureido)naphthalen-1-yl)oxy)methyl)pyridin-2-yl)amino)-N-methylpyrazine-2-carboxamide;

5-((4-(((4-(3-(3-(tert-butyl)-1-(m-tolyl)-1H-pyrazol-5-yl)ureido)naphthalen-1-yl)oxy)methyl)pyridin-2-yl)amino)-N-(2-methoxyethyl)-N-methylpyrazine-2-carboxamide;

1-(3-(tert-butyl)-1-(m-tolyl)-1H-pyrazol-5-yl)-3-(4-((2-((5-(4-methoxypiperidine-1-carbonyl)pyrazin-2-yl)amino)pyridin-4-yl)methoxy)naphthalen-1-yl)urea;

1-(3-(tert-butyl)-1-(6-methoxypyridin-3-yl)-1H-pyrazol-5-yl)-3-(4-((2-((5,6-dimethylpyrazin-2-yl)amino)pyridin-4-yl)methoxy)naphthalen-1-yl)urea;

1-(3-(tert-butyl)-1-(3-methoxy-4-methylphenyl)-1H-pyrazol-5-yl)-3-(4-((2-((5,6-dimethylpyrazin-2-yl)amino)pyridin-4-yl)methoxy)naphthalen-1-yl)urea;

2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-(2-methoxyethyl)acetamide;

1-(3-(tert-butyl)-1-(4-(methoxymethyl)phenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-fluoro-5-methoxyphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3,5-dimethylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(4-fluorophenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-((2S,6R)-2,6-dimethylmorpholine-4-carbonyl)pyrazin-2-yl)amino)pyridin-4-yl)methoxy)naphthalen-1-yl)urea;

1-(3-(tert-butyl)-1-(4-fluorophenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(3-methoxyphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(4-(methoxymethyl)phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(3,5-dimethylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(6-methoxypyridin-3-yl)-1H-pyrazol-5-yl)-3-(4-((2-((5-(pyrrolidine-1-carbonyl)pyrazin-2-yl)amino)pyridin-4-yl)methoxy)naphthalen-1-yl)urea;

1-(3-(tert-butyl)-1-(3-fluoro-5-methoxyphenyl)-1H-pyrazol-5-yl)-3-(4-((2-(pyrazin-2-ylamino)pyridin-4-yl)methoxy)naphthalen-1-yl)urea;

1-(3-(tert-butyl)-1-(3-methoxy-5-methylphenyl)-1H-pyrazol-5-yl)-3-(4-((2-((6-ethylpyrazin-2-yl)amino)pyridin-4-yl)methoxy)naphthalen-1-yl)urea;

1-(3-(tert-butyl)-1-(3-(methoxymethyl)phenyl)-1H-pyrazol-5-yl)-3-(4-((2-((6-ethylpyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)
ureido)naphthalen-1-yl)oxy)methyl)pyridin-2-yl)amino)-
N-(3-hydroxypropyl)-N-methylpyrazine-2-carboxamide;

1-(3-(tert-butyl)-1-(m-tolyl)-1H-pyrazol-5-yl)-3-(4-((2-((5-
(3-methoxyazetidine-1-carbonyl)pyrazin-2-yl)amino)
pyridin-4-yl)methoxy)naphthalen-1-yl)urea;

1-(3-(tert-butyl)-1-(p-tolyl)-1H-pyrazol-5-yl)-3-(4-((2-((5-
(3-(methoxymethyl)azetidine-1-carbonyl)pyrazin-2-yl)
amino)pyridin-4-yl)methoxy)naphthalen-1-yl)urea;

1-(3-(tert-butyl)-1-(3-methoxy-4-methylphenyl)-1H-pyra-
zol-5-yl)-3-(4-((2-((5-(pyrrolidine-1-carbonyl)pyrazin-2-
yl)amino)pyridin-4-yl)methoxy)naphthalen-1-yl)urea;

1-(3-(tert-butyl)-1-(3-methoxy-5-methylphenyl)-1H-pyra-
zol-5-yl)-3-(4-((2-((5-(pyrrolidine-1-carbonyl)pyrazin-2-
yl)amino)pyridin-4-yl)methoxy)naphthalen-1-yl)urea;

1-(3-(tert-butyl)-1-(3-fluoro-4-methoxyphenyl)-1H-pyra-
zol-5-yl)-3-(4-((2-((5-(pyrrolidine-1-carbonyl)pyrazin-2-
yl)amino)pyridin-4-yl)methoxy)naphthalen-1-yl)urea;

1-(3-(tert-butyl)-1-(4-ethylphenyl)-1H-pyrazol-5-yl)-3-(4-
((2-((5-(pyrrolidine-1-carbonyl)pyrazin-2-yl)amino)pyri-
din-4-yl)methoxy)naphthalen-1-yl)urea;

1-(3-(tert-butyl)-1-(3-ethylphenyl)-1H-pyrazol-5-yl)-3-(4-
((2-((5-(pyrrolidine-1-carbonyl)pyrazin-2-yl)amino)pyri-
din-4-yl)methoxy)naphthalen-1-yl)urea;

5-((4-(((4-(3-(3-(tert-butyl)-1-(m-tolyl)-1H-pyrazol-5-yl)
ureido)naphthalen-1-yl)oxy)methyl)pyridin-2-yl)amino)-
N-(3-hydroxypropyl)pyrazine-2-carboxamide;

(S)-1-(3-(tert-butyl)-1-(p-tolyl)-1H-pyrazol-5-yl)-3-(4-((2-
((5-(3-hydroxypiperidine-1-carbonyl)pyrazin-2-yl)
amino)pyridin-4-yl)methoxy)naphthalen-1-yl)urea;

(R)-1-(3-(tert-butyl)-1-(p-tolyl)-1H-pyrazol-5-yl)-3-(4-((2-
((5-(3-hydroxypiperidine-1-carbonyl)pyrazin-2-yl)
amino)pyridin-4-yl)methoxy)naphthalen-1-yl)urea;

1-(3-(tert-butyl)-1-(3-ethylphenyl)-1H-pyrazol-5-yl)-3-(4-
((2-((6-ethylpyrazin-2-yl)amino)pyridin-4-yl)methoxy)
naphthalen-1-yl)urea;

1-(3-(tert-butyl)-1-(3-fluoro-4-methylphenyl)-1H-pyrazol-
5-yl)-3-(4-((2-((5-(pyrrolidine-1-carbonyl)pyrazin-2-yl)
amino)pyridin-4-yl)methoxy)naphthalen-1-yl)urea;

1-(3-(tert-butyl)-1-(3-fluoro-5-methylphenyl)-1H-pyrazol-
5-yl)-3-(4-((2-((5-(pyrrolidine-1-carbonyl)pyrazin-2-yl)
amino)pyridin-4-yl)methoxy)naphthalen-1-yl)urea;

1-(3-(tert-butyl)-1-(3-(2-hydroxyethyl)phenyl)-1H-pyrazol-
5-yl)-3-(4-((2-(pyrazin-2-ylamino)pyridin-4-yl)methoxy)
naphthalen-1-yl)urea;

(S)-1-(3-(tert-butyl)-1-(p-tolyl)-1H-pyrazol-5-yl)-3-(4-((2-
((5-(3-methoxypiperidine-1-carbonyl)pyrazin-2-yl)
amino)pyridin-4-yl)methoxy)naphthalen-1-yl)urea;

(R)-1-(3-(tert-butyl)-1-(p-tolyl)-1H-pyrazol-5-yl)-3-(4-((2-
((5-(3-methoxypiperidine-1-carbonyl)pyrazin-2-yl)
amino)pyridin-4-yl)methoxy)naphthalen-1-yl)urea;

1-(4-((2-((5-(4-acetylpiperazine-1-carbonyl)pyrazin-2-yl)
amino)pyridin-4-yl)methoxy)naphthalen-1-yl)-3-(3-(tert-
butyl)-1-(p-tolyl)-1H-pyrazol-5-yl)urea;

1-(3-(tert-butyl)-1-(p-tolyl)-1H-pyrazol-5-yl)-3-(4-((2-((5-
(5-oxo-1,4-diazepane-1-carbonyl)pyrazin-2-yl)amino)
pyridin-4-yl)methoxy)naphthalen-1-yl)urea;

(S)-1-(3-(tert-butyl)-1-(p-tolyl)-1H-pyrazol-5-yl)-3-(4-((2-
((5-(3-fluoropyrrolidine-1-carbonyl)pyrazin-2-yl)amino)
pyridin-4-yl)methoxy)naphthalen-1-yl)urea;

1-(3-(tert-butyl)-1-(p-tolyl)-1H-pyrazol-5-yl)-3-(4-((2-((5-
(1,1-dioxidothiomorpholine-4-carbonyl)pyrazin-2-yl)
amino)pyridin-4-yl)methoxy)naphthalen-1-yl)urea;

1-(3-(tert-butyl)-1-(p-tolyl)-1H-pyrazol-5-yl)-3-(4-((2-((5-
(4-methyl-3-oxopiperazine-1-carbonyl)pyrazin-2-yl)
amino)pyridin-4-yl)methoxy)naphthalen-1-yl)urea;

(R)-1-(3-(tert-butyl)-1-(p-tolyl)-1H-pyrazol-5-yl)-3-(4-((2-
((5-(3-fluoropyrrolidine-1-carbonyl)pyrazin-2-yl)amino)
pyridin-4-yl)methoxy)naphthalen-1-yl)urea;

1-(3-(tert-butyl)-1-(p-tolyl)-1H-pyrazol-5-yl)-3-(4-((2-((5-
(4,4-difluoropiperidine-1-carbonyl)pyrazin-2-yl)amino)
pyridin-4-yl)methoxy)naphthalen-1-yl)urea;

1-(3-(tert-butyl)-1-(p-tolyl)-1H-pyrazol-5-yl)-3-(4-((2-((5-
((3S,4S)-3,4-dihydroxypyrrolidine-1-carbonyl)pyrazin-2-
yl)amino)pyridin-4-yl)methoxy)naphthalen-1-yl)urea;

1-(3-(tert-butyl)-1-(p-tolyl)-1H-pyrazol-5-yl)-3-(4-((2-((5-
((3R,4R)-3,4-dihydroxypyrrolidine-1-carbonyl)pyrazin-
2-yl)amino)pyridin-4-yl)methoxy)naphthalen-1-yl)urea;

1-(3-(tert-butyl)-1-(p-tolyl)-1H-pyrazol-5-yl)-3-(4-((2-((5-
(3-oxopiperazine-1-carbonyl)pyrazin-2-yl)amino)pyri-
din-4-yl)methoxy)naphthalen-1-yl)urea;

1-(3-(tert-butyl)-1-(3-fluoro-5-methoxyphenyl)-1H-pyra-
zol-5-yl)-3-(4-((2-((5-(pyrrolidine-1-carbonyl)pyrazin-2-
yl)amino)pyridin-4-yl)methoxy)naphthalen-1-yl)urea;

1-(3-(tert-butyl)-1-(4-ethylphenyl)-1H-pyrazol-5-yl)-3-(4-
((2-((5,6-dimethylpyrazin-2-yl)amino)pyridin-4-yl)
methoxy)naphthalen-1-yl)urea;

1-(3-(tert-butyl)-1-(3-fluoro-4-methoxyphenyl)-1H-pyra-
zol-5-yl)-3-(4-((2-((5,6-dimethylpyrazin-2-yl)amino)
pyridin-4-yl)methoxy)naphthalen-1-yl)urea;

1-(3-(tert-butyl)-1-(3-fluorophenyl)-1H-pyrazol-5-yl)-3-(4-
((2-((5-(hydroxymethyl)pyrazin-2-yl)amino)pyridin-4-
yl)methoxy)naphthalen-1-yl)urea;

1-(3-(tert-butyl)-1-(3-fluoro-5-methylphenyl)-1H-pyrazol-
5-yl)-3-(4-((2-((6-ethylpyrazin-2-yl)amino)pyridin-4-yl)
methoxy)naphthalen-1-yl)urea;

1-(3-(tert-butyl)-1-(3-fluorophenyl)-1H-pyrazol-5-yl)-3-(4-
((2-((6-propylpyrazin-2-yl)amino)pyridin-4-yl)methoxy)
naphthalen-1-yl)urea;

1-(3-(tert-butyl)-1-(3-chlorophenyl)-1H-pyrazol-5-yl)-3-(4-
((2-((5-(hydroxymethyl)pyrazin-2-yl)amino)pyridin-4-
yl)methoxy)naphthalen-1-yl)urea;

1-(3-(tert-butyl)-1-(3-(2-methoxyethyl)phenyl)-1H-pyrazol-
5-yl)-3-(4-((2-(pyrazin-2-ylamino)pyridin-4-yl)methoxy)
naphthalen-1-yl)urea;

(S)-1-(3-(tert-butyl)-1-(p-tolyl)-1H-pyrazol-5-yl)-3-(4-((2-
((5-(3-(dimethylamino)pyrrolidine-1-carbonyl)pyrazin-2-
yl)amino)pyridin-4-yl)methoxy)naphthalen-1-yl)urea;

(R)-1-(3-(tert-butyl)-1-(p-tolyl)-1H-pyrazol-5-yl)-3-(4-((2-
((5-(3-(dimethylamino)pyrrolidine-1-carbonyl)pyrazin-2-
yl)amino)pyridin-4-yl)methoxy)naphthalen-1-yl)urea;

5-((4-(((4-(3-(3-(tert-butyl)-1-(p-tolyl)-1H-pyrazol-5-yl)
ureido)naphthalen-1-yl)oxy)methyl)pyridin-2-yl)amino)-
N-(2-(4-methylpiperazin-1-yl)ethyl)pyrazine-2-carbox-
amide;

1-(3-(tert-butyl)-1-(3-((dimethylamino)methyl)phenyl)-1H-
pyrazol-5-yl)-3-(4-((2-(pyrazin-2-ylamino)pyridin-4-yl)
methoxy)naphthalen-1-yl)urea;

1-(3-(tert-butyl)-1-(3-(methoxymethyl)phenyl)-1H-pyrazol-
5-yl)-3-(4-((2-((5-(morpholinomethyl)pyrazin-2-yl)
amino)pyridin-4-yl)methoxy)naphthalen-1-yl)urea;

1-(3-(tert-butyl)-1-(p-tolyl)-1H-pyrazol-5-yl)-3-(4-((2-((5-
(morpholinomethyl)pyrazin-2-yl)amino)pyridin-4-yl)
methoxy)naphthalen-1-yl)urea;

1-(3-(tert-butyl)-1-(2-methoxypyridin-4-yl)-1H-pyrazol-5-
yl)-3-(4-((2-(pyrazin-2-ylamino)pyridin-4-yl)methoxy)
naphthalen-1-yl)urea;

1-(3-(tert-butyl)-1-(2-methylpyridin-4-yl)-1H-pyrazol-5-
yl)-3-(4-((2-(pyrazin-2-ylamino)pyridin-4-yl)methoxy)
naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(1-methylpiperidin-4-yl)ethyl)pyrazine-2-carboxamide;

1-(3-(tert-butyl)-1-(4-((dimethylamino)methyl)phenyl)-1H-pyrazol-5-yl)-3-(4-((2-(pyrazin-2-ylamino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(dimethylamino)ethyl)pyrazine-2-carboxamide;

1-(3-(tert-butyl)-1-(3-(methoxymethyl)phenyl)-1H-pyrazol-5-yl)-3-(4-((2-((5-(4-methylpiperazine-1-carbonyl)pyrazin-2-yl)amino)pyridin-4-yl)methoxy)naphthalen-1-yl)urea;

5-((4-(((4-(3-(3-(tert-butyl)-1-(3-(methoxymethyl)phenyl)-1H-pyrazol-5-yl)ureido)naphthalen-1-yl)oxy)methyl)pyridin-2-yl)amino)-N-(2-morpholinoethyl)pyrazine-2-carboxamide;

1-(3-(tert-butyl)-1-(p-tolyl)-1H-pyrazol-5-yl)-3-(4-((2-((5-(4-ethylpiperazine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-(dimethylamino)piperidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-(2-(dimethylamino)ethyl)piperazine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-(4-methyl-1,4-diazepane-1-carbonyl)pyrazin-2-yl)amino)pyridin-4-yl)methoxy)naphthalen-1-yl)urea;

(S)-1-(3-(tert-butyl)-1-(p-tolyl)-1H-pyrazol-5-yl)-3-(4-((2-((5-(octahydropyrrolo[1,2-a]pyrazine-2-carbonyl)pyrazin-2-yl)amino)pyridin-4-yl)methoxy)naphthalen-1-yl)urea;

1-(3-(tert-butyl)-1-(3-(methoxymethyl)phenyl)-1H-pyrazol-5-yl)-3-(4-((2-((5-((4-methylpiperazin-1-yl)methyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((5-((4-methylpiperazin-1-yl)methyl)pyrazin-2-yl)amino)pyridin-4-yl)methoxy)naphthalen-1-yl)urea;

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-morpholinopropan-2-yl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-morpholinopropyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-(4-methylpiperazin-1-yl)propyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methyl-2-morpholinopropyl)pyrazine-2-carboxamide;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-(2-methoxyethyl)piperidin-4-yl)pyrazine-2-carboxamide;

1-(3-(tert-butyl)-1-(3-(methoxymethyl)phenyl)-1H-pyrazol-5-yl)-3-(4-((2-((5-(4-ethylpiperazine-1-carbonyl)pyrazin-2-yl)amino)pyridin-4-yl)methoxy)naphthalen-1-yl)urea;

1-(3-(tert-butyl)-1-(3-(methoxymethyl)phenyl)-1H-pyrazol-5-yl)-3-(4-((2-((5-(4-(dimethylamino)piperidine-1-carbonyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(morpholinomethyl)pyrazin-2-yl)amino)pyridin-4-yl)methoxy)naphthalen-1-yl)urea;

1-(3-(tert-butyl)-1-(p-tolyl)-1H-pyrazol-5-yl)-3-(4-((2-((6-(1-methylpiperidin-4-yl)pyrazin-2-yl)amino)pyridin-4-yl)methoxy)naphthalen-1-yl)urea;

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methyl-1-morpholinopropan-2-yl)pyrazine-2-carboxamide; and 5-((4-(((4-(3-(3-(tert-butyl)-1-(p-tolyl)-1H-pyrazol-5-yl)ureido)naphthalen-1-yl)oxy)methyl)pyridin-2-yl)amino)-N-((1-methyl-1H-imidazol-2-yl)methyl)pyrazine-2-carboxamide;

and pharmaceutically acceptable salts of any one thereof.

In an embodiment, the compound of formula (I) is not 1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea or a pharmaceutically acceptable salt thereof.

Compounds of formula (I) may be prepared or employed in the form of a pharmaceutically acceptable salt, including the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like. Conversely said salt forms can be converted by treatment with an appropriate base into the free base form. Other salts of acid compounds of formula (I) include metal salts from periodic table groups 1 and 2 such as sodium, potassium, calcium and magnesium salts, and ammonium salts. These pharmaceutically acceptable salts can conveniently be obtained by treating the free acid form with such appropriate bases in a suitable solvent or mixture of solvents.

The invention provided herein extends to all stereoisomers of compounds of formula (I). The term stereoisomers as employed herein refers to isomeric molecules that have the same molecular formula and sequence of bonded atoms (constitution), but that differ only in the three-dimensional orientations of their atoms in space.

As employed herein the definition of compounds of formula (I) is intended to include all tautomers of said compounds, and solvates of said compounds (including solvates of salts of said compounds) unless the context specifically indicates otherwise. Examples of solvates include hydrates.

The invention provided herein extends to prodrugs of the compound of formula (I), that is to say compounds which break down and/or are metabolised in vivo to provide an active compound of formula (I). General examples of prodrugs include simple esters, and other esters such as mixed carbonate esters, carbamates, glycosides, ethers, acetals and ketals.

In a further aspect of the invention there is provided one or more metabolites of the compound of formula (I), in particular a metabolite that retains one or more of the therapeutic activities of the compound of formula (I). A metabolite, as employed herein, is a compound that is produced in vivo from the metabolism of the compound of formula (I), such as, without limitation, oxidative metabolites and/or metabolites generated, for example, from O-dealkylation.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The disclosure also extends to all polymorphic forms of the compounds herein defined.

A first process for preparing a compound of formula (I) or a protected derivative thereof comprises reacting a compound of formula (II)

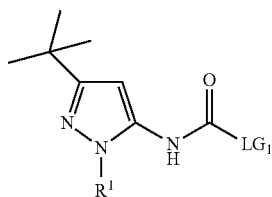

(II)

or a protected derivative thereof
wherein $LG^1$ represents a leaving group;
with a compound of formula (III)

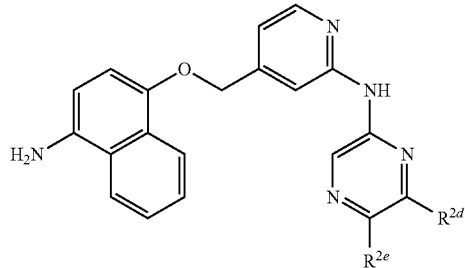

(III)

or a protected derivative thereof;
and optionally deprotecting the product to yield a compound of formula (I).

In compounds of formula (II), examples of leaving groups $LG^1$ include halo (especially Cl, Br) and aryloxy-, especially phenoxy-.

Compounds of formula (II) may optionally be used in a form in which sidechain $R^1$ is protected.

Compounds of formula (III) may optionally be used in a form in which sidechain $R^{2d}$ or $R^{2e}$ are protected.

Suitable protecting groups and means for their removal are described infra.

Suitable conditions for the reaction of compounds of formula (II) and (III) include treating a mixture of (II) and (III) in a suitable solvent such as THF, DCM or isopropyl acetate with triethylamine or Hunig's base and warming the reaction to a temperature such as 40° C.

A second process for preparing a compound of formula (I) comprises modifying another compound of formula (I). Thus a compound of formula (I) having a certain $R^{2d}$ or $R^{2e}$ group may be converted to a compound of formula (I) having a different $R^{2d}$ or $R^{2e}$ group.

By way of illustration, a compound of formula (I) in which $R^{2d}$ contains a carboxylic acid group can be converted to a corresponding amide by reaction with an amine. Conditions for the reaction of an amine and an acid to form an amide are well known to a skilled person and include treating a mixture of the amine and the acid with a coupling agent such as HATU in a solvent such as DCM optionally in the presence of a base such as Hunig's base. Other methods include conversion of the acid to an acid chloride or anhydride followed by treatment with an amine in the presence of a base such as Hunig's base in a solvent such as DCM. Similarly, a compound of formula (I) in which $R^{2d}$ contains a primary or secondary amine group can be converted to a corresponding amide by reaction with an activated carboxylic acid (e.g. in the form of an anhydride). Certain compounds of formula (I) in which $R^{2e}$ represents —CO—K'-Het may be prepared from compounds of formula (I) in which $R^{2e}$ represents CO-J'.

A third process for preparing a compound of formula (I) comprises reacting a compound of formula (IV)

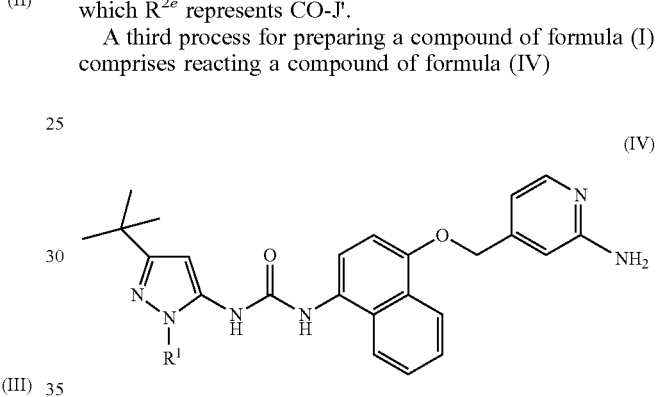

(IV)

or a protected derivative thereof,
with a compound of formula (V)

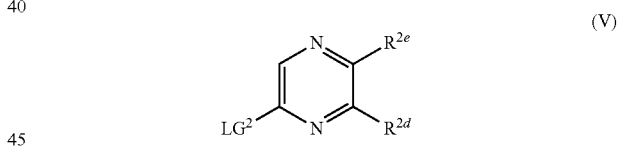

(V)

wherein $LG^2$ represents leaving group, such as halo and especially Cl
or a protected derivative thereof
and optionally deprotecting the product to yield a compound of formula (I).

Compounds of formula (IV) may optionally be used in a form in which sidechain $R^1$ is protected.

Compounds of formula (V) may optionally be used in a form in which sidechain $R^{2d}$ or $R^{2e}$ are protected.

Suitable protecting groups and means for their removal are described infra.

Suitable conditions for the reaction of compounds of formula (IV) and (V) include those normally employed for the Buchwald reaction i.e. treatment of a solution of (IV) and (V) in a solvent such as 1,4-dioxane with a palladium source and ligand such as $Pd_2(dba)_3$ and BINAP and a base such as sodium tert-butoxide or cesium carbonate at elevated temperature.

Alternative ligands include diphenylphosphinoferrocene and triphenylphosphine; alternative palladium sources include palladium (II) acetate and tetrakis(triphenylphosphine)palladium(0); alternative bases include lithium bis(trimethylsilyl)amide and potassium phosphate; alternative solvents include THF and toluene. For a wider range of conditions, see Surry, D. S.; Buchwald, S. L. (2008), "Biaryl Phosphane Ligands in Palladium-Catalyzed Amination", Angew. Chem. Int. Ed. 47:6338-6361, and references therein.

A fourth process for preparation of compounds of formula (I) in which $R^{2e}$ represents —CO-J' in which the atom of J' attached to CO is N comprises reacting a compound of formula (VI)

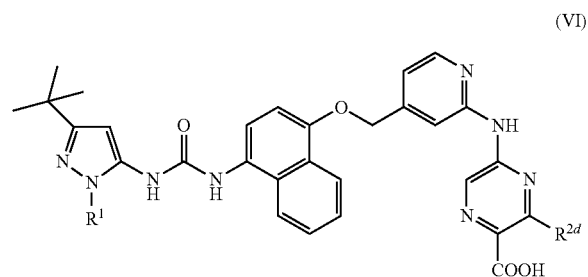

(VI)

with a compound of formula HNJ" wherein J" represents the remainder of the moiety J'.

Suitable conditions for the reaction of a compound of formula (VI) with a compound of formula HNJ" include treating a mixture of HNJ" and (VI) with a coupling agent such as HATU in a solvent such as DCM optionally in the presence of a base such as Hunig's base.

Compounds of formula HNJ" are known or may be prepared by methods known to a skilled person.

Compounds of formula (VI) may be prepared by methods analogous to those described herein for preparing compounds of formula (I).

Optionally a compound of formula (VI) or intermediates in the steps of preparation thereof which carry the —COOH substituted pyrazine may be prepared in a form in which said COOH group is protected, e.g. as an alkyl ester such as a methyl or ethyl ester of the carboxylic acid. The carboxylic acid may be regenerated from an alkyl ester derivative thereof by treatment with base (e.g. LiOH).

Thus, for example, a compound of formula (VI) may be prepared by reaction of a compound of formula (II) with a compound of formula (III'):

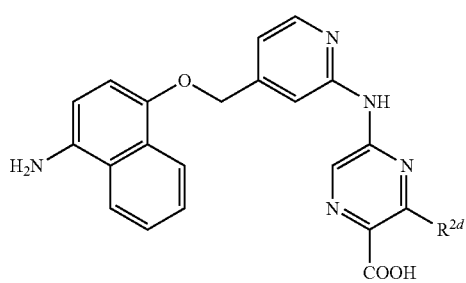

(III')

Compounds of formula (III') may be prepared by hydrolysis of the corresponding alkyl ester derivative thereof (e.g. methyl ester derivative thereof) by treatment with base (e.g. LiOH).

Compounds of formula (II) may be prepared by reaction of a compound of formula (VII)

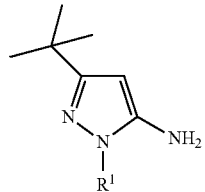

(VII)

with a compound of formula $LG^1C(=O)LG^3$ wherein $LG^3$ represents a leaving group such as halo and especially Cl.

Suitable conditions for the reaction of a compound of formula (VII) with a compound of formula $LG^1C(=O)LG^3$ where $LG^1$ is PhO and $LG^3$ is Cl comprise treatment of a mixture of a solution of compound of formula (VII) in a solvent such as isopropyl acetate and an aqueous solution of an inorganic base such as sodium carbonate with phenyl chloroformate.

Compounds of formula (VII) are known or may be prepared by methods to persons skilled in the art.

A first process for preparing a compound of formula (III) comprises reducing a compound of formula (VIII)

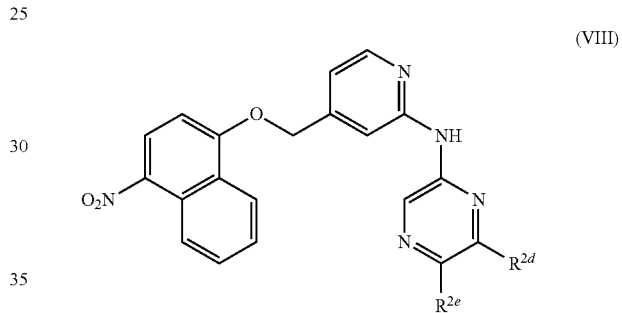

(VIII)

Suitable conditions for the reduction of a compound of formula (VIII) include treatment with hydrogen gas over platinum on carbon catalyst. This reaction may be carried out at elevated pressure in a solvent such as THF acidified with acetic acid. Alternatively it may be performed in a solvent such as DCM/MeOH under flow conditions using an H-cube hydrogenator.

This process is also suitable for preparing compounds of formula (III') or an alkyl ester (e.g. the methyl ester) derivative of the —COOH group thereof. In such a case an analogue of a compound of formula (VIII) having $R^{2e}$=COOH (or an alkyl ester e.g. the methyl ester derivative thereof) would be employed.

A second process for preparing a compound of formula (III) comprises deprotecting a compound of formula (IX)

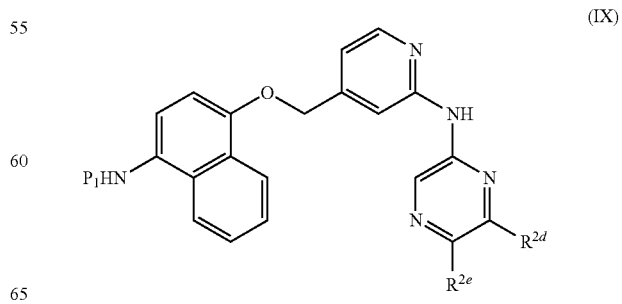

(IX)

wherein $P_1$ represents an amine protecting group.

Suitable protecting groups and means for their removal are described infra. A most suitable protecting group is Boc which can be removed by treatment with acid such as TFA or HCl.

This process is also suitable for preparing compounds of formula (III') or an alkyl ester (e.g. the methyl ester) derivative of the —COOH group thereof. In such a case an analogue of a compound of formula (IX) having $R^{2e}$=COOH (or an alkyl ester e.g. the methyl ester derivative thereof) would be employed. Such compounds are referred to herein as compounds of formula (IX').

A process for preparing a compound of formula (IV) comprises reacting a compound of formula (X)

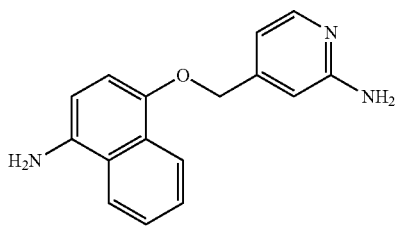

(X)

with a compound of formula (II).

Suitable conditions for the reaction of compounds of formula (X) and (II) include those mentioned above for the reaction of compounds of formula (II) and (III).

A first process for preparing a compound of formula (VIII) comprises reacting a compound of formula (XI)

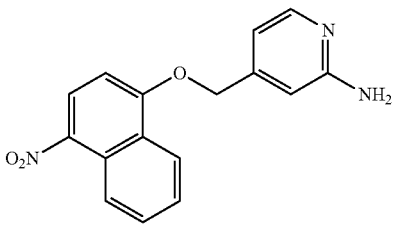

(XI)

with a compound of formula (V)
wherein $LG^2$ represents halogen, especially Cl.

Suitable conditions for the reaction of compounds of formula (XI) and (V) include those mentioned above for the reaction of compounds of formula (IV) and (V).

A second process for preparing a compound of formula (VIII) comprises reacting a compound of formula (XII)

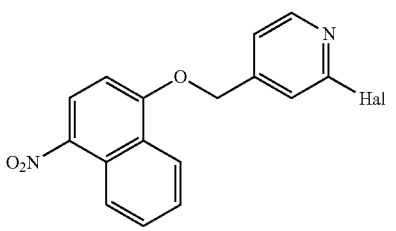

(XII)

wherein Hal represents halogen, especially Cl with a compound of formula (XIII)

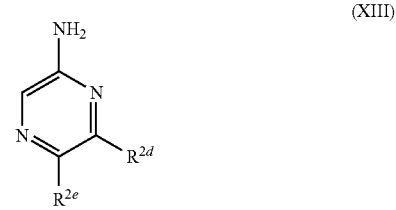

(XIII)

Suitable conditions for the reaction of compounds of formula (XII) and (XIII) include treatment of a solution of (XII) and (XIII) in a solvent such as 1,4-dioxane with a palladium source and ligand such as $Pd_2(dba)_3$ and BINAP and a base such as sodium tert-butoxide or cesium carbonate at elevated temperature.

This process is also suitable for preparing analogues of compounds of formula (VIII) referred to above having $R^{2e}$=COOH (or an alkyl ester e.g. methyl ester derivative thereof). In such a case an analogue of a compound of formula (XIII) having $R^{2e}$=COOH (or an alkyl ester e.g. the methyl ester derivative thereof) would be employed.

A third process for preparing a compound of formula (VIII) in which in which $R^{2e}$ represents —$CH_2$-J and J represents —$COJ^a$ ($J^a$ being the remainder of moiety J) in which the atom of $J^a$ attached to CO is N comprises reacting a compound of formula (XIVa)

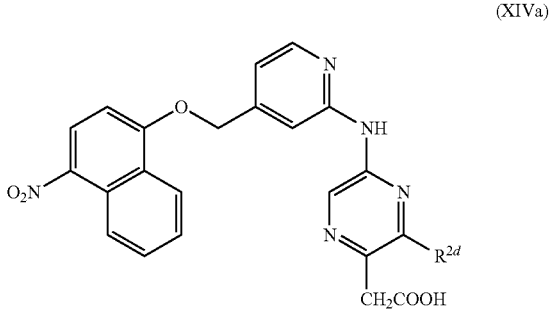

(XIVa)

with a compound of formula $HNJ^b$ wherein $J^b$ represents the remainder of moiety $J^a$.

Suitable conditions for the reaction of a compound of formula (XIVa) with a compound of formula $HNJ^b$ include treating a mixture of $HNJ^b$ and (XIVa) with a coupling agent such as HATU in a solvent such as DCM optionally in the presence of a base such as Hunig's base.

Compounds of formula $HNJ^b$ are known or may be prepared by methods known to a skilled person.

A fourth process for preparing a compound of formula (VIII) in which in which $R^{2d}$ represents —$CH_2$-J and J represents —$COJ^a$ ($J^a$ being the remainder of moiety J) in which the atom of $J^a$ attached to CO is N comprises reacting a compound of formula (XIVb)

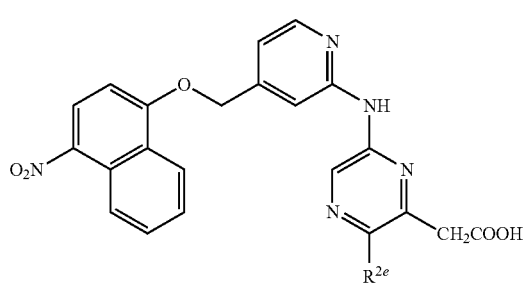
(XIVb)

with a compound of formula HNJ$^b$ wherein J$^b$ represents the remainder of moiety J$^a$.

Suitable conditions for the reaction of a compound of formula (XIVb) with a compound of formula HNJ$^b$ are the same as those described above for the reaction of a compound of formula (XIVa) with a compound of formula HNJ$^b$.

Compounds of formula (XIVa) and (XIVb) may be prepared by methods analogous to those described herein for preparing compounds of formula (VIII). Conveniently a compound of formula (XIVa) or (XIVb) may be prepared in protected form, e.g. as an alkyl ester such as a methyl or ethyl ester of the carboxylic acid. The carboxylic acid may be regenerated from an alkyl ester derivative thereof by treatment with base (e.g. LiOH). Thus a compound of formula (XIVa) or (XIVb) in which the —COOH group is protected as an alkyl (e.g. methyl) ester may be prepared by reaction of a compound of formula (XI) with an analogue of a compound of formula (V) having R$^{2e}$ or R$^{2d}$=CH$_2$COOalkyl (e.g. alkyl=methyl).

A first process for preparing compounds of formula (IX) comprises reacting a compound of formula (XV)

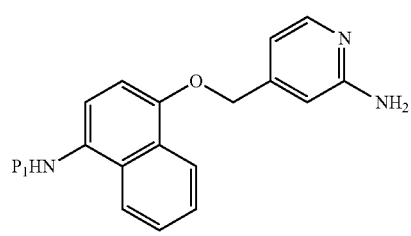
(XV)

with a compound of formula (V)

wherein LG$^2$ represents halogen, especially Cl.

Suitable conditions for the reaction of compounds of formula (XV) and (V) are the same as those described above for the reaction of compounds of formula (XI) and (V).

This process is also suitable for preparing compounds of formula (IX') (being compounds of formula (IX) having R$^{2e}$=COOH or an alkyl ester e.g. the methyl ester derivative thereof). In such a case an analogue of a compound of formula (V) having R$^{2e}$=COOH (or an alkyl ester e.g. the methyl ester derivative thereof) would be employed. Such compounds are referred to herein compounds of formula (XI').

A second process for preparing compounds of formula (IX) comprises reacting a compound of formula (XVI)

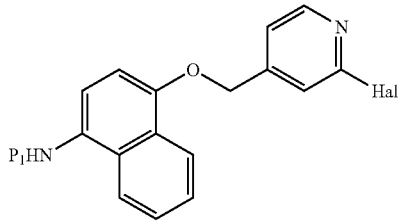
(XVI)

wherein Hal represents halogen, especially Cl with a compound of formula (XIII)

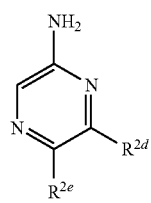
(XIII)

Suitable conditions for the reaction of compounds of formula (XVI) and (XIII) are the same as those described above for the reaction of compounds of formula (XII) and (XIII).

This process is also suitable for preparing compounds of formula (IX') (being compounds of formula (IX) having R$^{2e}$=COOH or an alkyl ester e.g. the methyl ester derivative thereof). In such a case an analogue of a compound of formula (XIII) having R$^{2e}$=COOH (or an alkyl ester e.g. the methyl ester derivative thereof) would be employed. Such compounds are referred to herein compounds of formula (XIII').

Certain compounds of formula (IX) in which R$^{2e}$ represents CO—K-Cyc or CO—K'-Het in which the first atom of K or K' is N may also be prepared from corresponding compounds of formula (IX') in which R$^{2e}$=COOH by standard amide formation processes (i.e. by reaction of said compound of formula (IX') or an activated derivative thereof with a compound of formula HNK$^c$ wherein K$^c$ represents the remainder of moiety R$^{2e}$).

Certain compounds of formula (IX) in which R$^{2d}$ represents —CH$_2$-J and J represents —COJ$^a$(J$^a$ being the remainder of moiety J) in which the atom of J$^a$ attached to CO is N may also be prepared from corresponding compounds of formula (IX") in which R$^{2d}$=CH$_2$COOH by standard amide formation processes (i.e. by reaction of said compound of formula (IX") or an activated derivative thereof with a compound of formula HNJ$^b$ wherein J$^b$ represents the remainder of moiety J$^a$). Compounds of formula (IX") may be prepared from compounds of formula (XIVb) in the form of its alkyl ester (e.g. the methyl ester) via processes described herein (i.e. reduction of the NO$_2$ group to the corresponding amine, protection of the amine, and hydrolysis of the ester).

Compounds of formula (XI) may be prepared as shown in the scheme below:

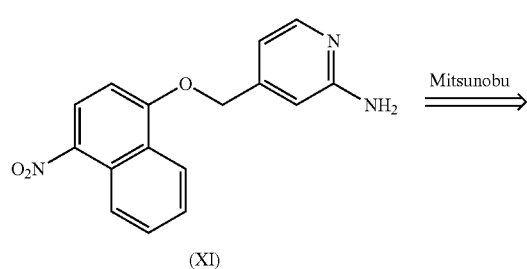

(XI)

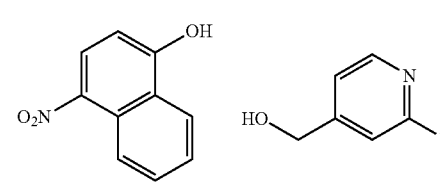

The reagents of this process are known compounds. Mitsunobu conditions include treatment of a mixture of a phenol and an alcohol with triphenylphosphine and diisopropylazodicarboxylate in a solvent such as THF. For a wider range of conditions, see Swamy, K. C.; Kumar, N. N.; Balaraman, E.; Kumar, K. V. (2009). "Mitsunobu and Related Reactions: Advances and Applications" *Chem. Rev.* 109(6):2551-2651, and references therein.

Compounds of formula (X) may be prepared by reduction of compounds of formula (XI). Suitable conditions include those mentioned above for reduction of compounds of formula (VIII).

Compounds of formula (XII) may be prepared as shown in the scheme below:

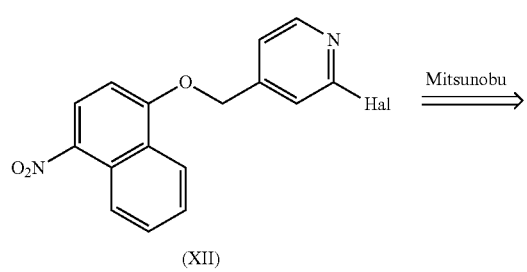

(XII)

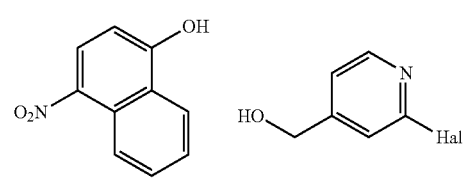

The reagents of this process are known compounds. Mitsunobu conditions include those given above.

Compounds of formula (XV) may be prepared as shown in the scheme below:

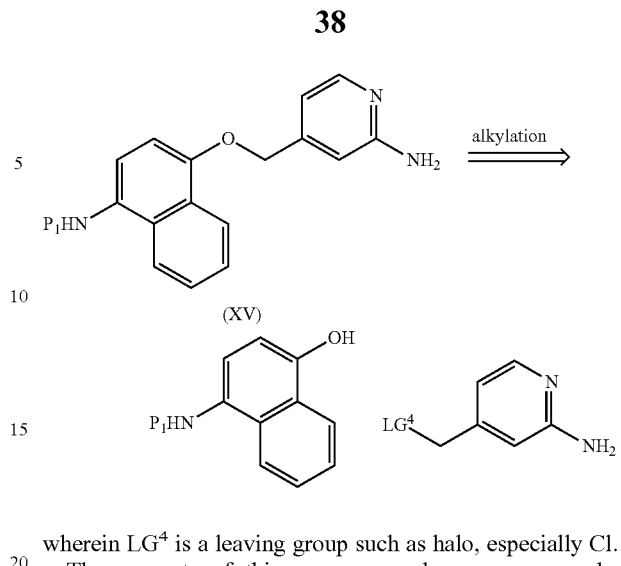

wherein $LG^4$ is a leaving group such as halo, especially Cl.

The reagents of this process are known compounds. Alkylation conditions include treatment of a mixture of a phenol and an alkyl halide with a base such as cesium or potassium carbonate in a solvent such as acetonitrile or DMF optionally at elevated temperature.

Compounds of formula (XVI) may be prepared as shown in the scheme below:

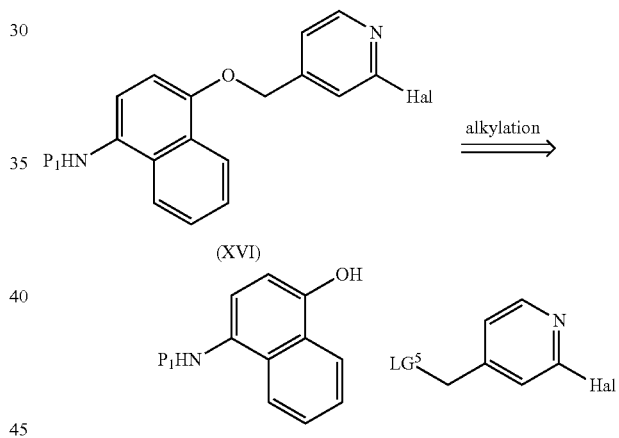

wherein $LG^5$ is a leaving group such as those mentioned above for $LG^4$.

The reagents of this process are known compounds. Alkylation conditions include those given above.

In general, compounds of formula (V), (XI'), (XIII) and (XIII') are either known or may be prepared by methods known to the skilled person. Specific methods for preparing compounds of formula (V) and (XIII) that may be mentioned include treatment of a compound of formula (V) where $R^{2e}$ is COOH with an amine to form an amide. Suitable conditions for this transformation include conversion of the acid to the acid chloride with a chlorinating agent such as oxalyl chloride followed by treatment with an amine in the presence of a base such as Hunig's base in a solvent such as DCM.

Protecting groups may be required to protect chemically sensitive groups during one or more of the reactions described above, to ensure that the process is efficient. Thus if desired or necessary, intermediate compounds (including compounds of formula (II) to (V) as highlighted above as well as compounds of formula (VI) to (XVI)) may be protected by the use of conventional protecting groups. Protecting groups and means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540. Thus exemplary amine protecting groups include Boc which may be removed by TFA and exemplary alcohol protecting groups are THP which may be removed by HCl.

Compounds of formula (III), (III'), (VI), (VIII), (IX), (XIVa) and (XIVb) are novel and certain compounds of formula (V) and (XIII) are novel. These novel compounds, together with their salts (including pharmaceutically acceptable salts) are claimed as aspects of the invention.

The compounds of formula (I) are p38 MAP kinase inhibitors (especially inhibitors of the alpha subtype) and in one aspect the compounds of the present invention are provided for use as a medicament e.g. in the treatment of inflammatory diseases, for example COPD and/or asthma.

Surprisingly, in at least some embodiments, the compounds of formula (I) exhibit a long duration of action and/or persistence of action in comparison to other previously disclosed allosteric p38 MAP kinase inhibitors such as, for example, BIRB-796 (Pargellis, C et al., *Nature Struct. Biol.*, 2002, 9(4):268-272).

In one embodiment the compounds of formula (I) do not strongly inhibit, or bind to GSK 3α, for example they have an $IC_{50}$ value against GSK 3α of 1000 nM or greater; such as 1,500, 2,000, 3,000, 4,000, 5,000, 6,000, 7,000, 8,000, 9,000 or 10,000 nM or greater.

In one embodiment the compounds of formula (I) have inhibitory activity against GSK 3α at least 10 times (e.g. at least 100 times) weaker than that against p38MAPKα (i.e. the $IC_{50}$ value against GSK 3α is at least 10 times (e.g. at least 100 times) that of the $IC_{50}$ value against pMAPK38α).

Persistence of action as used herein is related to the dissociation rate or dissociation constant of the compound from the target (such as a receptor). A low dissociation rate may lead to persistence.

A low dissociation rate in combination with a high association rate tends to provide potent therapeutic entities.

The compounds of formula (I) are expected to be potent in vivo.

Typically, the prior art compounds developed to date have been intended for oral administration. This strategy involves optimizing the pharmacokinetic profile of drug substances in order to achieve an adequate duration of action. In this manner a sufficiently high drug concentration is established and maintained between doses to provide sustained clinical benefit. The inevitable consequence of this approach is that all bodily tissues, and especially the liver and the gut, are likely to be exposed to supra-therapeutically active concentrations of the drug, whether or not they are adversely affected by the disease being treated.

An alternative strategy is to design treatment paradigms in which the drug is dosed directly to the inflamed organ, that is, to exploit topical administration. Whilst this approach is not suitable for treating all chronic inflammatory diseases, it has been exploited in lung disorders, such as asthma and COPD; in skin diseases, for example against atopic dermatitis and psoriasis; for nasal conditions, typified by allergic rhinitis; and in gastrointestinal diseases, such as ulcerative colitis, IBD and Crohn's disease and inflammatory diseases of the eye, such as uveitis.

In topical therapy, one way in which efficacy can be achieved is by the use of a drug that has a sustained duration of action and is retained in the relevant organ, thereby minimizing the risk of systemic toxicity. Alternatively, in some cases, a formulation can be developed that generates a "reservoir" of the active drug which is available to sustain its desired effects. The first approach is exemplified by the anticholinergic drug tiotropium (Spiriva). This compound is administered topically to the lung as a treatment for COPD, and has an exceptionally high affinity for its target receptor resulting in a very slow off rate and consequently displays a sustained duration of action.

In one aspect of the disclosure the compounds of formula (I) is particularly suitable for topical delivery, such as topical delivery to the lungs, in particular for the treatment of respiratory disease, for example chronic respiratory diseases such as COPD and/or asthma.

In one embodiment the compounds of formula (I) is suitable for sensitizing patients to treatment with a corticosteroid who have become refractory to such treatment regimens.

The compounds of formula (I) may have antiviral properties, for example the ability to prevent the infection of cells (such as respiratory epithelial cells) with a picornavirus, in particular a rhinovirus, influenza or respiratory syncytial virus.

Thus the compounds are thought to be antiviral agents, in particular suitable for the prevention, treatment or amelioration of picornavirus infections, such as rhinovirus infection, influenza or respiratory syncytial virus.

In one embodiment the compounds of formula (I) are able to reduce inflammation induced by viral infection, such as rhinovirus infection and in particular viral infections that result in the release of cytokines such as IL-8, especially in vivo. This activity may, for example, be tested in vitro employing a rhinovirus induced IL-8 assay as described in the Examples herein.

In one embodiment the compounds of formula (I) are able to reduce ICAM1 expression induced by rhinovirus, especially in vivo. ICAM1 is the receptor mechanism used by so-called major groove rhinovirus serotypes to infect cells. This activity may be measured, for example by a method described in the Examples herein.

It is expected that the above properties render the compounds of formula (I) particularly suitable for use in the treatment (including prophylaxis) of exacerbations of inflammatory diseases, in particular viral exacerbations, or in the treatment of viral infections, in patients with one or more chronic conditions such as congestive heart failure, COPD, asthma, diabetes, cancer and/or in immunosuppressed patients, for example post-organ transplant.

Such use may be in combination with anti-viral agents such as zanamivir, oseltamivir (for example oseltamivir phosphate), peramivir or laninamivir.

In general, the compounds of formula (I) may be useful in the treatment of one or more conditions having an inflammatory component which, suitably, may be treated by topical or local therapy.

In particular, the compounds of formula (I) may be useful in the treatment of one or more respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema).

Thus the compounds of formula (I) may be useful in the treatment of lung inflammation (and symptoms thereof) in subjects suffering from cystic fibrosis.

The compounds of formula (I) may be useful in the treatment of eye diseases or disorders including keratoconjunctivitis sicca (dry eye), allergic conjunctivitis, conjunctivitis, diabetic retinopathy, macular oedema (including wet macular oedema and dry macular oedema), post-operative cataract inflammation or, particularly, uveitis (including posterior, anterior and pan uveitis).

The compounds of formula (I) may be useful in the treatment of skin diseases or disorders including allergic dermatitis, contact dermatitis, atopic dermatitis or psoriasis.

The compounds of formula (I) may be useful in the treatment of gastrointestinal diseases or disorders including ulcerative colitis, IBD or Crohn's disease.

The compounds of formula (I) may be useful in the treatment of joint diseases or disorders including rheumatoid arthritis or osteoarthritis and particularly inflamed joints secondary to such conditions.

The compounds of formula (I) may be useful in the treatment of cancers including cancer of the stomach and in the inhibition of the growth and metastasis of tumours including lung cancers such as non-small cell lung carcinoma, gastric carcinoma, colorectal carcinomas and malignant melanoma.

It is also expected that the compounds of formula (I) may be useful in the treatment of certain other conditions including periodontitis, gingivitis and pharyngitis.

Compounds of formula (I) may also re-sensitise the patient's condition to treatment with a corticosteroid, when the patient's condition has become refractory to the same.

Furthermore, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

The present invention also provides a process for preparing such a pharmaceutical composition (for example a pharmaceutical composition for parenteral, oral, topical, mucosal or rectal administration), said process comprising mixing the ingredients.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules or in the form of liquid solutions or suspensions; for topical e.g. pulmonary or intranasal administration, particularly in the form of powders, aqueous solutions or suspensions, nasal drops or aqueous or non-aqueous aerosols, and for transdermal administration e.g. patches, creams, ointments; for mucosal administration e.g. to buccal, sublingual or vaginal mucosa, and for rectal administration e.g. in the form of a suppository, cream, ointment or foam.

The compositions may conveniently be administered in unit or multi-dose dosage forms and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like.

Formulations for nasal administration may be solid and may contain excipients, for example, lactose or dextran, or may be aqueous or oily solutions or suspensions for use in the form of nasal drops or metered sprays. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably a compound of formula (I) is administered topically to the lung, eye or bowel. Hence we provide according to the invention a pharmaceutical composition comprising a compound of the present invention optionally in combination with one or more topically acceptable diluents or carriers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. These may be administered by means of a nebuliser e.g. one that can be hand-held and portable or for home or hospital use (ie non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean diameter (MMAD) of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. a mass mean diameter (MMAD) of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients. Thus in one embodiment a dry powder formulation according the present disclosure comprises magnesium or calcium stearate. Such formulations may have superior chemical and/or physical stability especially when such formulations also contain lactose.

A dry powder formulation is typically delivered using a dry powder inhaler (DPI) device. Example dry powder delivery systems include SPINHALER®, DISKHALER®, TURBOHALER®, DISKUS®, SKYEHALER®, ACCUHALER® and CLICKHALER®. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided as a micronized dry powder formulation, for example comprising lactose of a suitable grade.

In one embodiment a compound of the present invention is provided as a micronized dry powder formulation, comprising lactose of a suitable grade and magnesium stearate, filled into a device such as DISKUS. Suitably, such a device is a multidose device, for example the formulation is filled into blisters for use in a multi-unit dose device such as DISKUS.

In another embodiment a compound of the present invention is provided as a micronized dry powder formulation, for example comprising lactose of a suitable grade, filled into hard shell capsules for use in a single dose device such as AEROLISER.

In another embodiment a compound of the present invention is provided as a micronized dry powder formulation, comprising lactose of a suitable grade and magnesium stearate, filled into hard shell capsules for use in a single dose device such as AEROLISER.

In another embodiment compounds of the present invention are provided as a fine powder for use in an inhalation dosage form wherein the powder is in fine particles with a $D_{50}$ of 0.5-10 µm e.g. around 1-5 µm, that have been produced by a size reduction process other than jet mill micronisation e.g. spray drying, spray freezing, microfluidisation, high pressure homogenisation, super critical fluid crystallisation, ultrasonic crystallisation or combinations of these methods thereof, or other suitable particle formation methods known in the art that are used to produce fine particles with an aerodynamic particle size of 0.5-10 µm. The resultant particle size distribution may be measured using laser diffraction (e.g. with a Malvern Mastersizer 2000S instrument). The particles may either comprise the compound alone or in combination with suitable other excipients that may aid the processing. The resultant fine particles may form the final formulation for delivery to humans or may optionally be further formulated with other suitable excipients to facilitate delivery in an acceptable dosage form.

The compounds of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

An alternative for administration to the eye is intravitreal injection of a solution or suspension of the compound of the present invention. In addition, the compound of the present invention may also be introduced by means of ocular implants or inserts.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of compounds the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of compounds of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the present invention, and hence the amount of the compound of the invention that should be included in any particular pharmaceutical formulation (whether in unit dosage form or otherwise).

A compound of formula (I) has therapeutic activity. Thus, in a further aspect, the present invention provides a compound as described herein for use in the treatment of one or more of the above mentioned conditions.

In a further aspect, the present invention provides use of a compound as described herein for the manufacture of a medicament for the treatment of one or more of the above mentioned conditions.

In a further aspect, the present invention provides a method of treatment of one or more of the above mentioned conditions which comprises administering to a subject an effective amount of a compound of the present invention or a pharmaceutical composition comprising the compound.

The word "treatment" is intended to embrace prophylaxis as well as therapeutic treatment. Treatment of conditions or disorders also embraces treatment of exacerbations thereof.

A compound of the present invention may also be administered in combination with one or more other active ingredients e.g. active ingredients suitable for treating the above mentioned conditions.

For example, possible combinations for treatment of respiratory disorders include combinations with steroids (e.g. budesonide, beclomethasone dipropionate, fluticasone propionate, mometasone furoate, fluticasone furoate, ciclesonide), beta agonists (e.g. terbutaline, salbutamol, salmeterol, formoterol, vilanterol, olodaterol, indacaterol, reproterol, fenoterol), xanthines (e.g. theophylline), anticholinergics or muscarinic antagonists (e.g. ipratropium, tiotropium, aclidinium, umeclidinium or glycopyrronium for example as the bromide salt), PI3 kinase inhibitors and anti-viral agents (e.g. zanamivir, oseltamivir, for example as the phosphate, peramivir and laninamivir).

In one embodiment there is provided a compound of the invention for use as a medicament to be administered in combination with one or more further active ingredients e.g. selected from corticosteroids, beta agonists, xanthines, muscarinic antagonists and PI3 kinase inhibitors. Suitably the beta agonist is a beta2 agonist.

In one embodiment the compound of the disclosure is administered by inhalation and a corticosteroid is administered orally or by inhalation either in combination or separately.

In one embodiment the compound of the disclosure is administered by inhalation and a beta2 agonist is administered orally or by inhalation either in combination or separately.

In one embodiment the compound of the disclosure is administered by inhalation and a muscarinic antagonist is administered orally or by inhalation either in combination or separately.

In one embodiment the compound of the disclosure is administered by inhalation either in combination or separately with one or more of a corticosteroid, a beta2 agonist and a muscarinic antagonist, all administered either orally or by inhalation.

Further, for the treatment of gastrointestinal disorders (such as Crohn's disease or ulcerative colitis), possible combinations include combinations with, for example, one or more agents selected from the list comprising:

5-aminosalicylic acid, or a prodrug thereof (such as sulfasalazine, olsalazine or bisalazide);
corticosteroids (e.g. prednisolone, methylprednisolone, or budesonide); immunosuppressants (e.g. cyclosporin, tacrolimus, methotrexate, azathioprine or 6-mercaptopurine);
anti-TNFα antibodies (e.g. infliximab, adalimumab, certolizumab pegol or golimumab); anti-IL12/IL23 antibodies (e.g. ustekinumab) or small molecule IL12/IL23 inhibitors (e.g., apilimod);
Anti-α4β7 antibodies (e.g. vedolizumab);
MAdCAM-1 blockers (e.g. PF-00547659);
antibodies against the cell adhesion molecule α4-integrin (e.g. natalizumab);
antibodies against the IL2 receptor a subunit (e.g. daclizumab or basiliximab);
JAK3 inhibitors (e.g. tofacitinib or R348);
Syk inhibitors and prodrugs thereof (e.g. fostamatinib and R-406);
Phosphodiesterase-4 inhibitors (e.g. tetomilast);
HMPL-004;
probiotics;
Dersalazine;
semapimod/CPSI-2364; and
protein kinase C inhibitors (e.g. AEB-071).

For the treatment of eye disorders (such as keratoconjunctivitis sicca or uveitis), possible combinations include combinations with, for example, one or more agents selected from the list comprising:

corticosteroids (e.g. dexamethasone, prednisolone, triamcinolone acetonide, difluprednate or fluocinolone acetonide);
immunosuppressants (e.g. cyclosporin, voclosporin, azathioprine, methotrexate, mycophenolate mofetil or tacrolimus);
anti-TNFα antibodies (e.g. infliximab, adalimumab, certolizumab pegol, ESBA-105 or golimumab);
anti-IL-17A antibodies (e.g. secukinumab);
mTOR inhibitors (e.g. sirolimus);
VGX-1027;
JAK3 inhibitors (e.g. tofacitinib or R348); and
protein kinase C inhibitors (e.g. AEB-071).

Hence another aspect of the invention provides a compound of formula (I) in combination with one or more further active ingredients, for example one or more active ingredients described above.

Similarly, another aspect of the invention provides a combination product comprising:
(A) a compound of the present invention; and
(B) one or more other therapeutic agents,
wherein each of components (A) and (B) is formulated in admixture with a pharmaceutically-acceptable adjuvant, diluent or carrier.

In this aspect of the invention, the combination product may be either a single (combination) pharmaceutical formulation or a kit of parts.

Thus, this aspect of the invention encompasses a pharmaceutical formulation including a compound of the present invention and another therapeutic agent, in admixture with a pharmaceutically acceptable adjuvant, diluent or carrier (which formulation is hereinafter referred to as a "combined preparation").

It also encompasses a kit of parts comprising components:
(i) a pharmaceutical formulation including a compound of the present invention in admixture with a pharmaceutically acceptable adjuvant, diluent or carrier; and
(ii) a pharmaceutical formulation including one or more other therapeutic agents, in admixture with a pharmaceutically-acceptable adjuvant, diluent or carrier,
which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

The one or more other therapeutic agents (i.e. component (B) above) may be, for example, any of the agents mentioned above in connection with the treatment of respiratory, gastrointestinal and eye disorders.

If component (B) is more than one further therapeutic agent, these further therapeutic agents can be formulated with each other or formulated with component (A) or they may be formulated separately.

In one embodiment component (B) is one other therapeutic agent. In another embodiment component (B) is two other therapeutic agents.

The combination product (either a combined preparation or kit of parts) of this aspect of the invention may be used in the treatment or prevention of an inflammatory disease e.g. the inflammatory diseases mentioned above, such as:

respiratory disorders including COPD (including chronic bronchitis and emphysema), asthma, paediatric asthma, cystic fibrosis, sarcoidosis, idiopathic pulmonary fibrosis, allergic rhinitis, rhinitis and sinusitis, especially asthma, or COPD (including chronic bronchitis and emphysema);
eye diseases or disorders including allergic conjunctivitis, conjunctivitis, keratoconjunctivitis sicca (dry eye), glaucoma, diabetic retinopathy, macular oedema (including diabetic macular oedema), central retinal vein occlusion (CRVO), dry and/or wet age related macular degeneration (AMD), post-operative cataract inflammation or, particularly, uveitis (including posterior, anterior and pan uveitis), corneal graft and limbal cell transplant rejection;
skin diseases or disorders including allergic dermatitis, contact dermatitis, atopic dermatitis or psoriasis; and
gastrointestinal diseases or disorders including gluten sensitive enteropathy (coeliac disease), eosinophilic esophagitis, intestinal graft versus host disease or, particularly, ulcerative colitis or Crohn's disease.

The aspects of the invention described herein (e.g. the above-mentioned compound, combinations, methods and uses) may have the advantage that, in the treatment of the conditions described herein, they may be more convenient for the physician and/or patient than, be more efficacious than, be less toxic than, be longer acting than, have better selectivity over, have a broader range of activity than, be more potent than, produce fewer side effects than, have a better pharmacokinetic and/or pharmacodynamic profile than, have more suitable solid state properties than, have better stability than, or may have other useful pharmacological properties over, similar compounds, combinations, methods (treatments) or uses known in the prior art for use in the treatment of those conditions or otherwise.

Relative to compounds of the prior art, the compounds of formula (I) in at least some embodiments may additionally (or alternatively):

- exhibit properties that are particularly suited to topical/local administration (e.g. following topical/local administration, the generation of high target tissue concentrations but low plasma or systemic concentrations of the compounds of formula (I) and/or rapid clearance of the compounds of formula (I) from plasma or the systemic circulation);
- have a reduced risk of extravascular exposure following intravenous administration (e.g. due to a low volume of distribution for the compounds of formula (I));
- exhibit superior potency with respect to selected kinases and/or a panel of kinases, such as p38 MAPKα, p38 MAPKγ, Src and p59-HCK);
- exhibit low or no inhibitory activity against Olaharsky kinases, particularly GSK3α;
- exhibit reduced β-catenin induction and/or inhibition of mitosis in cells;
- exhibit no or less time-dependent inhibition of members of the cytochrome P450 superfamily; and/or
- produce less problematic (e.g. less toxic) metabolites, e.g. following administration to a patient.

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| Ac$_2$O | acetic anhydride |
| aq | aqueous |
| b | broad |
| BEH | ethylene bridged hybrid |
| BINAP | 1,1'-binaphthyl-2,2'-diamine |
| Boc | tert-butoxycarbonyl |
| CSH | charged surface hybrid |
| d | doublet |
| δ | chemical shift |
| DCM | dichloromethane |
| DIAD | diisopropyl azodicarboxylate |
| DMF | N,N-dimethylformamide |
| DMSO | dimethyl sulfoxide |
| (ES$^+$) | electrospray ionization, positive mode |
| (ES$^-$) | electrospray ionization, negative mode |
| Et | ethyl |
| EtOAc | ethyl acetate |
| EtOH | ethanol |
| h | hour(s) |
| HATU | 1-[bis(dimethylamino)methylene]-1H-1,2,3-triazolo[4,5-b]pyridinium 3-oxid hexafluorophosphate |

TABLE 1-continued

| Abbreviations | |
|---|---|
| Hunig's base | N,N-diisopropylethylamine |
| IPA | isopropyl alcohol |
| $^i$PrOAc | isopropyl acetate |
| m | multiplet |
| (M + H)$^+$ | protonated molecular ion |
| (M − H)$^-$ | deprotonated molecular ion |
| Me | methyl |
| MeCN | acetonitrile |
| MeOH | methanol |
| MHz | megahertz |
| min | minute(s) |
| m/z | mass-to-charge ratio |
| NMR | nuclear magnetic resonance (spectroscopy) |
| Pd$_2$(dba)$_3$ | tris(dibenzylideneacetone)dipalladium(0) |
| Ph | phenyl |
| q | quartet |
| RT | room temperature |
| HPLC | high performance liquid chromatography |
| s | singlet |
| sat | saturated |
| SCX | solid supported cation exchange (resin) |
| t | triplet |
| $^t$Bu | tert-butyl |
| THF | tetrahydrofuran |
| TFA | trifluoroacetic acid |
| UV | ultra-violet |
| AKT | v-akt murine thymoma viral oncogene homolog 1 |
| ATP | adenosine-5'-triphosphate |
| BALF | bronchoalveolar lavage fluid |
| BSA | bovine serum albumin |
| COPD | chronic obstructive pulmonary disease |
| CXCL1 | chemokine (C—X—C motif) ligand 1 |
| COX2 | cytochrome c oxidase subunit II |
| DSS | dextran sodium sulfate |
| DTT | dithiothreitol |
| d-U937 cells | PMA differentiated U-937 cells |
| DVS | dynamic vapour sorption |
| dsRNA | double stranded RNA |
| ELISA | enzyme-linked immunosorbent assay |
| FACS | fluorescence-activated cell sorting |
| FBS | foetal bovine serum |
| FRET | fluorescence resonance energy transfer |
| GM-CSF | CSF2: granulocyte-macrophage colony-stimulating factor |
| GSK3α | glycogen synthase kinase 3α |
| GSK3β | glycogen synthase kinase 3β |
| HBSS | Hank's balanced salt solution |
| HCK | hemopoietic cell kinase |
| HRV | human rhinovirus |
| IBD | inflammatory bowel disease |
| IC50 | 50% inhibitory concentration |
| ICAM-1 | inter-cellular adhesion molecule 1 |
| IFN | interferon |
| IL-2 | interleukin 2 |
| IL-8 | interleukin 8 |
| JNK | c-Jun N-terminal kinase |
| KC | keratinocyte chemoattractant |
| LPMC | lamina propria mononuclear cell |
| LPS | lipopolysaccharide |
| MAPK | mitogen-activated protein kinase |
| MAPKAP-K2 | mitogen-activated protein kinase-activated protein kinase-2 |
| MKK4 | mitogen-activated protein kinase kinase 4 |
| MKK6 | mitogen-activated protein kinase kinase 6 |
| MOI | multiplicity of infection |
| MTT | 3-(4,5-dimethylthiazol-2-yl)-2,5-diphenyltetrazolium bromide |
| OD | optical density |
| PBMC | peripheral blood mononuclear cell |
| PBS | Dulbecco's phosphate buffered saline |
| PHA | phytohaemagglutinin |
| PI3 | phosphoinositide 3 kinase |
| PMA | phorbol 12-myristate 13-acetate |
| REC50 | relative 50% effective concentration |
| RNA | ribonucleic acid |
| RNAi | RNA interference |
| RT | room temperature |
| RSV | respiratory syncytial virus |
| SDS | sodium dodecyl sulphate |

TABLE 1-continued

Abbreviations

| | |
|---|---|
| SRC | v-src sarcoma (Schmidt-Ruppin A-2) viral oncogene homolog (avian) |
| Syk | spleen tyrosine kinase |
| TCID50 | 50% tissue culture infectious dose |
| TLR3 | toll-like receptor 3 |
| TNBS | 2,4,6-trinitrobenzenesulphonic acid |
| TNFα | tumor necrosis factor alpha |
| URTI | Upper respiratory tract infection |

Chemistry Examples

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μm) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 0.7 M $NH_3$ in MeOH.

Preparative Reverse Phase High Performance Liquid Chromatography

Performed using UV detection at 215 and 254 nm with either a Waters X-Select Prep-C18, 5 μm, 19×50 mm column eluting with a $H_2O$-MeCN gradient containing 0.1% v/v formic acid over 10 min, or a Waters X-Bridge Prep-C18, 5 μm, 19×50 mm column eluting with a $H_2O$-MeCN gradient containing 0.1% ammonium bicarbonate over 10 min.

Analytical Methods

Reverse Phase High Performance Liquid Chromatography

Method 1:

Waters XSelect CSH C18 2.5 μm (4.6×30 mm) at 40° C.; flow rate 2.5-4.5 mL min$^{-1}$ eluted with a $H_2O$-MeCN gradient containing 0.1% v/v formic acid over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^1$.

Method 2:

Waters XBridge BEH C18, 2.5 μm (4.6×30 mm) at 40° C.; flow rate 2.5-4.5 mL min$^{-1}$ eluted with a $H_2O$-MeCN gradient containing 10 mM ammonium bicarbonate over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min-1'.

$^1$H NMR Spectroscopy $^1$H NMR spectra were acquired on a Bruker Avance III spectrometer at 400 MHz using residual undeuterated solvent as reference and unless specified otherwise were run in DMSO-$d_6$.

Compound Examples of the Invention

Example 1: 1-(3-(tert-Butyl)-1-(p-tolyl)-1H-pyrazol-5-yl)-3-(4-((2-(pyrazin-2-ylamino) pyridin-4-yl)methoxy)naphthalen-1-yl)urea Intermediate A: 2-Chloro-4-(((4-nitronaphthalen-1-yl)oxy)methyl)pyridine

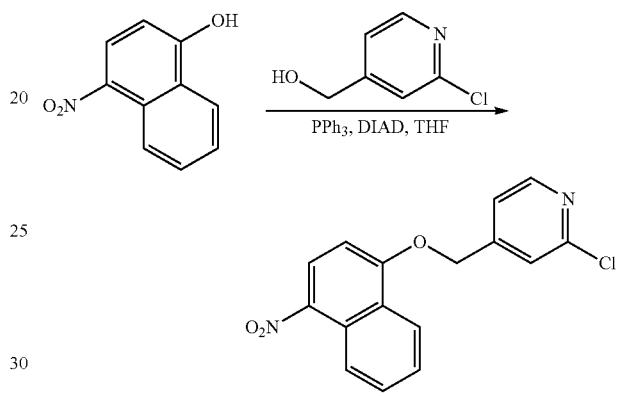

A mixture of (2-chloropyridin-4-yl)methanol (2.52 g, 17.6 mmol), 4-nitronaphthalen-1-ol (3.01 g, 15.9 mmol) and PPh$_3$ (5.58 g, 21.3 mmol) was dissolved in THF (30 mL) under a nitrogen atmosphere and cooled in a dry ice/acetone bath. DIAD (4.30 mL, 22.1 mmol) was added over 10 min to the cooled stirred mixture which was then allowed to warm to ambient temperature. After stirring for 19 h at ambient temperature MeOH (6 mL) was added and the mixture was evaporated in vacuo. Methanol (12 mL) was added to the resulting dark residue which was then sonicated for 20 min. The resulting solid was collected by filtration and washed with MeOH (50 mL) and ether (50 mL) to afford a dark yellow gum. The crude material was purified by silica gel chromatography (80 g, gradient 0-50% EtOAc in isohexane) to yield the subtitle compound 2-chloro-4-(((4-nitronaphthalen-1-yl)oxy)methyl)pyridine as a yellow solid. (2.66 g, 48%); R$^t$ 2.50 min (Method 1); m/z 315 (M+H)$^+$ (ES$^+$); $^1$H NMR δ: 5.58 (2H, s), 7.18 (1H, d), 7.62 (1H, m), 7.70 (1H, bs), 7.76 (1H, m), 7.87 (1H, m), 8.45-8.49 (3H, overlapping m), 8.59 (1H, d).

Intermediate B: N-(4-(((4-Nitronaphthalen-1-yl)oxy)methyl)pyridin-2-yl)pyrazin-2-amine

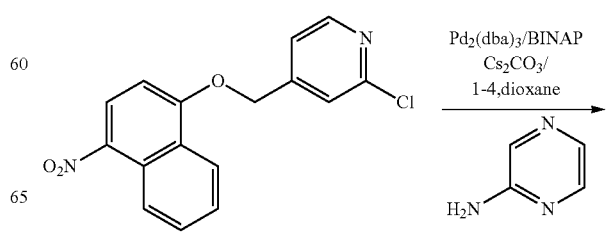

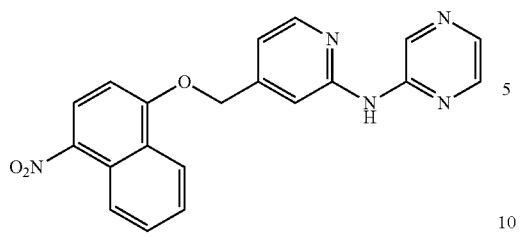

A mixture of 2-chloro-4-(((4-nitronaphthalen-1-yl)oxy)methyl)pyridine (Intermediate A) (308 mg, 0.88 mmol), 2-aminopyrazine (125 mg, 1.31 mmol), BINAP (110 mg, 0.18 mmol) and cesium carbonate (556 mg, 1.71 mmol) in 1,4-dioxane was purged under a nitrogen atmosphere for 10 min. Pd$_2$(dba)$_3$ (77 mg, 0.08 mmol) was added and the mixture was purged with nitrogen for a further 10 min and then heated to 90° C. After stirring for 19 h at 90° C. the reaction mixture was cooled to ambient temperature and partitioned between EtOAc (50 mL) and water (50 mL). The layers were separated and the organic phase was washed with water (2×50 mL), brine (2×50 mL) and then dried (MgSO$_4$), filtered and concentrated in vacuo to afford the crude product as an orange solid. The solid was triturated with MeOH (20 mL) and washed with MeOH (2×20 mL) to yield the subtitle compound N-(4-(((4-nitronaphthalen-1-yl)oxy)methyl)pyridin-2-yl)pyrazin-2-amine as an orange solid (156 mg, 36%); R$^t$ 1.69 min (Method 1); m/z 374 (M+H)$^+$ (ES$^+$).

Intermediate C: N-(4-(((4-Aminonaphthalen-1-yl)oxy)methyl)pyridin-2-yl)pyrazin-2-amine

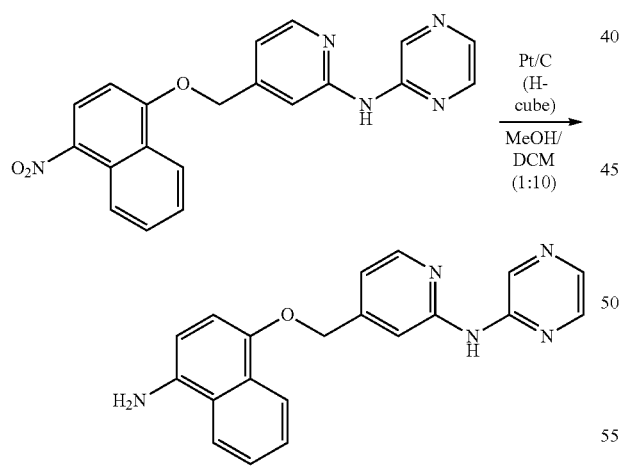

A solution of N-(4-(((4-nitronaphthalen-1-yl)oxy)methyl)pyridin-2-yl)pyrazin-2-amine (Intermediate B) (156 mg, 0.32 mmol) in a mixture of DCM (10 mL) and MeOH (1 mL) was passed through a Thales H-cube (10% Pt/C, 30×4 mm, Full hydrogen, 40° C., 1 mL/min). The volatiles were removed in vacuo to yield the subtitle compound N-(4-(((4-aminonaphthalen-1-yl)oxy)methyl)pyridin-2-yl)pyrazin-2-amine as a tan solid (121 mg, 88%); R$^t$ 0.81 min (Method 1); m/z 344 (M+H)$^+$ (ES$^+$).

Intermediate D: 3-tert-Butyl-1-p-tolyl-1H-pyrazol-5-amine

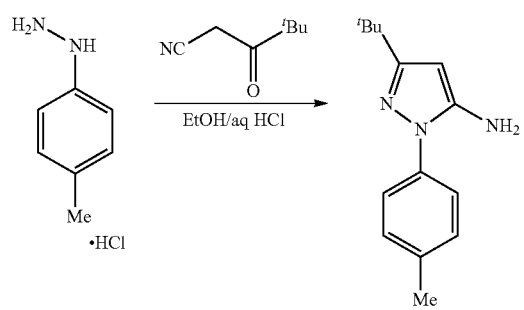 [SMILES: Cc1ccc(NN)cc1 ; Cl ; CC(C)(C)C(=O)CC#N ; Cc1ccc(-n2nc(C(C)(C)C)cc2N)cc1]

To a stirred solution of p-tolylhydrazine hydrochloride (100 g, 630 mmol) in EtOH (1251 mL) was added 4,4-dimethyl-3-oxopentanenitrile (88 g, 699 mmol) and HCl (62.5 mL, 750 mmol). The resulting mixture was stirred at reflux overnight. The reaction mixture was cooled to room temperature and concentrated in vacuo to c.a. ⅓ of the original volume. The reaction mixture was then cooled in an ice-bath and taken to c.a. pH 8-9 with 6M aq NaOH. The reaction mixture was extracted with diethyl ether (500 mL) and the organic phase washed with water (2×300 mL) before being dried over magnesium sulphate and concentrated in vacuo to afford an orange solid. The solid was suspended in iso-hexane and stirred at reflux for 2.5 h before being cooled and filtered whilst still hot to yield the subtitle product 3-tert-butyl-1-p-tolyl-1H-pyrazol-5-amine as a pale brown solid (76.5 g, 52%); R$^t$ 1.31 min (Method 1); m/z 230 (M+H)$^+$ (ES$^+$); $^1$H NMR δ: 1.20 (9H, s), 2.32 (3H, s), 5.10 (2H, br s), 5.35 (1H, s), 7.24 (2H, d), 7.42 (2H, m).

Intermediate E: Phenyl (3-(tert-butyl)-1-(p-tolyl)-1H-pyrazol-5-yl)carbamate

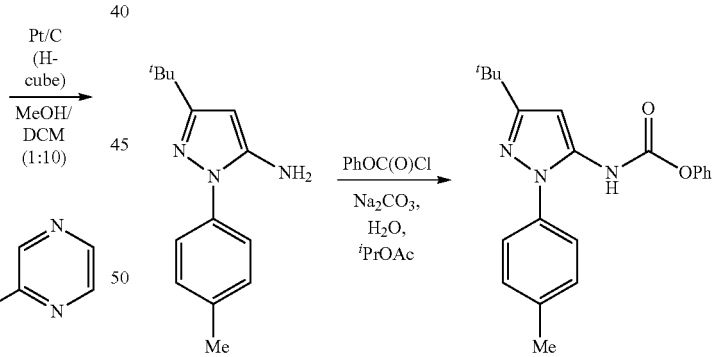

A solution of 3-(tert-butyl)-1-(p-tolyl)-1H-pyrazol-5-amine (Intermediate D) (20 g, 87.0 mmol) in isopropyl acetate (240 mL) was added to a stirred solution of sodium carbonate (11.3 g, 106 mmol) in water (80 mL). After 10 min phenyl chloroformate (12.1 mL, 96 mmol) was added and the resulting mixture was stirred at ambient temperature overnight. The reaction mixture was diluted with water (160 mL), the layers were separated and the organics were washed with water (2×80 mL), brine (80 mL), dried (MgSO$_4$) and concentrated in vacuo. The resulting yellow solid was suspended in 10% ether/iso-hexane (320 mL) and stirred until a uniform suspension was obtained. The solid was collected by filtration and washed with iso-hexane to yield the subtitle compound phenyl (3-(tert-butyl)-1-(p-tolyl)-1H-pyrazol-5-yl)carbamate as a white powder (27.3 g, 88%); R$^t$ 2.65 min (Method 1); m/z 350 (M+H)$^+$ (ES$^+$); $^1$H NMR δ: 1.29 (9H, s), 2.37 (3H, s), 6.35 (1H, s), 7.10-7.23 (3H, overlapping m), 7.33-7.46 (6H, overlapping m), 9.99 (1H, s).

Intermediate F: tert-Butyl (4-((2-chloropyridin-4-yl)methoxy)naphthalen-1-yl)carbamate

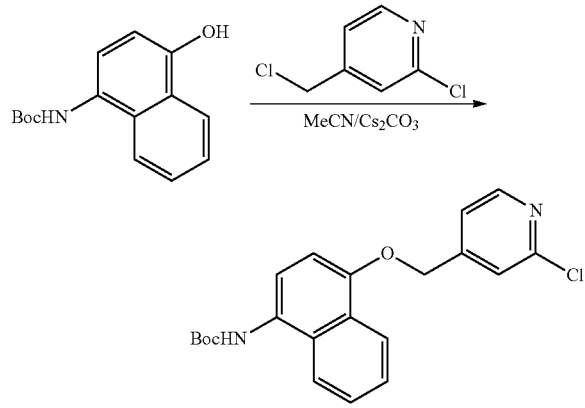

To a mixture of 2-chloro-4-(chloromethyl)pyridine (30 g, 185 mmol) and tert-butyl (4-hydroxynaphthalen-1-yl)carbamate (40.0 g, 154 mmol) in acetonitrile (200 mL) was added caesium carbonate (75 g, 231 mmol) and the resulting mixture was heated to 55° C. After 16 h the reaction mixture was diluted with 30% MeOH in DCM (600 mL) and water (400 mL). The layers were separated and the aqueous layer was extracted with a further amount of 30% MeOH in DCM (2×600 mL) and the organics were concentrated in vacuo to afford the crude product. The crude product was triturated with MeOH (200 mL), sonicated for c.a. 5 min and slurried for 1 day. The resulting solid was collected by filtration and washed with MeOH (2×10 mL) to yield the subtitle compound tert-butyl(4-((2-chloropyridin-4-yl)methoxy)naphthalen-1-yl)carbamate as a yellow solid (43 g, 70%); R$^t$ 2.60 min (Method 1); m/z 383 (M−H)$^-$ (ES$^-$); $^1$H NMR δ: 1.47 (9H, s), 5.41 (2H, s), 6.98 (1H, d), 7.36 (1H, d), 7.55-7.61 (3H, overlapping m), 7.65 (1H, m), 7.94 (1H, m), 8.29 (1H, m), 8.45 (1H, m), 9.00 (1H, bs).

Intermediate C (protected): tert-Butyl(4-((2-(pyrazin-2-ylamino)pyridin-4-yl)methoxy) naphthalen-1-yl)carbamate

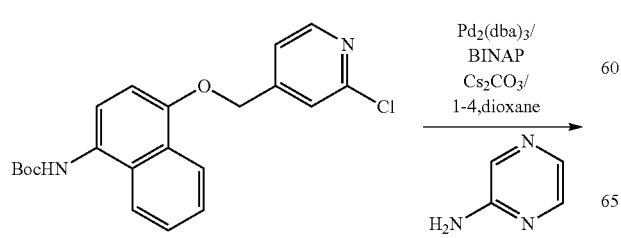

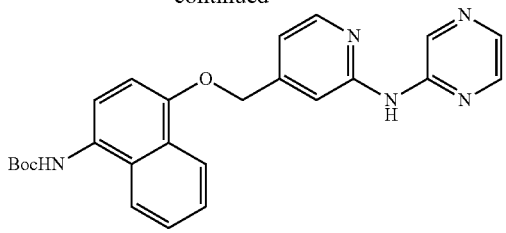

The following procedure was carried out twice: a suspension of tert-butyl (4-((2-chloropyridin-4-yl)methoxy)naphthalen-1-yl)carbamate (Intermediate F) (10.0 g, 25.5 mmol), 2-aminopyrazine (7.27 g, 76.0 mmol) and caesium carbonate (16.6 g, 50.9 mmol) in 1,4-dioxane (100 mL) was purged with nitrogen for 10 min. Pd$_2$(dba)$_3$ (1.17 g, 1.27 mmol) and BINAP (1.59 g, 2.55 mmol) in 1,4-dioxane (40 mL) was added and the resulting mixture was heated to 90° C. After 6.5 h both reaction mixtures were allowed to cool to ambient temperature, combined, diluted with 10% MeOH in DCM (300 mL) and filtered through a plug of Celite. The Celite pad was washed with 10% MeOH in DCM (300 mL), the solvents were concentrated in vacuo and the residue was dissolved in MeOH (200 mL) and stirred at ambient temperature for 2 h. The resulting solid was collected by filtration and washed with MeOH (20 mL) and diethyl ether (20 mL) to afford the impure product as bright orange solid. The crude material was combined, slurried in a mixture of MeOH (200 mL) and EtOH (200 mL) for 16 h. The solids were collected by filtration and dried (94% purity). The solid was treated with MeOH (200 mL) and EtOH (200 mL) and slurried for a further 16 h. The solids were collected by filtration and washed with iso-hexane (2×100 mL) to yield the subtitle compound tert-butyl(4-((2-(pyrazin-2-ylamino)pyridin-4-yl)methoxy)naphthalen-1-yl)carbamate as a tan solid (13.7 g, 60%); R$^t$ 2.4 min (Method 2); m/z 444 (M+H)$^+$ (ES$^+$); $^1$H NMR δ: 1.47 (9H, s), 5.36 (2H, s), 7.01 (1H, d), 7.07 (1H, m), 7.36 (1H, d), 7.57-7.62 (2H, overlapping m), 7.95 (1H, m), 8.01 (1H, bs), 8.09 (1H, m), 8.22 (1H, m), 8.29 (1H, m), 8.38 (1H, m), 8.99 (1H, bs), 9.08 (1H, m), 10.2 (1H, s).

Intermediate C (alternative method): N-(4-(((4-Aminonaphthalen-1-yl)oxy)methyl) pyridin-2-yl)pyrazin-2-amine

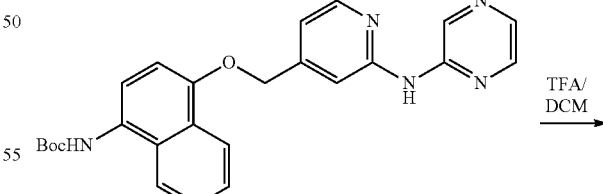

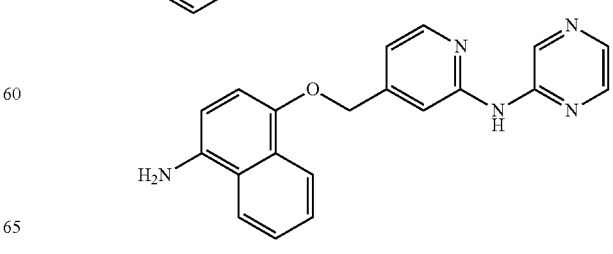

To a suspension of tert-butyl(4-((2-(pyrazin-2-ylamino)pyridin-4-yl)methoxy)naphthalen-1-yl)carbamate (Intermediate C (protected)) (13.9 g, 31.3 mmol) in DCM (140 mL) at ambient temperature was added TFA (24 mL) and the resulting solution was stirred at ambient temperature. After 3 h the solvent was removed in vacuo and the residue was poured onto sat. aq. NaHCO$_3$ (500 mL). The resulting mixture was sonicated for 2 min, slurried for 16 h and the resulting precipitate was collected by filtration and washed with water (300 mL) and acetonitrile (100 mL) to yield the subtitle compound N-(4-(((4-aminonaphthalen-1-yl)oxy)methyl)pyridin-2-yl)pyrazin-2-amine as a tan solid, partial TFA salt (10 g, 92%); R$^t$ 1.9 min (Method 2); m/z 344 (M+H)$^+$ (ES$^+$); $^1$H NMR δ: 5.20 (2H, s), 5.23 (2H, s), 6.60 (1H, d), 6.84 (1H, d), 7.06 (1H, m), 7.43-7.51 (2H, overlapping m), 7.98 (1H, s), 8.05 (1H, d), 8.08 (1H, m), 8.22 (1H, m), 8.25-8.29 (2H, overlapping m), 9.07 (1H, m), 10.1 (1H, s).

1-(3-(tert-Butyl)-1-(p-tolyl)-1H-pyrazol-5-yl)-3-(4-((2-(pyrazin-2-ylamino)pyridin-4-yl)methoxy)naphthalen-1-yl)urea

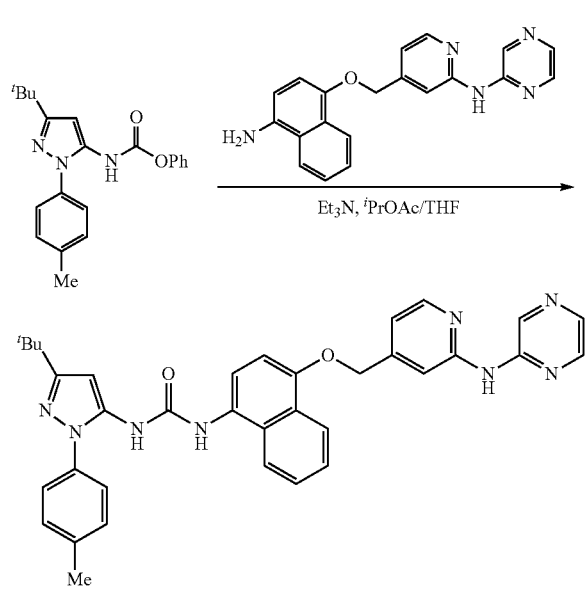

To a mixture of phenyl (3-(tert-butyl)-1-(p-tolyl)-1H-pyrazol-5-yl)carbamate (Intermediate E) (14.1 g, 40.4 mmol) and N-(4-(((4-aminonaphthalen-1-yl)oxy)methyl)pyridin-2-yl)pyrazin-2-amine (Intermediate C) (10 g, 28.8 mmol) in isopropyl acetate (400 mL) heated to 40° C. was added triethylamine (0.804 mL, 5.77 mmol). The resulting mixture was stirred for 1 h and then cooled to ambient temperature and stirred for a further 16 h. The excess solvents were removed in vacuo and the residue was dissolved in 20% MeOH in DCM (1000 mL) and washed with sat. aq. NaHCO$_3$ (300 mL). The aqueous layer was extracted with a further amount of 20% MeOH in DCM (200 mL) and the combined organics were washed with brine (200 mL) and concentrated in vacuo. The material obtained was combined with acetonitrile (200 mL) and slurried for 5 h. The resulting mixture was warmed to 50° C. and allowed to cool to ambient temperature (cycle repeated twice) and the solid was collected by filtration to afford a grey lumpy solid. The material was recombined with acetonitrile (700 mL), warmed to 50° C. for 30 min, cooled to ambient temperature, stirred for 3 h and filtered. The solid was recombined with acetonitrile (300 mL) and slurried for a further 72 h. The resulting solid was collected by filtration to yield the title compound 1-(3-(tert-butyl)-1-(p-tolyl)-1H-pyrazol-5-yl)-3-(4-((2-(pyrazin-2-ylamino)pyridin-4-yl)methoxy)naphthalen-1-yl)urea as a beige solid (14 g, 80%); R$^t$ 1.97 min (Method 1); m/z 599 (M+H)$^+$ (ES$^+$); $^1$H NMR δ: 1.27 (9H, s), 2.39 (3H, s), 5.35 (2H, s), 6.36 (1H, s), 7.04 (1H, d), 7.08 (1H, dd), 7.36 (2H, m), 7.44 (2H, m), 7.59-7.66 (3H, overlapping m), 7.95 (1H, m), 8.01 (1H, bs), 8.09 (1H, d), 8.21 (1H, m), 8.30 (1H, d), 8.40 (1H, m), 8.59 (1H, s), 8.80 (1H, s), 9.08 (1H, d), 10.15 (1H, s).

Example 2: 1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea Intermediate G (protected): tert-Butyl (4-((2-((6-ethylpyrazin-2-yl)amino)pyridin-4-yl)methoxy)naphthalen-1-yl)carbamate

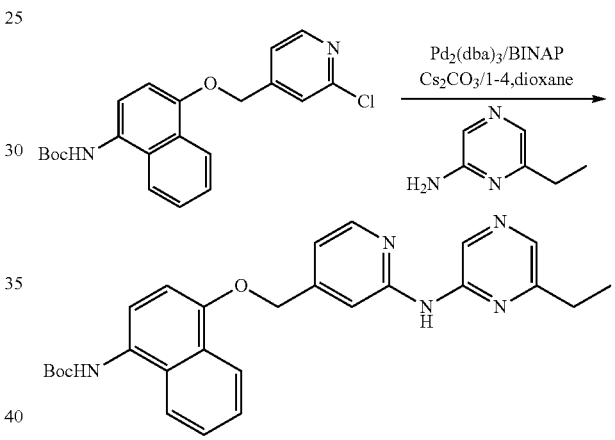

A mixture of tert-butyl(4-((2-chloropyridin-4-yl)methoxy)naphthalen-1-yl)carbamate (Intermediate F) (1050 mg, 2.73 mmol), 6-ethylpyrazin-2-amine (437 mg, 3.55 mmol), and cesium carbonate (1333 mg, 4.09 mmol) in 1,4-dioxane (15 mL) was degassed with nitrogen for 5 min. A solution of Pd$_2$(dba)$_3$ (125 mg, 0.136 mmol) and BINAP (170 mg, 0.273 mmol) in 1,4-dioxane (5 mL) was added, and the reaction mixture stirred at 90° C. for 6 h. The reaction mixture was allowed to cool and was stirred at room temperature for 16 h, then diluted with 10% MeOH/DCM (25 mL) and filtered through a plug of Celite, washing with additional 10% MeOH/DCM (15 mL). The solvent was removed in vacuo and the crude product was combined with MeOH (15 mL) and slurried for 3 h. The resulting orange solid was isolated by filtration, then combined with MeOH/EtOH (5 mL) solution and stirred for 72 h. Again the resulting orange solid was isolated by filtration, then acetone (20 mL) was added and the mixture was slurried for 2 h. The residual solid was filtered off, and the filtrate was evaporated to give the subtitle compound tert-butyl(4-((2-((6-ethylpyrazin-2-yl)amino)pyridin-4-yl)methoxy)naphthalen-1-yl)carbamate (360 mg, 27%); R$^t$ 2.6 min (Method 2); m/z 472 (M+H)$^+$ (ES$^+$); $^1$H NMR δ: 1.18 (3H, t), 1.47 (9H, s), 2.63 (2H, q), 5.36 (2H, s), 6.99 (1H, d), 7.06 (1H, d), 7.36 (1H, d), 7.53-7.63 (2H, m), 7.90-8.06 (3H, overlapping m), 8.29 (1H, d), 8.36 (1H, m), 8.91 (1H, s), 8.96 (1H, s), 10.06 (1H, s).

Intermediate G: N-(4-(((4-aminonaphthalen-1-yl)oxy)methyl)pyridin-2-yl)-6-ethylpyrazin-2-amine

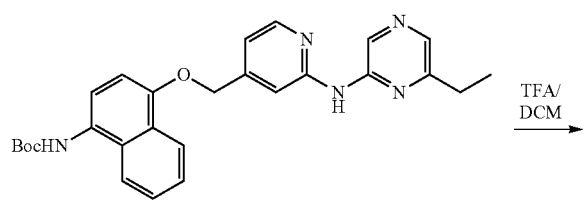

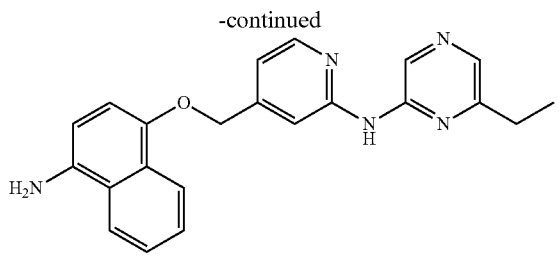

TFA (1.485 mL, 19.09 mmol) was added to a solution of tert-butyl(4-((2-((6-ethylpyrazin-2-yl)amino)pyridin-4-yl)methoxy)naphthalen-1-yl)carbamate (Intermediate G (protected)) (360 mg, 0.763 mmol) in DCM (15 mL), and the reaction mixture stirred at room temperature for 4 h, then concentrated in vacuo. The residue was combined with sat. sodium hydrogencarbonate solution and stirred at room temperature for 16 h. The solid was filtered, washing with acetonitrile, and dried under vacuum to give the subtitle compound N-(4-(((4-aminonaphthalen-1-yl)oxy)methyl)pyridin-2-yl)-6-ethylpyrazin-2-amine as a beige solid (200 mg, 69%); $R^t$ 2.14 min (Method 2); m/z 372 (M+H)$^+$ (ES$^+$); $^1$H NMR δ: 1.20 (3H, t), 2.64 (2H, q), 5.18-5.24 (4H, overlapping m), 6.59 (1H, d), 6.82 (1H, d), 7.03 (1H, d), 7.41-7.51 (2H, overlapping m), 7.98-8.01 (2H, m), 8.04 (1H, m), 8.22-8.29 (2H, overlapping m), 8.91 (1H, s), 10.04 (1H, s).

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea

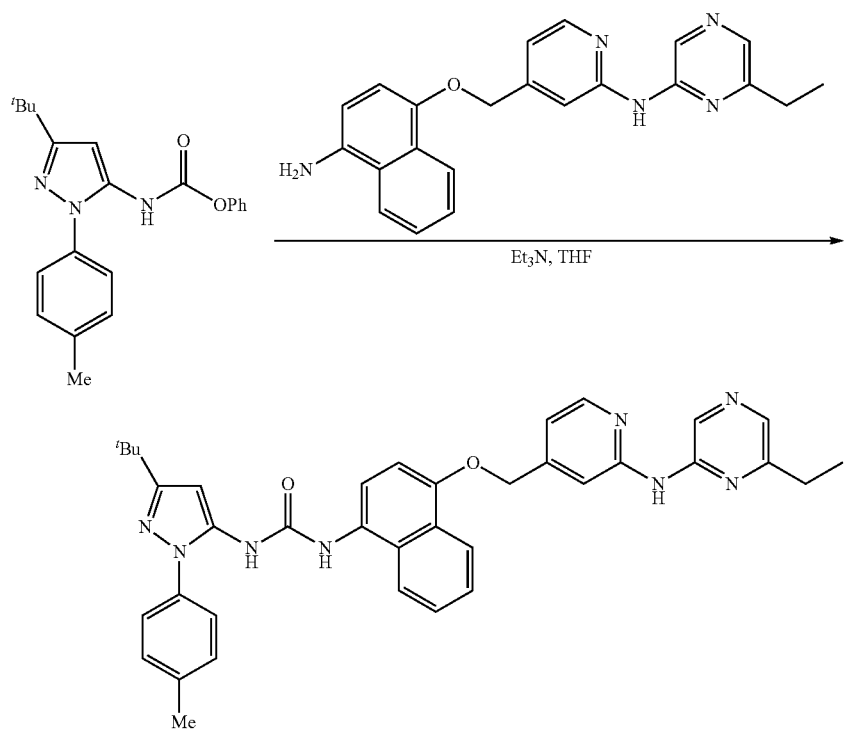

Triethylamine (0.013 mL, 0.093 mmol) was added to a solution of phenyl(3-(tert-butyl)-1-(p-tolyl)-1H-pyrazol-5-yl)carbamate (Intermediate E) (0.042 g, 0.121 mmol) and N-(4-(((4-aminonaphthalen-1-yl)oxy)methyl)pyridin-2-yl)-6-ethylpyrazin-2-amine (Intermediate G) (0.093 g, 0.250 mmol) in THF (1.5 mL) at 40° C. The reaction mixture was stirred at 40° C. for 40 min then cooled to RT and stirred for 3 days, and then concentrated in vacuo. The crude product was purified by silica gel chromatography (12 g column, 0 to 5% MeOH in DCM) to give an off white-brown solid. The product was re-purified by preparative HPLC (Gilson, Acidic (0.1% Formic acid), Acidic, Waters X-Select Prep-C18, 5 μm, 19×50 mm column, 45-75% MeCN in water) to afford the title compound 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea as an off white solid (0.029 g, 49%); $R^t$ 2.26 min (Method 1); m/z 627 (M+H)$^+$ (ES+), 625 (M−H)− (ES−); ¹H NMR δ: 1.18 (3H, t), 1.28 (9H, s), 2.40 (3H, s), 2.63 (2H, q), 5.36 (2H, s), 6.36 (1H, s), 7.02 (1H, d), 7.07 (1H, dd), 7.37 (2H, m), 7.45 (2H, m), 7.56-7.67 (3H, overlapping m), 7.94 (1H, m), 7.99 (1H, s), 8.02 (1H, s), 8.30 (1H, d), 8.39 (1H, m), 8.60 (1H, s), 8.81 (1H, s), 8.92 (1H, s), 10.08 (1H, s).

Example 2A: 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (free base and maleate)

Intermediate G(i): tert-butyl N-[4-[(2-chloro-4-pyridyl)methoxy]-1-naphthyl]carbamate

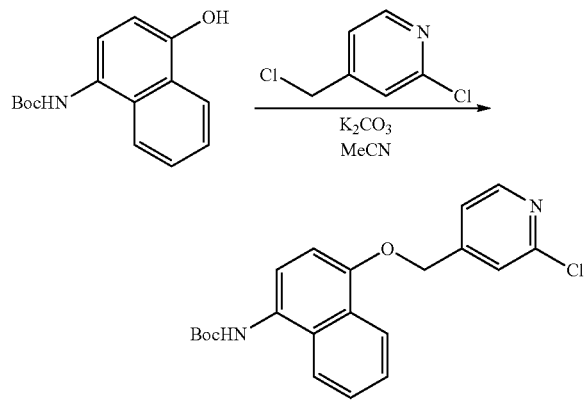

Acetonitrile (420 mL) was added to 2-chloro-4-(chloromethyl)pyridine (59.5 g) (1.05 eq), and the mixture stirred at 20° C. tert-Butyl (4-hydroxynaphthalen-1-yl)carbamate (90.8 g) was added to the mixture then potassium carbonate (72.6 g) was added. The heterogeneous mixture was warmed to 55° C. at a rate of 1.0 K/min.

The mixture was stirred for 16 h at 55° C. then the reaction mixture was cooled to 22° C. Water (1260 mL) was added over 30 min and the mixture was stirred for 30 min at 22° C. The precipitate was filtered and washed with water (2×200 mL). The product was dried in vacuo at 50° C. for 20 h to give tert-butyl N-[4-[(2-chloro-4-pyridyl)methoxy]-1-naphthyl]carbamate (100.0 g, 90.6%).

Intermediate G(ii) (protected): tert-butyl (4-((2-((6-ethylpyrazin-2-yl)amino)pyridin-4-yl)methoxy)naphthalen-1-yl)carbamate

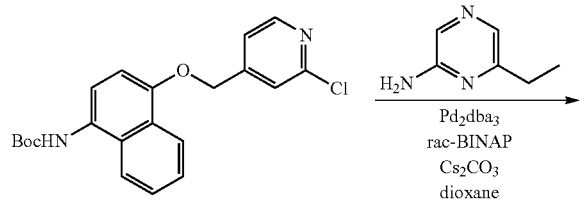

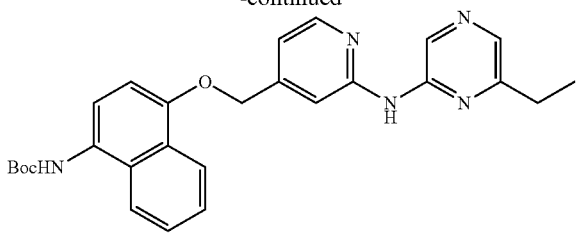

1,4-Dioxane (125 mL) was added to tert-butyl-N-[4-[(2-chloro-4-pyridyl)methoxy]-1-naphthyl]carbamate (Intermediate G(i)) (9.6 g) and the mixture stirred at 20° C. Cesium carbonate (16.3 g) (2 eq) and 2-amino-6-ethylpyrazine (4.8 g) (1.5 eq) were added to the stirred mixture at 20° C. Argon was purged through the reaction mixture. Tris(dibenzylideneacetone)dipalladium(0) (1.14 g) (0.05 eq) and racemic BINAP (1.56 g) (0.10 eq) were added to the reaction mixture. The mixture was stirred for an additional 15 min at 20° C. The mixture was heated to 90° C. at a rate of 1.5 K/min, then stirred for 12 h at 90° C. The mixture was cooled to 20° C. and stirring continued for an additional 6 h. The heterogeneous mixture was filtered over Celite, and the filter washed with 1,4-dioxane (twice 5 mL). The filtrate was concentrated in vacuo at 20 mbar and 50° C. The residue was dissolved in ethanol (150 mL). Spontaneous crystallisation occurred. The heterogeneous mixture was stirred for 3 h at 22° C. The precipitate was filtered and washed with ethanol (10 mL). The product was dried in vacuo at 50° C. for 20 h to give tert-butyl(4-((2-((6-ethylpyrazin-2-yl)amino)pyridin-4-yl)methoxy)naphthalen-1-yl)carbamate (9.05 g, 76.8%).

Intermediate G(ii): N-[4-[(4-amino-1-naphthyl)oxymethyl]-2-pyridyl]-6-ethyl-pyrazin-2-amine

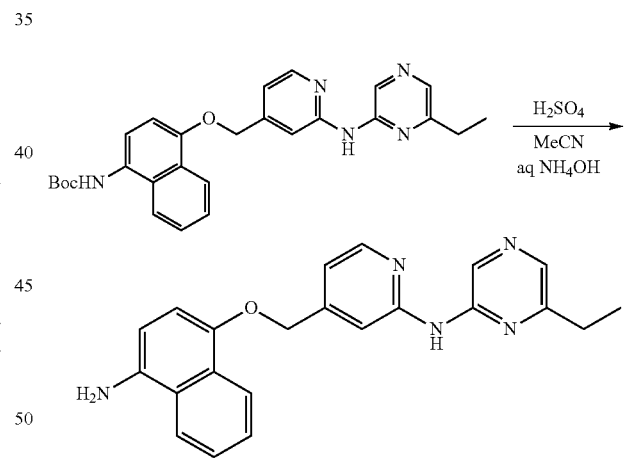

Acetonitrile (200 mL) was added to tert-butyl-N-[4-[[2-[(6-ethylpyrazin-2-yl)amino]-4-pyridyl]methoxy]-1-naphthyl]carbamate (Intermediate D (protected)) (10.5 g) and the heterogeneous mixture stirred at 20° C. Sulfuric acid (5.5 mL) (4.5 eq) was added over 2 h at 20° C. The heterogeneous mixture was stirred for an additional 2 h at 20° C. Aqueous ammonia (17 mL) (10 eq) was added to the reaction mixture over 15 min, keeping the temperature at 20° C. by cooling. Water (33.4 mL) was added to the heterogeneous mixture over 5 min at 20° C. After stirring for 30 min at 20° C., the mixture was cooled to 5° C. and stirred for an additional 2 h at 5° C. The precipitate was filtered and washed with water (33.4 mL) and 2-propanol (18 mL). The product was dried at 50° C. in vacuo for 24 h to give N-[4-[(4-amino-1-naphthyl)oxymethyl]-2-pyridyl]-6-ethyl-pyrazin-2-amine (6.2 g, 75%).

1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea

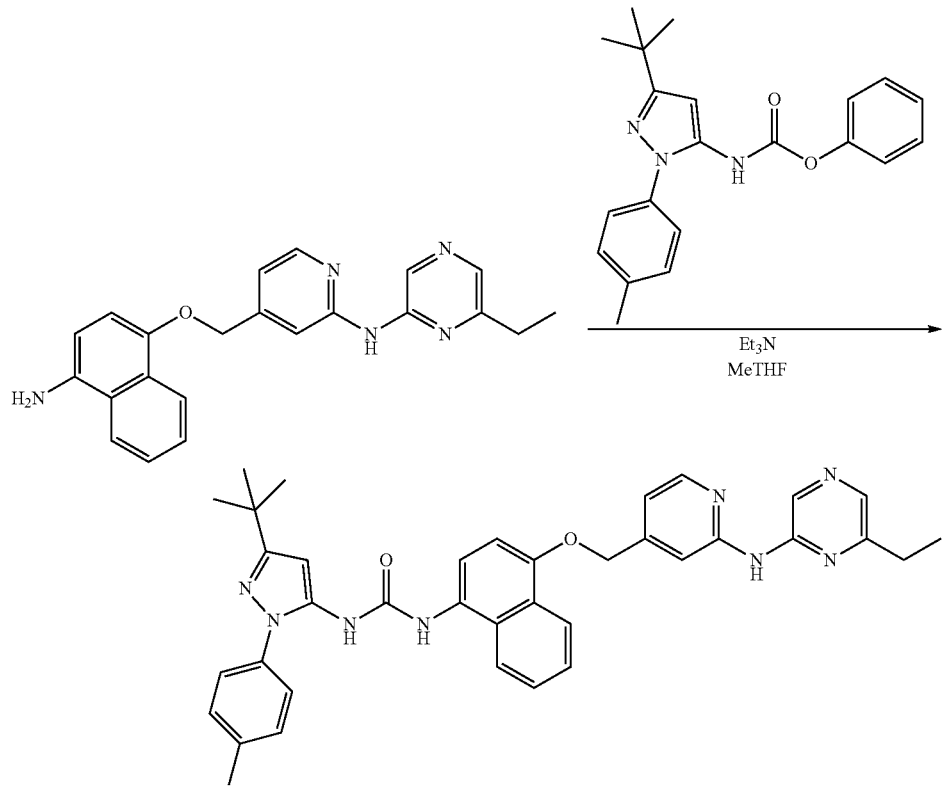

2-methyltetrahydrofuran (1809 mL) was added to N-(4-(((4-aminonaphthalen-1-yl)oxy)methyl)pyridin-2-yl)-6-ethylpyrazin-2-amine (Intermediate D) (41.3 g) and the mixture was stirred at 20° C. Phenyl (3-(tert-butyl)-1-(p-tolyl)-1H-pyrazol-5-yl)carbamate (51.3 g) (1.2 eq) was added to the mixture. Triethylamine (3.9 mL) (0.25 eq) was added and the mixture stirred for an additional 10 min at 20° C. The heterogeneous reaction mixture was warmed to 48° C. over 30 min and kept at 48° C. for 3.5 h. After 10 min at 48° C., the mixture became homogeneous, and was seeded with crystalline 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (60 mg). The reaction mixture was allowed to cool to 20° C. and stirred for an additional 16 h. The formed precipitate was filtered and washed with 2-methyltetrahydrofuran (twice 139 mL). The product was dried for 18 h at 45° C. in vacuo to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (54.1 g, 77.5%).

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2)

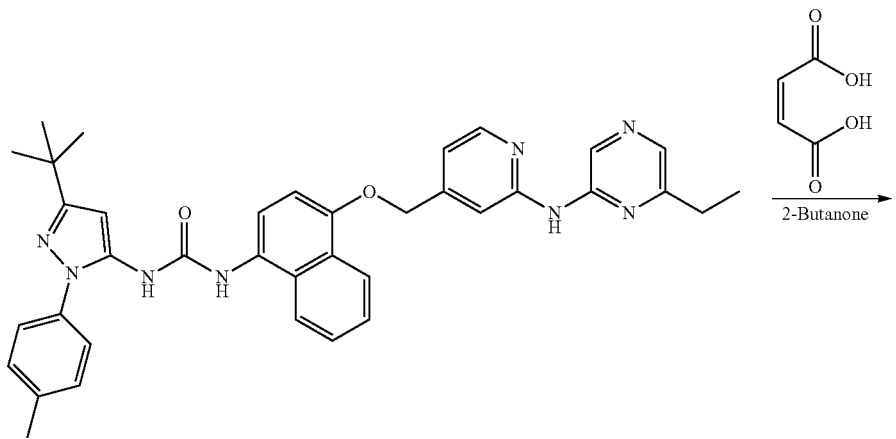

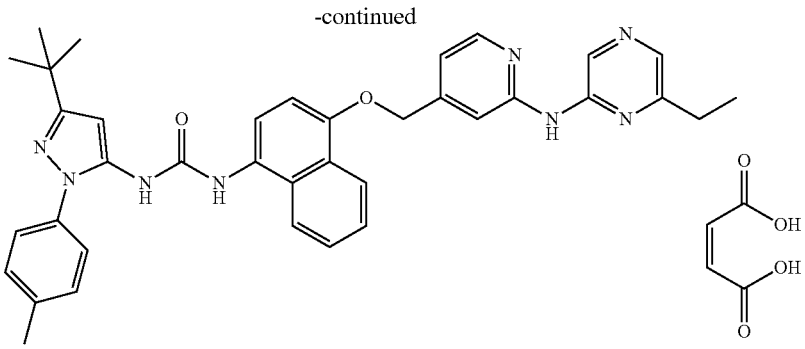

2-Butanone (4442 mL) was added to 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (111.04 g) and stirred at 20° C. The heterogeneous mixture was warmed to 65° C. and became a homogeneous solution. SilicaMetS Thiol (metal scavenger) (5.55 g) was added and the mixture stirred for 30 min at 65° C. Norit A Supra (activated charcoal) (5.55 g) added and the mixture stirred for an additional 20 min at 65° C. The mixture was filtered warm over Celite. The filter was washed with warm (60° C.) 2-butanone (1555 mL). 2-Butanone (2887 mL) was added to the filtrate and brought to 60° C. while stirring.

Maleic acid (20.56 g) (1.0 eq) was dissolved in 2-butanone (555 mL). The maleic acid solution was added to the 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea solution over 80 min at 65° C. After 10% of the maleic acid solution is added, the mixture was seeded with crystalline 1-(3-(tert-butyl)-1-(p-tolyl)-1H-pyrazol-5-yl)-3-(4-((2-((6-ethylpyrazin-2-yl)amino) pyridin-4-yl)methoxy)naphthalen-1-yl)urea maleate Form 2. The mixture was kept stirring for 1 h at 60° C., then cooled non-linearly with an exponent of 2.3 over 6 h to 5° C. The precipitate was filtered and washed twice with 2-butanone (278 mL). The product was dried at 45° C. in vacuo for 20 h to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate Form 2 (113.8 g, 86.5%).

The powder XRD pattern (CuKα radiation) of a sample of this material showed diffraction peaks at 4.2, 8.4, 8.7, 11.0, 11.5, 12.6, 14.4, 14.9, 16.0, 17.0, 17.4, 18.8, 19.5, 20.2, 21.7, 22.4, 23.8, 25.8 and 26.3 (±0.2) degrees 2-theta without the presence of a halo, indicating that the compound is present as a crystalline product (Form 2 polymorph).

Example 2B: 1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2) (different batch)

2-Butanone (750 mL) was added to 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea (7.50 g) and the mixture was stirred. The mixture was warmed to 60° C. over 20 min. A solution of maleic acid (1.39 g) in 2-butanone (12 mL) was added to the mixture over 5 min. Spontaneous crystallisation occurred after approximately half of the maleic acid solution was added. The mixture was stirred for 30 min at 60° C. then cooled to 5° C. over 6 h with an exponential ramp (exponent=2.3) then stirred for 30 min at 5° C. then heated to 65° C. over 30 min then stirred for 30 min at 65° C. then cooled to 5° C. over 6 h with an exponential ramp (exponent=2.3) then stirred for 30 min at 5° C. then heated to 65° C. over 30 min then stirred for 30 min at 65° C. then cooled to 5° C. over 6 h with an exponential ramp (exponent=2.3). The product was filtered and washed twice with 2-butanone (50 mL), subsequently dried at 45° C. in vacuo to give 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 2) (7.0 g).

Example 2C: 1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 1)

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (15 mg) was dissolved in THF (100 vol.) at 50° C. and temperature cycled between 50° C. and room temperature over 24 h (4 h at each temperature). The solution was then kept in the fridge for 24 h after which the solid material (Form 1) was isolated.

Example 2D: 1-(3-(tert-butyl)-1-(p-tolyl)-1H-pyrazol-5-yl)-3-(4-((2-((6-ethylpyrazin-2-yl)amino)pyridin-4-yl)methoxy)naphthalen-1-yl)urea maleate (Form 1) (different batch)

1-(3-(tert-Butyl)-1-(p-tolyl)-1H-pyrazol-5-yl)-3-(4-((2-((6-ethylpyrazin-2-yl)amino)pyridin-4-yl)methoxy)naphthalen-1-yl)urea was dissolved in THF (40 vol.) at 50° C. and 1 equivalent of maleic acid was added. The sample was left to mature between RT and 50° C. (4 h at each temperature) for 2 days. Solid material (Form 1) was isolated.

The powder XRD pattern (CuKα radiation) of a sample of this material showed diffraction peaks at 3.8, 6.3, 7.8, 9.3, 9.9, 10.7, 11.2, 12.7, 15.4, 16.5, 17.9, 19.2 and 19.6 (±0.2) degrees without the presence of a halo, indicating that the compound is present as a crystalline product (Form 1 polymorph).

Example 3: 5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-methoxyethyl)pyrazine-2-carboxamide Intermediate H: 4-(((4-Nitronaphthalen-1-yl)oxy)methyl)pyridin-2-amine

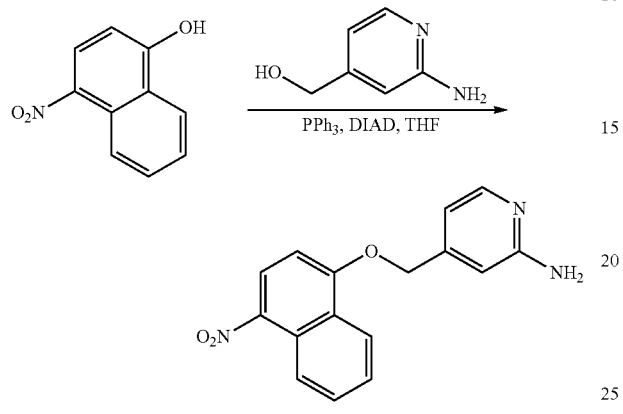

4-Nitronaphthalen-1-ol (60 g, 317 mmol), (2-aminopyridin-4-yl)methanol (44.6 g, 359 mmol) and triphenylphosphine (120 g, 458 mmol) were dissolved in tetrahydrofuran (616 mL, 7516 mmol) and cooled in a dry ice/acetone bath. (E)-Diisopropyl diazene-1,2-dicarboxylate (89 mL, 458 mmol) was added drop-wise over 20 min. The reaction mixture was allowed to warm to RT and was left to stir overnight. The reaction mixture was diluted with MeOH (80 mL) and concentrated to a black gel. The gel was taken up in MeOH (430 mL), sonicated for 40 min and stirred at room temperature for 3 h. The solid was collected via vacuum filtration, washing with MeOH (300 mL), to afford the subtitle compound 4-(((4-nitronaphthalen-1-yl)oxy)methyl)pyridin-2-amine as a black-yellow solid (28 g, 27%); R$^t$ 1.31 min (Method 1); m/z 296 (M+H)$^+$ (ES$^+$).

Intermediate I:
5-Chloro-N-(2-methoxyethyl)pyrazine-2-carboxamide

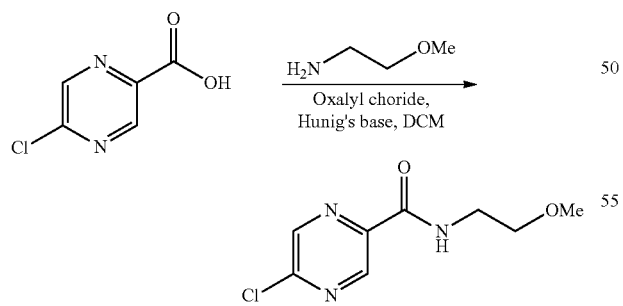

Oxalyl chloride (0.974 mL, 11.35 mmol) and few drops of DMF were added to a suspension of 5-chloropyrazine-2-carboxylic acid (1.5 g, 9.46 mmol), in dichloromethane (20 mL) and the reaction mixture was stirred for 2 h at room temperature under an atmosphere of nitrogen. The reaction mixture was concentrated in vacuo and dissolved in dichloromethane (10 mL) and cooled to 0° C. 2-methoxyethanamine (0.905 mL, 10.41 mmol) was then added dropwise to the solution, followed by Hunig's base (1.756 mL, 10.41 mmol). The reaction mixture was stirred overnight at room temperature, before being partitioned between water and dichloromethane, The organic layer was dried (MgSO$_4$), filtered and concentrated in vacuo. The crude product was purified by silica gel chromatography (40 g column, isohexane-ethyl acetate 0-50%) to afford the subtitle compound 5-chloro-N-(2-methoxyethyl)pyrazine-2-carboxamide as colourless solid (1.67 g, 78%); R$^t$ 1.86 min (Method 1); m/z 216 (M+H)$^+$ (ES$^+$).

Intermediate J: N-(2-Methoxyethyl)-5-((4-(((4-nitronaphthalen-1-yl)oxy)methyl)pyridin-2-yl)amino)pyrazine-2-carboxamide

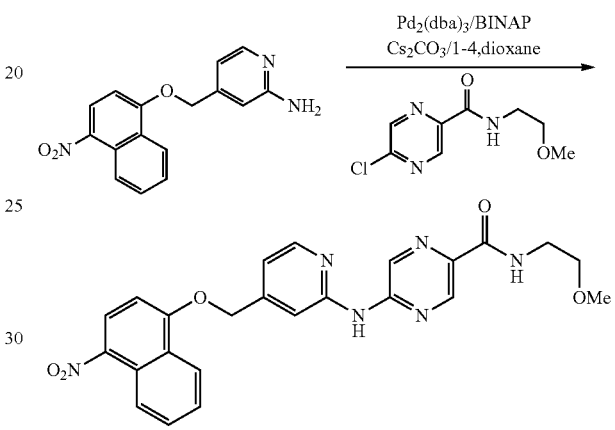

4-(((4-Nitronaphthalen-1-yl)oxy)methyl)pyridin-2-amine (Intermediate H) (2.410 g, 8.16 mmol), 5-chloro-N-(2-methoxyethyl)pyrazine-2-carboxamide (Intermediate I) (1.6 g, 7.42 mmol), Pd$_2$(dba)$_3$ (0.340 g, 0.371 mmol), 2,2'-bis(diphenylphosphino)-1,1'-binaphthalene (0.462 g, 0.742 mmol) and cesium carbonate (3.63 g, 11.13 mmol) were flushed with nitrogen and suspended in 1,4-dioxane (35 mL). The resultant mixture was degassed with nitrogen for 10 min and the dark brown mixture heated at 90° C. for 15 h. The crude mixture was cooled and then diluted with 10% MeOH/DCM (10 mL) and filtered through Celite, washing with further 10% MeOH/DCM (50 mL). The solvent was removed to yield the crude as a dark brown residue. This was triturated with methanol and filtered to afford the subtitle compound N-(2-methoxyethyl)-5-((4-(((4-nitronaphthalen-1-yl)oxy)methyl)pyridin-2-yl)amino) pyrazine-2-carboxamide as a brown solid (3 g, 75%); R$^t$ 1.93 min (Method 1); m/z 475 (M+H)$^+$ (ES$^+$).

Intermediate K: 5-((4-(((4-Aminonaphthalen-1-yl)oxy)methyl)pyridin-2-yl)amino)-N-(2-methoxyethyl)pyrazine-2-carboxamide

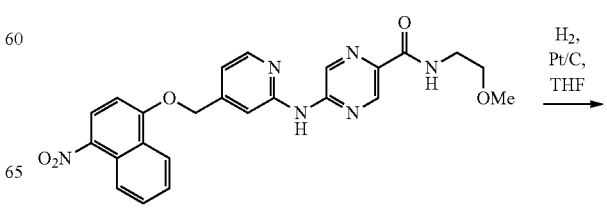

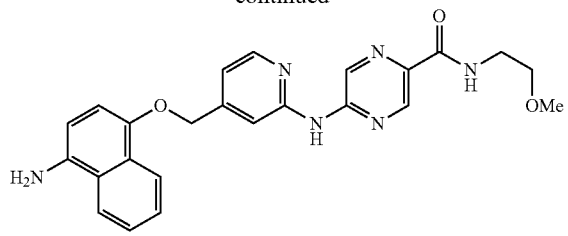

To a stirred solution of N-(2-methoxyethyl)-5-((4-(((4-nitronaphthalen-1-yl)oxy)methyl)pyridin-2-yl)amino)pyrazine-2-carboxamide (Intermediate J) (1 g, 2.108 mmol) in THF (25 mL), a few drops of acetic acid were added and the resulting mixture was degassed for 10 min with nitrogen. Pt/C (0.1 g) was then added. The resulting mixture was stirred under hydrogen at 5 bar overnight. The suspension was filtered through Celite, and the solvent removed in vacuo to yield the crude as dark brown residue. This was dissolved in a mixture of MeOH/DCM/THF and absorbed onto SCX, washed with MeOH and released with 1% $NH_3$ in MeOH. The 1% $NH_3$ in MeOH fraction was concentrated under reduced pressure to afford the subtitle compound 5-((4-(((4-aminonaphthalen-1-yl)oxy)methyl)pyridin-2-yl)amino)-N-(2-methoxyethyl)pyrazine-2-carboxamide as a brown solid (0.7 g, 61%); $R^r$ 1.13 min (Method 1); m/z 445 $(M+H)^+$ $(ES^+)$.

5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-methoxyethyl)pyrazine-2-carboxamide

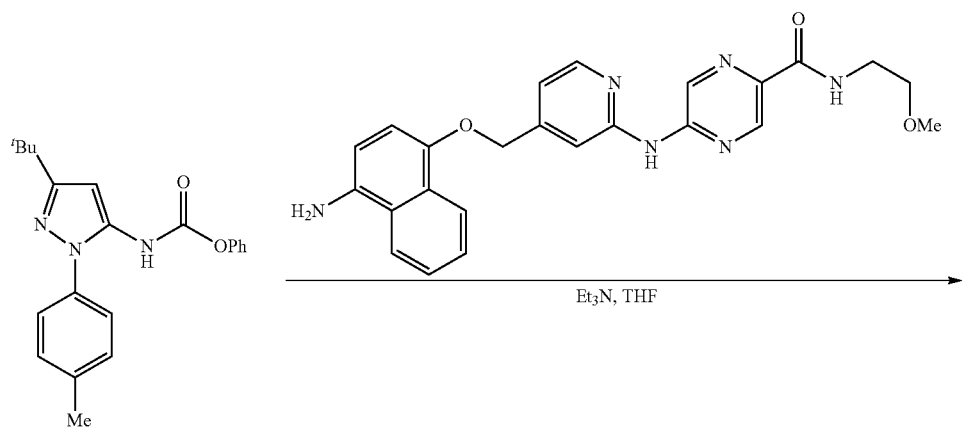

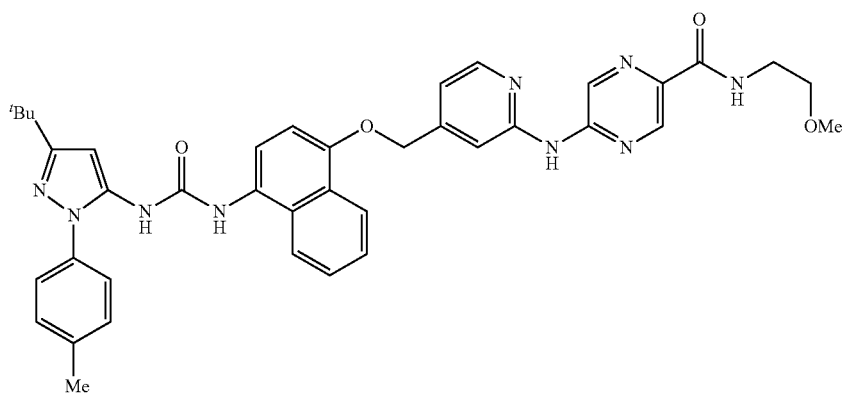

Phenyl (3-(tert-butyl)-1-(p-tolyl)-1H-pyrazol-5-yl)carbamate (Intermediate E) (259 mg, 0.742 mmol) was added to a solution of 5-((4-(((4-aminonaphthalen-1-yl)oxy)methyl)pyridin-2-yl)amino)-N-(2-methoxyethyl)pyrazine-2-carboxamide (Intermediate K) (300 mg, 0.675 mmol), in tetrahydrofuran (6 mL). The reaction mixture was heated to 40° C. and triethylamine (0.033 mL, 0.240 mmol) was then added. The reaction mixture was left to heat at 40° C. for 1 h then allowed to cool to room temperature and left to stir overnight. Methanol (3 mL) was added and the product was collected by filtration to afford the title compound 5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methoxyethyl)pyrazine-2-carboxamide (120 mg, 25%); R$^t$ 1.88 min (Method 1); m/z 700 (M+H)$^+$ (ES$^+$); $^1$H NMR δ: 1.28 (9H, s), 2.40 (3H, s), 3.28 (3H, s), 3.43-3.49 (4H, m), 5.39 (2H, s), 6.35 (1H, s), 7.05 (1H, d), 7.17 (1H, m), 7.37 (2H, m), 7.46 (2H, m), 7.58-7.68 (3H, overlapping m), 7.95 (1H, m), 8.10 (1H, s), 8.34 (1H, d), 8.41 (1H, d), 8.47 (1H, m), 8.59 (1H, s), 8.75 (1H, s), 8.94 (1H, s), 9.06 (1H, s), 10.61 (1H, s).

Example 4: 1-(3-(tert-Butyl)-1-(p-tolyl)-1H-pyrazol-5-yl)-3-(4-((2-((5,6-dimethylpyrazin-2-yl)amino)pyridin-4-yl)methoxy)naphthalen-1-yl)urea Intermediate L (protected): tert-Butyl (4-((2-((5,6-dimethylpyrazin-2-yl)amino)pyridin-4-yl)methoxy)naphthalen-1-yl)carbamate

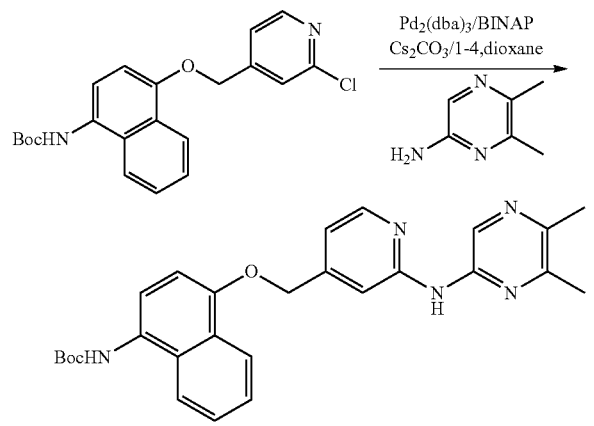

The reaction was carried out on an identical scale twice:—

Cesium carbonate (13.23 g, 40.6 mmol) was added to a suspension of tert-butyl(4-((2-chloropyridin-4-yl)methoxy)naphthalen-1-yl)carbamate (Intermediate F) (10.42 g, 27.1 mmol), 5,6-dimethylpyrazin-2-amine (5 g, 40.6 mmol), Pd$_2$(dba)$_3$ (1.239 g, 1.353 mmol) and BINAP (1.685 g, 2.71 mmol) in 1,4-dioxane (100 mL) at room temperature under nitrogen. The suspension was sonicated for 5 min and degassed with nitrogen for 10 min before being stirred at 90° C. overnight. The reaction mixture was cooled to room temperature and diluted with a solution of 10% MeOH in DCM (500 mm) before being filtered through a pad of Celite, washing with additional 10% MeOH in DCM (100 mL). The filtrate was concentrated in vacuo. At this stage the two identical reactions were combined. The combined residues were suspended in MeOH (125 mL) before being stirred for 16 h. The solid was collected via filtration. The residue was slurried in MeOH (100 mL) for 2 h and the solid filtered (3×). The material was slurried in a 1:1 mixture of 10% MeOH in DCM/EtOH (100 mL) for 1 hr twice, filtered and dried. The solid was dried overnight to afford the subtitle compound tert-butyl(4-((2-((5,6-dimethylpyrazin-2-yl)amino)pyridin-4-yl)methoxy)naphthalen-1-yl)carbamate) as a beige solid (13.3 g, 51%); R$^t$ 2.56 min (Method 2); m/z 472 (M+H)$^+$ (ES$^+$).

Intermediate L: N-(4-(((4-aminonaphthalen-1-yl)oxy)methyl)pyridin-2-yl)-5,6-dimethyl pyrazin-2-amine

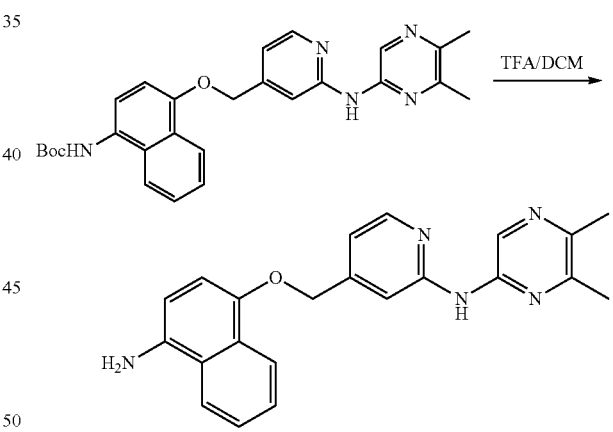

Trifluoroacetic acid (41.8 mL, 543 mmol) was added to a stirring solution of tert-butyl(4-((2-((5,6-dimethylpyrazin-2-yl)amino)pyridin-4-yl)methoxy)naphthalen-1-yl)carbamate (Intermediate L (protected)) (13.2 g, 27.2 mmol) in dichloromethane (608 mL). The reaction was stirred at room temperature for 2 h. The reaction mixture was concentrated under reduced pressure, and DCM (100 mL) was added to the residue, and solvent once again removed in vacuo. The residue was slurried in NaHCO$_3$ solution (700 mL), sonicated and stirred for 1 h and the solid was filtered off. The solid was washed with water (300 mL) and dried under vacuum for 16 h to give the subtitle compound N-(4-(((4-aminonaphthalen-1-yl)oxy)methyl)pyridin-2-yl)-5,6-dimethylpyrazin-2-amine as an off-white solid (9.33 g, 92%); R$^t$ 2.0 min (Method 2); m/z 372 (M+H)$^+$ (ES$^+$).

1-(3-(tert-Butyl)-1-(p-tolyl)-1H-pyrazol-5-yl)-3-(4-((2-((5,6-di methylpyrazin-2-yl)amino)pyridin-4-yl)methoxy)naphthalen-1-yl)urea

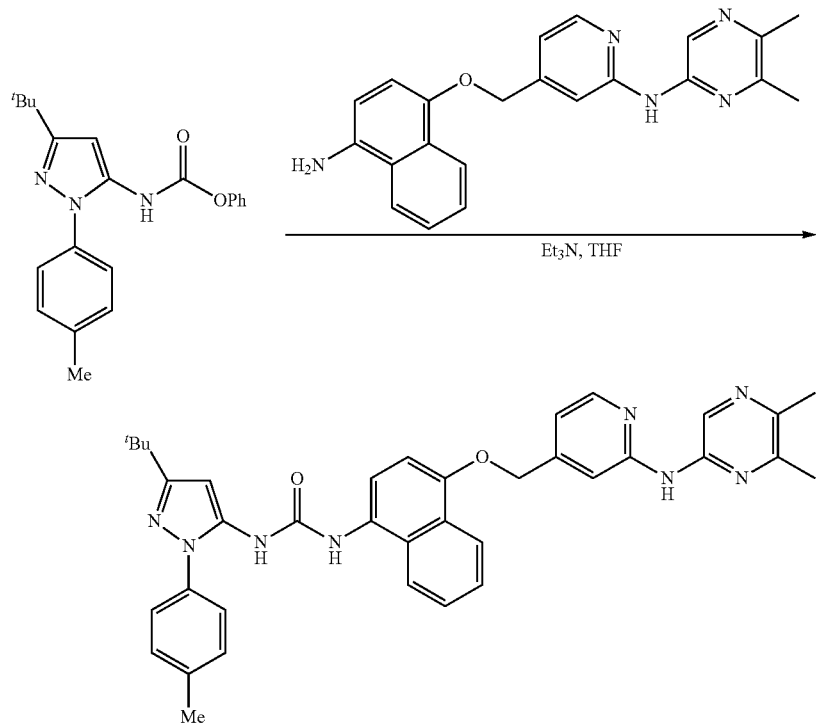

Phenyl (3-(tert-butyl)-1-(p-tolyl)-1H-pyrazol-5-yl)carbamate (Intermediate E) (6.95 g, 19.69 mmol), was added to a solution of N-(4-(((4-aminonaphthalen-1-yl)oxy)methyl)pyridin-2-yl)-5,6-dimethylpyrazin-2-amine (Intermediate L) (7 g, 17.90 mmol) in tetrahydrofuran (150 mL), The reaction mixture was heated to 40° C. and triethylamine (0.886 mL, 6.36 mmol) was added. The reaction mixture was left to heat at 40° C. for 1 h then allowed to cool to room temperature and left to stir overnight. The reaction mixture was diluted with 20% MeOH in DCM solution (250 mL) and the mixture was washed with saturated aqueous sodium hydrogencarbonate solution (200 mL) and water (300 mL), and the organic layer combined with silica (25 g) and the solvent was evaporated. The crude product was purified first by silica gel chromatography (2×220 g Hi loading Si column, 0-5% MeOH in DCM), and secondly by slurrying in acetone (200 mL) for 16 h. The solid obtained was collected by filtration and dried under vacuum to give the title compound 1-(3-(tert-butyl)-1-(p-tolyl)-1H-pyrazol-5-yl)-3-(4-((2-((5,6-dimethylpyrazin-2-yl)amino)pyridin-4-yl)methoxy)naphthalen-1-yl)urea as a white solid (5.2 g, 46%); R$^r$ 2.60 min (Method 2); m/z 627 (M+H)$^+$ (ES$^+$); $^1$H NMR δ: 1.28 (9H, s), 2.37 (3H, s), 2.39 (3H, s), 2.40 (3H, s), 5.34 (2H, s), 6.37 (1H, s), 6.99-7.06 (2H, overlapping m), 7.37 (2H, m), 7.45 (2H, m), 7.58-7.67 (3H, overlapping m), 7.88 (1H, s), 7.94 (1H, m), 8.27 (1H, d), 8.41 (1H, m), 8.60 (1H, s), 8.80 (1H, s), 8.89 (1H, s), 9.90 (1H, s).

Example 5: 1-(4-((2-((5-(Aminomethyl)pyrazin-2-yl)amino)pyridin-4-yl)methoxy) naphthalen-1-yl)-3-(3-(tert-butyl)-1-(p-tolyl)-1H-pyrazol-5-yl)urea Intermediate M: tert-Butyl ((5-chloropyrazin-2-yl)methyl)carbamate

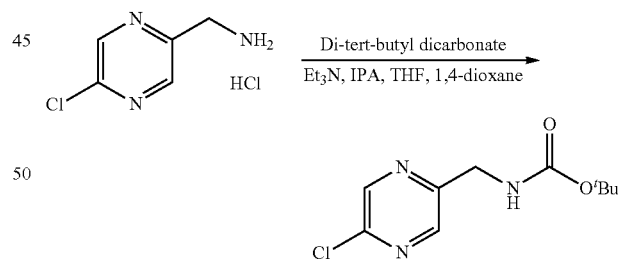

(5-chloropyrazin-2-yl)methanamine hydrochloride (0.100 g, 0.555 mmol) was suspended in isopropyl alcohol (1.0 mL, 12.98 mmol). Triethylamine (0.100 mL, 0.717 mmol) and then di-tert-butyl dicarbonate (0.160 mL, 0.689 mmol) were added. The resulting mixture was stirred at room temperature for 2 h, then 1,4-dioxane (1 mL) was added, followed by further triethylamine (0.100 mL, 0.717 mmol) and THF (2 mL). After a total of 5 h, the reaction mixture was concentrated under reduced pressure to afford the crude product as a brown solid, which was purified by silica gel chromatography (12 g column, iso-hexane-ethyl acetate 0-50%) to give the subtitle compound tert-butyl((5-chloropyrazin-2-yl)methyl)carbamate as a white solid (106 mg, 77%); R' 1.76 min (Method 1); m/z 143 (M+H−Boc)+ (ES+), m/z 188 (M+H−'Bu)+ (ES+).

Intermediate N: tert-Butyl ((5-((4-(((4-nitronaphthalen-1-yl)oxy)methyl)pyridin-2-yl)amino)pyrazin-2-yl)methyl)carbamate

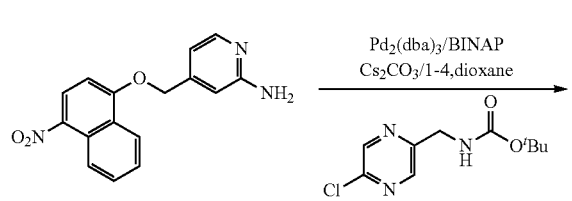

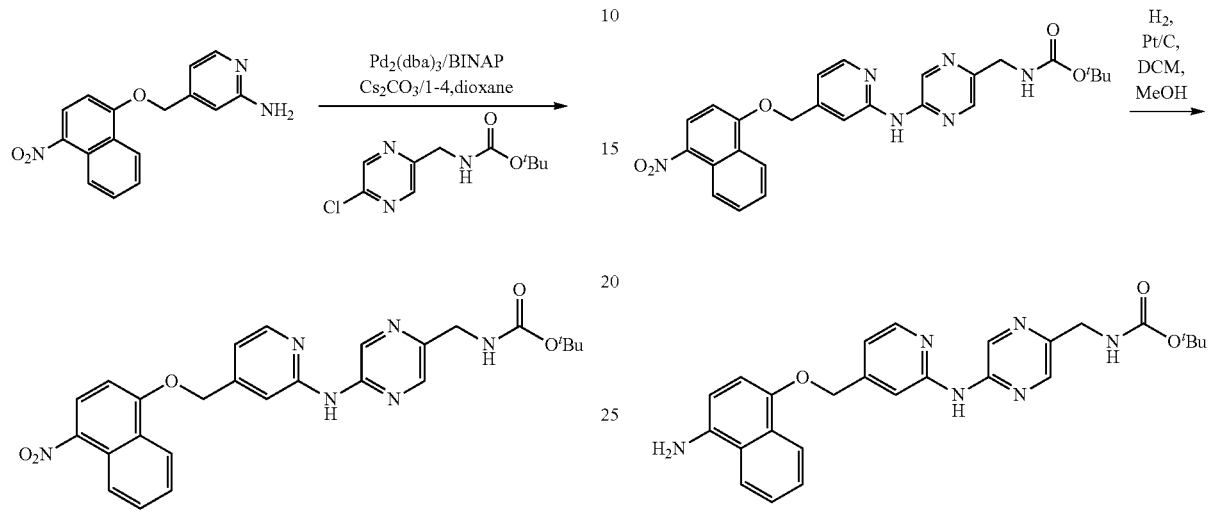

4-(((4-Nitronaphthalen-1-yl)oxy)methyl)pyridin-2-amine (Intermediate H) (0.129 g, 0.419 mmol), tert-butyl((5-chloropyrazin-2-yl)methyl)carbamate (Intermediate M) (0.106 g, 0.426 mmol), cesium carbonate (0.218 g, 0.669 mmol), BINAP (0.033 g, 0.053 mmol) and Pd₂(dba)₃ (0.020 g, 0.022 mmol) were suspended in 1,4-dioxane (3.2 mL). The reaction mixture was degassed with nitrogen for 15 min and then stirred at 90° C. for 24 h. The reaction mixture was allowed to cool, then diluted with 10% MeOH in DCM (25 mL), and filtered through Celite, washing through with 10% MeOH in DCM (2×25 mL). The combined filtrate was concentrated under reduced pressure to afford a dark residue, which was triturated with MeOH. The solid obtained was filtered and washed with MeOH (2×20 mL), then purified by silica gel chromatography (12 g column, 10% MeOH in DCM-DCM 0-50%) to give the subtitle compound tert-butyl((5-((4-(((4-nitronaphthalen-1-yl)oxy)methyl)pyridin-2-yl)amino) pyrazin-2-yl)methyl)carbamate as a yellow solid (91 mg, 32%); R' 1.97 min (Method 1); m/z 503 (M+H)+ (ES+), 501 (M−H)− (ES−).

Intermediate O: tert-Butyl ((5-((4-(((4-aminonaphthalen-1-yl)oxy)methyl)pyridin-2-yl)amino)pyrazin-2-yl)methyl)carbamate tert-Butyl((5-((4-(((4-nitronaphthalen-1-yl)oxy)methyl) pyridin-2-yl)amino)pyrazin-2-yl)methyl) carbamate (Intermediate N) (0.091 g, 0.136 mmol) was dissolved in 10% MeOH in DCM (10.0 mL). The reaction mixture was hydrogenated in the H-Cube (10% Pt/C, 30×4 mm, Full hydrogen, 40° C., 1 mL/min). The reaction mixture was reduced in volume under reduced pressure and then absorbed onto SCX, washed with MeOH and released with 1% NH₃ in MeOH. The 1% NH₃ in MeOH fraction was concentrated under reduced pressure to afford the subtitle compound tert-butyl((5-((4-(((4-aminonaphthalen-1-yl)oxy) methyl)pyridin-2-yl)amino)pyrazin-2-yl)methyl)carbamate as a yellow glassy solid (53 mg, 74%); R' 1.26 min (Method 1); m/z 473 (M+H)+ (ES+), 471 (M−H)− (ES−).

Intermediate P: tert-Butyl ((5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)methyl)carbamate

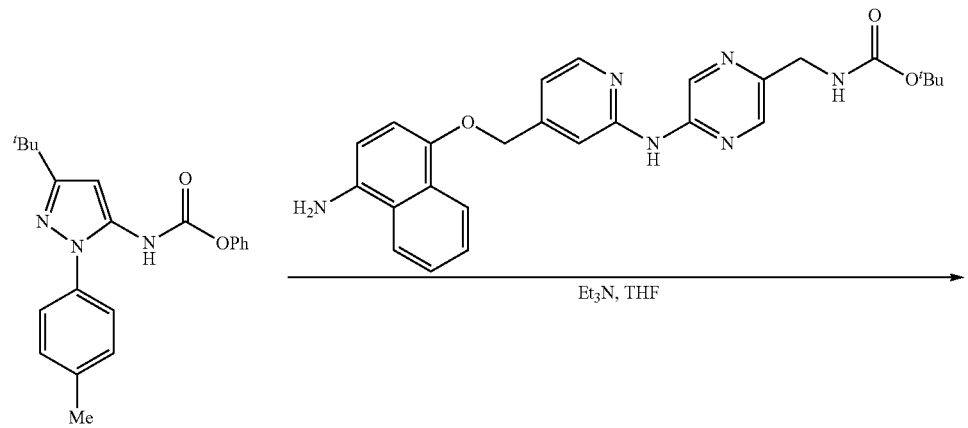

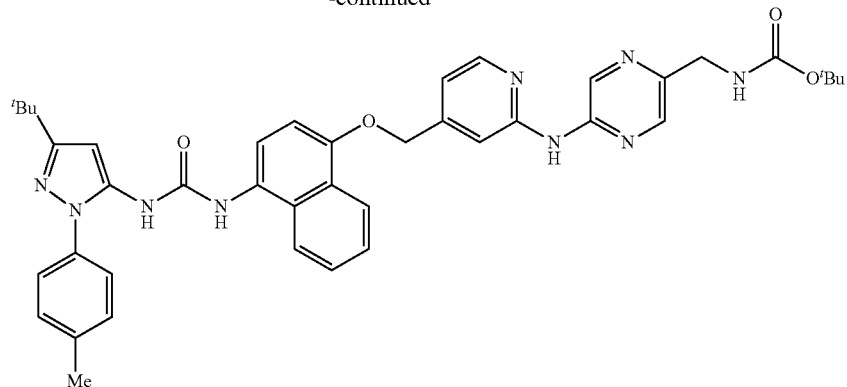

tert-Butyl((5-((4-(((4-aminonaphthalen-1-yl)oxy)methyl)pyridin-2-yl)amino)pyrazin-2-yl)methyl)carbamate (Intermediate O) (0.053 g, 0.101 mmol) and phenyl (3-(tert-butyl)-1-(p-tolyl)-1H-pyrazol-5-yl)carbamate (Intermediate E) (0.041 g, 0.116 mmol) were dissolved in THF (1.0 mL). The reaction mixture was heated to 40° C. and then triethylamine (0.005 mL, 0.036 mmol) was added. The reaction mixture was left to heat at 40° C. for 1 h then allowed to cool to room temperature and left to stir overnight. After a total of 21.5 h the reaction mixture was diluted with MeOH (2 mL), evaporated onto silica and purified by silica gel chromatography (12 g column, 10% MeOH in DCM-DCM 0-50%) to give the subtitle compound tert-butyl((5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)methyl)carbamate as a pale tan solid (54 mg, 66%); $R^t$ 2.19 min (Method 1); m/z 728 (M+H)$^+$ (ES$^+$), 726 (M−H)$^−$ (ES$^−$).

1-(4-((2-((5-(Aminomethyl)pyrazin-2-yl)amino)pyridin-4-yl)methoxy)naphthalen-1-yl)-3-(3-(tert-butyl)-1-(p-tolyl)-1H-pyrazol-5-yl)urea

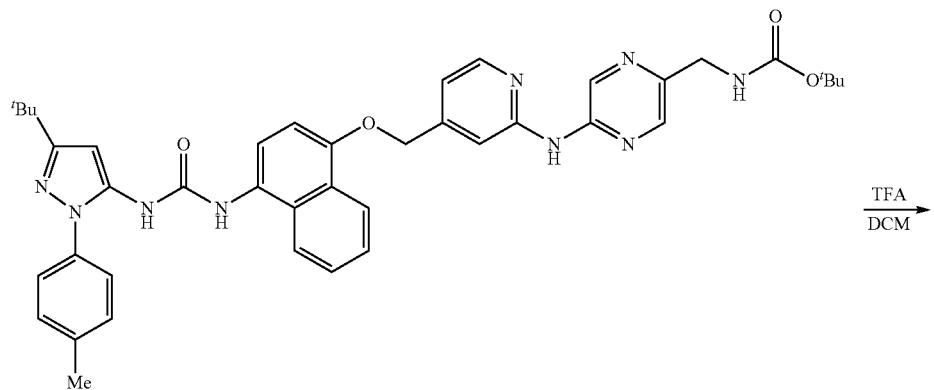

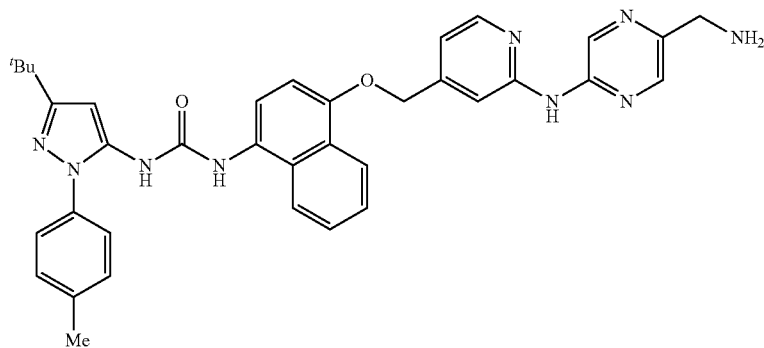

TFA (0.200 mL, 2.60 mmol) was added to a solution of tert-butyl ((5-(((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)methyl)carbamate (Intermediate P) (0.054 g, 0.067 mmol) in DCM (1.0 mL). The resulting solution was stirred at room temperature for 2.5 h, then the reaction mixture was concentrated under reduced pressure. The residue was dissolved in MeOH, absorbed onto SCX, washed with MeOH and released with 1% $NH_3$ in MeOH. The 1% $NH_3$ in MeOH fraction was concentrated under reduced pressure to afford the crude product as a yellow solid. This was purified by silica gel chromatography (4 g column, 10% (1% $NH_3$ in MeOH) in DCM-DCM 0-100%) to give the title compound 1-(4-((2-((5-(aminomethyl)pyrazin-2-yl)amino)pyridin-4-yl)methoxy)naphthalen-1-yl)-3-(3-(tert-butyl)-1-(p-tolyl)-1H-pyrazol-5-yl)urea as a pale yellow solid (20 mg, 45%); $R^t$ 1.57 min (Method 1); m/z 628 (M+H)$^+$ (ES$^+$), 626 (M−H)$^−$ (ES$^−$); $^1$H NMR δ: 1.27 (9H, s), 2.39 (3H, s), 3.77 (2H, s), 5.34 (2H, s), 6.36 (1H, s), 7.00-7.07 (2H, overlapping m), 7.34 (2H, m), 7.44 (2H, m), 7.59-7.67 (3H, overlapping m), 7.93-7.95 (2H, overlapping m), 8.25-8.30 (2H, overlapping m), 8.40 (1H, m), 8.59 (1H, s), 8.80 (1H, s), 9.03 (1H, d), 10.04 (1H, s).

Example 6: N-((5-(((4-(((4-(3-(3-(tert-Butyl)-1-(p-tolyl)-1H-pyrazol-5-yl)ureido)naphthalen-1-yl)oxy)methyl)pyridin-2-yl)amino)pyrazin-2-yl)methyl)acetamide Acetic anhydride (0.005 mL, 0.053 mmol) was added to a mixture of 1-(4-((2-((5-(aminomethyl)pyrazin-2-yl)amino)pyridin-4-yl)methoxy)naphthalen-1-yl)-3-(3-(tert-butyl)-1-(p-tolyl)-1H-pyrazol-5-yl)urea (Example 5) (0.017 g, 0.026 mmol) and triethylamine (0.010 mL, 0.072 mmol) in DCM (1.0 mL). The reaction mixture was stirred at room temperature for 90 min and then concentrated under reduced pressure. The residue was dissolved in MeOH/DCM and absorbed onto SCX, washed with MeOH and released with 1% $NH_3$ in MeOH. The 1% $NH_3$ in MeOH fraction was concentrated under reduced pressure to afford the title product N-((5-((4-(((4-(3-(3-(tert-butyl)-1-(p-tolyl)-1H-pyrazol-5-yl)ureido)naphthalen-1-yl)oxy) methyl)pyridin-2-yl)amino)pyrazin-2-yl)methyl)acetamide as a pale yellow solid (15 mg, 84%); $R^t$ 1.81 min (Method 1); m/z 670 (M+H)$^+$ (ES$^+$), 668 (M−H)$^−$ (ES$^−$); $^1$H NMR δ: 1.28 (9H, s), 1.89 (3H, s), 2.40 (3H, s), 4.30 (2H, d), 5.35 (2H, s), 6.37 (1H, s), 7.01-7.10 (2H, overlapping m), 7.37 (2H, m), 7.44 (2H m), 7.60-7.67 (3H, overlapping m), 7.93 (1H, dd), 8.00 (1H, s), 8.16 (1H, d), 8.29 (1H, m), 8.42 (2H, overlapping m), 8.60 (1H, s), 8.81 (1H, s), 9.03 (1H, d), 10.13 (1H, s).

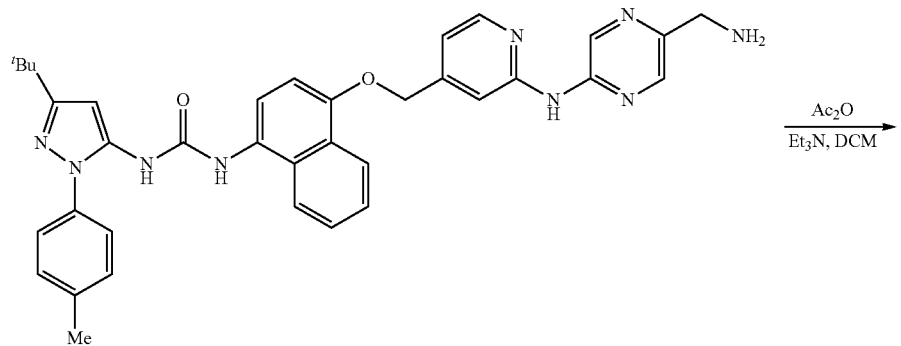

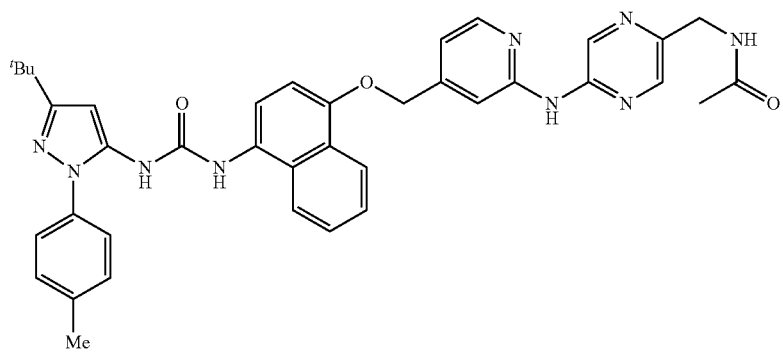

Example 7: 5-((4-(((4-(3-(3-(tert-butyl)-1-(p-tolyl)-1H-pyrazol-5-yl)ureido)naphthalen-1-yl)oxy)methyl)pyridin-2-yl)amino)-N-methylpyrazine-2-carboxamide Intermediate Q: Methyl 5-((4-(((4-nitronaphthalen-1-yl)oxy)methyl)pyridin-2-yl)amino)pyrazine-2-carboxylate

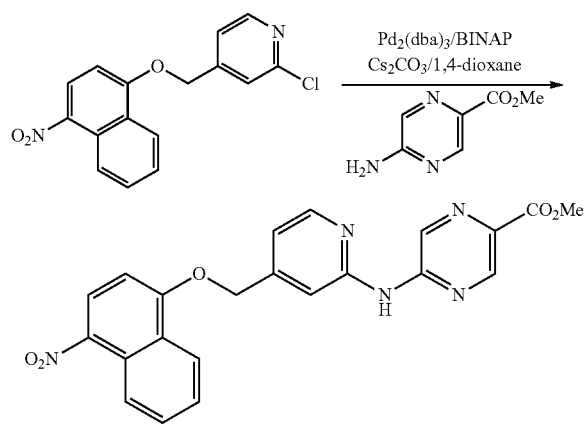

A solution of Pd$_2$(dba)$_3$ (0.299 g, 0.327 mmol), 2-chloro-4-(((4-nitronaphthalen-1-yl)oxy)methyl)pyridine (Intermediate A), methyl 5-aminopyrazine-2-carboxylate (1.00 g, 6.53 mmol), BINAP (0.407 g, 0.653 mmol) and cesium carbonate (3.19 g, 9.80 mmol) in 1,4-dioxane (20 mL) was degassed with nitrogen for 10 min and then heated to 90° C. for 16 h.

The reaction mixture was cooled, diluted with MeOH (30 mL) and the suspension was filtered through a Celite pad, washing with 1% NH$_3$ in MeOH (100 mL). The filtrate was concentrated under reduced pressure. The residue was suspended in DCM (20 mL), MeOH (100 mL) and the resulting solid was captured and rinsed with MeOH (50 mL) and hexane (50 mL) to give the subtitle compound methyl 5-((4-(((4-nitronaphthalen-1-yl)oxy)methyl)pyridin-2-yl)amino)pyrazine-2-carboxylate (0.58 g, 18%); R$^t$ 2.09 min (Method 1); m/z 432 (M+H)$^+$ (ES$^+$).

Intermediate R: Methyl 5-((4-(((4-aminonaphthalen-1-yl)oxy)methyl)pyridin-2-yl)amino)pyrazine-2-carboxylate

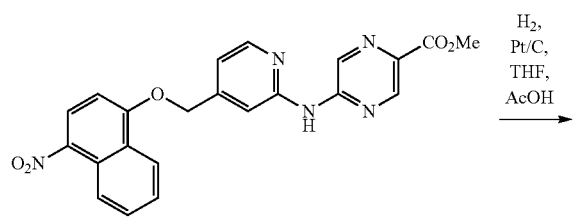

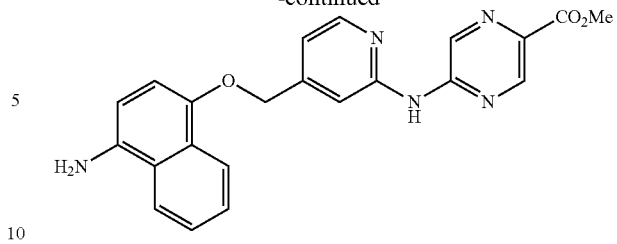

Wet Pt/C (0.267 g, 0.065 mmol) was added to a solution of methyl 5-((4-(((4-nitronaphthalen-1-yl)oxy)methyl)pyridin-2-yl)amino)pyrazine-2-carboxylate (Intermediate Q) (0.557 g, 1.291 mmol) in THF (20 mL) and AcOH (3 drops). The reaction mixture was stirred under 5 bar hydrogen for 5 h. The reaction was diluted with MeOH (20 mL) and filtered through a Celite pad, washing with MeOH (20 mL). The combined filtrate was concentrated under reduced pressure to give the subtitle compound methyl 5-((4-(((4-aminonaphthalen-1-yl)oxy)methyl)pyridin-2-yl)amino)pyrazine-2-carboxylate (0.28 g, 35%); R$^t$ 1.16 min (Method 1); m/z 402 (M+H)$^+$ (ES$^+$).

Intermediate S: 5-((4-(((4-Aminonaphthalen-1-yl)oxy)methyl)pyridin-2-yl)amino)pyrazine-2-carboxylic acid hydrochloride

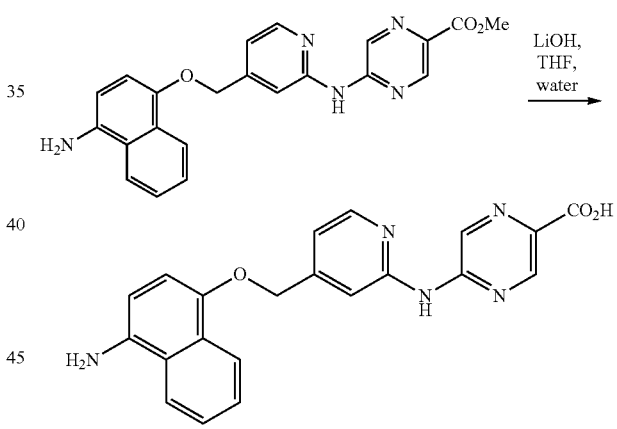

Lithium hydroxide (0.034 g, 1.420 mmol) was added to a solution of methyl 5-((4-(((4-aminonaphthalen-1-yl)oxy)methyl)pyridin-2-yl)amino)pyrazine-2-carboxylate (Intermediate R) (0.228 g, 0.568 mmol) in THF:Water (10 mL:3 mL) and the reaction mixture heated at 40° C. for 3 h, then concentrated under reduced pressure. To the residue was added 1M HCl (10 mL) and the suspension was filtered, washing with water (10 mL) and diethyl ether (10 mL). A brown hydroscopic solid was obtained, which was dissolved in MeOH (30 mL), dried (Na$_2$SO$_4$), filtered, and concentrated under reduced pressure to give the subtitle compound 5-((4-(((4-aminonaphthalen-1-yl)oxy)methyl)pyridin-2-yl)amino)pyrazine-2-carboxylic acid hydrochloride as a dark brown solid (0.208 g, 82%); R$^t$ 0.97 min (Method 1); m/z 388 (M+H)$^+$ (ES$^+$).

Intermediate T: 5-((4-(((4-(3-(3-(tert-Butyl)-1-(p-tolyl)-1H-pyrazol-5-yl)ureido)naphthalen-1-yl)oxy)methyl)pyridin-2-yl)amino)pyrazine-2-carboxylic acid

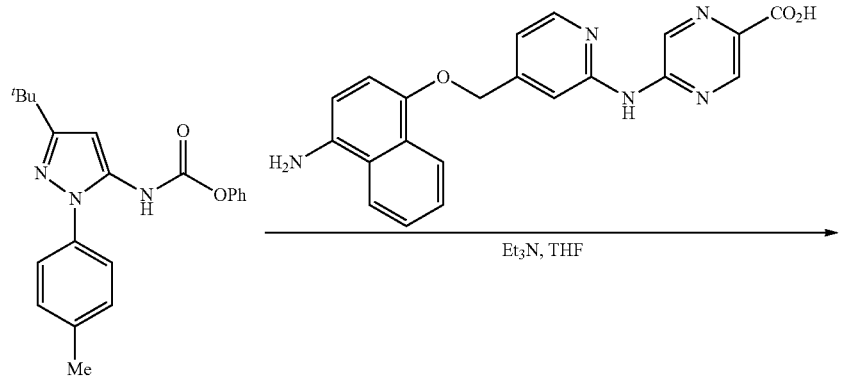

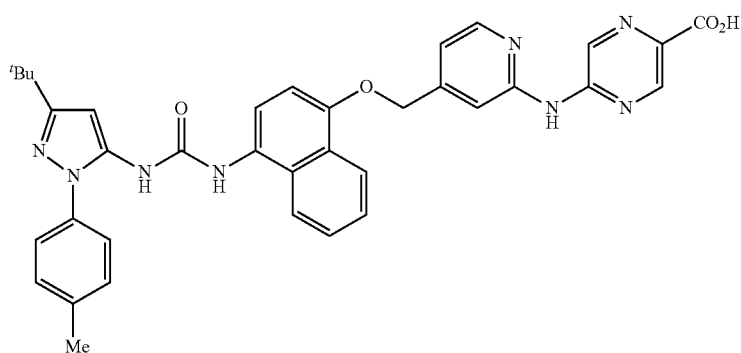

Triethylamine (0.374 mL, 2.68 mmol) was added to a solution of phenyl (3-(tert-butyl)-1-(p-tolyl)-1H-pyrazol-5-yl)carbamate (Intermediate E) (0.281 g, 0.805 mmol) and 5-((4-(((4-aminonaphthalen-1-yl)oxy)methyl)pyridin-2-yl)amino)pyrazine-2-carboxylic acid hydrochloride (Intermediate S) (0.208 g, 0.491 mmol) in THF (10 mL) and the reaction mixture stirred at 40° C. for 5 h. The reaction was concentrated under reduced pressure and the residue was triturated with DCM (10 mL) and diethyl ether (20 mL). The resulting suspension was filtered, washing with diethyl ether (20 mL), to give the subtitle compound 5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxylic acid (0.215 g, 56%); R$^t$ 2.08 min (Method 1); m/z 643 (M+H)$^+$ (ES$^+$).

5-((4-(((4-(3-(3-(tert-Butyl)-1-(p-tolyl)-1H-pyrazol-5-yl)ureido)naphthalen-1-yl)oxy)methyl)pyridin-2-yl)amino)-N-methylpyrazine-2-carboxamide

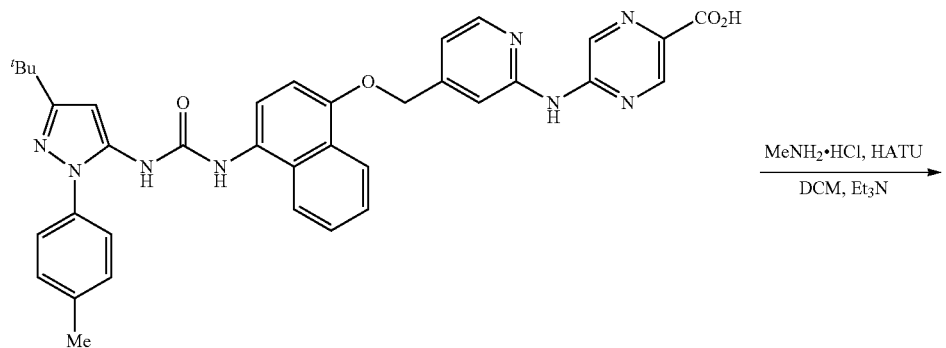

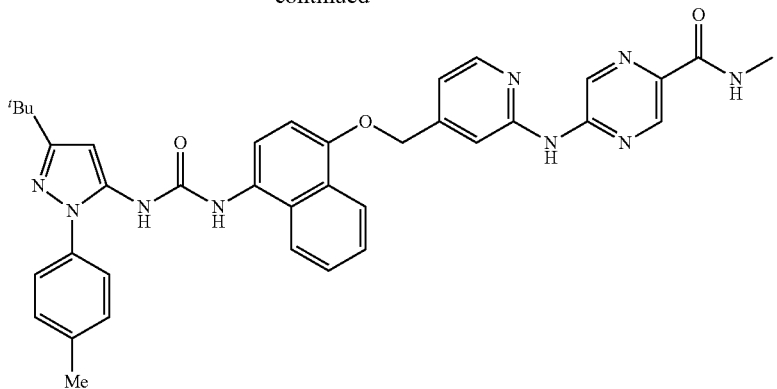

Hunig's Base (0.109 mL, 0.622 mmol) was added to a stirring solution of 5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxylic acid (Intermediate T) (0.080 g, 0.124 mmol), HATU (0.062 g, 0.162 mmol) and methylamine hydrochloride (0.042 g, 0.622 mmol) in DCM (3 mL). The reaction mixture was stirred at 40° C. for 16 h. Water (10 mL) was added and the solution sonicated, before a solid was collected by filtration. The crude product was purified by preparative HPLC (Gilson, Basic (0.1% Ammonium Bicarbonate), Basic, Waters X-Bridge Prep-C18, 5 m, 19×50 mm column, 25-70% MeCN in water) to afford the title compound 5-((4-(((4-(3-(3-(tert-butyl)-1-(p-tolyl)-1H-pyrazol-5-yl)ureido)naphthalen-1-yl)oxy)methyl)pyridin-2-yl)amino)-N-methylpyrazine-2-carboxamide as a pale brown solid (3 mg, 3.6%); $R^t$ 2.17 min (Method 1); m/z 656 (M+H)$^+$ (ES$^+$); $^1$H NMR δ: 1.28 (9H, s), 2.40 (3H, s), 2.83 (3H, d), 5.39 (2H, s), 6.36 (1H, s), 7.05 (1H, d), 7.16 (1H, d), 7.38 (2H, m), 7.44 (2H, m), 7.59-7.66 (3H, overlapping m), 7.95 (1H, m), 8.10 (1H, s), 8.36 (1H, s), 8.41 (1H, m), 8.54 (1H, q), 8.65 (1H, br s), 8.75 (1H, d), 8.85 (1H, s), 9.05 (1H, s), 10.57 (1H, s).

Example 8: 2-(6-((4-(((4-(3-(3-(tert-Butyl)-1-(p-tolyl)-1H-pyrazol-5-yl)ureido)naphthalen-1-yl)oxy)methyl)pyridin-2-yl)amino)pyrazin-2-yl)-N,N-dimethylacetamide Intermediate U: Methyl 2-(6-chloropyrazin-2-yl)acetate

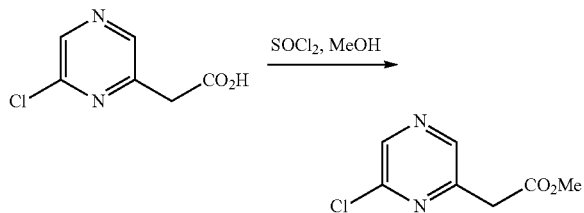

To an ice-cold solution (0-4° C.) of 2-(6-chloropyrazin-2-yl)acetic acid (0.6 g, 3.48 mmol) in MeOH (7 mL) was added thionyl chloride (0.508 mL, 6.95 mmol) dropwise. The resulting solution was allowed to warm to room temperature and stirred for 2 h. The reaction mixture was concentrated in vacuo and the solid residue was dissolved in EtOAc (50 mL) and treated with sat. aq. NaHCO$_3$ (50 mL). The layers were separated and the organic phase dried over MgSO$_4$, then filtered and concentrated in vacuo to afford the subtitle compound methyl 2-(6-chloropyrazin-2-yl)acetate as a yellow oil (0.647 g, 95%); $R^t$ 1.21 min (Method 1); m/z 187 (M+H)$^+$ (ES$^+$).

Intermediate V: Methyl 2-(6-((4-(((4-nitronaphthalen-1-yl)oxy)methyl)pyridin-2-yl)amino)pyrazin-2-yl)acetate

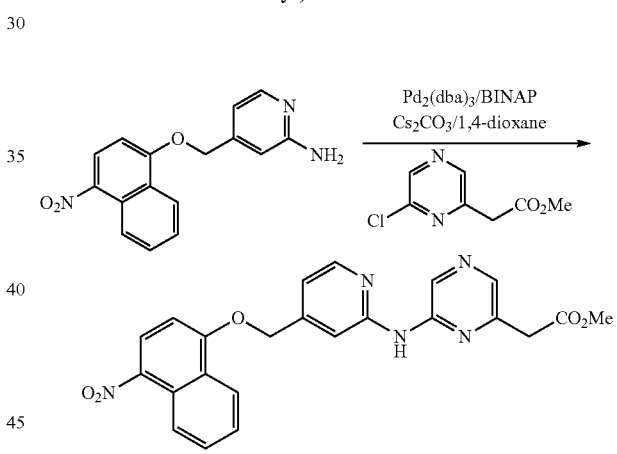

A flask was charged with 4-(((4-nitronaphthalen-1-yl)oxy)methyl)pyridin-2-amine (Intermediate H) (1 g, 3.39 mmol), methyl 2-(6-chloropyrazin-2-yl)acetate (Intermediate U) (0.632 g, 3.39 mmol), BINAP (0.211 g, 0.339 mmol), cesium carbonate (1.655 g, 5.08 mmol) and Pd$_2$(dba)$_3$ (0.155 g, 0.169 mmol). To this was added 1,4-dioxane (25 mL) and the resulting mixture was purged with nitrogen for 5 min and then heated to 90° C. for 2 h. The reaction mixture was cooled to room temperature and taken up in a mixture of 10% MeOH in DCM and passed through a Celite pad and concentrated in vacuo to afford a brown semi solid. This was triturated with MeOH (10 mL) to afford the subtitle compound methyl 2-(6-((4-(((4-nitronaphthalen-1-yl)oxy)methyl)pyridin-2-yl)amino)pyrazin-2-yl)acetate as a brown solid (856 mg, 53%); $R^t$ 1.83 min (Method 1); m/z 446 (M+H)$^+$ (ES$^+$).

Intermediate W: 2-(6-((4-(((4-Nitronaphthalen-1-yl)oxy)methyl)pyridin-2-yl)amino)pyrazin-2-yl)acetic acid

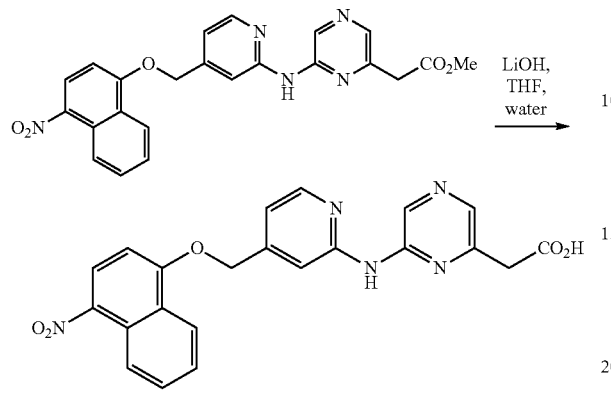

A solution of LiOH (0.056 g, 2.357 mmol) in water (1.8 mL) was added to a solution of methyl 2-(6-((4-(((4-nitronaphthalen-1-yl)oxy)methyl)pyridin-2-yl)amino)pyrazin-2-yl)acetate (Intermediate V) (0.7 g, 1.572 mmol) in THF (6 mL). The resulting mixture was heated to 40° C. for 2 h and then stirred at room temperature for a further 1 h. The reaction mixture was concentrated in vacuo and the residue was treated with 1M aq HCl to afford a tan coloured precipitate. This was collected under vacuum filtration, washing with water (2×5 mL), to afford the subtitle compound 2-(6-((4-(((4-nitronaphthalen-1-yl)oxy)methyl)pyridin-2-yl)amino)pyrazin-2-yl)acetic acid as a tan coloured solid (682 mg, 89%); $R^t$ 1.60 min (Method 1); m/z 432 $(M+H)^+$ $(ES^+)$.

Intermediate X: N,N-Dimethyl-2-(6-((4-(((4-nitronaphthalen-1-yl)oxy)methyl)pyridin-2-yl)amino)pyrazin-2-yl)acetamide

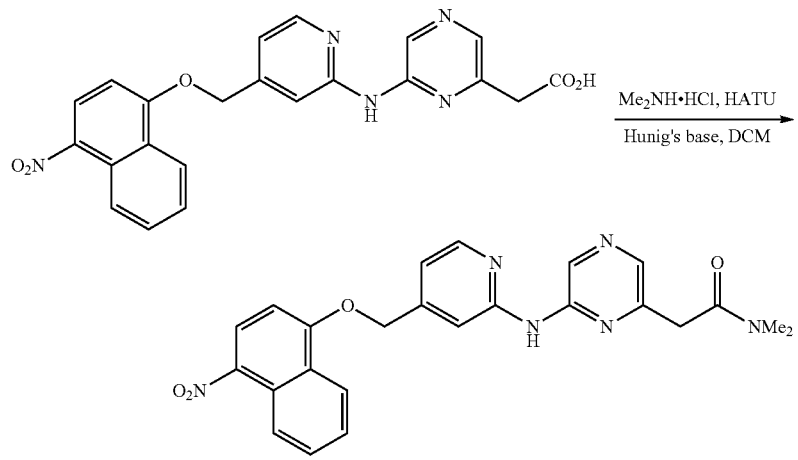

To a stirred solution of 2-(6-((4-(((4-nitronaphthalen-1-yl)oxy)methyl)pyridin-2-yl)amino)pyrazin-2-yl)acetic acid (Intermediate W) (0.151 g, 0.350 mmol) in DCM (5 mL) was added dimethylamine hydrochloride (0.143 g, 1.750 mmol) and Hunig's base (0.306 mL, 1.750 mmol), followed by HATU (0.200 g, 0.525 mmol), and the resulting mixture was stirred at room temperature overnight. The reaction mixture was treated with 1M HCl, the layers separated, and the organic phase was washed with sat. aq. $NaHCO_3$ (10 mL) and brine (2×20 mL), and passed through a phase sep. cartridge to afford a brown viscous oil after solvent evaporation. The oil was purified by silica gel chromatography (12 g column, 0-5% MeOH in DCM) to afford the subtitle compound N,N-dimethyl-2-(6-((4-(((4-nitronaphthalen-1-yl)oxy)methyl)pyridin-2-yl)amino)pyrazin-2-yl)acetamide as a yellow solid (64 mg, 38%); $R^t$ 1.61 min (Method 1); m/z 459 $(M+H)^+$ $(ES^+)$, 457 $(M-H)^-$ $(ES^-)$.

Intermediate Y: 2-(6-((4-(((4-Aminonaphthalen-1-yl)oxy)methyl)pyridin-2-yl)amino)pyrazin-2-yl)-N,N-di methylacetamide

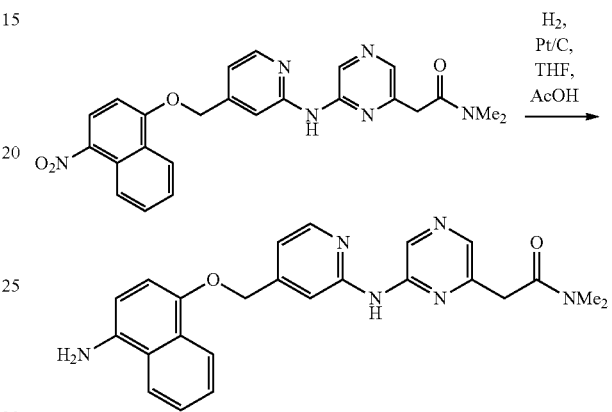

Platinum/C paste (25.5 mg, 0.013 mmol) was added to a solution of N,N-dimethyl-2-(6-((4-(((4-nitronaphthalen-1-yl)oxy)methyl)pyridin-2-yl)amino)pyrazin-2-yl)acetamide (Intermediate X) (60 mg, 0.131 mmol) in THF (5 mL) with a drop of AcOH. The resulting mixture was stirred under an atmosphere of hydrogen at 5 bar for 5 h. The reaction mixture was passed through a pad of Celite and concentrated in vacuo to afford a brown glass. The crude product was loaded onto a column of SCX (2 g) in MeOH. The column was washed with MeOH and then the product was eluted with 0.7M ammonia in MeOH. The resultant mixture was concentrated in vacuo to afford the subtitle compound 2-(6-((4-(((4-aminonaphthalen-1-yl)oxy)methyl)pyridin-2-yl)amino)pyrazin-2-yl)-N,N-dimethylacetamide as a brown glass (56 mg, 80%); $R^t$ 0.95 min (Method 1); m/z 429 $(M+H)^+$ $(ES^+)$.

2-(6-((4-(((4-(3-(3-(tert-Butyl)-1-(p-tolyl)-1H-pyrazol-5-yl)ureido)naphthalen-1-yl)oxy)methyl)pyridin-2-yl)amino)pyrazin-2-yl)-N,N-dimethylacetamide

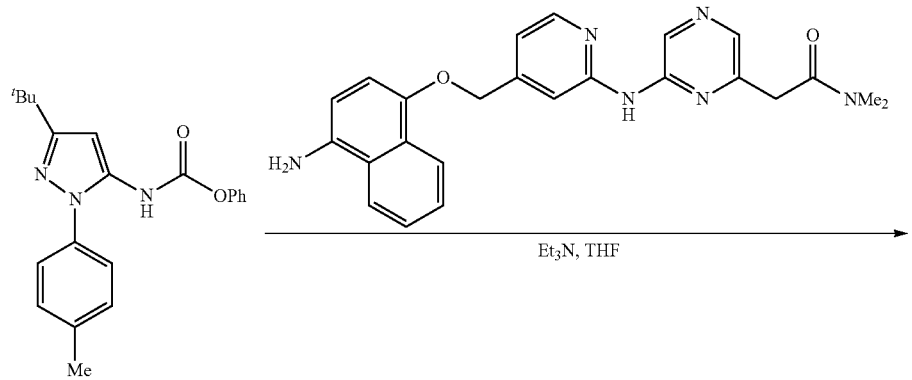

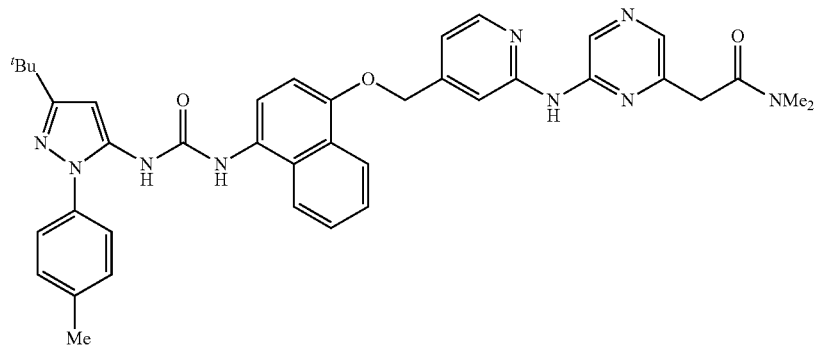

To a stirred solution of 2-(6-((4-(((4-aminonaphthalen-1-yl)oxy)methyl)pyridin-2-yl)amino)pyrazin-2-yl)-N,N-dimethylacetamide (Intermediate Y) (50 mg, 0.093 mmol) and phenyl (3-(tert-butyl)-1-(p-tolyl)-1H-pyrazol-5-yl)carbamate (Intermediate E) (42.4 mg, 0.121 mmol) in THF (1.5 mL) was added triethylamine (13.01 μl, 0.093 mmol). The resulting mixture was heated to 40° C. for 3 h, then quenched with MeOH and concentrated in vacuo to give a pink solid. This was triturated with MeOH (2 mL) to afford the title compound 2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N,N-dimethylacetamide as pale pink solid (22 mg, 33.8%); R$^t$ 1.88 min (Method 1); m/z 684 (M+H)$^+$ (ES$^+$); $^1$H NMR δ: 1.27 (9H, s), 2.39 (3H, s), 2.81 (3H, s), 3.00 (3H, s), 3.78 (2H, s), 5.33 (2H, s), 6.35 (1H, s), 7.02 (1H, d), 7.07 (1H, dd), 7.36 (2H, d), 7.44 (2H, m), 7.56-7.61 (2H, overlapping m), 7.64 (1H, d), 7.88 (1H, s), 7.93 (1H, m), 7.99 (1H, s), 8.30 (1H, m), 8.36 (1H, m), 8.58 (1H, s), 8.79 (1H, s), 9.03 (1H, s), 10.10 (1H, s).

Example 9: 5-((4-(((4-(3-(3-(tert-Butyl)-1-(p-tolyl)-1H-pyrazol-5-yl)ureido)naphthalen-1-yl)oxy)methyl)pyridin-2-yl)amino)-N,N-dimethylpyrazine-2-carboxamide Intermediate Z: 5-((4-(((4-Nitronaphthalen-1-yl)oxy)methyl)pyridin-2-yl)amino)pyrazine-2-carboxylic acid

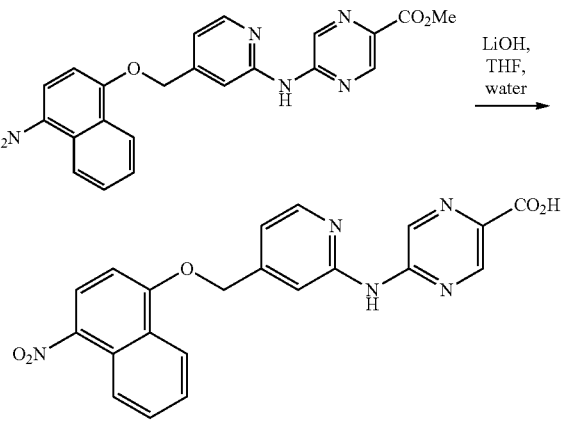

Lithium hydroxide (0.024 g, 0.985 mmol) was added to a solution of methyl 5-((4-(((4-nitronaphthalen-1-yl)oxy)methyl)pyridin-2-yl)amino)pyrazine-2-carboxylate (Intermediate Q) (0.085 g, 0.197 mmol) in THF/Water (5 mL, 1:1). The reaction mixture was heated at 40° C. for 16 h, then concentrated under reduced pressure. Water (2 mL) was added to the residue and the aqueous was made acidic with 1M aq HCl (2 mL), giving a precipitate, which was isolated by filtration, to give the subtitle compound 5-((4-(((4-nitronaphthalen-1-yl)oxy)methyl)pyridin-2-yl)amino)pyrazine-2-carboxylic acid as a pale tan solid (80 mg, 88%); $R^t$ 1.85 min (Method 1); m/z 418 (M+H)$^+$ (ES$^+$).

Intermediate AA: N,N-Dimethyl-5-((4-(((4-nitronaphthalen-1-yl)oxy)methyl)pyridin-2-yl)amino)pyrazine-2-carboxamide

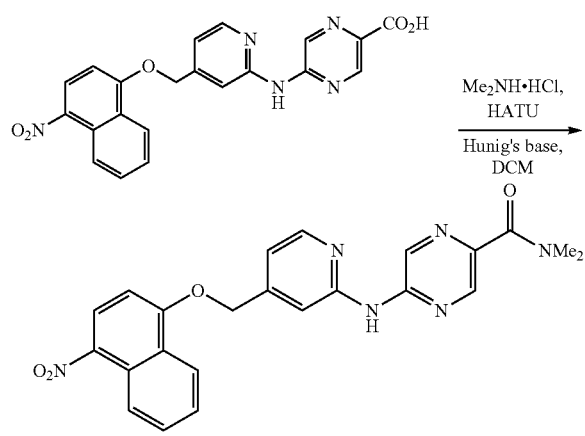

Hunig's base (0.335 mL, 1.917 mmol) was added to a stirring solution of 5-((4-(((4-nitronaphthalen-1-yl)oxy)methyl)pyridin-2-yl)amino)pyrazine-2-carboxylic acid (Intermediate Z) (0.08 g, 0.192 mmol), HATU (0.095 g, 0.249 mmol) and dimethylamine hydrochloride (0.156 g, 1.917 mmol) in DCM (5 mL) and the reaction mixture stirred for 16 h. The reaction was concentrated under reduced pressure and water (20 mL) was added to the residue. The resulting suspension was filtered to give the subtitle compound N,N-dimethyl-5-((4-(((4-nitronaphthalen-1-yl)oxy)methyl)pyridin-2-yl)amino)pyrazine-2-carboxamide as a brown solid (80 mg, 85%); $R^t$ 1.78 min (Method 1); m/z 445 (M+H)$^+$ (ES$^+$), 443 (M−H)$^-$ (ES$^-$).

Intermediate BB: 5-((4-(((4-Aminonaphthalen-1-yl)oxy)methyl)pyridin-2-yl)amino)-N,N-dimethylpyrazine-2-carboxamide

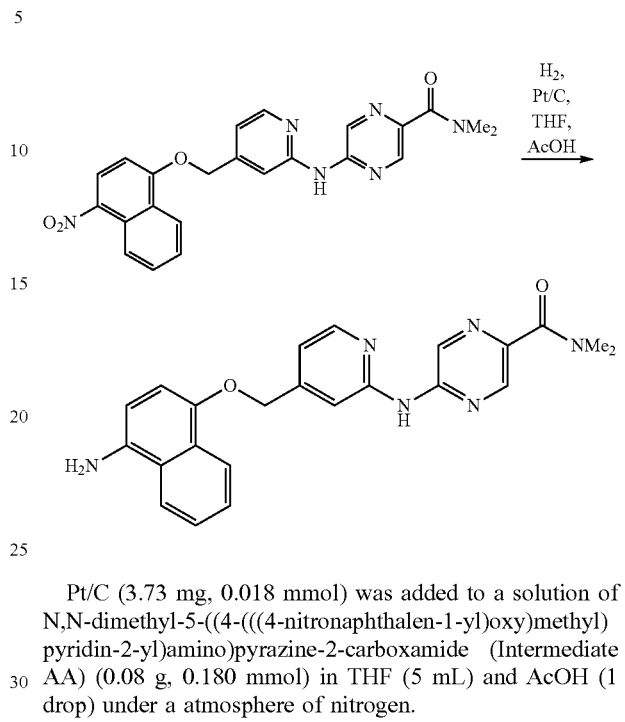

Pt/C (3.73 mg, 0.018 mmol) was added to a solution of N,N-dimethyl-5-((4-(((4-nitronaphthalen-1-yl)oxy)methyl)pyridin-2-yl)amino)pyrazine-2-carboxamide (Intermediate AA) (0.08 g, 0.180 mmol) in THF (5 mL) and AcOH (1 drop) under a atmosphere of nitrogen.

The reaction mixture was then stirred under an atmosphere of 1 bar hydrogen at room temperature for 24 h. The reaction was filtered through Celite and rinsed with MeOH (20 mL) and DCM (20 mL). The filtrate was concentrated under reduced pressure and the residue was diluted with MeOH (5 mL) and loaded onto a SCX cartridge. The cartridge was rinsed with MeOH (3 column volumes) and product eluted with 1% NH$_3$ MeOH (3 column volumes). The ammonia/methanol solution was concentrated under reduced pressure to give the subtitle compound 5-((4-(((4-aminonaphthalen-1-yl)oxy)methyl)pyridin-2-yl)amino)-N,N-dimethylpyrazine-2-carboxamide (22 mg, 22%); $R^t$ 1.01 min (Method 1); m/z 415 (M+H)$^+$ (ES$^+$).

5-((4-(((4-(3-(3-(tert-Butyl)-1-(p-tolyl)-1H-pyrazol-5-yl)ureido)naphthalen-1-yl)oxy)methyl)pyridin-2-yl)amino)-N,N-dimethylpyrazine-2-carboxamide

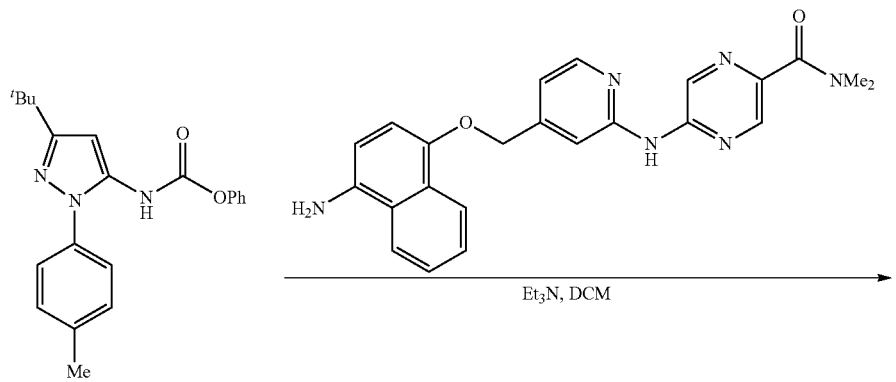

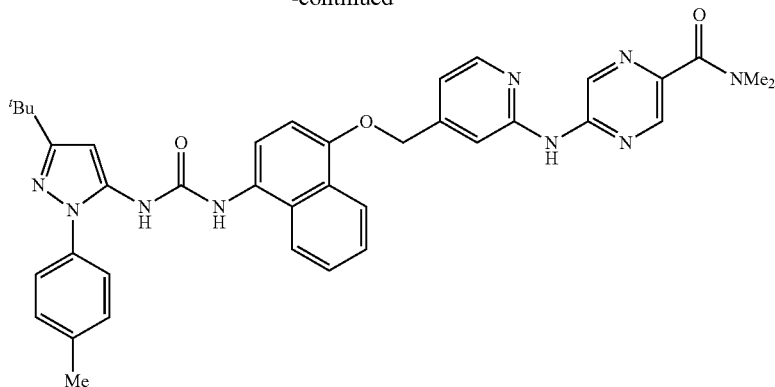

Triethylamine (8.32 μl, 0.060 mmol) was added to a stirring solution of phenyl (3-(tert-butyl)-1-(p-tolyl)-1H-pyrazol-5-yl)carbamate (Intermediate E) (0.021 g, 0.060 mmol) and 5-((4-(((4-aminonaphthalen-1-yl)oxy)methyl)pyridin-2-yl)amino)-N,N-dimethylpyrazine-2-carboxamide (Intermediate BB) (0.022 g, 0.040 mmol) in DCM (5 mL) and the reaction mixture was stirred at 40° C. for 16 h. The reaction mixture was concentrated under reduced pressure and loaded onto a silica pad and the crude product was purified by chromatography on silica gel (12 g column, gradient 0-5% MeOH in DCM) to afford the title compound 5-((4-(((4-(3-(3-(tert-butyl)-1-(p-tolyl)-1H-pyrazol-5-yl)ureido)naphthalen-1-yl)oxy)methyl)pyridin-2-yl)amino)-N,N-dimethylpyrazine-2-carboxamide as a pale tan solid (7 mg, 24%); $R^t$ 2.03 min (Method 1); m/z 670 (M+H)$^+$ (ES$^+$); $^1$H NMR δ: 1.28 (9H, s), 2.40 (3H, s), 3.02 (3H, s), 3.10 (3H, s), 5.38 (2H, s), 6.36 (1H, s), 7.05 (1H, d), 7.14 (1H, d), 7.37 (2H, m), 7.44 (2H, m), 7.59-7.66 (3H, overlapping m), 7.94 (1H, m), 8.01 (1H, s), 8.35 (1H, d), 8.41 (1H, m), 8.47 (1H, d), 8.59 (1H, s), 8.80 (1H, s), 9.08 (1H, s), 10.47 (1H, s).

Example 10: 1-(3-(tert-Butyl)-1-(p-tolyl)-1H-pyrazol-5-yl)-3-(4-((2-((5-(hydroxymethyl) pyrazin-2-yl)amino)pyridin-4-yl)methoxy)naphthalen-1-yl)urea Intermediate CC: (5-((4-(((4-Nitronaphthalen-1-yl)oxy)methyl)pyridin-2-yl)amino) pyrazin-2-yl)methanol

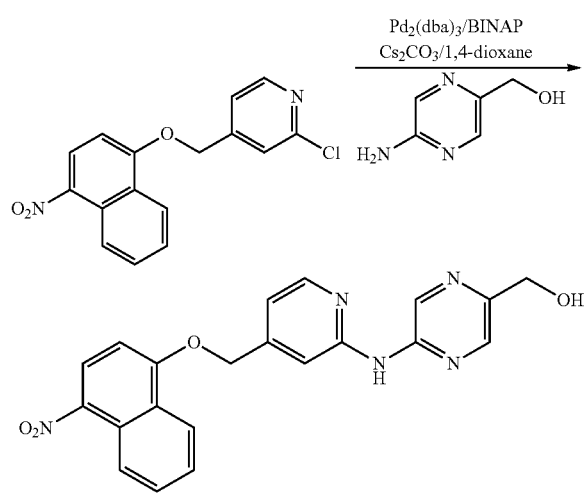

A mixture of 2-chloro-4-(((4-nitronaphthalen-1-yl)oxy)methyl)pyridine (Intermediate A) (0.265 g, 0.842 mmol), (5-aminopyrazin-2-yl)methanol (0.105 g, 0.842 mmol), BINAP (0.052 g, 0.084 mmol), cesium carbonate (0.412 g, 1.263 mmol) and Pd$_2$(dba)$_3$ (0.039 g, 0.042 mmol) in 1,4-dioxane (6 mL) was purged with nitrogen for 10 min, then kept under a nitrogen atmosphere and heated to 90° C. for 2 h. The reaction mixture was cooled to room temperature, diluted with 10% MeOH in DCM (100 mL), and passed through a pad of Celite, washing with further 10% MeOH in DCM (2×30 mL). The filtrate was concentrated in vacuo and triturated with MeOH (10 mL) to afford the subtitle compound (5-((4-(((4-nitronaphthalen-1-yl)oxy)methyl)pyridin-2-yl)amino)pyrazin-2-yl)methanol as a burnt orange solid (274 mg, 77%); $R^t$ 1.57 min (Method 1); m/z 404 (M+H)$^+$ (ES$^+$).

Intermediate DD: (5-((4-(((4-Aminonaphthalen-1-yl)oxy)methyl)pyridin-2-yl)amino)pyrazin-2-yl)methanol

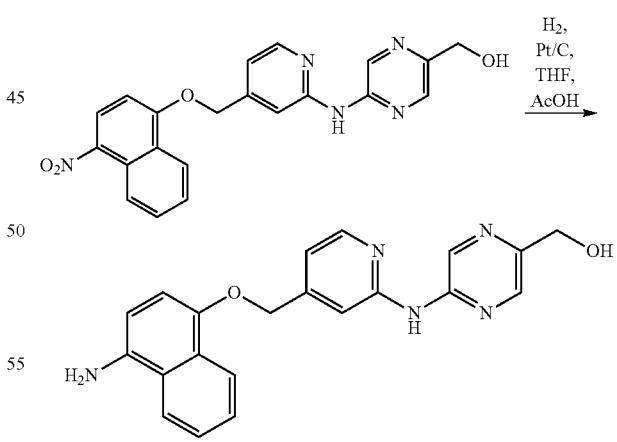

(5-((4-(((4-nitronaphthalen-1-yl)oxy)methyl)pyridin-2-yl)amino)pyrazin-2-yl)methanol (Intermediate CC) (0.27 g, 0.669 mmol) was taken up in 5% AcOH in THF (15 mL) and the reaction mixture was hydrogenated in the H-Cube (10% Pt/C, 30×4 mm, Full hydrogen, ambient temp, 1 mL/min; 2 passes). The reaction mixture was then concentrated in vacuo to give a purple solid. The crude product was loaded onto a column of SCX (4 g) in 5% AcOH in MeOH/DCM.

The column was washed with MeOH (2×10 mL) and then the product was eluted with 0.7M ammonia in MeOH (2×20 mL). The product fractions were concentrated in vacuo to afford the subtitle compound (5-((4-(((4-aminonaphthalen-1-yl)oxy)methyl)pyridin-2-yl)amino)pyrazin-2-yl)methanol as a dark purple solid (150 mg, 33%); R$^t$ 1.70 min (Method 1); m/z 374 (M+H)$^+$ (ES$^+$).

1-(3-(tert-Butyl)-1-(p-tolyl)-1H-pyrazol-5-yl)-3-(4-((2-((5-(hydroxymethyl)pyrazin-2-yl)amino)pyridin-4-yl)methoxy)naphthalen-1-yl)urea

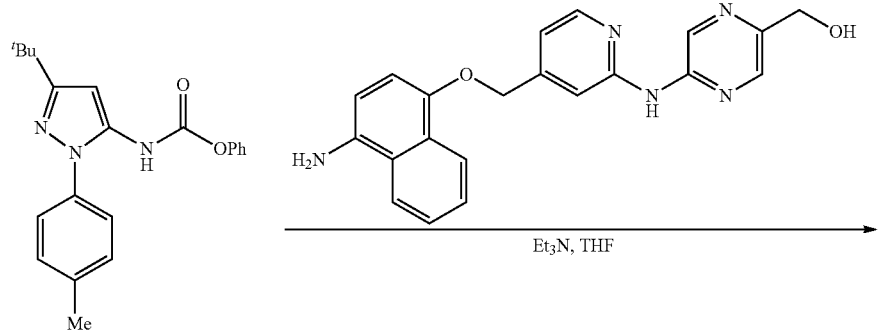

Triethylamine (0.024 mL, 0.175 mmol) was added to a solution of (5-((4-(((4-aminonaphthalen-1-yl)oxy)methyl)pyridin-2-yl)amino)pyrazin-2-yl)methanol (Intermediate DD) (119 mg, 0.175 mmol) and phenyl (3-(tert-butyl)-1-(p-tolyl)-1H-pyrazol-5-yl)carbamate (Intermediate E) (80 mg, 0.228 mmol) in THF (2.5 mL). The resulting mixture was heated to 40° C. for 2 h. The reaction mixture was cooled to room temperature, quenched with MeOH (2 mL) and concentrated in vacuo to afford a dark purple solid. This was taken up in a mixture of MeOH/DCM, concentrated onto silica and was purified by silica gel chromatography (12 g column, 0-5% MeOH in DCM) to afford the title compound 1-(3-(tert-butyl)-1-(p-tolyl)-1H-pyrazol-5-yl)-3-(4-((2-((5-(hydroxymethyl)pyrazin-2-yl)amino)pyridin-4-yl)methoxy)naphthalen-1-yl)urea as a pink solid (19 mg, 16%); R$^t$ 1.79 min (Method 1); m/z 629 (M+H)$^+$ (ES$^+$); $^1$H NMR δ: 1.27 (9H, s), 2.39 (3H, s), 4.54 (2H, d), 5.35 (1H, s), 5.37 (2H, t), 6.36 (1H, s), 6.99-7.12 (2H, overlapping m), 7.36 (2H, d), 7.44 (2H, d), 7.56-7.70 (3H, overlapping m), 7.93 (1H, m), 7.97 (1H, s), 8.26 (1H, d), 8.29 (1H, dd), 8.40 (1H, m), 8.58 (1H, s), 8.79 (1H, s), 9.03 (1H, s), 10.09 (1H, s).

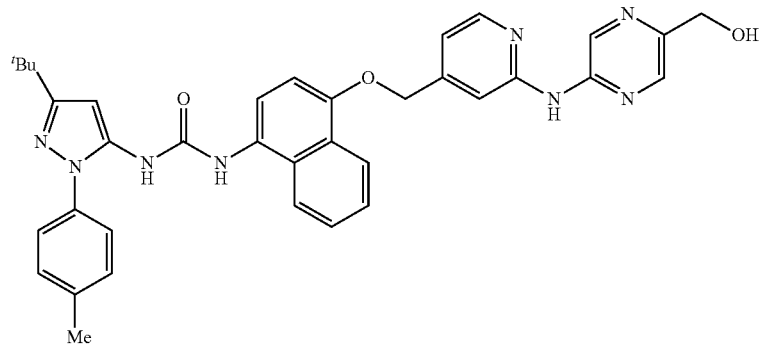

Examples 11-52

The following examples were prepared using methods analogous to those described above for the preparation of Examples 1-10:

Example 11:

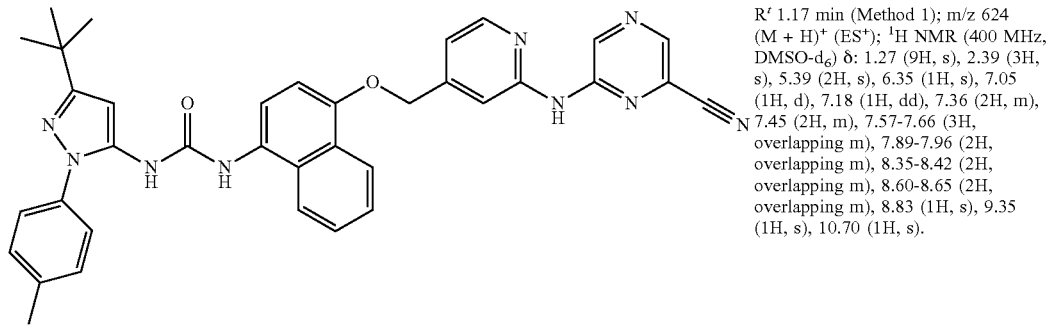

1-(3-(tert-butyl)-1-(p-tolyl)-1H-pyrazol-5-yl)-3-(4-((2-((6-cyanopyrazin-2-yl)
amino)pyridin-4-yl)methoxy)naphthalen-1-yl)urea.
Route code*: 3

R$^t$ 1.17 min (Method 1); m/z 624 (M + H)$^+$ (ES$^+$); $^1$H NMR (400 MHz, DMSO-d$_6$) δ: 1.27 (9H, s), 2.39 (3H, s), 5.39 (2H, s), 6.35 (1H, s), 7.05 (1H, d), 7.18 (1H, dd), 7.36 (2H, m), 7.45 (2H, m), 7.57-7.66 (3H, overlapping m), 7.89-7.96 (2H, overlapping m), 8.35-8.42 (2H, overlapping m), 8.60-8.65 (2H, overlapping m), 8.83 (1H, s), 9.35 (1H, s), 10.70 (1H, s).

Example 12:

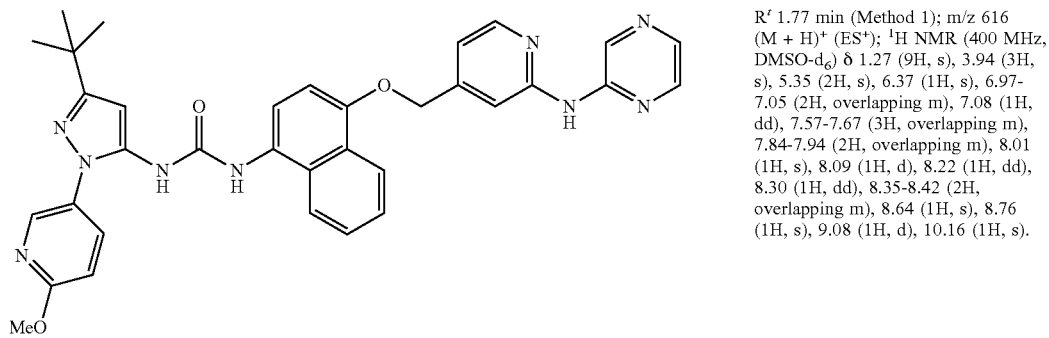

1-(3-(tert-butyl)-1-(6-methoxypyridin-3-yl)-1H-pyrazol-5-yl)-3-(4-((2-(pyrazin-2-
ylamino)pyridin-4-yl)methoxy)naphthalen-1-yl)urea.
Route code*: 3

R$^t$ 1.77 min (Method 1); m/z 616 (M + H)$^+$ (ES$^+$); $^1$H NMR (400 MHz, DMSO-d$_6$) δ 1.27 (9H, s), 3.94 (3H, s), 5.35 (2H, s), 6.37 (1H, s), 6.97-7.05 (2H, overlapping m), 7.08 (1H, dd), 7.57-7.67 (3H, overlapping m), 7.84-7.94 (2H, overlapping m), 8.01 (1H, s), 8.09 (1H, d), 8.22 (1H, dd), 8.30 (1H, dd), 8.35-8.42 (2H, overlapping m), 8.64 (1H, s), 8.76 (1H, s), 9.08 (1H, d), 10.16 (1H, s).

Example 13:

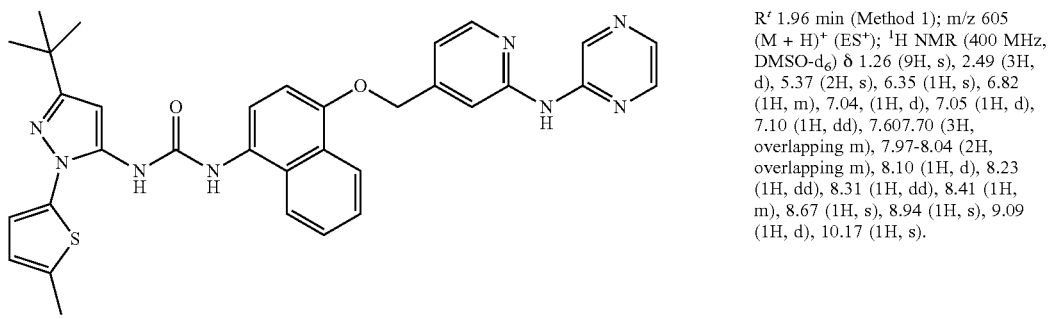

1-(3-(tert-butyl)-1-(5-methylthiophen-2-yl)-1H-pyrazol-5-yl)-3-(4-((2-(pyrazin-2-
ylamino)pyridin-4-yl)methoxy)naphthalen-1-yl)urea.
Route code*: 3

R$^t$ 1.96 min (Method 1); m/z 605 (M + H)$^+$ (ES$^+$); $^1$H NMR (400 MHz, DMSO-d$_6$) δ 1.26 (9H, s), 2.49 (3H, d), 5.37 (2H, s), 6.35 (1H, s), 6.82 (1H, m), 7.04 (1H, d), 7.05 (1H, d), 7.10 (1H, dd), 7.60-7.70 (3H, overlapping m), 7.97-8.04 (2H, overlapping m), 8.10 (1H, d), 8.23 (1H, dd), 8.31 (1H, dd), 8.41 (1H, m), 8.67 (1H, s), 8.94 (1H, s), 9.09 (1H, d), 10.17 (1H, s).

Example 14:

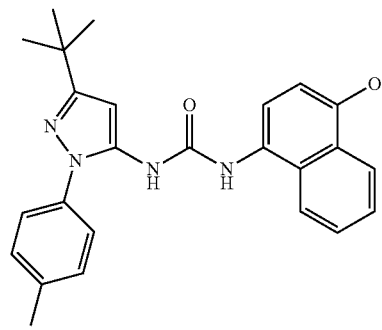

1-(3-(tert-butyl)-1-(p-tolyl)-1H-pyrazol-5-yl)-3-(4-((2-((6-(dimethylamino)pyrazin-2-yl)amino)pyridin-4-yl)methoxy)naphthalen-1-yl)urea.
Route code*: 1

R$^t$ 2.6 min (Method 2); m/z 642 (M + H)$^+$ (ES$^+$); $^1$H NMR (400 MHz, DMSO-d$_6$) δ: 1.27 (9H, s), 2.39 (3H, s), 2.97 (6H, s), 5.33 (2H, s), 6.35 (1H, s), 6.99 (1H, d), 7.03 (1H, m), 7.36 (2H, m), 7.44 (2H, m), 7.54-7.64 (4H, overlapping m), 7.93 (1H, m), 8.07 (1H, s), 8.11 (1H, s), 8.26 (1H, d), 8.31 (1H, m), 8.57 (1H, s), 8.78 (1H, s), 9.65 (1H, s).

Example 15:

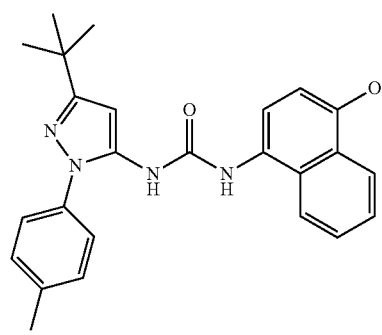

1-(3-(tert-butyl)-1-(p-tolyl)-1H-pyrazol-5-yl)-3-(4-((2-((6-cyclopropylpyrazin-2-yl)amino)pyridin-4-yl)methoxy)naphthalen-1-yl)urea.
Route code*: 1

R$^t$ 2.73 min (Method 2); m/z 639 (M + H)$^+$ (ES$^+$); $^1$H NMR (400 MHz, DMSO-d$_6$) δ: 0.85-0.94 (4H, overlapping m), 1.27 (9H, s), 1.98-2.06 (1H, m), 2.39 (3H, s), 5.34 (2H, s), 6.35 (1H, s), 6.99 (1H, d), 7.07 (1H, dd), 7.36 (2H, m), 7.44 (2H, m), 7.56-7.84 (3H, overlapping m), 7.89-7.95 (2H, overlapping m), 8.03 (1H, s), 8.28 (1H, d), 8.36 (1H, m), 8.58 (1H, s), 8.77-8.80 (2H, overlapping m), 9.94 (1H, s).

Example 16:

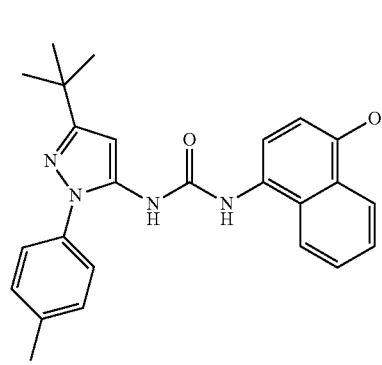

1-(3-(tert-butyl)-1-(p-tolyl)-1H-pyrazol-5-yl)-3-(4-((2-((5-cyclopropylpyrazin-2-yl)amino)pyridin-4-yl)methoxy)naphthalen-1-yl)urea
Route code*: 3

R$^t$ 2.11 min (Method 1); m/z 639 (M + H)$^+$ (ES$^+$); $^1$H NMR (400 MHz, DMSO-d$_6$) δ: 0.85 (2H, m), 0.94 (2H, m), 1.27 (9H, s), 2.10 (1H, ddd), 2.39 (3H, s), 5.33 (2H, s), 6.36 (1H, s), 6.97-7.08 (2H, overlapping m), 7.36 (2H, m), 7.44 (2H, m), 7.56-7.67 (3H, overlapping m), 7.86 (1H, s), 7.93 (1H, m), 8.17 (1H, d), 8.25 (1H, dd), 8.38 (1H, m), 8.58 (1H, s), 8.79 (1H, s), 8.96 (1H, d), 9.93 (1H, s).

Example 17:

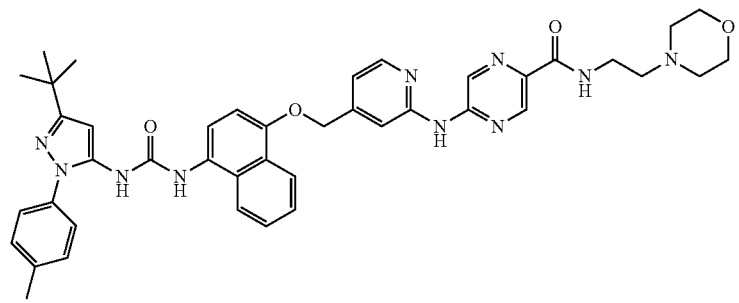

R' 1.68 min (Method 1); m/z 755 (M + H)⁺ (ES⁺); ¹H NMR (400 MHz, DMSO-d₆) δ: 1.28 (9H, s), 2.42-2.40 (7H, overlapping m), 3.40-3.35 (4H, overlapping m), 3.58 (4H, t), 5.39 (2H, s), 6.36 (1H, s), 7.05 (1H, d), 7.17 (1H, d), 7.37 (2H, m), 7.46 (2H, m), 7.59-7.66 (3H, overlapping m), 7.95 (1H, m), 8.10 (1H, s), 8.35 (1H, d), 8.41 (1H, m), 8.46 (1H, t), 8.64 (1H, s), 8.76 (1H, d), 8.85 (1H, d), 9.06 (1H, d), 10.59 (1H, s).

5-((4-(((4-(3-(3-(tert-butyl)-1-(p-tolyl)-1H-pyrazol-5-yl)ureido)naphthalen-1-yl)oxy)methyl) pyridin-2-yl)amino)-N-(2-morpholinoethyl)pyrazine-2-carboxamide.
Route code*: 4

Example 18:

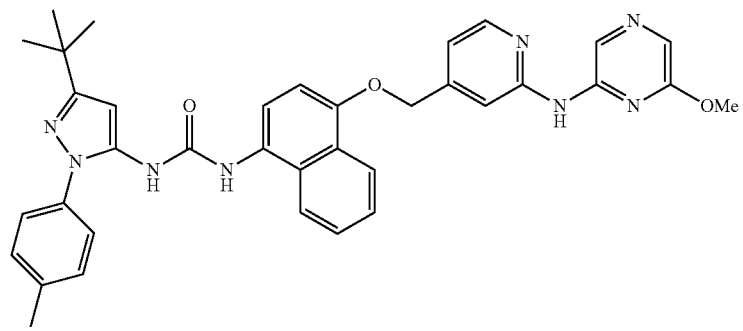

R' 2.36 min (Method 1); m/z 629 (M + H)⁺ (ES⁺); ¹H NMR (400 MHz, DMSO-d₆) δ: 1.29 (9H, s), 2.40 (3H, s), 3.80 (3H, s), 5.37 (2H, s), 6.36 (1H, s), 7.01 (1H, d), 7.10 (1H, d), 7.38 (2H, m), 7.44 (2H, m), 7.58-7.64 (3H, overlapping m), 7.33 (1H, s), 7.92-9.95 (2H, overlapping m), 8.32 (1H, d), 8.35 (1H, m), 8.59 (1H, s), 8.63 (1H, s), 8.80 (1H, s), 10.06 (1H, s).

1-(3-(tert-butyl)-1-(p-tolyl)-1H-pyrazol-5-yl)-3-(4-((2-(((6-methoxypyrazin-2-yl) amino)pyridin-4-yl)methoxy)naphthalen-1-yl)urea
Route code*: 1

Example 19:

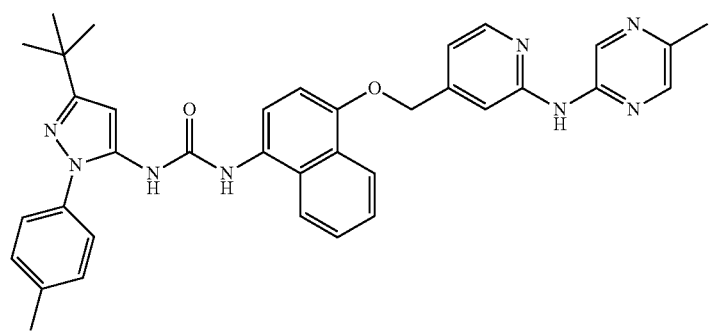

R' 2.03 min (Method 1); m/z 613 (M + H)⁺ (ES⁺); ¹H NMR (400 MHz, DMSO-d₆) δ: 1.27 (9H, s), 2.39 (3H, s), 2.40 (3H, s), 5.34 (2H, s), 6.35 (1H, s), 7.01-7.05 (2H, overlapping m), 7.36 (2H, m), 7.44 (2H, m), 7.58-7.65 (3H, overlapping m), 7.89 (1H, s), 7.93 (1H, m), 8.11 (1H, s), 8.27 (1H, d), 8.39 (1H, m), 8.61 (1H, s), 8.81 (1H, s), 9.02 (1H, s), 9.97 (1H, s).

1-(3-(tert-butyl)-1-(p-tolyl)-1H-pyrazol-5-yl)-3-(4-((2-((5-methylpyrazin-2-yl) amino)pyridin-4-yl)methoxy)naphthalen-1-yl)urea.
Route code*: 1

Example 20:

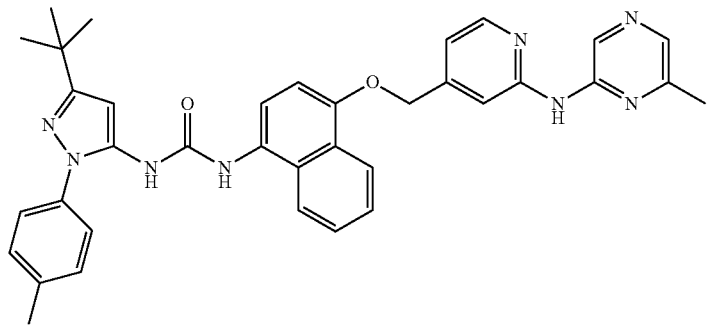

1-(3-(tert-butyl)-1-(p-tolyl)-1H-pyrazol-5-yl)-3-(4-((2-(((6-methylpyrazin-2-yl)amino)pyridin-4-yl)methoxy)naphthalen-1-yl)urea.
Route code*: 1

R$^t$ 2.10 min (Method 1); m/z 613 (M + H)$^+$ (ES$^+$); $^1$H NMR (400 MHz, DMSO-d$_6$) δ: 1.27 (9H, s), 2.35 (3H, s), 2.39 (3H, s), 5.35 (2H, s), 6.36 (1H, s), 7.01-7.06 (2H, overlapping m), 7.36 (2H, m), 7.43 (2H, m), 7.57-7.67 (3H, overlapping m), 7.93 (1H, m), 7.98 (2H, s), 8.29 (1H, d), 8.41 (1H, m), 8.60 (1H, s), 8.81 (1H, s), 8.94 (1H, s), 10.10 (1H, s).

Example 21:

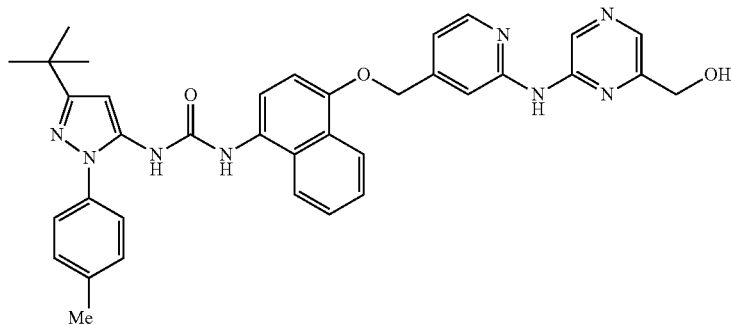

1-(3-(tert-butyl)-1-(p-tolyl)-1H-pyrazol-5-yl)-3-(4-((2-(((6-(hydroxymethyl)pyrazin-2-yl)amino)pyridin-4-yl)methoxy)naphthalen-1-yl)urea.
Route code*: 2

R$^t$ 1.82 min (Method 1); m/z 629 (M + H)$^+$ (ES$^+$); $^1$H NMR (400 MHz, DMSO-d$_6$) δ 1.27 (9H, s), 2.39 (3H, s), 4.53 (2H, d), 5.35 (2H, s), 5.48 (1H, s), 6.36 (1H, s), 7.03 (1H, d), 7.06 (1H, m), 7.36 (2H, d), 7.45 (2H, m), 7.59-7.68 (3H, overlapping m), 7.91-7.98 (2H, overlapping m), 8.16 (1H, s), 8.29 (1H, d), 8.40 (1H, m), 8.58 (1H, s), 8.79 (1H, s), 9.01 (1H, s), 10.13 (1H, s).

Example 22:

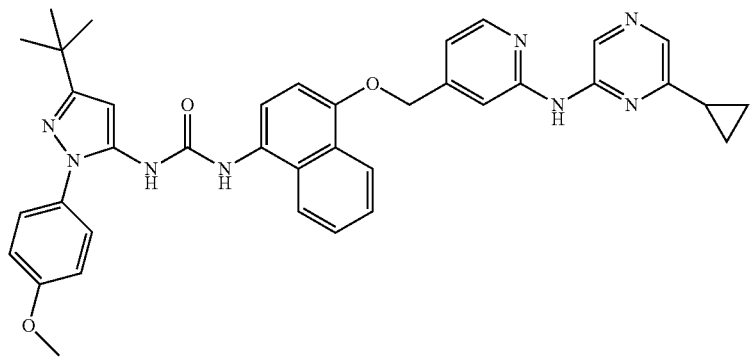 [SMILES: Cc1ccc(-n2nc(C(C)(C)C)cc2NC(=O)Nc2ccc(OCc3ccnc(Nc4cncc(C5CC5)n4)c3)c3ccccc23)cc1C]

1-(3-(tert-butyl)-1-(4-methoxyphenyl)-1H-pyrazol-5-yl)-3-(4-((2-(((6-cyclopropylpyrazin-2-yl)amino)pyridin-4-yl)methoxy)naphthalen-1-yl)urea.
Route code*: 1

R$^t$ 2.25 min (Method 1); m/z 655 (M + H)$^+$ (ES$^+$); $^1$H NMR (400 MHz, DMSO-d$_6$) δ: 0.85-0.93 (4H, overlapping m), 1.26 (9H, s), 2.02 (1H, m), 3.83 (3H, s), 5.34 (2H, s), 6.33 (1H, s), 6.99 (1H, d), 7.05-7.12 (3H, overlapping m), 7.45 (2H, m), 7.55-7.64 (3H, overlapping m), 7.90-7.93 (2H, overlapping m), 8.03 (1H, s), 8.28 (1H, d), 8.36 (1H, m), 8.52 (1H, br s), 8.77 (1H, br s), 8.78 (1H, br s), 9.94 (1H, br s).

Example 23:

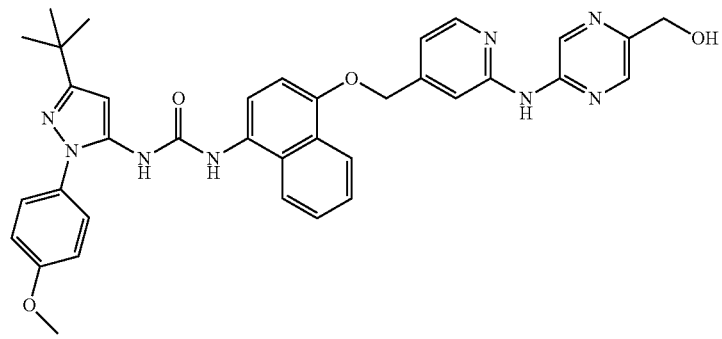 [SMILES: Cc1ccc(-n2nc(C(C)(C)C)cc2NC(=O)Nc2ccc(OCc3ccnc(Nc4cnc(CO)cn4)c3)c3ccccc23)cc1C]

R$^t$ 1.72 min (Method 1); m/z 645 (M + H)$^+$ (ES$^+$); 643 (M − H)$^-$ (ES$^-$); $^1$H NMR (400 MHz, DMSO-d$_6$) δ: 1.26 (9H, s), 3.83 (3H, s), 4.54 (2H, s), 5.30-5.42 (3H, overlapping m), 6.34 (1H, s), 7.01-7.13 (4H, overlapping m), 7.45 (2H, m), 7.59-7.66 (3H, overlapping m), 7.93 (1H, m), 7.97 (1H, br s), 8.26 (1H, s), 8.29 (1H, d), 8.40 (1H, m), 8.53 (1H, br s), 8.79 (1H, br s), 9.02 (1H, br s), 10.10 (1H, br s).

1-(3-(tert-butyl)-1-(4-methoxyphenyl)-1H-pyrazol-5-yl)-3-(4-((2-((5-(hydroxymethyl)pyrazin-2-yl)amino)pyridin-4-yl)methoxy)naphthalen-1-yl)urea.
Route code*: 1

Example 24:

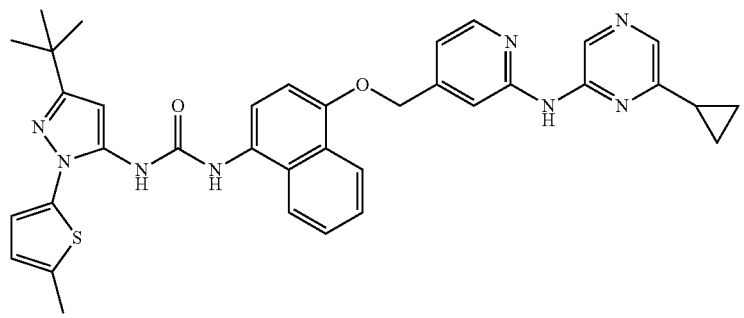

R$^t$ 2.39 min (Method 1); m/z 645 (M + H)$^+$ (ES$^+$); 643 (M − H)$^-$ (ES$^-$); $^1$H NMR (400 MHz, DMSO-d$_6$) δ: 0.85-0.95 (4H, overlapping m), 1.25 (9H, s), 2.02 (1H, m), 2.48 (3H, s), 5.35 (2H, s), 6.33 (1H, s), 6.81 (1H, m), 6.99-7.08 (3H, overlapping m), 7.56-7.66 (3H, overlapping m), 7.92 (1H, s), 7.98 (1H, d), 8.03 (1H, s), 8.29 (1H, d), 8.37 (1H, d), 8.64 (1H, br s), 8.78 (1H, br s), 8.92 (1H, br s), 9.94 (1H, br s).

1-(3-(tert-butyl)-1-(5-methylthiophen-2-yl)-1H-pyrazol-5-yl)-3-(4-((2-((6-cyclopropyl-pyrazin-2-yl)amino)pyridin-4-yl)methoxy)naphthalen-1-yl)urea
Route code*: 1

Example 25:

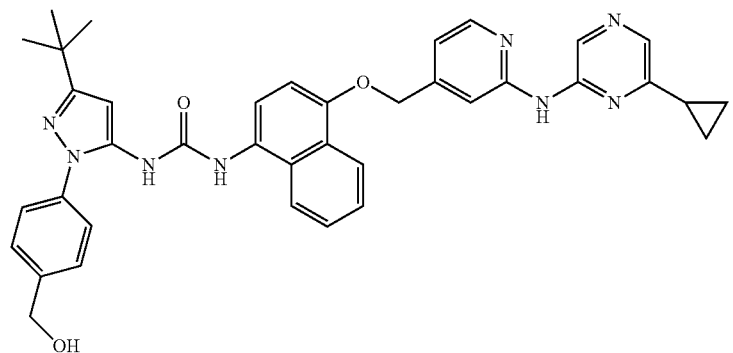

R$^t$ 2.01 min (Method 1); m/z 655 (M + H)$^+$ (ES$^+$); 653 (M − H)$^-$ (ES$^-$); $^1$H NMR (400 MHz, DMSO-d$_6$) δ: 0.85-0.94 (4H, overlapping m), 1.27 (9H, s), 2.02 (1H, m), 4.59 (2H, d), 5.30-5.36 (3H, overlapping m), 6.36 (1H, s), 6.99 (1H, d), 7.07 (1H, d), 7.46-7.53 (4H, overlapping m), 7.55-7.64 (3H, overlapping m), 7.91-7.95 (2H, overlapping m), 8.03 (1H, s), 8.28 (1H, d), 8.36 (1H, d), 8.61 (1H, s), 8.78 (1H, br s), 8.79 (1H, br s), 9.94 (1H, br s).

1-(3-(tert-butyl)-1-(4-(hydroxymethyl)phenyl)-1H-pyrazol-5-yl)-3-(4-((2-((6-cyclopropylpyrazin-2-yl)amino)pyridin-4-yl)methoxy)naphthalen-1-yl)urea.
Route code*: 1 with compound (II) protected through the process and deprotected as a final step Example 26:

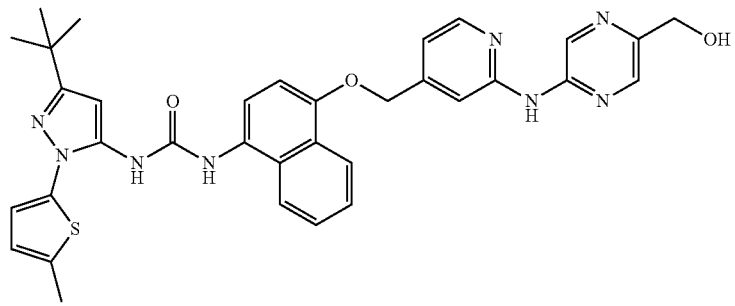

1-(3-(tert-butyl)-1-(5-methylthiophen-2-yl)-1H-pyrazol-5-yl)-3-(4-((2-((5-hydroxymethyl)pyrazin-2-yl)amino)pyridin-4-yl)methoxy)naphthalen-1-yl)urea.
Route code*: 1

$R^t$ 1.82 min (Method 1); m/z 635 (M + H)$^+$ (ES$^+$); 633 (M − H)$^−$ (ES$^−$); $^1$H NMR (400 MHz, DMSO-d$_6$) δ: 1.25 (9H, s), 2.48 (3H, br s), 4.54 (2H, s), 5.36 (3H, s), 6.34 (1H, s), 6.82 (1H, d), 7.02-7.08 (3H, overlapping m), 7.59-7.68 (3H, overlapping m), 7.96-8.02 (2H, overlapping m), 8.26 (1H, s), 8.29 (1H, d), 8.41 (1H, m), 8.65 (1H, br s), 8.93 (1H, br s), 9.02 (1H, br s), 10.10 (1H, br s).

Example 27:

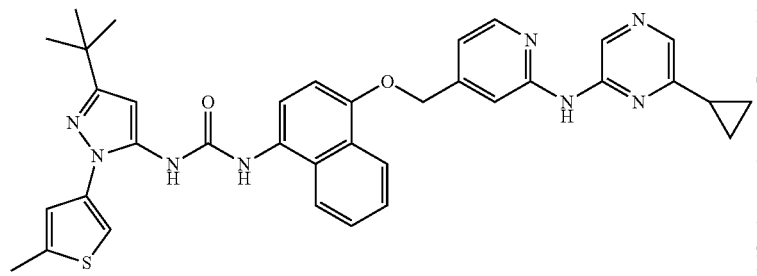

1-(3-(tert-butyl)-1-(5-methylthiophen-3-yl)-1H-pyrazol-5-yl)-3-(4-((2-((6-cyclopropylpyrazin-2-yl)amino)pyridin-4-yl)methoxy)naphthalen-1-yl)urea.
Route code*: 1

$R^t$ 2.36 min (Method 1); m/z 645 (M + H)$^+$ (ES$^+$); 643 (M − H)$^−$ (ES$^−$); $^1$H NMR (400 MHz, DMSO-d$_6$) δ: 0.85-0.95 (4H, overlapping m), 1.25 (9H, s), 2.02 (1H, m), 5.35 (2H, s), 6.31 (1H, s), 7.00 (1H, d), 7.06-7.08 (2H, overlapping m), 7.39 (1H, d), 7.56-7.65 (3H, overlapping m), 7.92 (1H, s), 7.99 (1H, d), 8.03 (1H, s), 8.29 (1H, d), 8.37 (1H, d), 8.60 (1H, br s), 8.78 (1H, br s), 8.86 (1H, br s), 9.94 (1H, br s). Missing CH$_3$ resonance presumed 2.50 ppm obscured by residual DMSO peak 2.49-2.51 ppm.

Example 28:

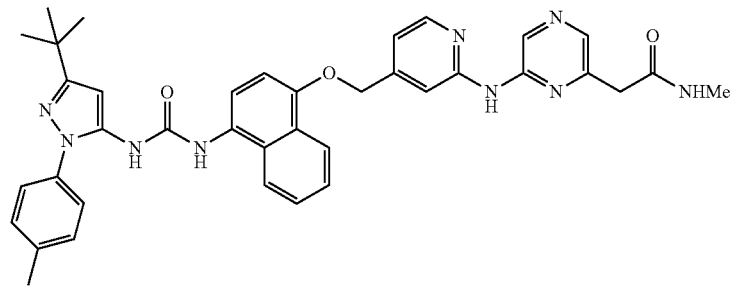

2-(6-(((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-methylacetamide
Route code*: 5

$R^t$ 1.82 min (Method 1); m/z 670 (M + H)$^+$ (ES$^+$); $^1$H NMR (400 MHz, DMSO-d$_6$) δ: 1.27 (9H, s), 2.39 (3H, s), 2.60 (3H, d), 3.55 (2H, s), 5.33 (2H, s), 6.35 (1H, s), 7.02 (1H, d), 7.07 (2H, overlapping dd), 7.36 (2H, m), 7.44 (2H, m), 7.60 (1H, m), 7.64 (1H, d), 7.84 (1H, s), 7.93 (1H, m), 8.01 (1H, m), 8.03 (1H, s), 8.29 (1H, d), 8.38 (1H, m), 8.58 (1H, s), 8.79 (1H, s), 9.09 (1H, s), 10.12 (1H, s).

Example 29:

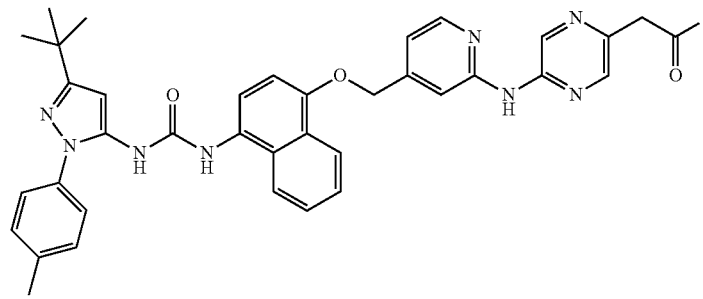

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N,N-dimethylacetamide
Route code*: 5

$R^t$ 1.88 min (Method 1); m/z 684 (M + H)$^+$ (ES$^+$); $^1$H NMR (400 MHz, DMSO-d$_6$) δ: 1.27 (9H, s), 2.39 (3H, s), 2.81 (3H, s), 3.00 (3H, s), 3.78 (2H, s), 5.33 (2H, s), 6.36 (1H, s), 7.02 (1H, d), 7.07 (2H, dd), 7.36 (2H, d), 7.44 (2H, m), 7.64-7.53 (2H, overlapping m), 7.64 (1H, d), 7.88 (1H, s), 7.93 (1H, m), 7.99 (1H, s), 8.30 (1H, d), 8.36 (1H, m), 8.58 (1H, s), 8.79 (1H, s), 9.03 (1H, s), 10.10 (1H, s).

Example 30:

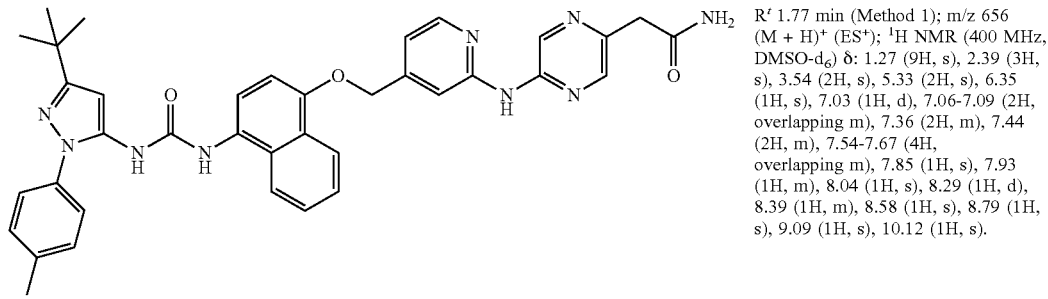

R$^t$ 1.77 min (Method 1); m/z 656 (M + H)$^+$ (ES$^+$); $^1$H NMR (400 MHz, DMSO-d$_6$) δ: 1.27 (9H, s), 2.39 (3H, s), 3.54 (2H, s), 5.33 (2H, s), 6.35 (1H, s), 7.03 (1H, d), 7.06-7.09 (2H, overlapping m), 7.36 (2H, m), 7.44 (2H, m), 7.54-7.67 (4H, overlapping m), 7.85 (1H, s), 7.93 (1H, m), 8.04 (1H, s), 8.29 (1H, d), 8.39 (1H, m), 8.58 (1H, s), 8.79 (1H, s), 9.09 (1H, s), 10.12 (1H, s).

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)acetamide
Route code*: 5

Example 31:

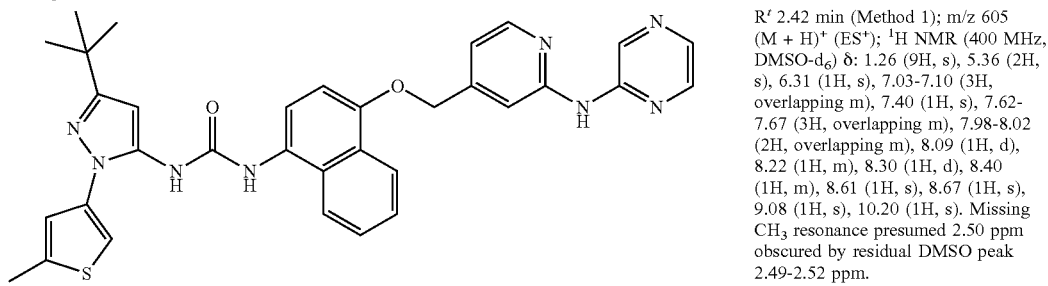

R$^t$ 2.42 min (Method 1); m/z 605 (M + H)$^+$ (ES$^+$); $^1$H NMR (400 MHz, DMSO-d$_6$) δ: 1.26 (9H, s), 5.36 (2H, s), 6.31 (1H, s), 7.03-7.10 (3H, overlapping m), 7.40 (1H, s), 7.62-7.67 (3H, overlapping m), 7.98-8.02 (2H, overlapping m), 8.09 (1H, d), 8.22 (1H, m), 8.30 (1H, d), 8.40 (1H, m), 8.61 (1H, s), 8.67 (1H, s), 9.08 (1H, s), 10.20 (1H, s). Missing CH$_3$ resonance presumed 2.50 ppm obscured by residual DMSO peak 2.49-2.52 ppm.

1-(3-(tert-butyl)-1-(5-methylthiophen-3-yl)-1H-pyrazol-5-yl)-3-(4-((2-(pyrazin-2-ylamino)pyridin-4-yl)methoxy)naphthalen-1-yl)urea.
Route code*: 1

Example 32:

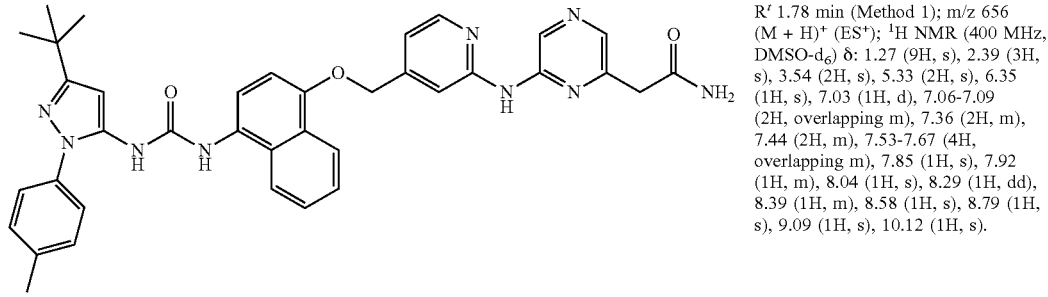

R$^t$ 1.78 min (Method 1); m/z 656 (M + H)$^+$ (ES$^+$); $^1$H NMR (400 MHz, DMSO-d$_6$) δ: 1.27 (9H, s), 2.39 (3H, s), 3.54 (2H, s), 5.33 (2H, s), 6.35 (1H, s), 7.03 (1H, d), 7.06-7.09 (2H, overlapping m), 7.36 (2H, m), 7.44 (2H, m), 7.53-7.67 (4H, overlapping m), 7.85 (1H, s), 7.92 (1H, m), 8.04 (1H, s), 8.29 (1H, dd), 8.39 (1H, m), 8.58 (1H, s), 8.79 (1H, s), 9.09 (1H, s), 10.12 (1H, s).

2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)acetamide
Route code*: 5

Example 33:

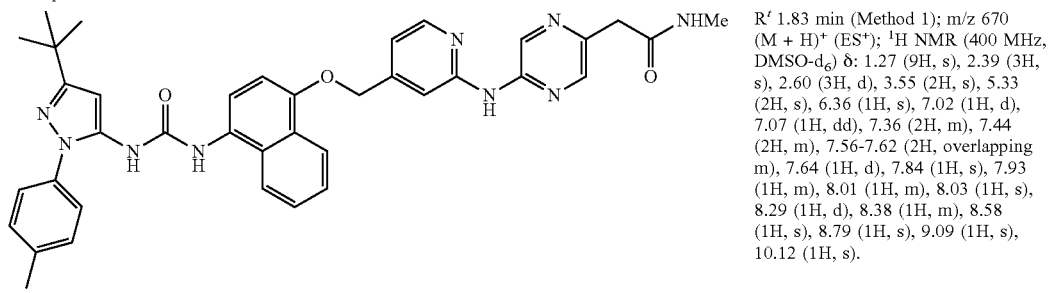

R$^t$ 1.83 min (Method 1); m/z 670 (M + H)$^+$ (ES$^+$); $^1$H NMR (400 MHz, DMSO-d$_6$) δ: 1.27 (9H, s), 2.39 (3H, s), 2.60 (3H, d), 3.55 (2H, s), 5.33 (2H, s), 6.36 (1H, s), 7.02 (1H, d), 7.07 (1H, dd), 7.36 (2H, m), 7.44 (2H, m), 7.56-7.62 (2H, overlapping m), 7.64 (1H, d), 7.84 (1H, s), 7.93 (1H, m), 8.01 (1H, m), 8.03 (1H, s), 8.29 (1H, d), 8.38 (1H, m), 8.58 (1H, s), 8.79 (1H, s), 9.09 (1H, s), 10.12 (1H, s).

2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-methylacetamide
Route: 5

Example 34:

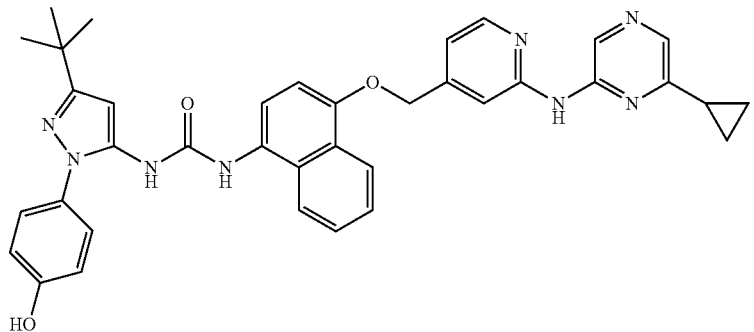 [SMILES: Cc1cccc(-n2nc(C(C)(C)C)cc2NC(=O)Nc2ccc(OCc3ccnc(Nc4cncc(C5CC5)n4)c3)c3ccccc23)c1]

1-(3-(tert-butyl)-1-(4-hydroxyphenyl)-1H-pyrazol-5-yl)-3-(4-((2-((6-cyclopropylpyrazin-2-yl)amino)pyridin-4-yl)methoxy)naphthalen-1-yl)urea.
Route code*: 1 with the hydroxy of compound (II) protected through the process and deprotected as a final step $R^t$ 2.07 min (Method 1); m/z 641 (M + H)$^+$ (ES$^+$); 639 (M − H)$^-$ (ES$^-$); $^1$H NMR (400 MHz, DMSO-d$_6$) δ: 0.85-0.95 (4H, overlapping m), 1.26 (9H, s), 2.02 (1H, m), 5.34 (2H, s), 6.31 (1H, s), 6.92 (2H, m), 6.99 (1H, d), 7.07 (1H, d), 7.32 (2H, m), 7.56-7.63 (3H, overlapping m), 7.89-7.94 (2H, overlapping m), 8.03 (1H, s), 8.28 (1H, d), 8.36 (1H, m), 8.48 (1H, br s), 8.77 (1H, br s), 8.78 (1H, br s), 9.77 (1H, br s), 9.94 (1H, br s).

Example 35:

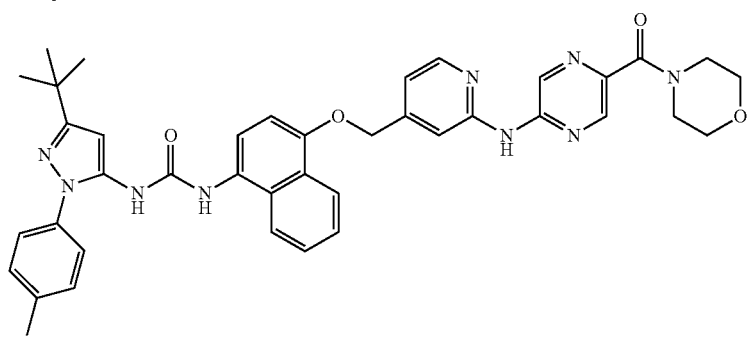

1-(3-(tert-butyl)-1-(p-tolyl)-1H-pyrazol-5-yl)-3-(4-((2-((5-(morpholine-4-carbonyl)pyrazin-2-yl)amino)pyridin-4-yl)methoxy)naphthalen-1-yl)urea
Route code*: 2

$R^t$ 2.08 min (Method 1); m/z 712.4 (M + H)$^+$ (ES$^+$); $^1$H NMR (400 MHz, DMSO-d$_6$) δ: 1.18 (9H, s), 2.31 (3H, s), 3.55-3.59 (8H, overlapping m), 5.30 (2H, m), 6.26 (1H, s), 6.98 (1H, d), 7.07 (1H, d), 7.27 (2H, m), 7.40 (2H, m), 7.50-7.53 (3 H, overlapping m), 7.90-7.93 (2H, overlapping m), 8.27 (1H, d), 8.40 (1H, s), 8.50 (1H, m), 8.93 (1H, s), 9.01 (1H, s), 9.06 (1H, s), 10.46 (1H, s).

Example 36:

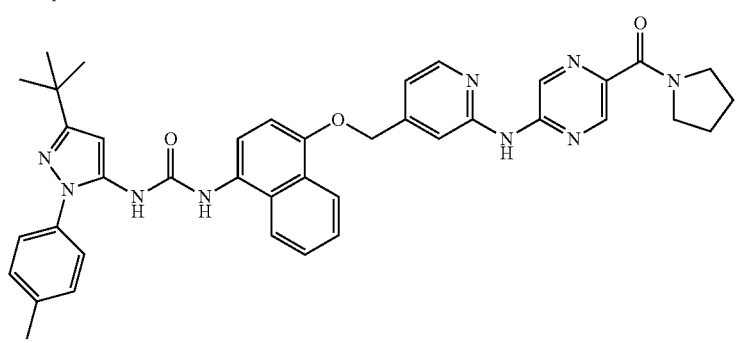

1-(3-(tert-butyl)-1-(p-tolyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
Route code*: 2

$R^t$ 2.29 min (Method 1); m/z 696.4 (M + H)$^+$ (ES$^+$); $^1$H NMR (400 MHz, DMSO-d6) δ: 1.27 (9H, s), 1.86 (4H, m), 2.34 (3H, s), 3.52 (2H, m), 3.76 (2H, m), 5.37 (2H, s), 6.34 (1H, s), 7.02 (1H, d), 7.14 (1H, d), 7.36 (2H, m), 7.44 (2H, m), 7.58-7.64 (3H, overlapping m), 7.96 (1H, m), 8.02 (1H, s), 8.34 (1H, d), 8.40 (1H, m), 8.62 (1H, s), 8.85 (1H, s), 9.02 (1H, s), 9.09 (1H, s), 10.53 (1H, s).

Example 37:

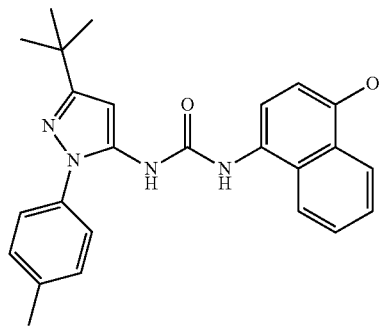

R$^t$ 2.11 min (Method 1); m/z 627 (M + H)$^+$ (ES$^+$); $^1$H NMR (400 MHz, DMSO-d$_6$) δ 1.22 (3H, t), 1.27 (9H, s), 2.39 (3H, s), 2.70 (2H, q), 5.34 (2H, s), 6.35 (1H, s), 7.00-7.07 (2H, overlapping m), 7.36 (2H, m), 7.44 (2H, m), 7.58-7.67 (3H, overlapping m), 7.91 (1H, s), 7.94 (1H, m), 8.11 (1H, d), 8.27 (1H, dd), 8.39 (1H, m), 8.59 (1H, s), 8.80 (1H, s), 9.02 (1H, d), 9.98 (1H, s).

1-(3-(tert-butyl)-1-(p-tolyl)-1H-pyrazol-5-yl)-3-(4-((2-((5-ethylpyrazin-2-yl)amino)pyridin-4-yl)methoxy)naphthalen-1-yl)urea.
Route code*: 1

Example 38:

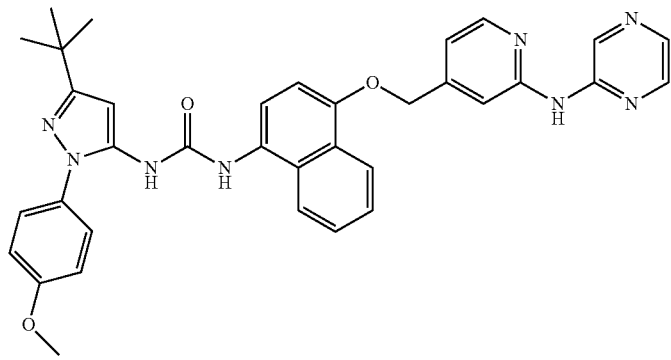

R$^t$ 2.40 min (Method 2); m/z 615 (M + H)$^+$ (ES$^+$); $^1$H NMR (400 MHz, DMSO-d$_6$) δ: 1.27 (9H, s), 3.83 (3H, s), 5.35 (2H, s), 6.34 (1H, s), 7.04 (1H, d), 7.07-7.13 (3H, overlapping m), 7.46 (2H, m), 7.58-7.65 (3H, overlapping m), 7.92 (1H, m), 8.01 (1H, s), 8.09 (1H, d), 8.22 (1H, m), 8.30 (1H, d), 8.40 (1H, m), 8.53 (1H, s), 8.78 (1H, s), 9.08 (1H, s), 10.14 (1H, s).

1-(3-(tert-butyl)-1-(4-methoxyphenyl)-1H-pyrazol-5-yl)-3-(4-((2-(pyrazin-2-ylamino)pyridin-4-yl)methoxy)naphthalen-1-yl)urea.
Route code*: 1

Example 39:

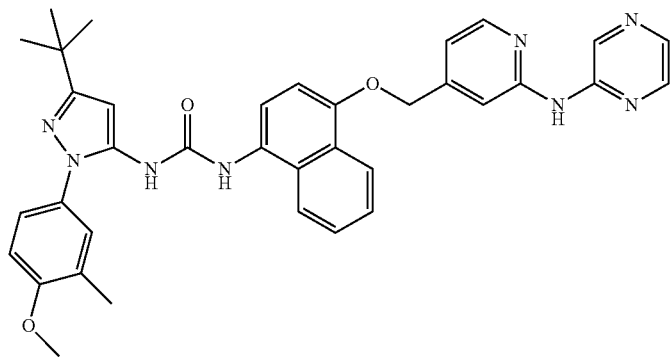

R$^t$ 2.53 min (Method 2); m/z 629 (M + H)$^+$ (ES$^+$); $^1$H NMR (400 MHz, DMSO-d$_6$) δ: 1.27 (9H, s), 2.24 (3H, s), 3.87 (3H, s), 5.36 (2H, s), 6.34 (1H, s), 7.04 (1H, d), 7.08-7.11 (2H, overlapping m), 7.32-7.34 (2H, overlapping m), 7.60-7.66 (3H, overlapping m), 7.93 (1H, m), 8.02 (1H, s), 8.09 (1H, d), 8.22 (1H, m), 8.30 (1H, d), 8.39 (1H, m), 8.52 (1H, s), 8.80 (1H, s), 9.09 (1H, s), 10.15 (1H, s).

1-(3-(tert-butyl)-1-(4-methoxy-3-methylphenyl)-1H-pyrazol-5-yl)-3-(4-((2-(pyrazin-2-ylamino)pyridin-4-yl)methoxy)naphthalen-1-yl)urea
Route code*: 1

Example 40:

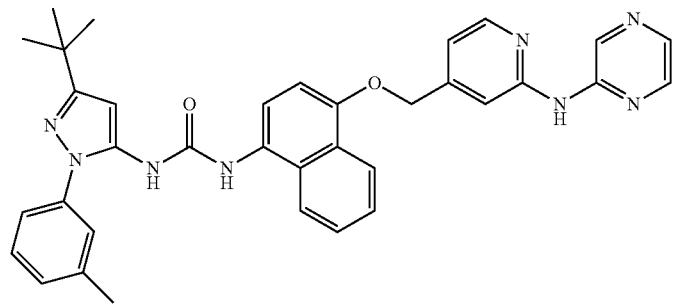

1-(3-(tert-butyl)-1-(m-tolyl)-1H-pyrazol-5-yl)-3-(4-((2-(pyrazin-2-ylamino)pyridin-4-yl)methoxy)naphthalen-1-yl)urea
Route code*: 1

R$^t$ 2.00 min (Method 1); m/z 599 (M + H)$^+$ (ES$^+$); $^1$H NMR (400 MHz, DMSO-d$_6$) δ: 1.28 (9H, s), 2.41 (3H, s), 5.36 (2H, s), 6.37 (1H, s), 7.05 (1H, d), 7.09 (1H, d), 7.26 (1H, d), 7.35-7.39 (2H, overlapping m), 7.44 (1H, t), 7.60-7.64 (3H, overlapping m), 7.95 (1H, m), 8.02 (1H, s), 8.09 (1H, d), 8.23 (1H, m), 8.31 (1H, d), 8.40 (1H, m), 8.61 (1H, s), 8.80 (1H, s), 9.08 (1H, s), 10.16 (1H, s).

Example 41:

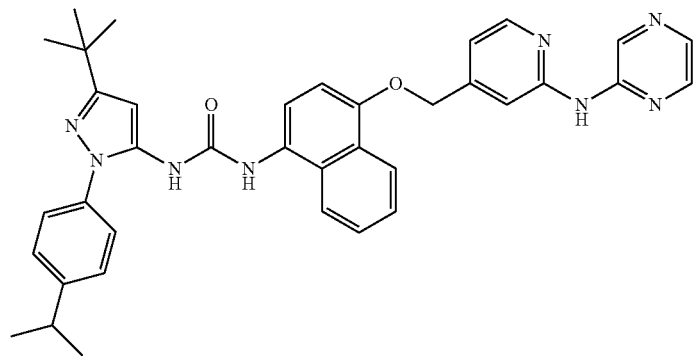

1-(3-(tert-butyl)-1-(4-isopropylphenyl)-1H-pyrazol-5-yl)-3-(4-((2-(pyrazin-2-ylamino)pyridin-4-yl)methoxy)naphthalen-1-yl)urea
Route code*: 1

R$^t$ 1.79 min (Method 1); m/z 627 (M + H)$^+$ (ES$^+$); $^1$H NMR (400 MHz, DMSO-d$_6$) δ: 1.26-1.28 (15H, overlapping m), 2.99 (1H, m), 5.37 (2H, s), 6.38 (1H, s), 7.06 (1H, d), 7.10 (1H, d), 7.44 (2H, m), 7.47 (2H, m), 7.62-7.67 (3H, overlapping m), 7.96 (1H, m), 8.02 (1H, s), 8.10 (1H, d), 8.22 (1H, m), 8.31 (1H, d), 8.40 (1H, m), 8.65 (1H, s), 8.83 (1H, s), 9.08 (1H, s), 10.16 (1H, s).

Example 42:

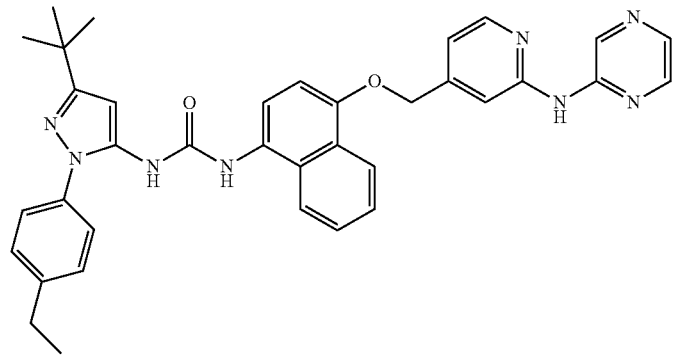

1-(3-(tert-butyl)-1-(4-ethylphenyl)-1H-pyrazol-5-yl)-3-(4-((2-(pyrazin-2-ylamino)pyridin-4-yl)methoxy)naphthalen-1-yl)urea
Route code*: 1

R$^t$ 2.60 min (Method 2); m/z 613 (M + H)$^+$ (ES$^+$); $^1$H NMR (400 MHz, DMSO-d$_6$) δ: 1.26-1.28 (12H, overlapping m), 2.70 (2H, q), 5.36 (2H, s), 6.37 (1H, s), 7.05 (1H, d), 7.09 (1H, d), 7.41 (2H, m), 7.46 (2H, m), 7.61-7.66 (3H, overlapping m), 7.96 (1H, m), 8.02 (1H, s), 8.09 (1H, s), 8.22 (1H, m), 8.32 (1H, d), 8.40 (1H, m), 8.62 (1H, s), 8.81 (1H, s), 9.09 (1H, s), 10.16 (1H, s).

Example 43:

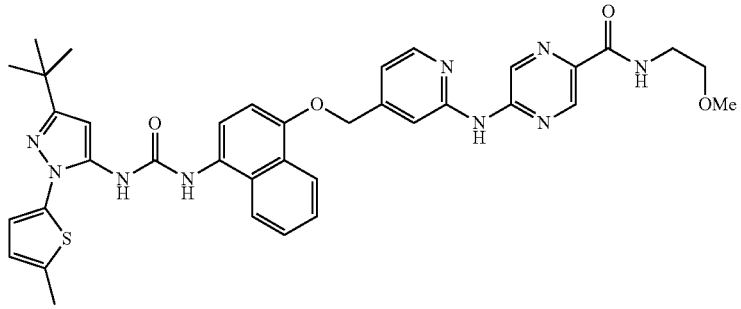

$R^t$ 2.22 min (Method 1); m/z 706 (M + H)$^+$ (ES$^+$); $^1$H NMR (400 MHz, DMSO-d$_6$) δ: 1.25 (9H, s), 2.49 (3H, s), 3.28 (3H, s), 3.48-3.45 (4H, m), 5.40 (2H, s), 6.35 (1H, s), 6.83 (1H, s), 7.03-7.08 (2H, overlapping m), 7.14 (1H, d), 7.57-7.62 (3H, overlapping m), 8.01 (1H, d), 8.11 (1H, s), 8.36 (1H, d), 8.42-8.47 (2H, overlapping m), 8.67 (1H, s), 8.76 (1H, s), 8.95 (1H, s), 9.06 (1H, s), 10.60 (1H, s).

5-((4-(((4-(3-(3-(tert-butyl)-1-(5-methylthiophen-2-yl)-1H-pyrazol-5-yl)ureido)naphthalen-1-yl)oxy)methyl)pyridin-2-yl)amino)-N-(2-methoxyethyl)pyrazine-2-carboxamide
Route code*: 2

Example 44:

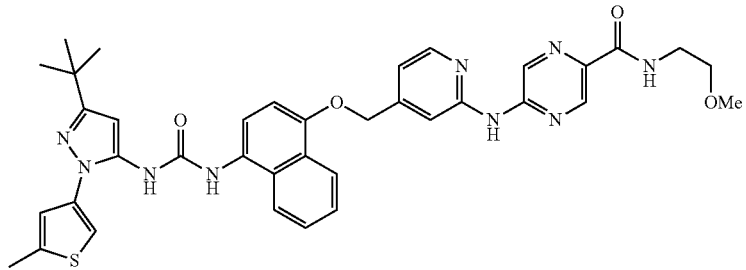

$R^t$ 2.20 min (Method 1); m/z 706 (M + H)$^+$ (ES$^+$); $^1$H NMR (400 MHz, DMSO-d$_6$) δ: 1.28 (9H, s), 3.28 (3H, s), 3.45-3.48 (4H, overlapping m), 5.40 (2H, s), 6.32 (1H, s), 7.08-7.04 (2H, overlapping m), 7.16 (1H, d), 7.40 (1H, s), 7.57-7.62 (3H, overlapping m), 8.01 (1H, d), 8.11 (1H, s), 8.36 (1H, d), 8.42-8.46 (2H, overlapping m), 8.62 (1H, s), 8.76 (1H, s), 8.88 (1H, s), 9.06 (1H, s), 10.60 (1H, s). 3H from CH$_3$—Ar assumed to be under DMSO.

5-((4-(((4-(3-(3-(tert-butyl)-1-(5-methylthiophen-3-yl)-1H-pyrazol-5-yl)ureido)naphthalen-1-yl)oxy)methyl)pyridin-2-yl)amino)-N-(2-methoxyethyl)pyrazine-2-carboxamide
Route code*: 2

Example 45:

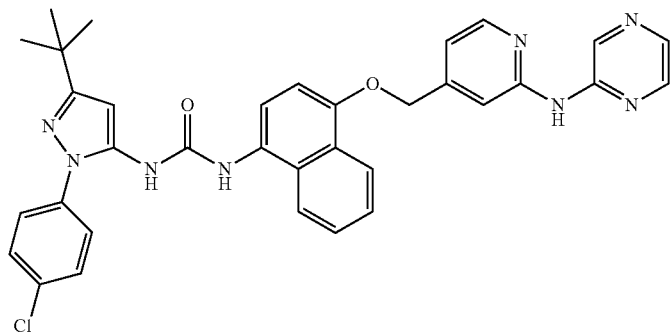

$R^t$ 2.00 min (Method 1); m/z 619 (M + H)$^+$ (ES$^+$); $^1$H NMR (400 MHz, DMSO-d$_6$) δ: 1.28 (9H, s), 5.36 (2H, s), 6.38 (1H, s), 7.05 (1H, d), 7.10 (1H, d), 7.60-7.64 (7H, overlapping m), 7.92 (1H, m), 8.02 (1H, s), 8.09 (1H, d), 8.22 (1H, m), 8.31 (1H, d), 8.40 (1H, m), 8.65 (1H, s), 8.77 (1H, s), 9.08 (1H, s), 10.16 (1H, s).

1-(3-(tert-butyl)-1-(4-chlorophenyl)-1H-pyrazol-5-yl)-3-(4-((2-(pyrazin-2-ylamino)pyridin-4-yl)methoxy)naphthalen-1-yl)urea
Route code*: 1

Example 46:

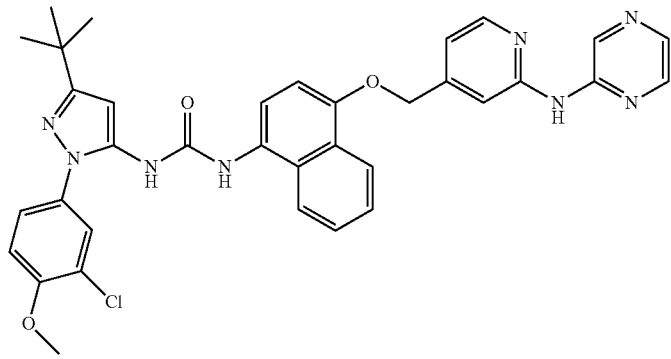

1-(3-(tert-butyl)-1-(3-chloro-4-methoxyphenyl)-1H-pyrazol-5-yl)-3-(4-((2-(pyrazin-2-ylamino)pyridin-4-yl)methoxy)naphthalen-1-yl)urea
Route code*: 1

$R^t$ 1.99 min (Method 1); m/z 649 (M + H)+ (ES+); 1H NMR (400 MHz, DMSO-$d_6$) δ: 1.28 (9H, s), 3.94 (3H, s), 5.36 (2H, s), 6.35 (1H, s), 7.04-7.13 (2H, overlapping m), 7.32 (1H, s), 7.34 (1H, s), 7.53 (1H, m), 7.58-7.68 (3H, overlapping m), 7.93 (1H, m), 8.01 (1H, s), 8.10 (1H, d), 8.22 (1H, m), 8.30 (1H, d), 8.42 (1H, m), 8.58 (1H, s), 8.77 (1H, s), 9.09 (1H, s), 10.16 (1H, s).

Example 47:

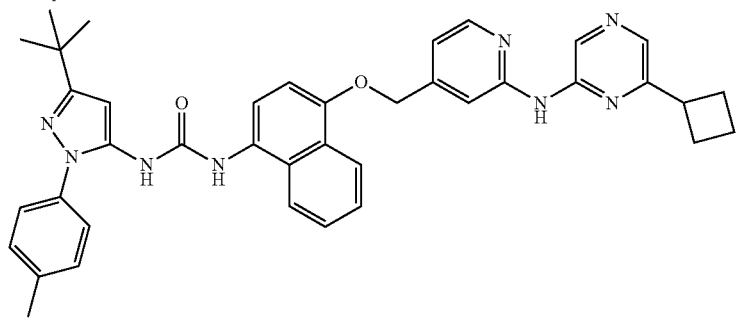

1-(3-(tert-butyl)-1-(p-tolyl)-1H-pyrazol-5-yl)-3-(4-((2-((6-cyclobutylpyrazin-2-yl)amino)pyridin-4-yl)methoxy)naphthalen-1-yl)urea.
Route code*: 1

$R^t$ 2.86 min (Method 2); m/z 653 (M + H)+ (ES+); 1H NMR (400 MHz, DMSO-$d_6$) δ: 1.28 (9H, s), 1.77 (1H, m), 1.93 (1H, m), 2.14-2.35 (4H, overlapping m), 2.40 (3H, s), 3.57 (1H, pentet), 5.35 (2H, s), 6.36 (1H, s), 7.02 (1H, d), 7.08 (1H, m), 7.37 (2H, m), 7.45 (2H, m), 7.55-7.67 (3H, overlapping m), 7.93 (1H, m), 7.97 (1H, s), 8.07 (1H, s), 8.31 (1H, dd), 8.37 (1H, m), 8.59 (1H, s), 8.80 (1H, s), 8.92 (1H, s), 10.09 (1H, s).

Example 48:

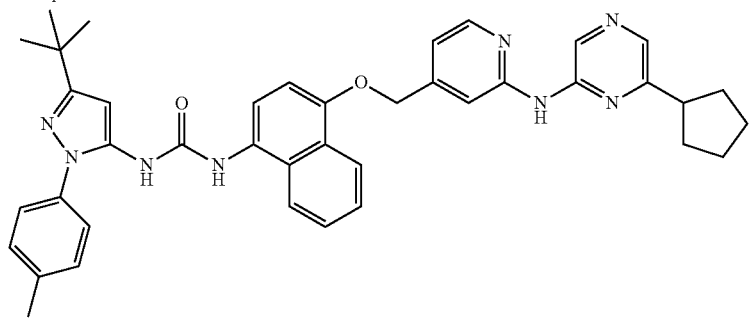

1-(3-(tert-butyl)-1-(p-tolyl)-1H-pyrazol-5-yl)-3-(4-((2-((6-cyclopentylpyrazin-2-yl)amino)pyridin-4-yl)methoxy)naphthalen-1-yl)urea.
Route code*: 1

$R^t$ 2.94 min (Method 2); m/z 667 (M + H)+ (space) (ES+); 1H NMR (400 MHz, DMSO-$d_6$) δ: 1.28 (9H, s), 1.46-1.58 (2H, overlapping m), 1.59-1.77 (4H, overlapping m), 1.87-2.02 (2H, overlapping m), 2.40 (3H, s), 3.08 (1H, pentet), 5.33 (2H, s), 6.36 (1H, s), 7.02 (1H, d), 7.08 (1H, d), 7.37 (2H, m), 7.45 (2H, m), 7.5-7.69 (3H, overlapping m), 7.94 (1H, d), 7.99 (1H, s), 8.09 (1H, s), 8.30 (1H, d), 8.34 (1H, m), 8.59 (1H, s), 8.80 (1H, s), 8.84 (1H, s), 10.04 (1H, s).

Example 49:

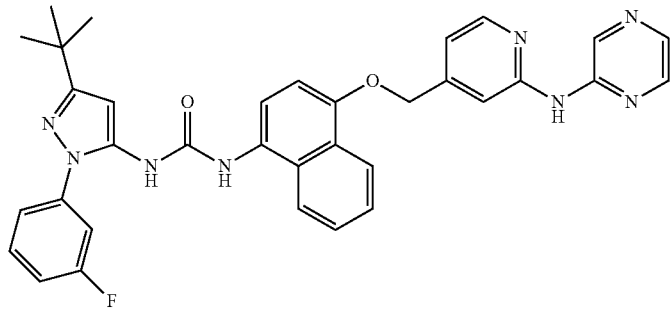

1-(3-(tert-butyl)-1-(3-fluorophenyl)-1H-pyrazol-5-yl)-3-(4-((2-(pyrazin-2-ylamino)
pyridin-4-yl)methoxy)naphthalen-1-yl)urea
Route code*: 1

$R^t$ 2.55 min (Method 2); m/z 603 (M + H)⁺ (ES⁺); ¹H NMR (400 MHz, DMSO-$d_6$) δ: 1.28 (9H, s), 5.36 (2H, s), 6.39 (1H, s), 7.04 (1H, d), 7.09 (1H, d), 7.28 (1H, t), 7.45-7.51 (2H, overlapping m), 7.58-7.68 (4H, overlapping m), 7.93 (1H, m), 8.01 (1H, s), 8.10 (1H, d), 8.21 (1H, m), 8.31 (1H, d), 8.40 (1H, m), 8.68 (1H, s), 8.81 (1H, s), 9.09 (1H, s), 10.16 (1H, s).

Example 50:

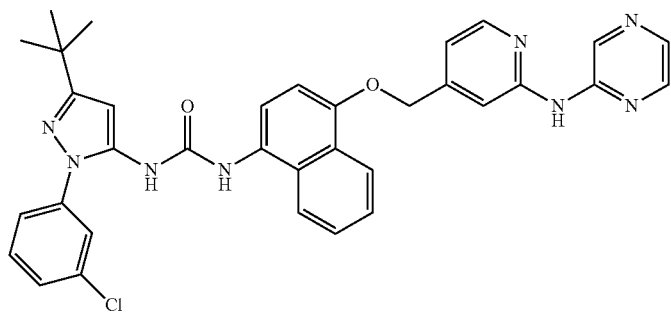

1-(3-(tert-butyl)-1-(3-chlorophenyl)-1H-pyrazol-5-yl)-3-(4-((2-(pyrazin-2-ylamino)
pyridin-4-yl)methoxy)naphthalen-1-yl)urea
Route code*: 1

$R^t$ 2.6 min (Method 2); m/z 619 (M + H)⁺ (ES⁺); ¹H NMR (400 MHz, DMSO-$d_6$) δ: 1.28 (9H, s), 5.36 (2H, s), 6.39 (1H, s), 7.04 (1H, d), 7.09 (1H, d), 7.48 (1H, m), 7.55-7.68 (6H, overlapping m), 7.93 (1H, m), 8.01 (1H, s), 8.10 (1H, d), 8.21 (1H, m), 8.30 (1H, d), 8.40 (1H, m), 8.67 (1H, s), 8.79 (1H, s), 9.08 (1H, s), 10.16 (1H, s).

Example 51:

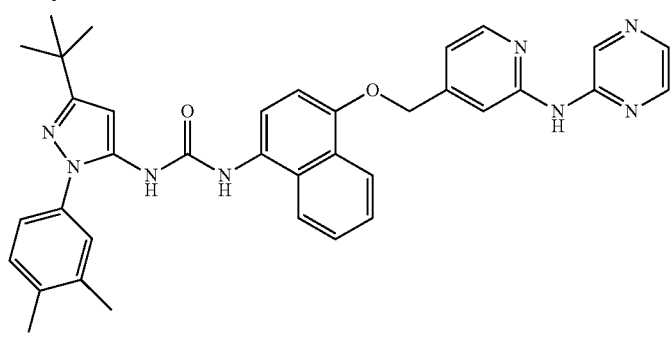

1-(3-(tert-butyl)-1-(3,4-dimethylphenyl)-1H-pyrazol-5-yl)-3-(4-((2-(pyrazin-2-ylamino)
pyridin-4-yl)methoxy)naphthalen-1-yl)urea
Route code*: 1

$R^t$ 2.6 min (Method 2); m/z 613 (M + H)⁺ (ES⁺); ¹H NMR (400 MHz, DMSO-$d_6$) δ: 1.28 (9H, s), 2.30 (3H, s), 2.31 (3H, s), 5.34 (2H, s), 6.35 (1H, s), 7.04 (1H, d), 7.09 (1H, d), 7.27 (1H, m), 7.30-7.33 (2H, overlapping m), 7.59-7.66 (3H, overlapping m), 7.93 (1H, m), 8.01 (1H, s), 8.10 (1H, d), 8.21 (1H, m), 8.31 (1 H, d), 8.40 (1H, m), 8.56 (1H, s), 8.80 (1H, s), 9.08 (1H, s), 10.16 (1H, s).

Example 52:

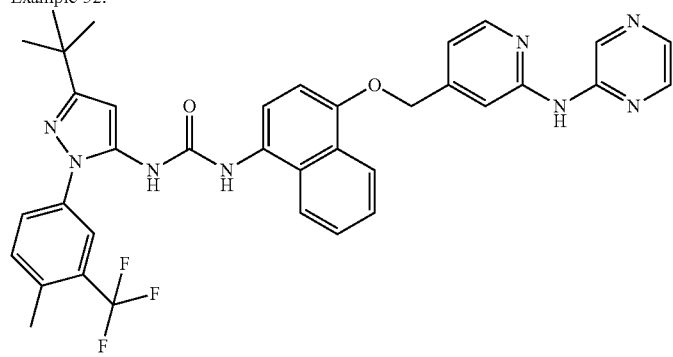

$R^t$ 2.7 min (Method 2); m/z 667 (M + H)+ (ES+); $^1$H NMR (400 MHz, DMSO-d$_6$) δ: 1.28 (9H, s), 5.36 (2H, s), 6.38 (1H, s), 7.04 (1H, d), 7.10 (1H, d), 7.55 (1H, d), 7.59-7.65 (3H, overlapping m), 7.79 (1H, d), 7.85-7.90 (2H, overlapping m), 8.01 (1H, s), 8.09 (1H, d), 8.21 (1H, m), 8.30 (1H, d), 8.39 (1H, m), 8.65 (1H, s), 8.76 (1H, s), 9.08 (1H, s), 10.16 (1H, s). 3H from CH$_3$—Ar assumed to be under DMSO.

1-(3-(tert-butyl)-1-(4-methyl-3-(trifluoromethyl)phenyl)-1H-pyrazol-5-yl)-3-(4-((2-(pyrazin-2-ylamino)pyridin-4-yl)methoxy)naphthalen-1-yl)urea
Route code*: 1

*Route codes:
1: compound (I) (which might optionally be protected) prepared by reaction of compound (II) with compound (III); compound (III) prepared by deprotection of compound (IX); compound (IX) prepared by reaction of compound (XVI) with compound (XIII). This route is illustrated in the synthesis of Example 2.
2: compound (I) (which might optionally be protected) prepared by reaction of compound (II) with compound (III); compound (III) prepared by reduction of compound (VIII); compound (VIII) prepared by reaction of compound (XI) with compound (V) This route is illustrated in the synthesis of Example 5.
3: compound (I) prepared by reaction of compound (II) with compound (III); compound (III) prepared by reduction of compound (VIII); compound (VIII) prepared by reaction of compound (XII) with compound (XIII). This route is illustrated in the synthesis of Example 1.
4: compound (I) prepared from a compound of formula (VI); compound of formula (VI) prepared by reaction of compound (II) with compound (III'). Compound (III') prepared by a process analogous to that for the preparation of compound (III) in route code 3 with the —COOH group protected as the methyl ester for the nitro reduction step. This route is illustrated in the synthesis of Example 7.
5: compound (I) prepared by reaction of compound (II) with compound (III); compound (III) prepared by reduction of compound (VIII); compound (VIII) prepared from a compound of formula (XIVa/b); compound of formula (XIVa/b) prepared by hydrolysis of the corresponding methyl ester; methyl ester prepared by a process analogous to that for the preparation of compound (VIII) in route code 2. This route is illustrated in the synthesis of Example 8.

Example 53: 5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-hydroxyethyl)pyrazine-2-carboxamide Intermediate EE: Ethyl 5-((4-(((4-((tert-butoxycarbonyl)amino)naphthalen-1-yl)oxy)methyl)pyridin-2-yl)amino)pyrazine-2-carboxylate

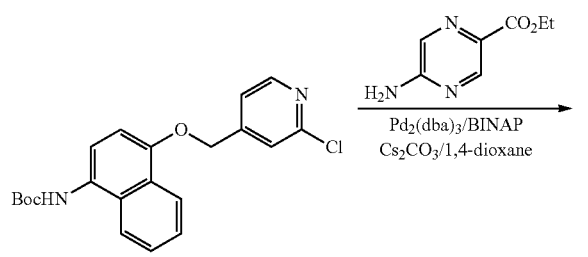

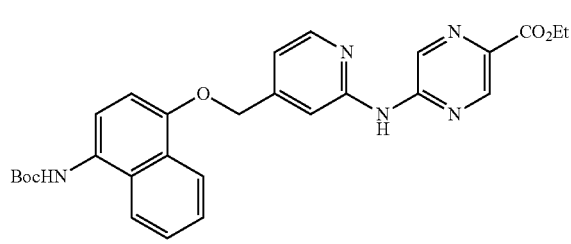

To a suspension of tert-butyl (4-((2-chloropyridin-4-yl)methoxy)naphthalen-1-yl)carbamate (12.5 g, 32.5 mmol), ethyl 5-aminopyrazine-2-carboxylate (6.52 g, 39.0 mmol), Pd$_2$(dba)$_3$ (1.487 g, 1.624 mmol) and BINAP (2.022 g, 3.25 mmol) in 1,4-dioxane (55 mL, 32.5 mmol) at room temperature and under nitrogen was added cesium carbonate (15.87 g, 48.7 mmol).

The suspension was sonicated for 5 min and degassed for 10 min before being stirred at 90° C. overnight. The reaction mixture was cooled to room temperature, and diluted with a solution of 10% MeOH in DCM (750 mL), methanol (100 mL) and 1,4-dioxane (100 mL) before being filtered through a pad of Celite. The filtrate was concentrated in vacuo to give a residue which was suspended in EtOH (500 mL) before being stirred for 16 h and the solid collected via filtration. The solid was dried in a vacuum oven at 40° C. for 3 h, then slurried in diethyl ether (30 mL) for 10 min and filtered to afford the subtitle compound 5-((4-(((4-((tert-butoxycarbonyl)amino)naphthalen-1-yl)oxy)methyl)pyridin-2-yl)amino)pyrazine-2-carboxylate as a light yellow solid (7 g, 37%); $R^t$ 2.62 min (Method 1); m/z 516 (M+H)+ (ES+).

Intermediate FF: 5-((4-(((4-((tert-Butoxycarbonyl)amino)naphthalen-1-yl)oxy)methyl) pyridin-2-yl)amino)pyrazine-2-carboxylic acid

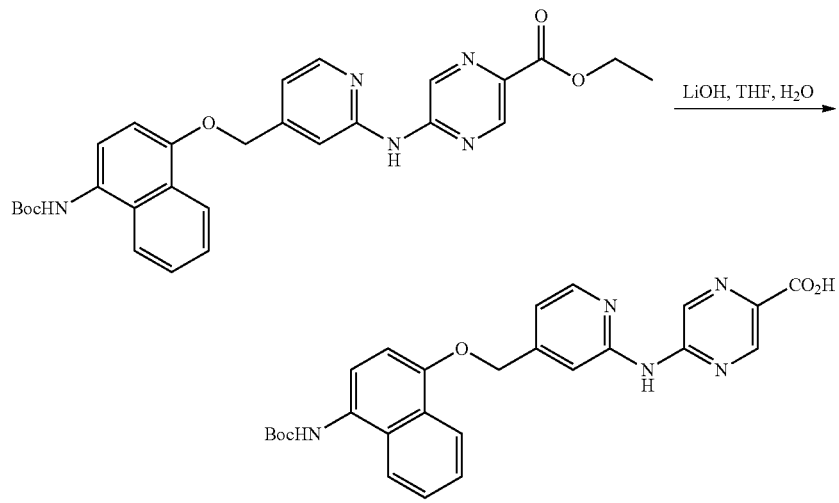

A solution of lithium hydroxide (1.463 g, 61.1 mmol) in water (100 mL) was added to a suspension of ethyl 5-((4-(((4-((tert-butoxycarbonyl)amino)naphthalen-1-yl)oxy)methyl) pyridin-2-yl)amino)pyrazine-2-carboxylate (Intermediate EE) (7 g, 13.58 mmol) in tetrahydrofuran (100 mL). The reaction mixture was heated at 40° C. for 4 h then stirred at room temperature overnight. The organic layer was evaporated, and the residual solid material isolated by filtration, washing with additional water. This solid was then taken up in water and the mixture acidified with 1M HCl. The resulting solid was isolated by filtration, washing with water (200 mL) and hexane (200 mL), and dried under vacuum at 40° C. to afford the subtitle compound 5-((4-(((4-((tert-butoxycarbonyl)amino)naphthalen-1-yl)oxy)methyl)pyridin-2-yl)amino)pyrazine-2-carboxylic acid as a light yellow solid (5 g, 68%); $R^t$ 1.91 min (Method 1); m/z 488 (M+H)$^+$ (ES$^+$).

Intermediate GG: tert-Butyl (4-((2-((5-((2-hydroxyethyl)carbamoyl)pyrazin-2-yl)amino)pyridin-4-yl)methoxy)naphthalen-1-yl)carbamate

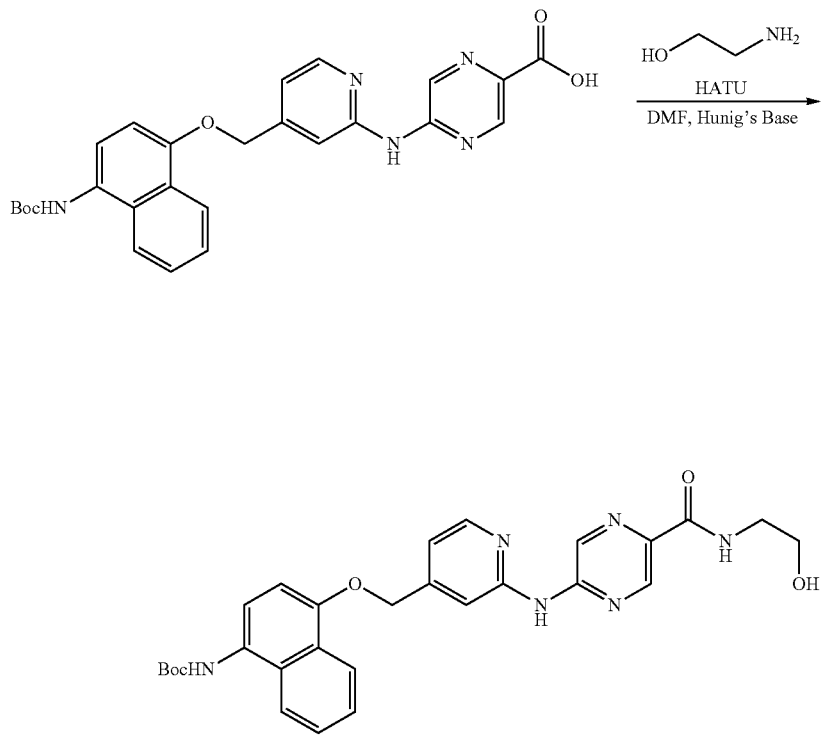

2-(3H-[1,2,3]Triazolo[4,5-b]pyridin-3-yl)-1,1,3,3-tetramethylisouronium hexafluorophosphate (V) (5.62 g, 14.77 mmol) was added to a suspension of 5-((4-(((4-((tert-butoxycarbonyl)amino)naphthalen-1-yl)oxy)methyl)pyridin-2-yl)amino)pyrazine-2-carboxylic acid (Intermediate FF) (4.8 g, 9.85 mmol) in dry DMF (144 mL, 1861 mmol). After 20 min of stirring at room temperature N-ethyl-N-isopropylpropan-2-amine (5.14 mL, 29.5 mmol) was added followed by 2-aminoethanol (1.783 mL, 29.5 mmol). The reaction mixture was heated to 40 t° overnight, then cooled to 0 w and saturated aqueous NaHCO$_3$ (350 mL) was added. The resultant slurry was stirred for 20 min, whereafter the solid was collected by filtration under reduced pressure and washed with water (100 mL). The solid was dried under vacuum overnight to afford the subtitle compound tert-butyl (4-((2-((5-((2-hydroxyethyl)carbamoyl)pyrazin-2-yl)amino)pyridin-4-yl)methoxy)naphthalen-1-yl)carbamate as a yellow solid (9 g, 153% yield), which was used in the next reaction without further purification; R$^t$ 1.73 min (Method 1); m/z 531 (M+H)$^+$ (ES$^+$).

Intermediate HH: 5-((4-(((4-Aminonaphthalen-1-yl)oxy)methyl)pyridin-2-yl)amino)-N-(2-hydroxyethyl)pyrazine-2-carboxamide

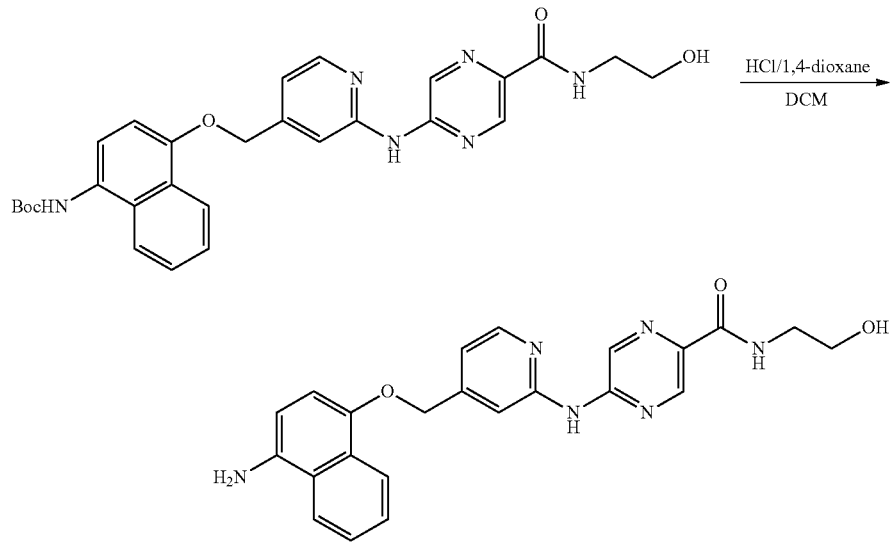

A suspension of tert-butyl (4-((2-((5-((2-hydroxyethyl)carbamoyl)pyrazin-2-yl)amino)pyridin-4-yl)methoxy)naphthalen-1-yl)carbamate (Intermediate GG) (5.23 g, 9.85 mmol) in DCM (44 mL) was treated with hydrogen chloride in 1,4-dioxane (49.3 mL, 197 mmol). The reaction mixture was allowed to stir at room temperature for 1 h. Saturated aqueous NaHCO$_3$ (250 mL) was added slowly and the quenched mixture was allowed to stir at room temperature overnight. The resultant solid was filtered and washed with water (2×200 mL), and dried under vacuum at 40° C. overnight to afford the subtitle compound 5-((4-(((4-aminonaphthalen-1-yl)oxy)methyl)pyridin-2-yl)amino)-N-(2-hydroxyethyl)pyrazine-2-carboxamide as a yellow solid (2.1 g, 48% yield); R$^t$ 1.00 min (Method 1); m/z 431 (M+H)$^+$ (ES$^+$).

5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-hydroxyethyl)pyrazine-2-carboxamide

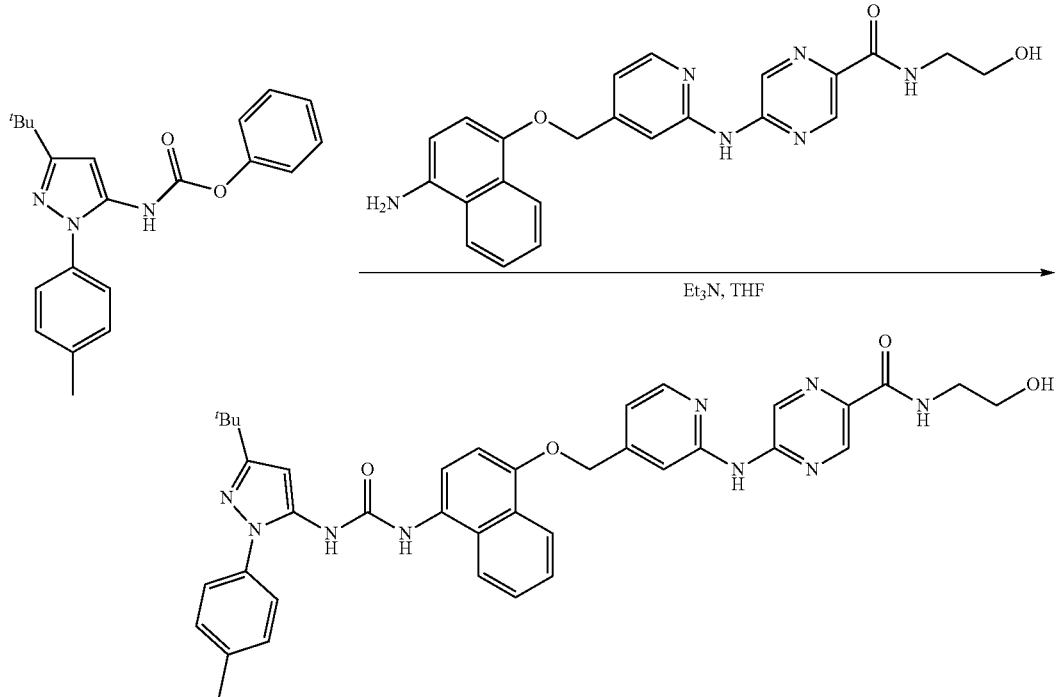

To a stirred slurry of 5-((4-(((4-aminonaphthalen-1-yl)oxy)methyl)pyridin-2-yl)amino)-N-(2-hydroxyethyl)pyrazine-2-carboxamide (Intermediate HH) (2 g, 4.65 mmol) in THF (57.1 mL) at room temperature under a nitrogen atmosphere was added phenyl (3-(tert-butyl)-1-(p-tolyl)-1H-pyrazol-5-yl)carbamate (1.786 g, 5.11 mmol). The reaction mixture was stirred for 5 min, then Et₃N (0.648 mL, 4.65 mmol) was added over 2 min and the reaction mixture stirred at 40° C. for 20 min. THF (50 mL) was then added and stirring continued overnight. Solvent was removed in vacuo and the solid was suspended in 10% MeOH, and adsorbed onto silica. The crude product was purified by chromatography on silica gel (80 g column, gradient 0-30% MeOH in DCM) to afford the title compound 5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-hydroxyethyl)pyrazine-2-carboxamide as a dark orange solid (2.5 g, 74%); R' 1.94 min (Method 1); m/z 686 (M+H)⁺ (ES⁺); ¹H NMR δ: 1.28 (9H, s), 2.40 (3H, s), 3.39 (2H, m), 3.54 (2H, m), 4.80 (1H, t), 5.39 (2H, s), 6.37 (1H, s), 7.05 (1H, d), 7.16 (1H, d), 7.36 (2H, m), 7.45 (2H, m), 7.56-7.68 (3H, overlapping m), 7.96 (1H, m), 8.10 (1H, s), 8.35 (1H, d), 8.39-8.47 (2H, overlapping m), 8.63 (1H, s), 8.77 (1H, d), 8.84 (1H, s), 9.06 (1H, d), 10.59 (1H, s).

Example 54: (S)-5-((4-(((4-(3-(3-(tert-Butyl)-1-(p-tolyl)-1H-pyrazol-5-I)ureido)naphthalen-1-yl)oxy)methyl)pyridin-2-yl)amino)-N-(2-(3-methoxypiperidin-1-yl)ethyl)pyrazine-2-carboxamide Intermediate II: N-(2-Bromoethyl)-5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamide

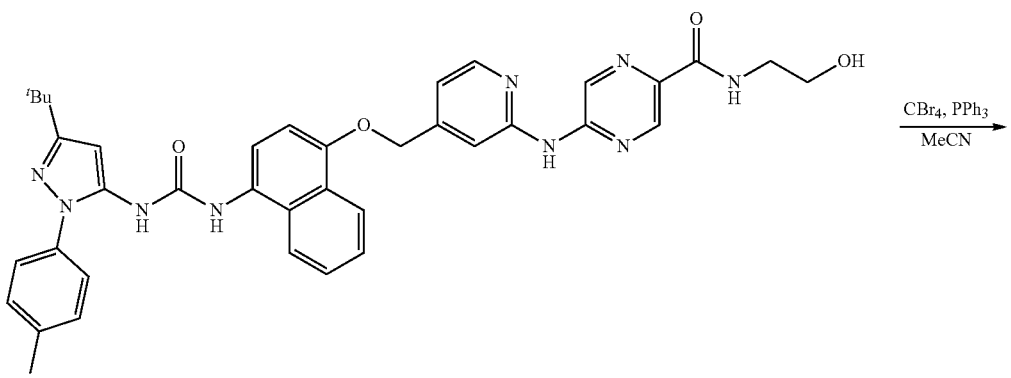

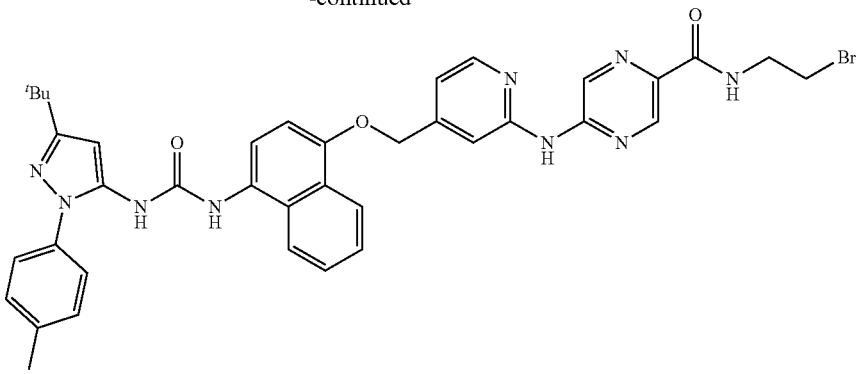

To a well stirred slurry of 5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-hydroxyethyl)pyrazine-2-carboxamide (Example 53) (0.254 g, 0.370 mmol) in anhydrous MeCN (12.7 mL) at room temperature under a nitrogen atmosphere were added triphenylphosphine (0.291 g, 1.111 mmol) and carbon tetrabromide (0.368 g, 1.111 mmol). The reaction mixture was stirred overnight. The resultant precipitate was isolated by filtration, washing with MeCN (50 mL), then dissolved in DMF and adsorbed onto silica gel. The crude product was purified by chromatography on silica gel (12 g column, gradient 0-15% MeOH in DCM) to afford the subtitle compound N-(2-bromoethyl)-5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamide as a pale yellow solid (0.1 g, 35%); R$^r$ 2.37 min (Method 1); m/z 748/750 (M+H)$^+$ (ES$^+$); $^1$H NMR (400 MHz, DMSO-d$_6$) δ 1.27 (9H, s), 2.39 (3H, s), 3.54-3.72 (4H, overlapping m), 5.40 (2H, s), 6.35 (1H, s), 7.04 (1H, d), 7.19 (1H, d), 7.36 (2H, m), 7.44 (2H, m), 7.56-7.69 (3H, overlapping m), 7.95 (1H, m), 8.08 (1H, s), 8.36 (1H, d), 8.41 (1H, m), 8.60 (1H, s), 8.77 (1H, d), 8.79-8.85 (2H, overlapping m), 9.02 (1H, d), 10.72 (1H, s).

(S)-5-((4-(((4-(3-(3-(tert-Butyl)-1-(p-tolyl)-1H-pyrazol-5-yl)ureido)naphthalen-1-yl)oxy)methyl)pyridin-2-yl)amino)-N-(2-(3-methoxypiperidin-1-yl)ethyl)pyrazine-2-carboxamide

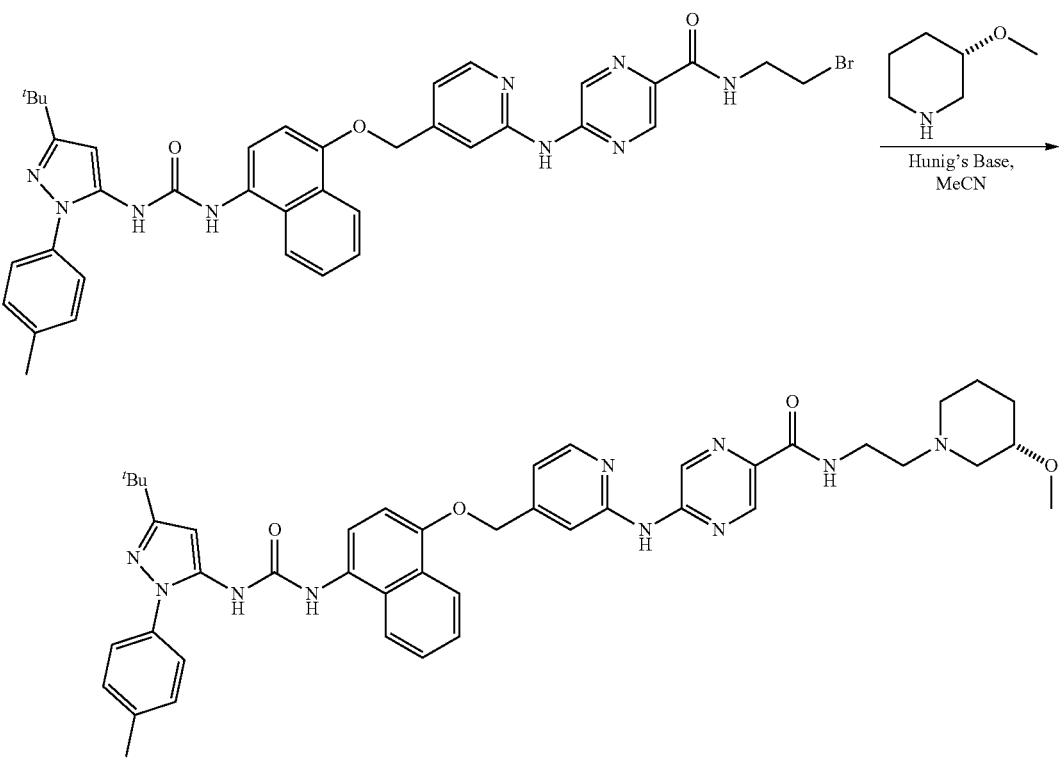

To a stirred solution of (S)-3-methoxypiperidine hydrochloride (0.608 g, 4.01 mmol) in anhydrous MeCN (15.0 mL) at room temperature under a nitrogen atmosphere was added Hunig's base (0.525 mL, 3.01 mmol) and the solution was stirred for 1 h before N-(2-bromoethyl)-5-((4-(((4-(3-

(3-(tert-butyl)-1-(p-tolyl)-1H-pyrazol-5-yl)ureido)naphthalen-1-yl)oxy)methyl)pyridin-2-yl)amino)pyrazine-2-carboxamide (0.150 g, 0.200 mmol) was added in a single portion. The stirring was continued for 2 days and then the resultant precipitate was isolated by filtration, washing with MeCN (10 mL). The crude product was purified by preparative HPLC (Waters, Acidic (0.1% Formic acid), Acidic, Waters X-Select Prep-C18, 5 μm, 19×50 mm column, 20-50% MeCN in Water) to afford the title compound (S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-methoxypiperidin-1-yl)ethyl)pyrazine-2-carboxamide as a pale orange solid (28 mg, 18%); R$^t$ 1.72 min (Method 1); m/z 783 (M+H)$^+$ (ES$^+$); $^1$H NMR δ: 1.00-1.24 (3H, overlapping m), 1.28 (9H, s), 1.42 (1H, m), 1.66 (1H, m), 1.81-2.04 (3H, overlapping m), 2.40 (3H, s), 2.69 (1H, m), 2.98 (1H, d), 3.20 (1H, dq), 3.26 (3H, s), 3.42 (2H, q), 5.39 (2H, s), 6.36 (1H, s), 7.05 (1H, d), 7.17 (1H, dd), 7.36 (2H, m), 7.45 (2H, m), 7.57-7.69 (3H, overlapping m), 7.95 (1H, m), 8.10 (1H, s), 8.35 (1H, m), 8.39-8.47 (2H, overlapping m), 8.64 (1H, s), 8.76 (1H, d), 8.84 (1H, s), 9.06 (1H, d), 10.59 (1H, s).

Example 55: 1-(3-(tert-Butyl)-1-(p-tolyl)-1H-pyrazol-5-yl)-3-(4-((2-((6-(pyrrolidin-1-yl)pyrazin-2-yl)amino)pyridin-4-yl)methoxy)naphthalen-1-yl)urea Intermediate JJ: 4-(((4-Aminonaphthalen-1-yl)oxy)methyl)pyridin-2-amine

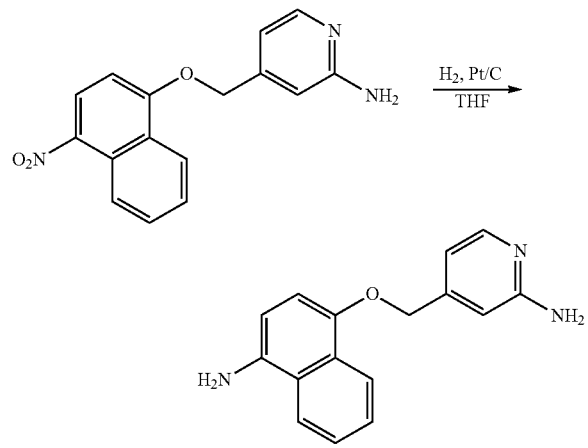

A solution of 4-(((4-nitronaphthalen-1-yl)oxy)methyl)pyridin-2-amine (3 g, 3.39 mmol) in THF (20 mL) and AcOH (few drops) was hydrogenated in the H-Cube (10% Pd/C, 55×4 mm, Full hydrogen, 45° C., 1 mL/min). The reaction mixture was concentrated in vacuo to afford the subtitle compound 4-(((4-aminonaphthalen-1-yl)oxy)methyl)pyridin-2-amine as a black solid (2.3 g, 71% yield); R$^t$ 0.35 min (Method 1); m/z 266 (M+H)$^+$ (ES$^+$).

Intermediate KK: 1-(4-((2-Aminopyridin-4-yl)methoxy)naphthalen-1-yl)-3-(3-(tert-butyl)-1-(p-tolyl)-1H-pyrazol-5-yl)urea

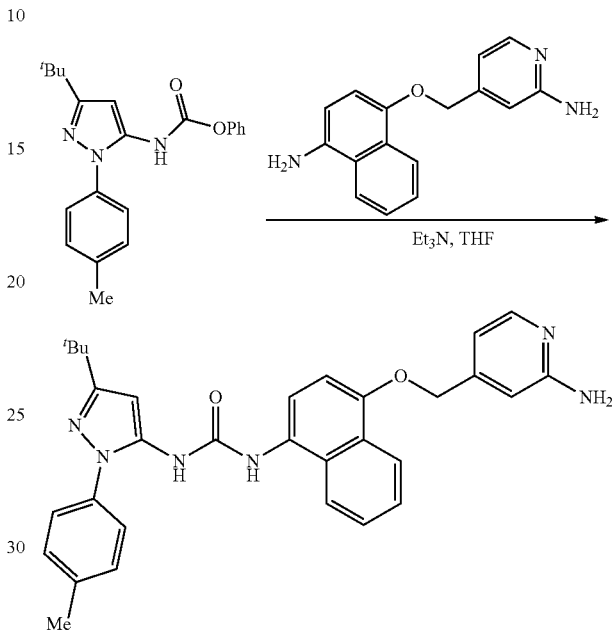

To a stirred solution of 4-(((4-aminonaphthalen-1-yl)oxy)methyl)pyridin-2-amine (Intermediate JJ) (2.3 g, 8.67 mmol) in THF (40 mL) was added phenyl (3-(tert-butyl)-1-(p-tolyl)-1H-pyrazol-5-yl)carbamate (3.33 g, 9.54 mmol) and triethylamine (0.224 mL, 1.734 mmol). The reaction mixture was stirred at 40° C. for 1 h before being allowed to cool and stirred at room temperature overnight. The reaction mixture was absorbed onto silica and purified by chromatography on silica gel (80 g column, gradient 0-10% MeOH in DCM) to afford the subtitle compound 1-(4-((2-aminopyridin-4-yl)methoxy)naphthalen-1-yl)-3-(3-(tert-butyl)-1-(p-tolyl)-1H-pyrazol-5-yl)urea as a black solid (441 mg, 9% yield); R$^t$ 1.81 min (Method 1); m/z 521 (M+H)$^+$ (ES+).

1-(3-(tert-Butyl)-1-(p-tolyl)-1H-pyrazol-5-yl)-3-(4-((2-((6-(pyrrolidin-1-yl)pyrazin-2-yl)amino)pyridin-4-yl)methoxy)naphthalen-1-yl)urea

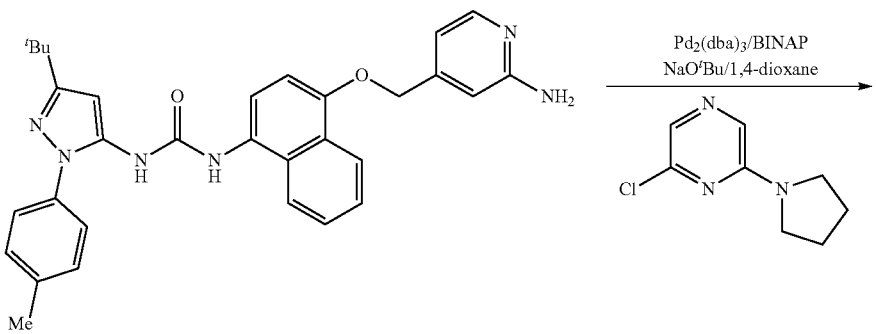

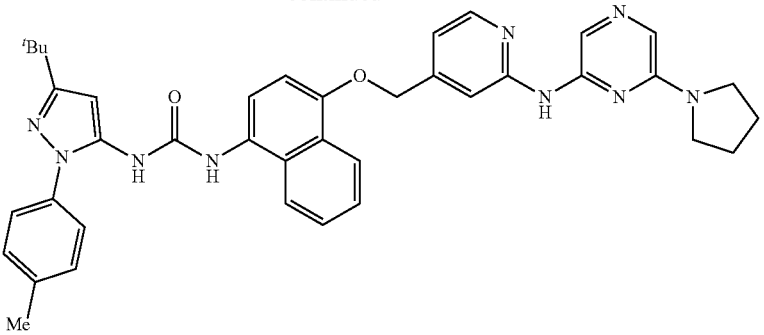

A mixture of 1-(4-((2-aminopyridin-4-yl)methoxy)naphthalen-1-yl)-3-(3-(tert-butyl)-1-(p-tolyl)-1H-pyrazol-5-yl)urea (150 mg, 0.288 mmol), 2-chloro-6-(pyrrolidin-1-yl)pyrazine (52.9 mg, 0.288 mmol), Pd$_2$(dba)$_3$ (13.19 mg, 0.014 mmol), BINAP (17.94 mg, 0.029 mmol) and sodium tert-butoxide (41.5 mg, 0.432 mmol) was flushed with nitrogen and suspended in 1,4-dioxane (2.1 mL). The resulting mixture was sonicated for 2 min, degassed with nitrogen for 5 min and heated at 90° C. for 3 h. The reaction mixture was allowed to cool to room temperature, diluted with 2 mL 10% MeOH in DCM, sonicated for 1 min, and filtered through Celite, washing with 10% MeOH in DCM (2×4 mL). The filtrate was concentrated in vacuo, and the crude product purified first by preparative HPLC (Waters, Acidic (0.1% Formic acid), Acidic, Waters X-Select Prep-C18, 5 μm, 19×50 mm column, 30-60% MeCN in Water), then by filtering through a column of with 0.7M ammonia in MeOH (25 mL), to give the title compound 1-(3-(tert-butyl)-1-(p-tolyl)-1H-pyrazol-5-yl)-3-(4-((2-((6-(pyrrolidin-1-yl)pyrazin-2-yl)amino)pyridin-4-yl)methoxy)naphthalen-1-yl)urea as a beige solid (36 mg, 18% yield); R$^r$ 2.12 min (Method 1); m/z 668 (M+H)$^+$ (ES$^+$); $^1$H NMR δ: 1.26 (9H, s), 1.70 (4H, m), 2.38 (3H, s), 5.32 (2H, s), 6.34 (1H, s), 6.97 (1H, d), 7.02 (1H, d), 7.32-7.36 (3H, overlapping m), 7.43 (2H, m), 7.53-7.63 (3H, overlapping m), 7.92 (1H, m), 7.98 (1H, s), 8.22-8.26 (2H, overlapping m), 8.29 (1H, m), 8.60 (1H, br s), 8.80 (1H, br s), 9.64 (1H, s), Missing (CH$_2$)$_2$ resonance presumed 3.31 ppm (4H, s) obscured by H$_2$O peak 3.29-3.34 ppm.

Examples 56-288

The following examples were prepared using methods analogous to those described above for the preparation of Examples 1-10 and 53-55:

Example 56:

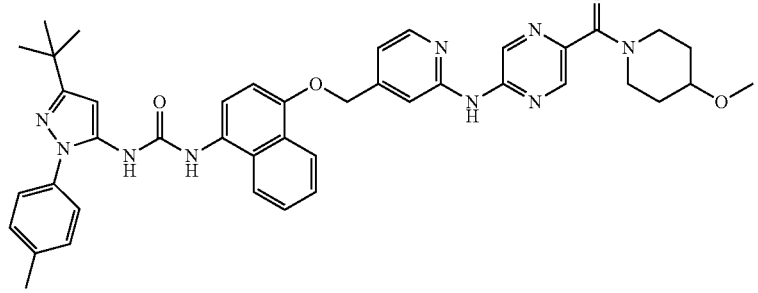

1-(3-(tert-butyl)-1-(p-tolyl)-1H-pyrazol-5-yl)-3-(4-((2-((5-(4-methoxypiperidine-1-carbonyl)pyrazin-2-yl)amino)pyridin-4-yl)methoxy)naphthalen-1-yl)urea
Route code*: 2

R$^r$ 2.15 min (Method 1); m/z 740 (M + H)$^+$ (ES$^+$); $^1$H NMR (400 MHz, DMSO-d$_6$) δ: 1.27 (9H, s), 1.46 (2H, m), 1.88 (2H, m), 2.39 (3H, s), 3.27 (3H, s), 3.29-3.50 (3H, overlapping m), 3.77 (1H, m), 3.93 (1H, m), 5.38 (2H, s), 6.35 (1H, s), 7.04 (1H, d), 7.15 (1H, d), 7.36 (2H, m), 7.44 (2H, m), 7.57-7.66 (3H, overlapping m), 7.92-8.00 (2H, overlapping m), 8.34 (1H, d), 8.39 (1H, m), 8.46 (1H, s), 8.61 (1H, s), 8.82 (1H, s), 9.05 (1H, s), 10.54 (1H, s).

Example 57:

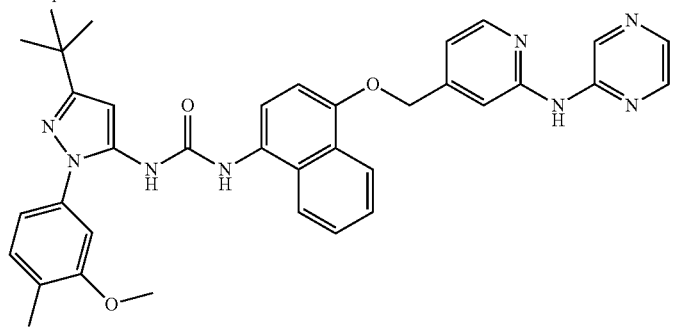

1-(3-(tert-butyl)-1-(3-methoxy-4-methylphenyl)-1H-pyrazol-5-yl)-3-(4-((2-(pyrazin-2-ylamino)pyridin-4-yl)methoxy)naphthalen-1-yl)urea.
Route code*: 1

Rt 2.57 min (Method 2); m/z 629 (M + H)$^+$ (ES$^+$); $^1$H NMR (400 MHz, DMSO-d$_6$) δ: 1.28 (9H, s), 2.22 (3H, s), 3.84 (3H, s), 5.35 (2H, s), 6.37 (1H, s), 7.00-7.13 (4H, overlapping m), 7.30 (1H, d), 7.57-7.68 (3H, overlapping m), 7.94 (1H, m), 8.01 (1H, s), 8.09 (1H, d), 8.21 (1H, dd), 8.30 (1H, d), 8.40 (1H, m), 8.60 (1H, s), 8.83 (1H, s), 9.08 (1H, d), 10.15 (1H, s).

Example 58:

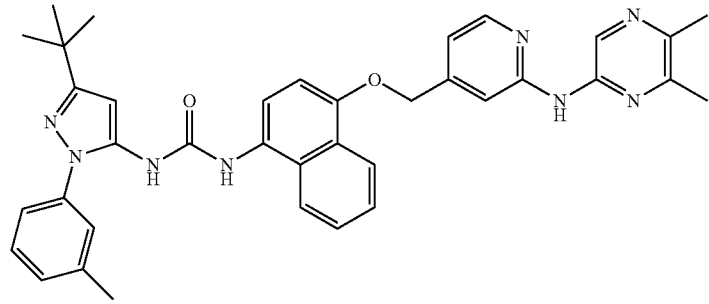

1-(3-(tert-butyl)-1-(m-tolyl)-1H-pyrazol-5-yl)-3-(4-((2-((5,6-dimethylpyrazin-2-yl)amino)pyridin-4-yl)methoxy)naphthalen-1-yl)urea.
Route code*: 1

$R^t$ 2.69 min (Method 2); m/z 627 (M + H)⁺ (ES⁺); ¹H NMR (400 MHz, DMSO-$d_6$) δ: 1.27 (9H, s), 2.36 (3H, s), 2.38 (3H, s), 2.40 (3H, s), 5.33 (2H, s), 6.36 (1H, s), 6.99-7.04 (2H, overlapping m), 7.25 (1H, d), 7.33-7.46 (3H, overlapping m), 7.56-7.65 (3H, overlapping m), 7.87 (1H, s), 7.93 (1H, m), 8.25 (1H, d), 8.40 (1H, m), 8.60 (1H, s), 8.79 (1H, s), 8.88 (1H, s), 9.88 (1H, s).

Example 59:

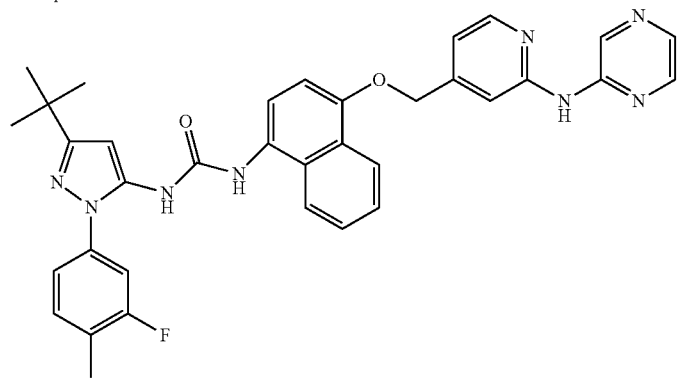

1-(3-(tert-butyl)-1-(3-fluoro-4-methylphenyl)-1H-pyrazol-5-yl)-3-(4-((2-(pyrazin-2-ylamino)pyridin-4-yl)methoxy)naphthalen-1-yl)urea
Route code*: 1

$R^t$ 2.02 min (Method 1); m/z 309 (M + H)²⁺ (ES⁺); ¹H NMR (400 MHz, DMSO-$d_6$) δ: 1.27 (9H, s), 2.31 (3H, s), 5.36 (2H, s), 6.36 (1H, s), 7.04 (1H, d), 7.08 (1H, d), 7.30-7.51 (3H, overlapping m), 7.56-7.65 (3H, overlapping m), 7.94 (1H, m), 8.01 (1H, s), 8.09 (1H, m), 8.21 (1H, d), 8.30 (1H, d), 8.40 (1H, m), 8.63 (1H, s), 8.79 (1H, s), 9.08 (1H, s), 10.15 (1H, s).

Example 60:

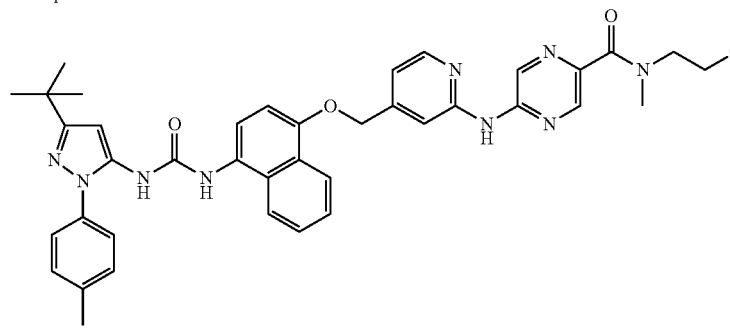

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methoxyethyl)-N-methylpyrazine-2-carboxamide
Route code*: 2

$R^t$ 1.88 min (Method 1); m/z 714 (M + H)⁺ (ES⁺); ¹H NMR (400 MHz, DMSO-$d_6$) δ: 1.27 (9H, s), 2.40 (3H, s), 3.03 (2H, s), 3.13 (1H, s), 3.16 (2H, s), 3.30 (1H, s), 3.55 (2H, m), 3.67 (2H, m), 5.39 (2H, s), 6.36 (1H, s), 7.04 (1H, d), 7.14 (1H, d), 7.35 (2H, m), 7.44 (2H, m), 7.59-7.66 (3H, overlapping, m), 7.95 (1H, m), 8.10 (1H, s), 8.34 (1H, d), 8.40 (1H, m), 8.45 (1H, m), 8.59 (1 H, s), 8.80 (1H, d), 9.09 (1H, d), 10.47 (1H, s).

Example 61:

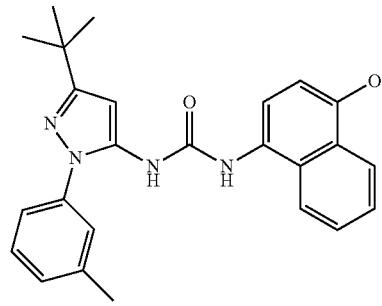

1-(3-(tert-butyl)-1-(m-tolyl)-1H-pyrazol-5-yl)-3-(4-((2-((5-(hydroxymethyl)pyrazin-2-yl)amino)pyridin-4-yl)methoxy)naphthalen-1-yl)urea.
Route code*: 1

Rt 2.36 min (Method 2); m/z 629 (M + H)+ (ES+); $^1$H NMR (400 MHz, DMSO-$d_6$) δ: 1.27 (9H, s), 2.41 (3H, s), 4.54 (2H, s), 5.35 (2H, s), 6.36 (1H, s), 7.01-7.08 (2H, overlapping m), 7.25 (1H, d), 7.32-7.47 (3H, overlapping m), 7.58-7.65 (3H, overlapping m), 7.93 (1H, m), 7.97 (1H, s), 8.26 (1H, s), 8.29 (1H, d), 8.40 (1H, m), 8.61 (1H, s), 8.80 (1H, s), 9.02 (1H, s), 10.11 (1H, s).

Example 62:

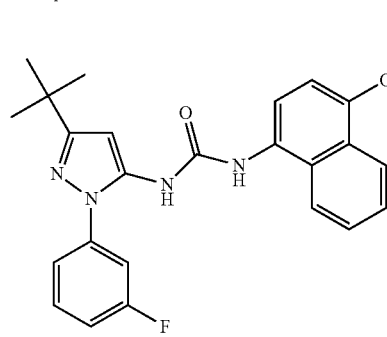

1-(3-(tert-butyl)-1-(3-fluorophenyl)-1H-pyrazol-5-yl)-3-(4-((2-((6-ethylpyrazin-2-yl)amino)pyridin-4-yl)methoxy)naphthalen-1-yl)urea
Route code*: 1

R$^t$ 2.10 min (Method 1); m/z 316 (M + 2H)$^{2+}$ (ES+); $^1$H NMR (400 MHz, DMSO-$d_6$) δ: 1.18 (3H, t), 1.28 (9H, s), 2.62 (2H, q), 5.35 (2H, s), 6.38 (1H, s), 7.01 (1H, d), 7.06 (1H, dd), 7.26 (1H, m), 7.47 (2H, m), 7.54-7.66 (4H, overlapping m), 7.93 (1H, m), 7.98 (1H, s), 8.02 (1H, s), 8.29 (1H, d), 8.38 (1H, m), 8.68 (1H, s), 8.80 (1H, s), 8.91 (1H, s), 10.07 (1H, s).

Example 63:

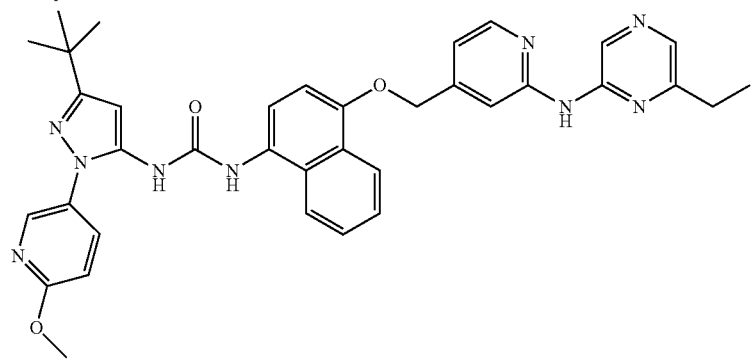

1-(3-(tert-butyl)-1-(6-methoxypyridin-3-yl)-1H-pyrazol-5-yl)-3-(4-((2-((6-ethylpyrazin-2-yl)amino)pyridin-4-yl)methoxy)naphthalen-1-yl)urea
Route code*: 1

R$^t$ 2.54 min (Method 2); m/z 644 (M + H)+ (ES+); $^1$H NMR (400 MHz, DMSO-$d_6$) δ: 1.17 (3H, t), 1.27 (9H, s), 2.62 (2H, q), 3.94 (3H, s), 5.35 (2H, s), 6.37 (1H, s), 6.99-7.03 (2H, overlapping m), 7.06 (1H, d), 7.54-7.64 (3H, overlapping m), 7.85-7.91 (2H, overlapping m), 7.98 (1H, s), 8.01 (1H, s), 8.29 (1H, d), 8.34-8.40 (2H, overlapping m), 8.63 (1H, s), 8.75 (1H, s), 8.91 (1H, s), 10.06 (1H, s).

Example 64:

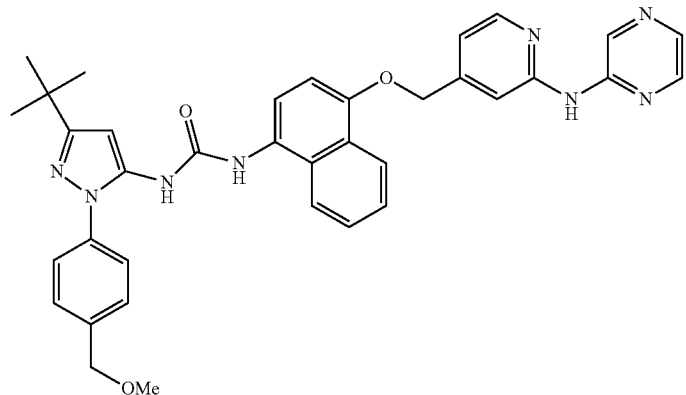

1-(3-(tert-butyl)-1-(4-(methoxymethyl)phenyl)-1H-pyrazol-5-yl)-3-(4-((2-(pyrazin-2-ylamino)pyridin-4-yl)methoxy)naphthalen-1-yl)urea
Route code*: 1

Rt 2.37 min (Method 1); m/z 315 (M + 2H)$^{2+}$ (ES+); 1H NMR (400 MHz, DMSO-d$_6$) δ: 1.28 (9H, s), 3.33 (3H, s), 4.50 (2H, s), 5.35 (2H, s), 6.37 (1H, s), 7.03 (1H, d), 7.08 (1H, d), 7.36 (1H, m), 7.49-7.54 (3H, overlapping m), 7.57-7.65 (3H, overlapping m), 7.94 (1H, m), 8.01 (1H, s), 8.09 (1H, d), 8.22 (1H, d), 8.30 (1H, d), 8.39 (1H, m), 8.71 (2H, s), 9.08 (1H, d), 10.15 (1H, s).

Example 65:

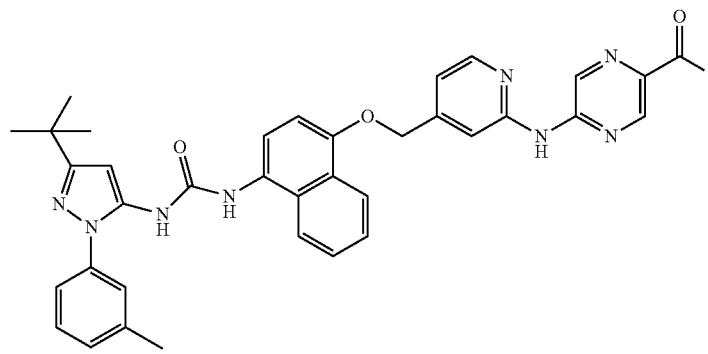

1-(3-(tert-butyl)-1-(m-tolyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
Route code*: 2

R$^t$ 2.14 min (Method 1); m/z 696 (M + H)$^+$ (ES$^+$); $^1$H NMR (400 MHz, DMSO-d$_6$) δ: 1.27 (9H, s), 1.86-1.89 (4H, m), 2.36 (3H, s), 3.51 (2H, t), 3.74 (2H, t), 5.36 (2H, s), 6.36 (1H, s), 7.04 (1H, d), 7.14 (1H, d), 7.25 (1H, d), 7.35-7.42 (2H, overlapping, m), 7.45 (1H, m), 7.60-7.64 (3H, overlapping, m), 7.95 (1H, m), 8.02 (1H, s), 8.35 (1H, d), 8.40 (1H, m), 8.59-8.62 (2H, overlapping, m), 8.78 (1H, s), 9.08 (1H, d), 10.50 (1H, s).

Example 66:

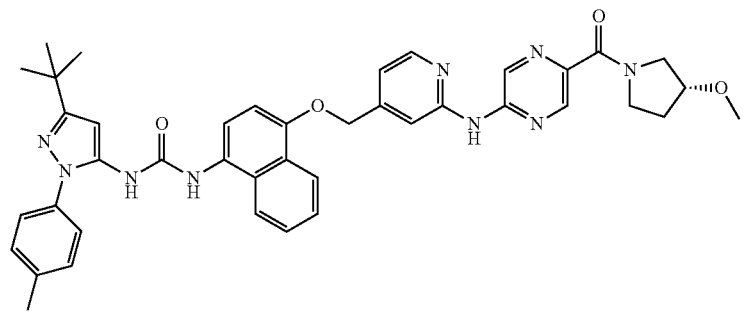

(R)-1-(3-(tert-butyl)-1-(p-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea
Route code*: 6

R$^t$ 2.20 min (Method 1); m/z 726 (M + H)$^+$ (ES$^+$); $^1$H NMR (400 MHz, DMSO-d$_6$) δ: 1.27 (9H, s), 1.86-2.08 (2H, overlapping m), 2.39 (3H, s), rotamers: 3.21 (1.5H, s), 3.26 (1.5H, s), 3.43-3.66 (2H, m), 3.72-3.90 (2H, overlapping m), 3.99 (1H, m), 5.38 (2H, s), 6.36 (1H, s), 7.04 (1H, d), 7.14 (1H, d), 7.36 (2H, m), 7.44 (2H, m), 7.57-7.68 (3H, overlapping m), 7.94 (1H, m), 8.02 (1H, s), 8.34 (1H, d), 8.41 (1H, m), 8.60 (1H, s), 8.62 (1H, m), 8.81 (1H, s), 9.09 (1H, d), 10.55 (1H, d).

Example 67:

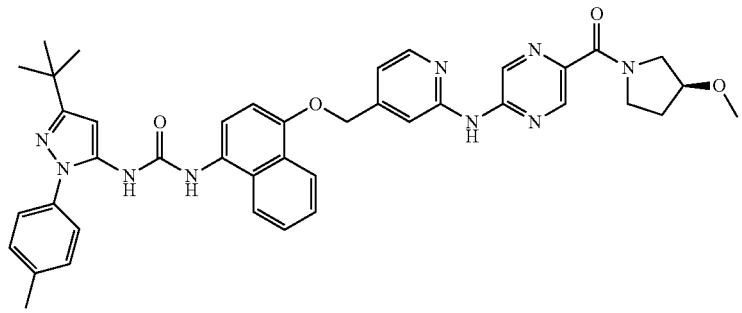

(S)-1-(3-(tert-butyl)-1-(p-tolyl)-1H-pyrazol-5-yl)-3-(4-((2-((5-(3-methoxypyrrolidine-1-carbonyl)pyrazin-2-yl)amino)pyridin-4-yl)methoxy)naphthalen-1-yl)urea
Route code*: 6

$R^t$ 2.19 min (Method 1); m/z 726 (M + H)⁺ (ES⁺); ¹H NMR (400 MHz, DMSO-d₆) δ: 1.27 (9H, s), 1.85-2.08 (2H, overlapping m), 2.39 (3H, s), rotamers: 3.21 (1.5H, s), 3.27 (1.5H, s), 3.45-3.65 (2H, m), 3.72-3.90 (2H, overlapping m), 3.99 (1H, m), 5.38 (2H, s), 6.36 (1H, s), 7.04 (1H, d), 7.14 (1H, d), 7.36 (2H, m), 7.44 (2H, m), 7.56-7.68 (3H, overlapping m), 7.94 (1H, m), 8.02 (1H, s), 8.34 (1H, d), 8.41 (1H, m), 8.61 (1H, s), 8.63 (1H m), 8.81 (1H, s), 9.09 (1H, d), 10.55 (1H, d).

Example 68:

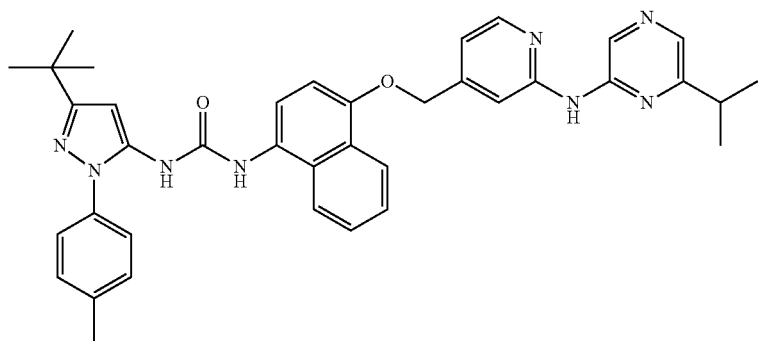

1-(3-(tert-butyl)-1-(p-tolyl)-1H-pyrazol-5-yl)-3-(4-((2-((6-isopropylpyrazin-2-yl)amino)pyridin-4-yl)methoxy)naphthalen-1-yl)urea
Route code*: 1

Rt 2.35 min (Method 1); m/z 641 (M + H)⁺ (ES+); 1H NMR (400 MHz, DMSO-d₆) δ: 1.17 (6H, d), 1.28 (9H, s), 2.40 (3H, s), 2.90 (1H, m), 5.36 (2H, s), 6.36 (1H, s), 7.00 (1H, d), 7.07 (1H, d), 7.37 (2H, m), 7.43 (2H, m), 7.56-7.64 (3H, overlapping m), 7.93 (1H, d), 7.99 (1H, s), 8.07 (1H, s), 8.30 (1H, d), 8.37 (1H, d), 8.58 (1H, s) , 8.79 (1H, s), 8.86 (1H, s), 10.04 (1H, s).

Example 69:

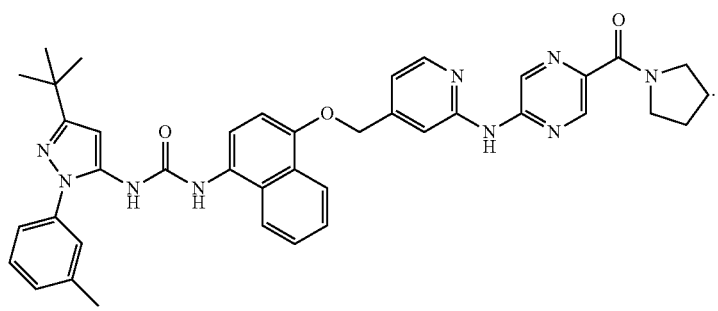

(R)-1-(3-(tert-butyl)-1-(m-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea
Route code*: 6

$R^t$ 1.97 min (Method 1); m/z 712 (M + H)⁺ (ES⁺); ¹H NMR (400 MHz, DMSO-d₆) δ: 1.27 (9H, s), 1.74-1.96 (2H, overlapping m), 2.40 (3H, s), 3.40-3.66 (3H, overlapping m), 3.84 (1H m), 4.31 (1H, m), 4.96 (1H, m), 5.38 (2H, s), 6.36 (1H, s), 7.04 (1H, d), 7.14 (1H, d), 7.24 (1H m), 7.33-7.46 (3H, overlapping m), 7.57-7.65 (3H, overlapping m), 7.94 (1H, m), 8.02 (1H, s), 8.35 (1H, d), 8.40 (1H, m), 8.62 (1H, m), 8.69 (1H, s), 8.87 (1H, s), 9.09 (1H, s), 10.51 (1H, s).

Example 70:

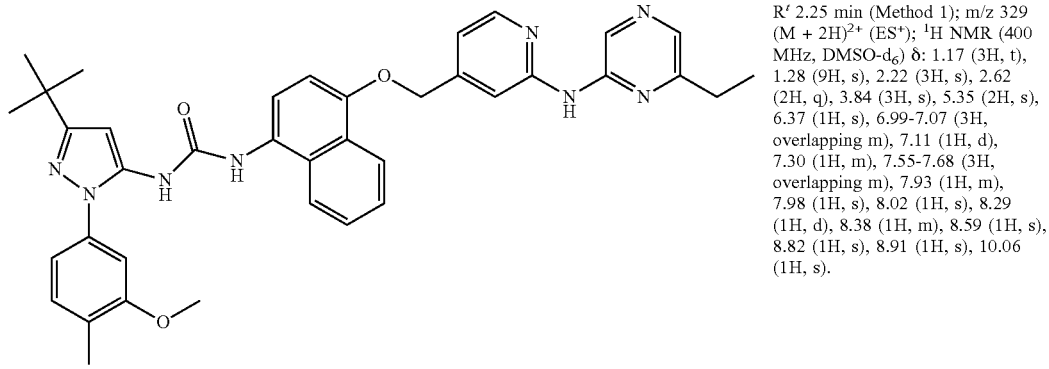

1-(3-(tert-butyl)-1-(3-methoxy-4-methylphenyl)-1H-pyrazol-5-yl)-3-(4-((2-((6-ethylpyrazin-2-yl)amino)pyridin-4-yl)methoxy)naphthalen-1-yl)urea
Route code*: 1

R$^t$ 2.25 min (Method 1); m/z 329 (M + 2H)$^{2+}$ (ES$^+$); $^1$H NMR (400 MHz, DMSO-d$_6$) δ: 1.17 (3H, t), 1.28 (9H, s), 2.22 (3H, s), 2.62 (2H, q), 3.84 (3H, s), 5.35 (2H, s), 6.37 (1H, s), 6.99-7.07 (3H, overlapping m), 7.11 (1H, d), 7.30 (1H, m), 7.55-7.68 (3H, overlapping m), 7.93 (1H, m), 7.98 (1H, s), 8.02 (1H, s), 8.29 (1H, d), 8.38 (1H, m), 8.59 (1H, s), 8.82 (1H, s), 8.91 (1H, s), 10.06 (1H, s).

Example 71:

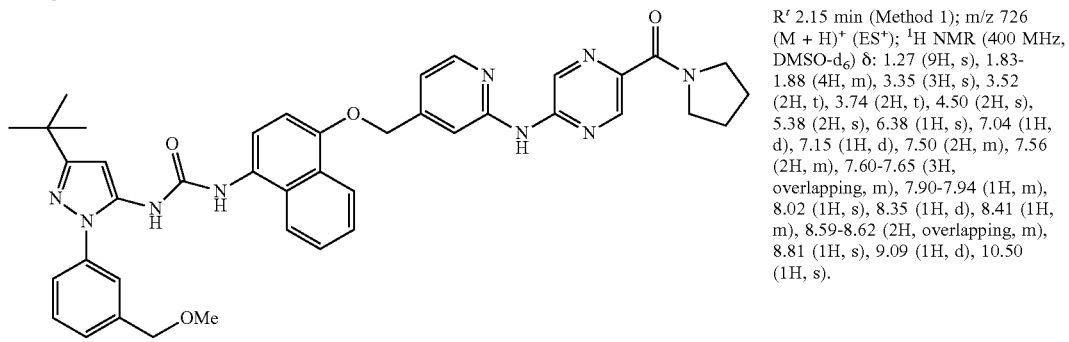

1-(3-(tert-butyl)-1-(3-(methoxymethyl)phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
Route code*: 2

R$^t$ 2.15 min (Method 1); m/z 726 (M + H)$^+$ (ES$^+$); $^1$H NMR (400 MHz, DMSO-d$_6$) δ: 1.27 (9H, s), 1.83-1.88 (4H, m), 3.35 (3H, s), 3.52 (2H, t), 3.74 (2H, t), 4.50 (2H, s), 5.38 (2H, s), 6.38 (1H, s), 7.04 (1H, d), 7.15 (1H, d), 7.50 (2H, m), 7.56 (2H, m), 7.60-7.65 (3H, overlapping, m), 7.90-7.94 (1H, m), 8.02 (1H, s), 8.35 (1H, d), 8.41 (1H, m), 8.59-8.62 (2H, overlapping, m), 8.81 (1H, s), 9.09 (1H, d), 10.50 (1H, s).

Example 72:

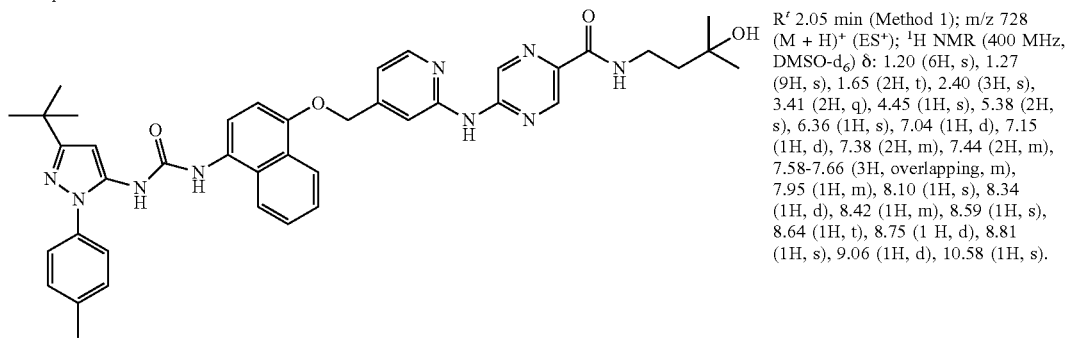

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-hydroxy-3-methylbutyl)pyrazine-2-carboxamide
Route code*: 6

R$^t$ 2.05 min (Method 1); m/z 728 (M + H)$^+$ (ES$^+$); $^1$H NMR (400 MHz, DMSO-d$_6$) δ: 1.20 (6H, s), 1.27 (9H, s), 1.65 (2H, t), 2.40 (3H, s), 3.41 (2H, q), 4.45 (1H, s), 5.38 (2H, s), 6.36 (1H, s), 7.04 (1H, d), 7.15 (1H, d), 7.38 (2H, m), 7.44 (2H, m), 7.58-7.66 (3H, overlapping, m), 7.95 (1H, m), 8.10 (1H, s), 8.34 (1H, d), 8.42 (1H, m), 8.59 (1H, s), 8.64 (1H, t), 8.75 (1 H, d), 8.81 (1H, s), 9.06 (1H, d), 10.58 (1H, s).

Example 73:

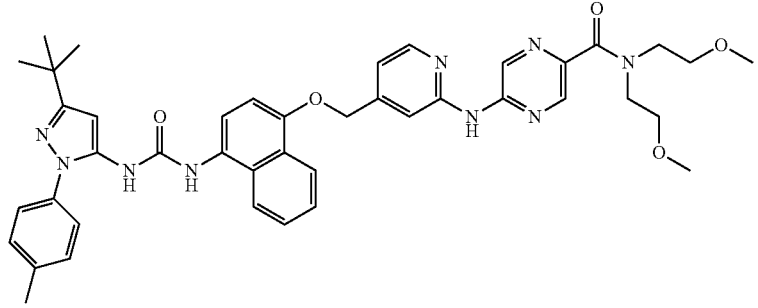

R$^t$ 2.16 min (Method 1); m/z 758 (M + H)$^+$ (ES$^+$); $^1$H NMR (400 MHz, DMSO-d$_6$) δ: 1.27 (9H, s), 2.39 (3H, s), 3.15 (3H, s), 3.29 (3H, s), 3.52 (4H, m), 3.68 (4H, m), 5.37 (2H, s), 6.35 (1H, s), 7.04 (1H, d), 7.14 (1H, d), 7.36 (2H, m), 7.44 (2H, m), 7.57-7.67 (3H, overlapping m), 7.94 (1H, m), 7.98 (1H, s), 8.34 (1H, d), 8.40 (1H, m), 8.45 (1H, s), 8.58 (1H, s), 8.79 (1H, s), 9.06 (1H, s), 10.46 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N,N-bis(2-methoxyethyl)pyrazine-2-carboxamide
Route code*: 6

Example 74:

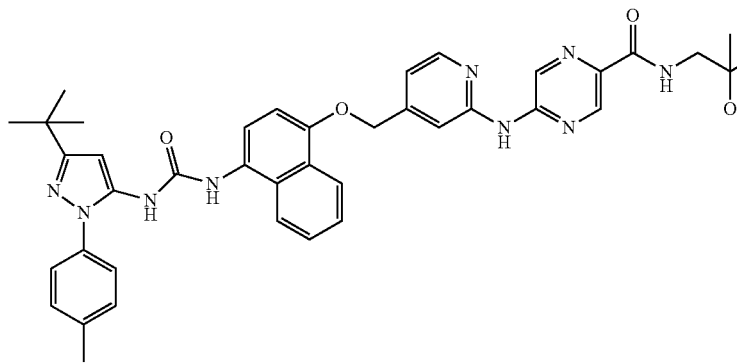

R$^t$ 2.10 min (Method 1); m/z 728 (M + H)$^+$ (ES$^+$); $^1$H NMR (400 MHz, DMSO-d$_6$) δ: 1.13 (6H, s), 1.27 (9H, s), 2.34 (3H, s), 3.17 (3H, s), 3.38 (2H, d), 5.39 (2H, s), 6.36 (1H, s), 7.04 (1H, d), 7.17 (1H, d), 7.35-7.40 (2H, overlapping, m), 7.43-7.48 (2H, overlapping, m), 7.60-7.67 (3H, overlapping, m), 7.92-7.97 (1H, m), 8.03 (1H, t), 8.08 (1H, s), 8.35 (1H, d), 8.39-8.44 (1H, m), 8.59 (1H, s), 8.77 (1H, d), 8.81 (1H, s), 9.10 (1H, d), 10.63 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methoxy-2-methylpropyl)pyrazine-2-carboxamide
Route code*: 6

Example 75:

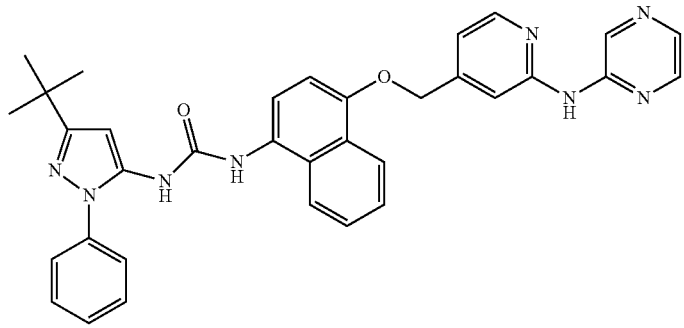

R$^t$ 1.9 min (Method 1); m/z 585 (M + H)$^+$ (ES$^+$); $^1$H NMR (400 MHz, DMSO-d$_6$) δ: 1.29 (9H, s), 5.36 (2H, s), 6.38 (1H, s), 7.04 (1H, d), 7.09 (1H, d), 7.44 (1H, m), 7.64-7.55 (7H, overlapping m), 7.94 (1H, m), 8.02 (1H, s), 8.10 (1H, d), 8.22 (1H, m), 8.31 (1H, d), 8.40 (1H, m), 8.65 (1H, s), 8.81 (1H, s), 9.09 (1H, d), 10.15 (1H, s).

1-(3-(tert-butyl)-1-phenyl-1H-pyrazol-5-yl)-3-(4-((2-(pyrazin-2-ylamino)pyridin-4-yl)methoxy)naphthalen-1-yl)urea
Route code*: 1

Example 76:

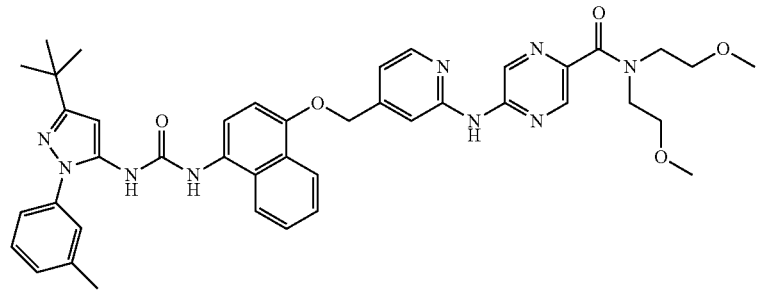

5-((4-(((4-(3-(3-(tert-butyl)-1-(m-tolyl)-1H-pyrazol-5-yl)ureido)naphthalen-1-yl)oxy)
methyl)pyridin-2-yl)amino)-N,N-bis(2-methoxyethyl)pyrazine-2-carboxamide
Route code*: 6

R$^t$ 2.22 min (Method 1); m/z 380 (M + 2H)$^{2+}$ (ES$^+$); $^1$H NMR (400 MHz, DMSO-d$_6$) δ: 1.28 (9H, s), 2.40 (3H, s), 3.15 (3H, s), 3.29 (3H, s), 3.52 (4H, dt), 3.68 (4H, dt), 5.37 (2H, s), 6.36 (1H, s), 7.04 (1H, d), 7.13 (1H, dd), 7.25 (1H, d), 7.33-7.47 (3H, overlapping m), 7.56-7.68 (3H, overlapping m), 7.93 (1H, m), 7.98 (1H, s), 8.34 (1H, d), 8.34 (1H, m), 8.46 (1H, d), 8.60 (1H, s), 8.79 (1H, s), 9.06 (1H, d), 10.46 (1H, s).

Example 77:

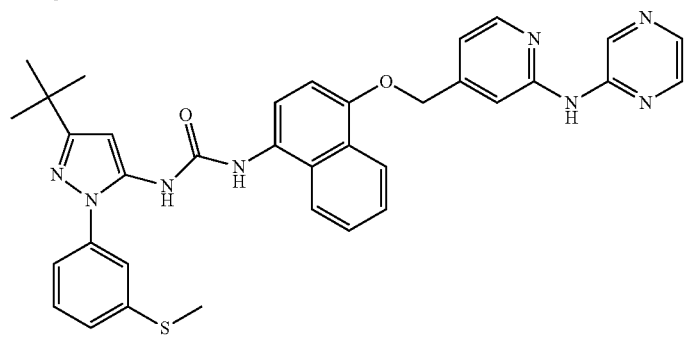

1-(3-(tert-butyl)-1-(3-(methylthio)phenyl)-1H-pyrazol-5-yl)-3-(4-((2-(pyrazin-2-ylamino)pyridin-4-yl)methoxy)naphthalen-1-yl)urea
Route code*: 1

R$^t$ 2.08 min (Method 1); m/z 316 (M + 2H)$^{2+}$ (ES$^+$); $^1$H NMR (400 MHz, DMSO-d$_6$) δ: 1.28 (9H, s), 2.53 (3H, s), 5.36 (2H, s), 6.37 (1H, s), 7.03 (1H, d), 7.08 (1H, dd), 7.26-7.37 (2H, m), 7.40-7.52 (2H, m), 7.56-7.65 (3H, m), 7.88-7.97 (1H, m), 8.01 (1H, s), 8.09 (1H, d), 8.19-8.24 (1H, m), 8.30 (1H, d), 8.36-8.43 (1H, m), 8.65 (1H, s), 8.81 (1H, s), 9.08 (1H, d), 10.17 (1H, s)

Example 78:

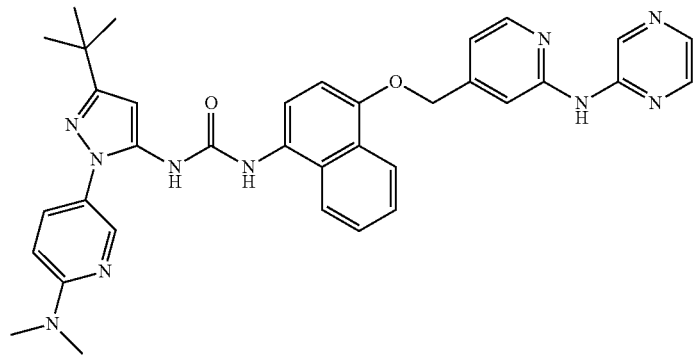

1-(3-(tert-butyl)-1-(6-(dimethylamino)pyridin-3-yl)-1H-pyrazol-5-yl)-3-(4-((2-(pyrazin-2-ylamino)pyridin-4-yl)methoxy)naphthalen-1-yl)urea
Route code*: 1

R$^t$ 1.53 min (Method 1); m/z 629 (M + H)$^+$ (ES$^+$); $^1$H NMR (400 MHz, DMSO-d$_6$) δ: 1.27 (9H, s), 3.12 (6H, s), 5.36 (2H, s), 6.35 (1H, s), 6.80 (1H, d) 7.04 (1H, d), 7.10 (1H, d), 7.68-7.57 (4H, overlapping m), 7.93 (1H, m), 8.01 (1H, s), 8.10 (1H, d), 8.24-8.20 (2H, overlapping m), 8.31 (1H, d), 8.40 (1H, m), 8.57 (1H, s), 8.81 (1H, s), 9.08 (1H, d), 10.19 (1H, s).

Example 79:

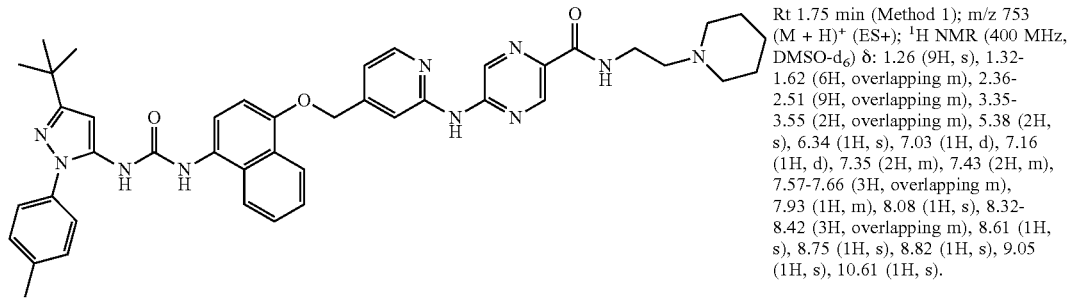

Rt 1.75 min (Method 1); m/z 753 (M + H)+ (ES+); ¹H NMR (400 MHz, DMSO-d₆) δ: 1.26 (9H, s), 1.32-1.62 (6H, overlapping m), 2.36-2.51 (9H, overlapping m), 3.35-3.55 (2H, overlapping m), 5.38 (2H, s), 6.34 (1H, s), 7.03 (1H, d), 7.16 (1H, d), 7.35 (2H, m), 7.43 (2H, m), 7.57-7.66 (3H, overlapping m), 7.93 (1H, m), 8.08 (1H, s), 8.32-8.42 (3H, overlapping m), 8.61 (1H, s), 8.75 (1H, s), 8.82 (1H, s), 9.05 (1H, s), 10.61 (1H, s).

5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(2-(piperidin-1-yl)ethyl)pyrazine-2-carboxamide
Route code*: 6

Example 80:

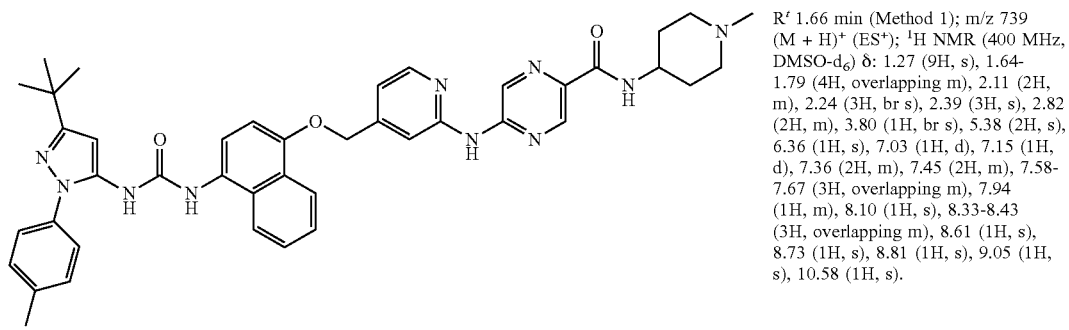

R' 1.66 min (Method 1); m/z 739 (M + H)+ (ES+); ¹H NMR (400 MHz, DMSO-d₆) δ: 1.27 (9H, s), 1.64-1.79 (4H, overlapping m), 2.11 (2H, m), 2.24 (3H, br s), 2.39 (3H, s), 2.82 (2H, m), 3.80 (1H, br s), 5.38 (2H, s), 6.36 (1H, s), 7.03 (1H, d), 7.15 (1H, d), 7.36 (2H, m), 7.45 (2H, m), 7.58-7.67 (3H, overlapping m), 7.94 (1H, m), 8.10 (1H, s), 8.33-8.43 (3H, overlapping m), 8.61 (1H, s), 8.73 (1H, s), 8.81 (1H, s), 9.05 (1H, s), 10.58 (1H, s).

5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(1-methylpiperidin-4-yl)pyrazine-2-carboxamide
Route code*: 6

Example 81:

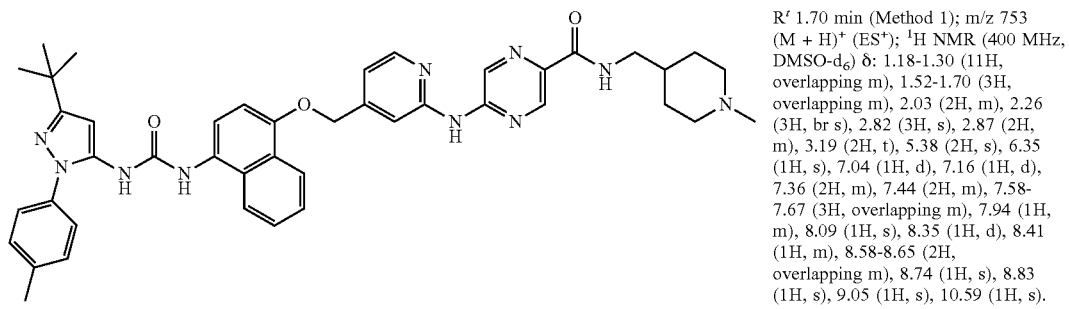

R' 1.70 min (Method 1); m/z 753 (M + H)+ (ES+); ¹H NMR (400 MHz, DMSO-d₆) δ: 1.18-1.30 (11H, overlapping m), 1.52-1.70 (3H, overlapping m), 2.03 (2H, m), 2.26 (3H, br s), 2.82 (3H, s), 2.87 (2H, m), 3.19 (2H, t), 5.38 (2H, s), 6.35 (1H, s), 7.04 (1H, d), 7.16 (1H, d), 7.36 (2H, m), 7.44 (2H, m), 7.58-7.67 (3H, overlapping m), 7.94 (1H, m), 8.09 (1H, s), 8.35 (1H, d), 8.41 (1H, m), 8.58-8.65 (2H, overlapping m), 8.74 (1H, s), 8.83 (1H, s), 9.05 (1H, s), 10.59 (1H, s).

5-((4-(((4-(3-(3-(tert-butyl)-1-(p-tolyl)-1H-pyrazol-5-yl)ureido)naphthalen-1-yl)oxy)
methyl)pyridin-2-yl)amino)-N-((1-methylpiperidin-4-yl)methyl)pyrazine-2-carboxamide
Route code*: 6

Example 82:

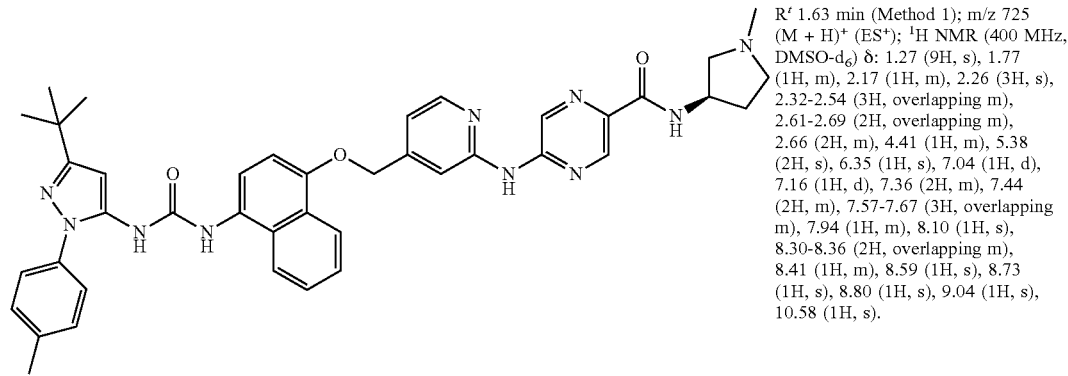

R$^t$ 1.63 min (Method 1); m/z 725 (M + H)$^+$ (ES$^+$); $^1$H NMR (400 MHz, DMSO-d$_6$) δ: 1.27 (9H, s), 1.77 (1H, m), 2.17 (1H, m), 2.26 (3H, s), 2.32-2.54 (3H, overlapping m), 2.61-2.69 (2H, overlapping m), 2.66 (2H, m), 4.41 (1H, m), 5.38 (2H, s), 6.35 (1H, s), 7.04 (1H, d), 7.16 (1H, d), 7.36 (2H, m), 7.44 (2H, m), 7.57-7.67 (3H, overlapping m), 7.94 (1H, m), 8.10 (1H, s), 8.30-8.36 (2H, overlapping m), 8.41 (1H, m), 8.59 (1H, s), 8.73 (1H, s), 8.80 (1H, s), 9.04 (1H, s), 10.58 (1H, s).

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpyrrolidin-3-yl)pyrazine-2-carboxamide
Route code*: 6

Example 83:

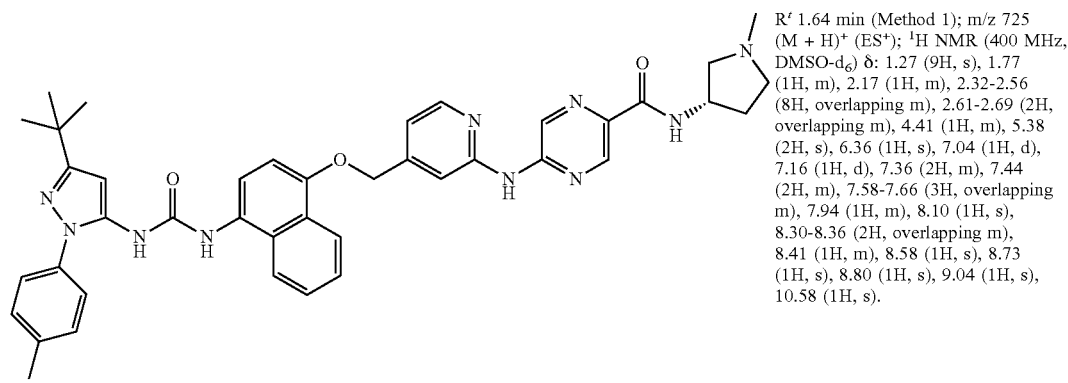

R$^t$ 1.64 min (Method 1); m/z 725 (M + H)$^+$ (ES$^+$); $^1$H NMR (400 MHz, DMSO-d$_6$) δ: 1.27 (9H, s), 1.77 (1H, m), 2.17 (1H, m), 2.32-2.56 (8H, overlapping m), 2.61-2.69 (2H, overlapping m), 4.41 (1H, m), 5.38 (2H, s), 6.36 (1H, s), 7.04 (1H, d), 7.16 (1H, d), 7.36 (2H, m), 7.44 (2H, m), 7.58-7.66 (3H, overlapping m), 7.94 (1H, m), 8.10 (1H, s), 8.30-8.36 (2H, overlapping m), 8.41 (1H, m), 8.58 (1H, s), 8.73 (1H, s), 8.80 (1H, s), 9.04 (1H, s), 10.58 (1H, s).

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpyrrolidin-3-yl)pyrazine-2-carboxamide
Route code*: 6

Example 84:

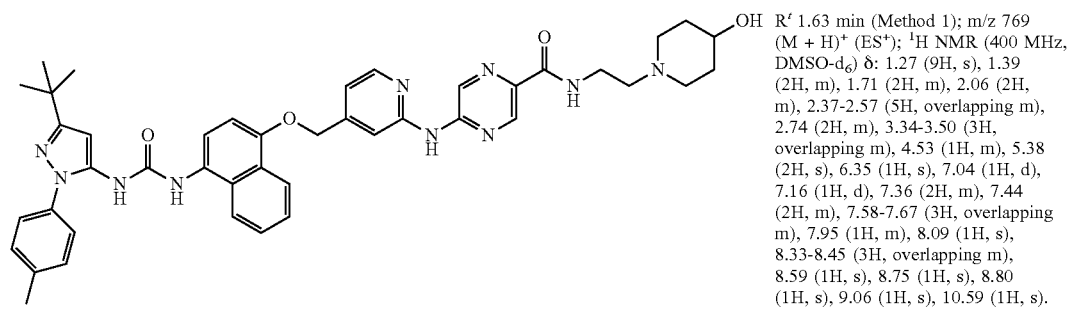

R$^t$ 1.63 min (Method 1); m/z 769 (M + H)$^+$ (ES$^+$); $^1$H NMR (400 MHz, DMSO-d$_6$) δ: 1.27 (9H, s), 1.39 (2H, m), 1.71 (2H, m), 2.06 (2H, m), 2.37-2.57 (5H, overlapping m), 2.74 (2H, m), 3.34-3.50 (3H, overlapping m), 4.53 (1H, m), 5.38 (2H, s), 6.35 (1H, s), 7.04 (1H, d), 7.16 (1H, d), 7.36 (2H, m), 7.44 (2H, m), 7.58-7.67 (3H, overlapping m), 7.95 (1H, m), 8.09 (1H, s), 8.33-8.45 (3H, overlapping m), 8.59 (1H, s), 8.75 (1H, s), 8.80 (1H, s), 9.06 (1H, s), 10.59 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-hydroxypiperidin-1-yl)ethyl)pyrazine-2-carboxamide
Route code*: 6

Example 85:

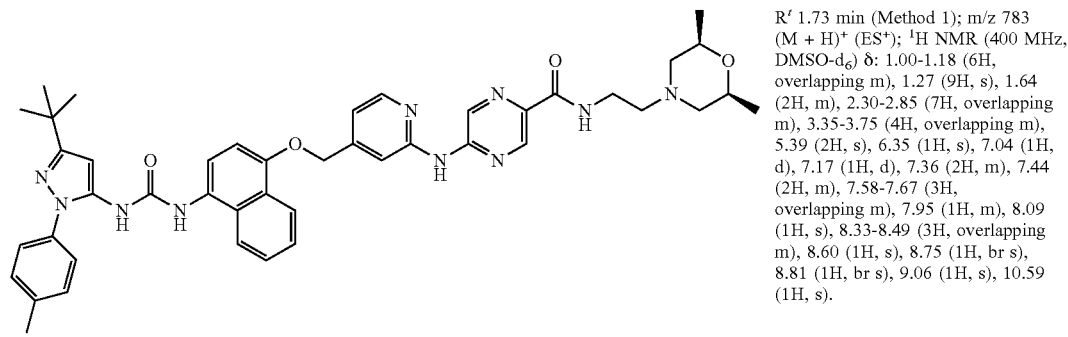

R' 1.73 min (Method 1); m/z 783 (M + H)+ (ES+); 1H NMR (400 MHz, DMSO-d6) δ: 1.00-1.18 (6H, overlapping m), 1.27 (9H, s), 1.64 (2H, m), 2.30-2.85 (7H, overlapping m), 3.35-3.75 (4H, overlapping m), 5.39 (2H, s), 6.35 (1H, s), 7.04 (1H, d), 7.17 (1H, d), 7.36 (2H, m), 7.44 (2H, m), 7.58-7.67 (3H, overlapping m), 7.95 (1H, m), 8.09 (1H, s), 8.33-8.49 (3H, overlapping m), 8.60 (1H, s), 8.75 (1H, br s), 8.81 (1H, br s), 9.06 (1H, s), 10.59 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-((2S,6R)-2,6-dimethylmorpholino)ethyl)pyrazine-2-carboxamide
Route code*: 6

Example 86:

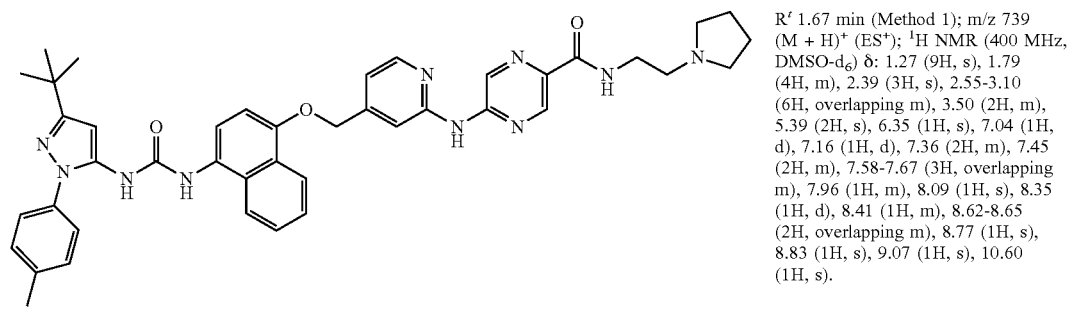

R' 1.67 min (Method 1); m/z 739 (M + H)+ (ES+); 1H NMR (400 MHz, DMSO-d6) δ: 1.27 (9H, s), 1.79 (4H, m), 2.39 (3H, s), 2.55-3.10 (6H, overlapping m), 3.50 (2H, m), 5.39 (2H, s), 6.35 (1H, s), 7.04 (1H, d), 7.16 (1H, d), 7.36 (2H, m), 7.45 (2H, m), 7.58-7.67 (3H, overlapping m), 7.96 (1H, m), 8.09 (1H, s), 8.35 (1H, d), 8.41 (1H, m), 8.62-8.65 (2H, overlapping m), 8.77 (1H, s), 8.83 (1H, s), 9.07 (1H, s), 10.60 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(pyrrolidin-1-yl)ethyl)pyrazine-2-carboxamide
Route code*: 6

Example 87:

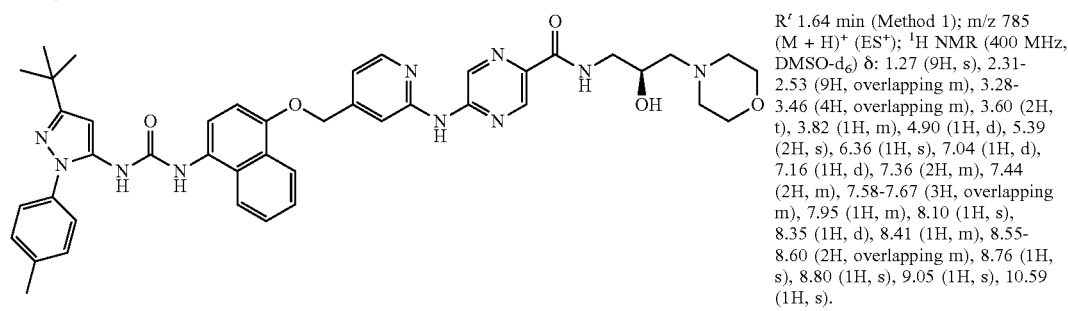

R' 1.64 min (Method 1); m/z 785 (M + H)+ (ES+); 1H NMR (400 MHz, DMSO-d6) δ: 1.27 (9H, s), 2.31-2.53 (9H, overlapping m), 3.28-3.46 (4H, overlapping m), 3.60 (2H, t), 3.82 (1H, m), 4.90 (1H, d), 5.39 (2H, s), 6.36 (1H, s), 7.04 (1H, d), 7.16 (1H, d), 7.36 (2H, m), 7.44 (2H, m), 7.58-7.67 (3H, overlapping m), 7.95 (1H, m), 8.10 (1H, s), 8.35 (1H, d), 8.41 (1H, m), 8.55-8.60 (2H, overlapping m), 8.76 (1H, s), 8.80 (1H, s), 9.05 (1H, s), 10.59 (1H, s).

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-hydroxy-3-morpholinopropyl)pyrazine-2-carboxamide
Route code*: 6

Example 88:

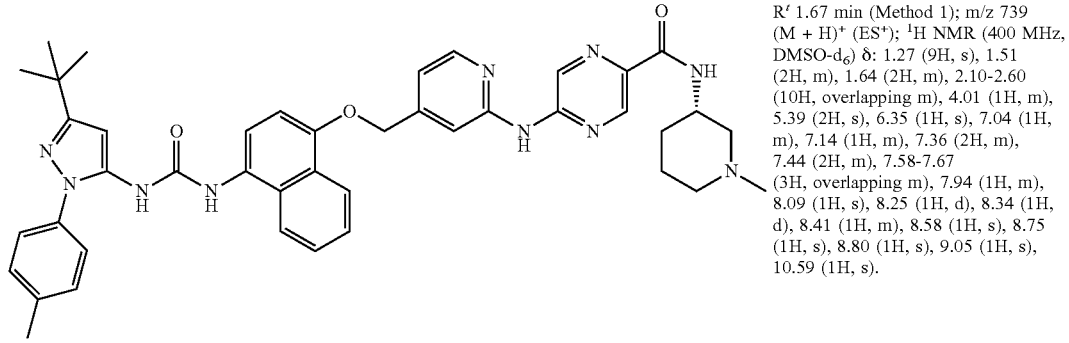

R$^t$ 1.67 min (Method 1); m/z 739 (M + H)$^+$ (ES$^+$); $^1$H NMR (400 MHz, DMSO-d$_6$) δ: 1.27 (9H, s), 1.51 (2H, m), 1.64 (2H, m), 2.10-2.60 (10H, overlapping m), 4.01 (1H, m), 5.39 (2H, s), 6.35 (1H, s), 7.04 (1H, m), 7.14 (1H, m), 7.36 (2H, m), 7.44 (2H, m), 7.58-7.67 (3H, overlapping m), 7.94 (1H, m), 8.09 (1H, s), 8.25 (1H, d), 8.34 (1H, d), 8.41 (1H, m), 8.58 (1H, s), 8.75 (1H, s), 8.80 (1H, s), 9.05 (1H, s), 10.59 (1H, s).

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylpiperidin-3-yl)pyrazine-2-carboxamide
Route code*: 6

Example 89:

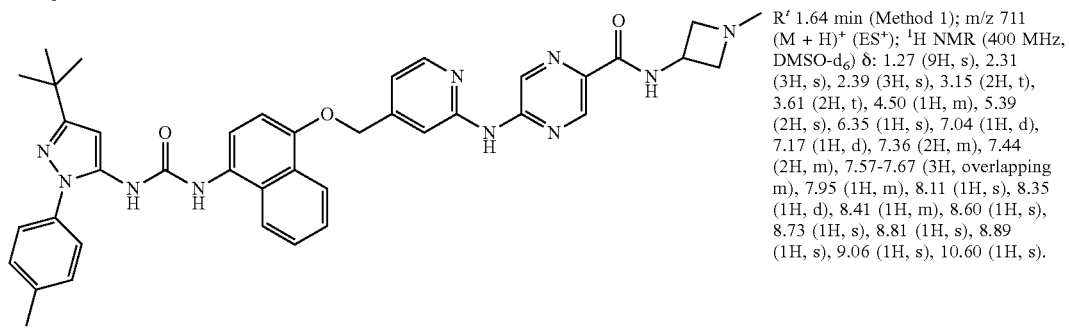

R$^t$ 1.64 min (Method 1); m/z 711 (M + H)$^+$ (ES$^+$); $^1$H NMR (400 MHz, DMSO-d$_6$) δ: 1.27 (9H, s), 2.31 (3H, s), 2.39 (3H, s), 3.15 (2H, t), 3.61 (2H, t), 4.50 (1H, m), 5.39 (2H, s), 6.35 (1H, s), 7.04 (1H, d), 7.17 (1H, d), 7.36 (2H, m), 7.44 (2H, m), 7.57-7.67 (3H, overlapping m), 7.95 (1H, m), 8.11 (1H, s), 8.35 (1H, d), 8.41 (1H, m), 8.60 (1H, s), 8.73 (1H, s), 8.81 (1H, s), 8.89 (1H, s), 9.06 (1H, s), 10.60 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-methylazetidin-3-yl)pyrazine-2-carboxamide
Route code*: 6

Example 90:

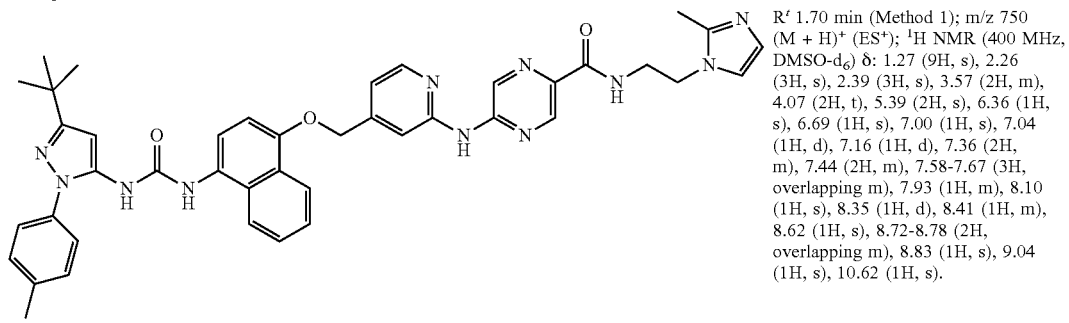

R$^t$ 1.70 min (Method 1); m/z 750 (M + H)$^+$ (ES$^+$); $^1$H NMR (400 MHz, DMSO-d$_6$) δ: 1.27 (9H, s), 2.26 (3H, s), 2.39 (3H, s), 3.57 (2H, m), 4.07 (2H, t), 5.39 (2H, s), 6.36 (1H, s), 6.69 (1H, s), 7.00 (1H, s), 7.04 (1H, d), 7.16 (1H, d), 7.36 (2H, m), 7.44 (2H, m), 7.58-7.67 (3H, overlapping m), 7.93 (1H, m), 8.10 (1H, s), 8.35 (1H, d), 8.41 (1H, m), 8.62 (1H, s), 8.72-8.78 (2H, overlapping m), 8.83 (1H, s), 9.04 (1H, s), 10.62 (1H, s).

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(2-methyl-1H-imidazol-1-yl)ethyl)pyrazine-2-carboxamide
Route code*: 6

Example 91:

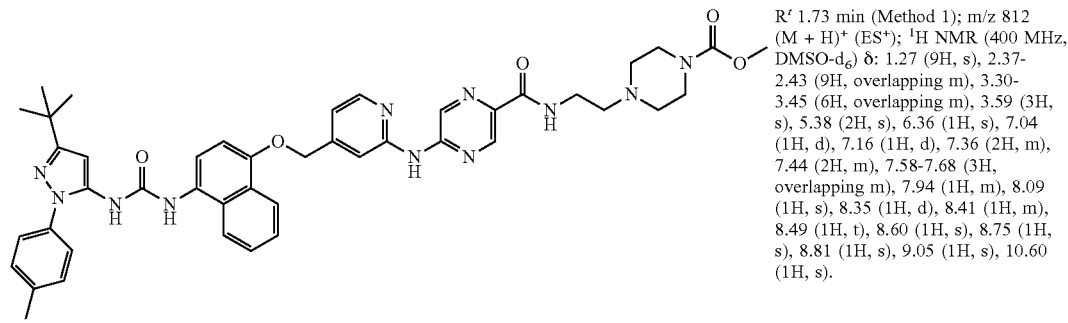

Methyl 4-(2-(5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamido)ethyl)piperazine-1-carboxylate
Route code*: 6

R$^t$ 1.73 min (Method 1); m/z 812 (M + H)$^+$ (ES$^+$); $^1$H NMR (400 MHz, DMSO-d$_6$) δ: 1.27 (9H, s), 2.37-2.43 (9H, overlapping m), 3.30-3.45 (6H, overlapping m), 3.59 (3H, s), 5.38 (2H, s), 6.36 (1H, s), 7.04 (1H, d), 7.16 (1H, d), 7.36 (2H, m), 7.44 (2H, m), 7.58-7.68 (3H, overlapping m), 7.94 (1H, m), 8.09 (1H, s), 8.35 (1H, d), 8.41 (1H, m), 8.49 (1H, t), 8.60 (1H, s), 8.75 (1H, s), 8.81 (1H, s), 9.05 (1H, s), 10.60 (1H, s).

Example 92:

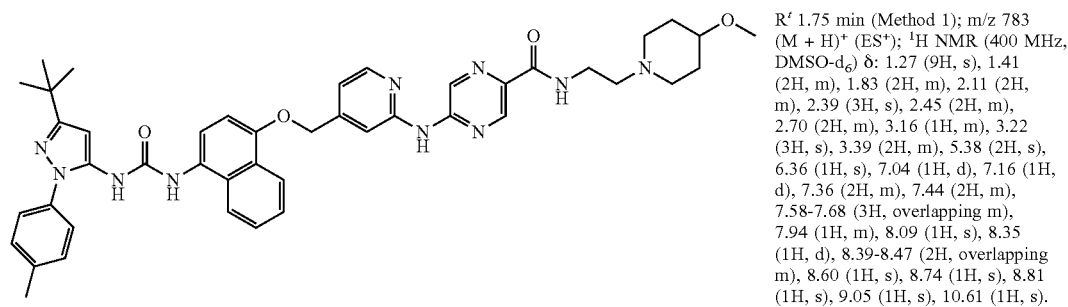

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-methoxypiperidin-1-yl)ethyl)pyrazine-2-carboxamide
Route code*: 6

R$^t$ 1.75 min (Method 1); m/z 783 (M + H)$^+$ (ES$^+$); $^1$H NMR (400 MHz, DMSO-d$_6$) δ: 1.27 (9H, s), 1.41 (2H, m), 1.83 (2H, m), 2.11 (2H, m), 2.39 (3H, s), 2.45 (2H, m), 2.70 (2H, m), 3.16 (1H, m), 3.22 (3H, s), 3.39 (2H, m), 5.38 (2H, s), 6.36 (1H, s), 7.04 (1H, d), 7.16 (1H, d), 7.36 (2H, m), 7.44 (2H, m), 7.58-7.68 (3H, overlapping m), 7.94 (1H, m), 8.09 (1H, s), 8.35 (1H, d), 8.39-8.47 (2H, overlapping m), 8.60 (1H, s), 8.74 (1H, s), 8.81 (1H, s), 9.05 (1H, s), 10.61 (1H, s).

Example 93:

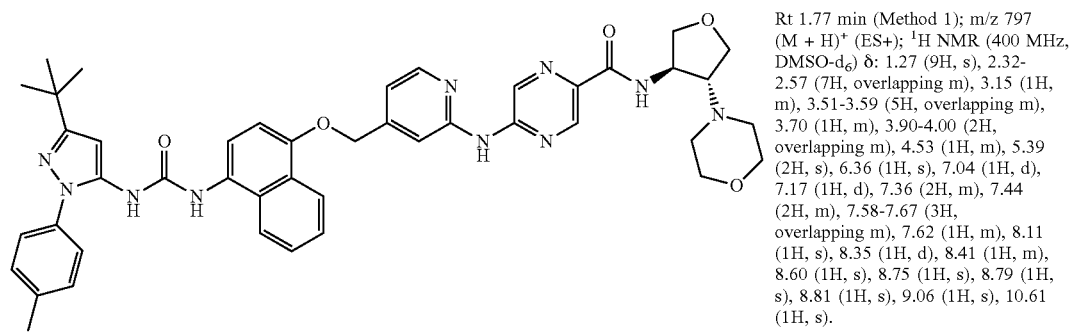

5-((4-(((4-(3-(3-(tert-butyl)-1-(p-tolyl)-1H-pyrazol-5-yl)ureido)naphthalen-1-yl)oxy)methyl)pyridin-2-yl)amino)-N-((3R,4R)-4-morpholinotetrahydrofuran-3-yl)pyrazine-2-carboxamide
Route code*: 6

Rt 1.77 min (Method 1); m/z 797 (M + H)$^+$ (ES+); $^1$H NMR (400 MHz, DMSO-d$_6$) δ: 1.27 (9H, s), 2.32-2.57 (7H, overlapping m), 3.15 (1H, m), 3.51-3.59 (5H, overlapping m), 3.70 (1H, m), 3.90-4.00 (2H, overlapping m), 4.53 (1H, m), 5.39 (2H, s), 6.36 (1H, s), 7.04 (1H, d), 7.17 (1H, d), 7.36 (2H, m), 7.44 (2H, m), 7.58-7.67 (3H, overlapping m), 7.62 (1H, m), 8.11 (1H, s), 8.35 (1H, d), 8.41 (1H, m), 8.60 (1H, s), 8.75 (1H, s), 8.79 (1H, s), 8.81 (1H, s), 9.06 (1H, s), 10.61 (1H, s).

Example 94:

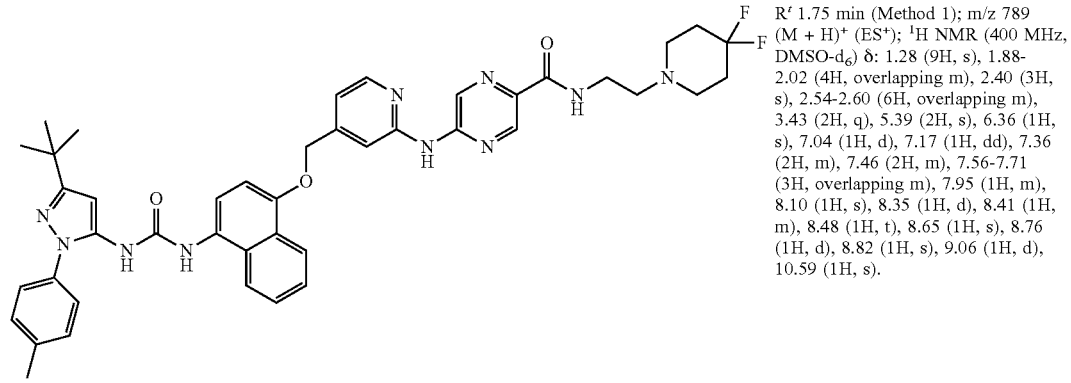

5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(2-(4,4-difluoropiperidin-1-yl)ethyl)pyrazine-2-carboxamide
Route code*: 7

$R^t$ 1.75 min (Method 1); m/z 789 (M + H)$^+$ (ES$^+$); $^1$H NMR (400 MHz, DMSO-d$_6$) δ: 1.28 (9H, s), 1.88-2.02 (4H, overlapping m), 2.40 (3H, s), 2.54-2.60 (6H, overlapping m), 3.43 (2H, q), 5.39 (2H, s), 6.36 (1H, s), 7.04 (1H, d), 7.17 (1H, dd), 7.36 (2H, m), 7.46 (2H, m), 7.56-7.71 (3H, overlapping m), 7.95 (1H, m), 8.10 (1H, s), 8.35 (1H, d), 8.41 (1H, m), 8.48 (1H, t), 8.65 (1H, s), 8.76 (1H, d), 8.82 (1H, s), 9.06 (1H, d), 10.59 (1H, s).

Example 95:

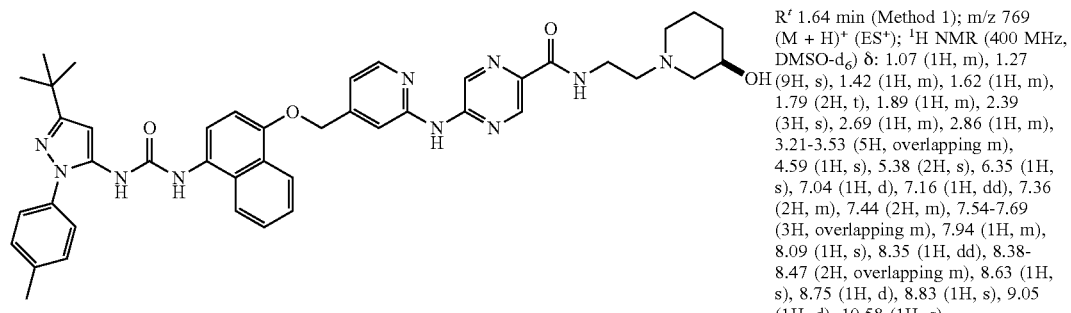

(R)-5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(2-(3-hydroxypiperidin-1-yl)ethyl)pyrazine-2-carboxamide
Route code*: 7

$R^t$ 1.64 min (Method 1); m/z 769 (M + H)$^+$ (ES$^+$); $^1$H NMR (400 MHz, DMSO-d$_6$) δ: 1.07 (1H, m), 1.27 (9H, s), 1.42 (1H, m), 1.62 (1H, m), 1.79 (2H, t), 1.89 (1H, m), 2.39 (3H, s), 2.69 (1H, m), 2.86 (1H, m), 3.21-3.53 (5H, overlapping m), 4.59 (1H, s), 5.38 (2H, s), 6.35 (1H, s), 7.04 (1H, d), 7.16 (1H, dd), 7.36 (2H, m), 7.44 (2H, m), 7.54-7.69 (3H, overlapping m), 7.94 (1H, m), 8.09 (1H, s), 8.35 (1H, dd), 8.38-8.47 (2H, overlapping m), 8.63 (1H, s), 8.75 (1H, d), 8.83 (1H, s), 9.05 (1H, d), 10.58 (1H, s).

Example 96:

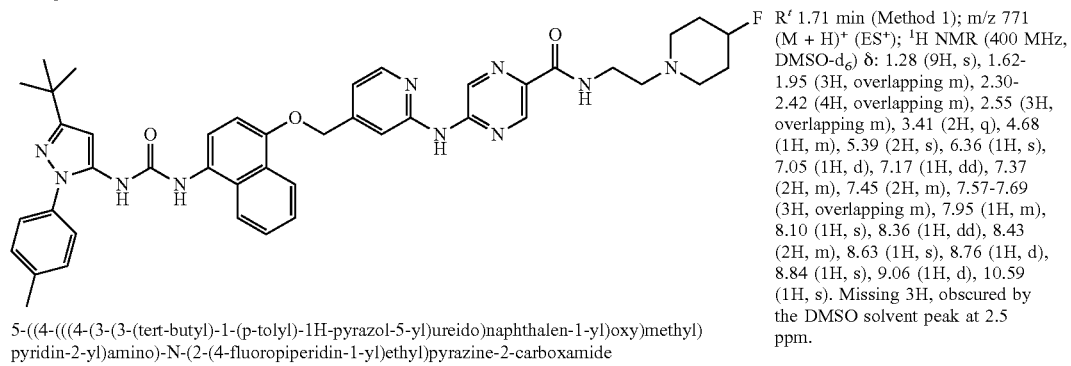

5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(2-(4-fluoropiperidin-1-yl)ethyl)pyrazine-2-carboxamide
Route code*: 7

$R^t$ 1.71 min (Method 1); m/z 771 (M + H)$^+$ (ES$^+$); $^1$H NMR (400 MHz, DMSO-d$_6$) δ: 1.28 (9H, s), 1.62-1.95 (3H, overlapping m), 2.30-2.42 (4H, overlapping m), 2.55 (3H, overlapping m), 3.41 (2H, q), 4.68 (1H, m), 5.39 (2H, s), 6.36 (1H, s), 7.05 (1H, d), 7.17 (1H, dd), 7.37 (2H, m), 7.45 (2H, m), 7.57-7.69 (3H, overlapping m), 7.95 (1H, m), 8.10 (1H, s), 8.36 (1H, dd), 8.43 (2H, m), 8.63 (1H, s), 8.76 (1H, d), 8.84 (1H, s), 9.06 (1H, d), 10.59 (1H, s). Missing 3H, obscured by the DMSO solvent peak at 2.5 ppm.

Example 97:

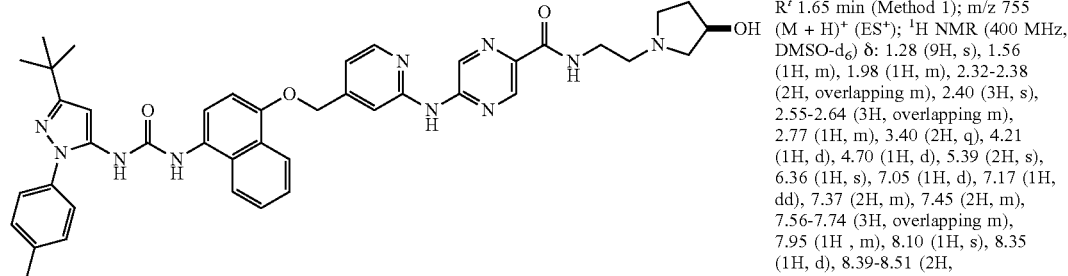

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-hydroxypyrrolidin-1-yl)ethyl)pyrazine-2-carboxamide
Route code*: 7

$R^t$ 1.65 min (Method 1); m/z 755 (M + H)$^+$ (ES$^+$); $^1$H NMR (400 MHz, DMSO-d$_6$) δ: 1.28 (9H, s), 1.56 (1H, m), 1.98 (1H, m), 2.32-2.38 (2H, overlapping m), 2.40 (3H, s), 2.55-2.64 (3H, overlapping m), 2.77 (1H, m), 3.40 (2H, q), 4.21 (1H, d), 4.70 (1H, d), 5.39 (2H, s), 6.36 (1H, s), 7.05 (1H, d), 7.17 (1H, dd), 7.37 (2H, m), 7.45 (2H, m), 7.56-7.74 (3H, overlapping m), 7.95 (1H , m), 8.10 (1H, s), 8.35 (1H, d), 8.39-8.51 (2H, overlapping m), 8.60 (1H, s), 8.76 (1H, d), 8.81 (1H, s), 9.06 (1H, d), 10.59 (1H, s).

Example 98:

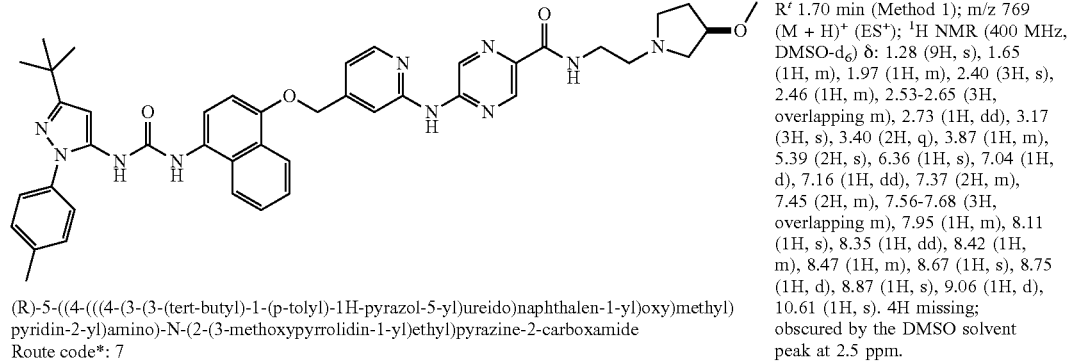

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-methoxypyrrolidin-1-yl)ethyl)pyrazine-2-carboxamide
Route code*: 7

$R^t$ 1.70 min (Method 1); m/z 769 (M + H)$^+$ (ES$^+$); $^1$H NMR (400 MHz, DMSO-d$_6$) δ: 1.28 (9H, s), 1.65 (1H, m), 1.97 (1H, m), 2.40 (3H, s), 2.46 (1H, m), 2.53-2.65 (3H, overlapping m), 2.73 (1H, dd), 3.17 (3H, s), 3.40 (2H, q), 3.87 (1H, m), 5.39 (2H, s), 6.36 (1H, s), 7.04 (1H, d), 7.16 (1H, dd), 7.37 (2H, m), 7.45 (2H, m), 7.56-7.68 (3H, overlapping m), 7.95 (1H, m), 8.11 (1H, s), 8.35 (1H, dd), 8.42 (1H, m), 8.47 (1H, m), 8.67 (1H, s), 8.75 (1H, d), 8.87 (1H, s), 9.06 (1H, d), 10.61 (1H, s). 4H missing; obscured by the DMSO solvent peak at 2.5 ppm.

Example 99:

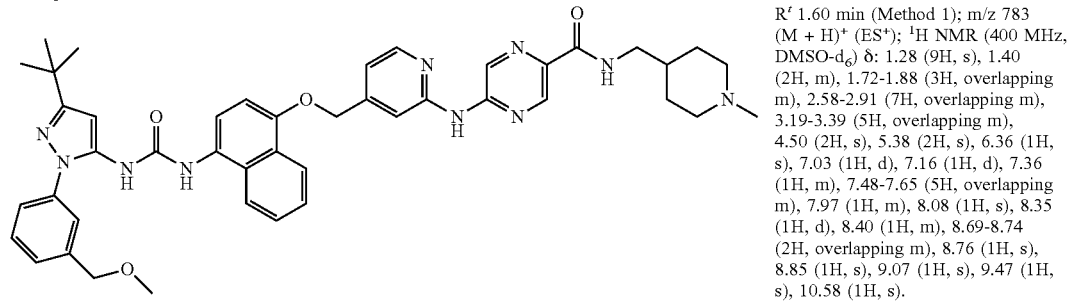

5-((4-(((4-(3-(3-(tert-butyl)-1-(3-(methoxymethyl)phenyl)-1H-pyrazol-5-yl)ureido)naphthalen-1-yl)oxy)methyl)pyridin-2-yl)amino)-N-((1-methylpiperidin-4-yl)methyl)pyrazine-2-carboxamide
Route code*: 6

$R^t$ 1.60 min (Method 1); m/z 783 (M + H)$^+$ (ES$^+$); $^1$H NMR (400 MHz, DMSO-d$_6$) δ: 1.28 (9H, s), 1.40 (2H, m), 1.72-1.88 (3H, overlapping m), 2.58-2.91 (7H, overlapping m), 3.19-3.39 (5H, overlapping m), 4.50 (2H, s), 5.38 (2H, s), 6.36 (1H, s), 7.03 (1H, d), 7.16 (1H, d), 7.36 (1H, m), 7.48-7.65 (5H, overlapping m), 7.97 (1H, m), 8.08 (1H, s), 8.35 (1H, d), 8.40 (1H, m), 8.69-8.74 (2H, overlapping m), 8.76 (1H, s), 8.85 (1H, s), 9.07 (1H, s), 9.47 (1H, s), 10.58 (1H, s).

Example 100:

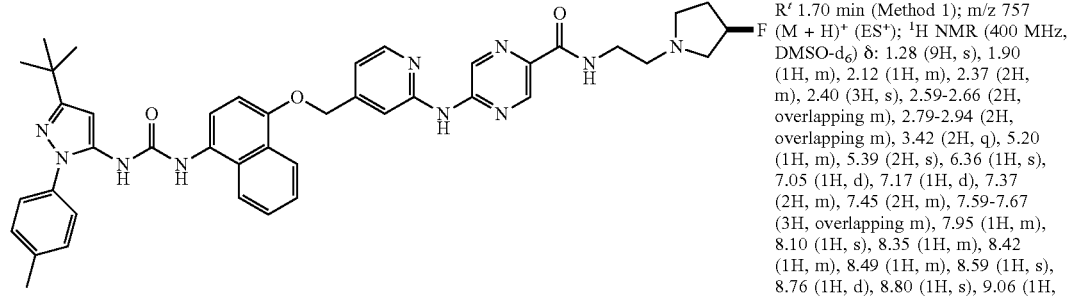

(R)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(3-fluoropyrrolidin-1-yl)ethyl)pyrazine-2-carboxamide
Route code*: 7

$R^t$ 1.70 min (Method 1); m/z 757 (M + H)$^+$ (ES$^+$); $^1$H NMR (400 MHz, DMSO-d$_6$) δ: 1.28 (9H, s), 1.90 (1H, m), 2.12 (1H, m), 2.37 (2H, m), 2.40 (3H, s), 2.59-2.66 (2H, overlapping m), 2.79-2.94 (2H, overlapping m), 3.42 (2H, q), 5.20 (1H, m), 5.39 (2H, s), 6.36 (1H, s), 7.05 (1H, d), 7.17 (1H, d), 7.37 (2H, m), 7.45 (2H, m), 7.59-7.67 (3H, overlapping m), 7.95 (1H, m), 8.10 (1H, s), 8.35 (1H, m), 8.42 (1H, m), 8.49 (1H, m), 8.59 (1H, s), 8.76 (1H, d), 8.80 (1H, s), 9.06 (1H, d), 10.59 (1H, s).

Example 101:

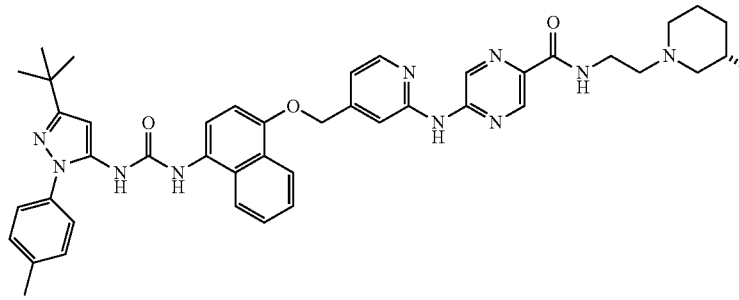

(S)-5-(((4-(((4-(3-(3-(tert-butyl)-1-(p-tolyl)-1H-pyrazol-5-yl)ureido)naphthalen-1-yl)oxy)methyl)
pyridin-2-yl)amino)-N-(2-(3-fluoropiperidin-1-yl)ethyl)pyrazine-2-carboxamide
Route code*: 7

R$^t$ 1.72 min (Method 1); m/z 771 (M + H)$^+$ (ES$^+$); $^1$H NMR (400 MHz, DMSO-d$_6$) δ: 1.28 (9H, s), 1.39-1.59 (2H, overlapping m), 1.65-1.92 (2H, overlapping m), 2.31 (1H, m), 2.40 (3H, s), 2.80 (1H, m), 3.42 (2H, q), 4.62 (1H, m), 5.39 (2H, s), 6.35 (1H, s), 7.04 (1H, d), 7.16 (1H, dd), 7.36 (2H, m), 7.45 (2H, m), 7.55-7.71 (3H, overlapping m), 7.96 (1H, m), 8.10 (1H, s), 8.35 (1H, m), 8.38-8.52 (3H, overlapping m), 8.67-8.81 (2H, overlapping m), 8.95 (1H, s), 9.06 (1H, d), 10.59 (1H, s). Missing 3H, obscured by the DMSO solvent peak at 2.5 ppm Example 102:

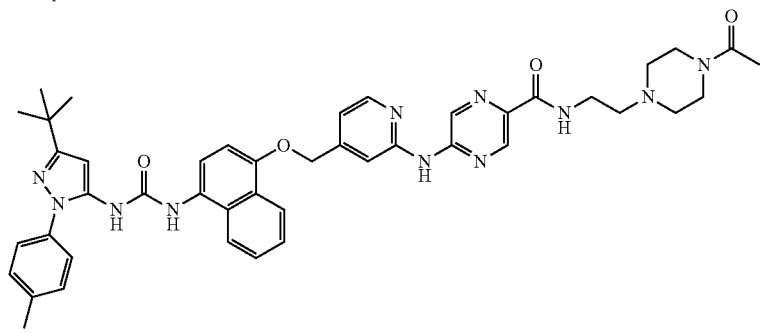

N-(2-(4-acetylpiperazin-1-yl)ethyl)-5-((4-(((4-(3-(3-(tert-butyl)-1-(p-tolyl)-1H-pyrazol-5-yl)ureido)
naphthalen-1-yl)oxy)methyl)pyridin-2-yl)amino)pyrazine-2-carboxamide
Route code*: 6

R$^t$ 1.66 min (Method 1); m/z 796 (M + H)$^+$ (ES$^+$); $^1$H NMR (400 MHz, DMSO-d$_6$) δ: 1.27 (9H, s), 1.98 (3H, s), 2.35-2.54 (9H, overlapping m), 3.38-3.47 (6H, overlapping m), 5.39 (2H, s), 6.36 (1H, s), 7.04 (1H, d), 7.16 (1H, d), 7.36 (2H, m), 7.44 (2H, m), 7.58-7.67 (3H, overlapping m), 7.94 (1H, m), 8.09 (1H, s), 8.35 (1H, d), 8.38 (1H, m), 8.50 (1H, t), 8.60 (1H, s), 8.75 (1H, s), 8.81 (1H, s), 9.05 (1H, s), 10.61 (1H, s).

Example 103:

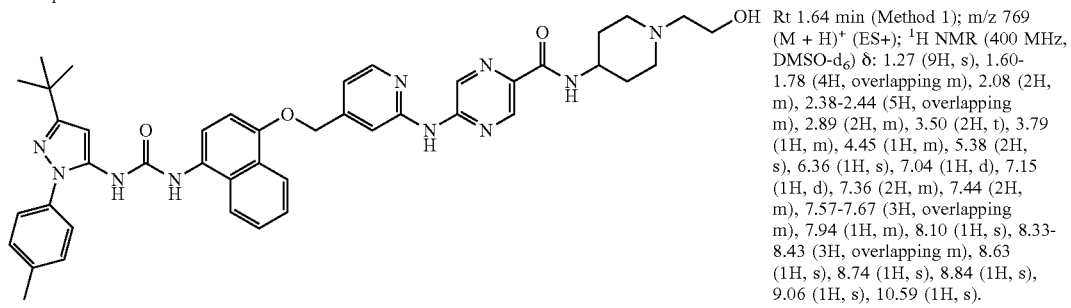

5-((4-(((4-(3-(3-(tert-butyl)-1-(p-tolyl)-1H-pyrazol-5-yl)ureido)naphthalen-1-yl)oxy)methyl)
pyridin-2-yl)amino)-N-(1-(2-hydroxyethyl)piperidin-4-yl)pyrazine-2-carboxamide
Route code*: 6

Rt 1.64 min (Method 1); m/z 769 (M + H)$^+$ (ES+); $^1$H NMR (400 MHz, DMSO-d$_6$) δ: 1.27 (9H, s), 1.60-1.78 (4H, overlapping m), 2.08 (2H, m), 2.38-2.44 (5H, overlapping m), 2.89 (2H, m), 3.50 (2H, t), 3.79 (1H, m), 4.45 (1H, m), 5.38 (2H, s), 6.36 (1H, s), 7.04 (1H, d), 7.15 (1H, d), 7.36 (2H, m), 7.44 (2H, m), 7.57-7.67 (3H, overlapping m), 7.94 (1H, m), 8.10 (1H, s), 8.33-8.43 (3H, overlapping m), 8.63 (1H, s), 8.74 (1H, s), 8.84 (1H, s), 9.06 (1H, s), 10.59 (1H, s).

Example 104:

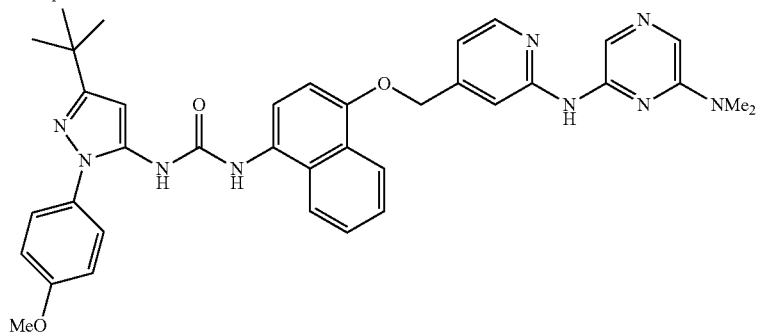

Route code*: 3

1-(3-(tert-butyl)-1-(4-methoxyphenyl)-1H-pyrazol-5-yl)-3-(4-((2-((6-(dimethylamino)pyrazin-2-yl)amino)pyridin-4-yl)methoxy)naphthalen-1-yl)urea
R$^t$ 1.92 min (Method 1); m/z 658 (M + H)$^+$ (ES$^+$).

Example 105:

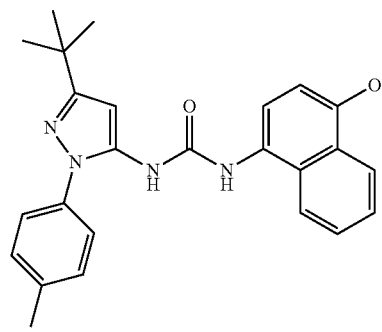

Route code*: 1

1-(3-(tert-butyl)-1-(p-tolyl)-1H-pyrazol-5-yl)-3-(4-((2-((5-methoxypyrazin-2-yl)amino)pyridin-4-yl)methoxy)naphthalen-1-yl)urea
R$^t$ 2.06 min (Method 1); m/z 629 (M + H)$^+$ (ES$^+$).

Example 106:

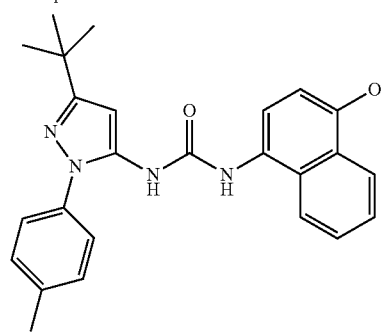

Route code*: 3

1-(4-((2-((6-aminopyrazin-2-yl)amino)pyridin-4-yl)methoxy)naphthalen-1-yl)-3-(3-(tert-butyl)-1-(p-tolyl)-1H-pyrazol-5-yl)urea
R$^t$ 1.83 min (Method 1); m/z 614 (M + H)$^+$ (ES$^+$).

Example 107:

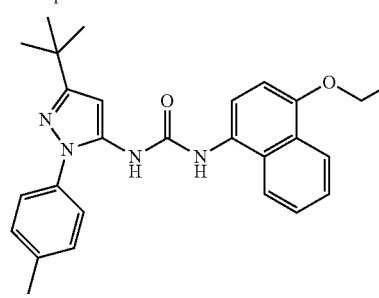

Route code*: 3

N-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-2-methoxyacetamide
R$^t$ 1.94 min (Method 1); m/z 686 (M + H)$^+$ (ES$^+$).

Example 108:

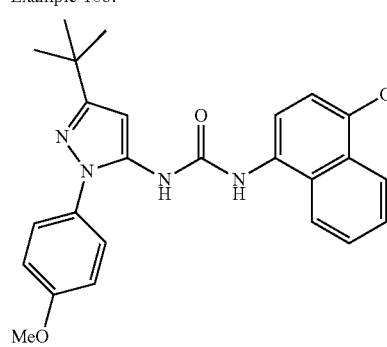

Route code*: 1

1-(3-(tert-butyl)-1-(4-methoxyphenyl)-1H-pyrazol-5-yl)-3-(4-((2-((6-methoxypyrazin-2-yl)amino)pyridin-4-yl)methoxy)naphthalen-1-yl)urea
R$^t$ 2.25 min (Method 1); m/z 645 (M + H)$^+$ (ES$^+$).

Example 109:

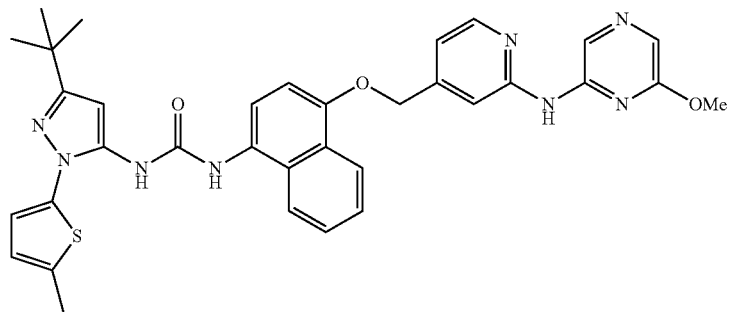

Route code*: 1

1-(3-(tert-butyl)-1-(5-methylthiophen-2-yl)-1H-pyrazol-5-yl)-3-(4-((2-((6-methoxypyrazin-2-yl)amino)pyridin-4-yl)methoxy)naphthalen-1-yl)urea
R$^t$ 2.39 min (Method 1); m/z 635 (M + H)$^+$ (ES$^+$).

Example 110:

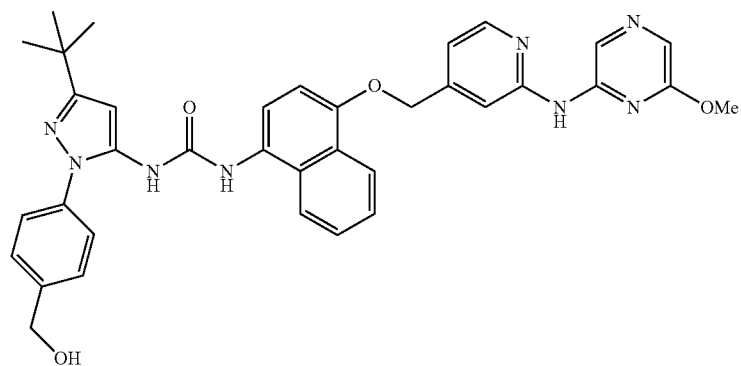

Route code*: 1

1-(3-(tert-butyl)-1-(4-(hydroxymethyl)phenyl)-1H-pyrazol-5-yl)-3-(4-((2-((6-methoxypyrazin-2-yl)amino)pyridin-4-yl)methoxy)naphthalen-1-yl)urea
R$^t$ 1.96 min (Method 1); m/z 645 (M + H)$^+$ (ES$^+$).

Example 111:

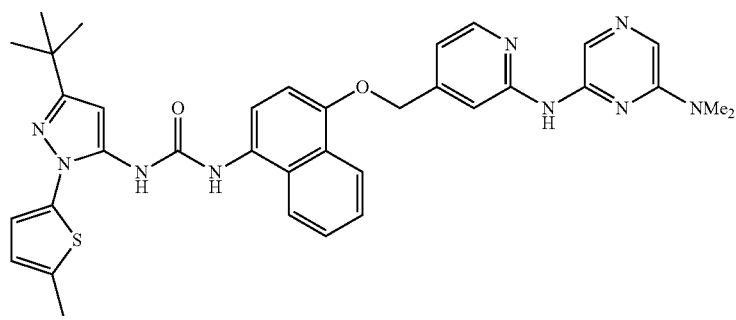

Route code*: 1

1-(3-(tert-butyl)-1-(5-methylthiophen-2-yl)-1H-pyrazol-5-yl)-3-(4-((2-((6-(dimethylamino)pyrazin-2-yl)amino)pyridin-4-yl)methoxy)naphthalen-1-yl)urea
R$^t$ 2.05 min (Method 1); m/z 648 (M + H)$^+$ (ES$^+$).

Example 112:

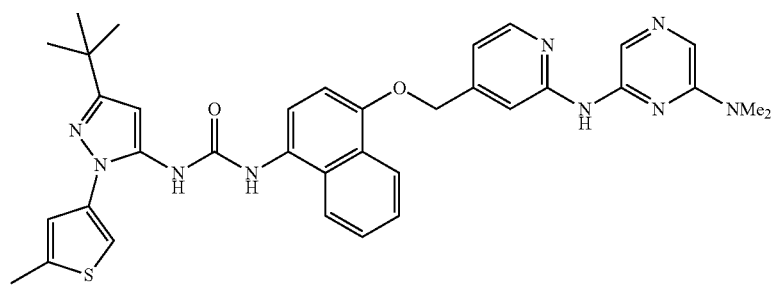

Route code*: 1

1-(3-(tert-butyl)-1-(5-methylthiophen-3-yl)-1H-pyrazol-5-yl)-3-(4-((2-((6-(dimethylamino)pyrazin-2-yl)amino)pyridin-4-yl)methoxy)naphthalen-1-yl)urea
R$^t$ 2.03 min (Method 1); m/z 648 (M + H)$^+$ (ES$^+$).

Example 113:

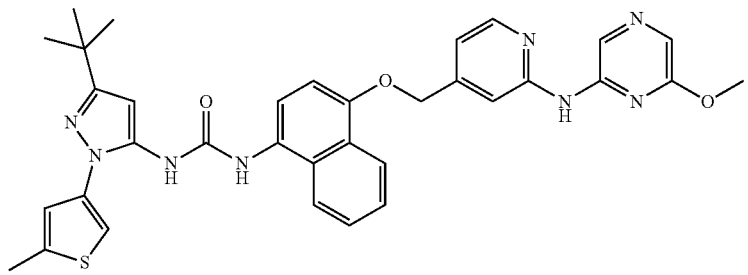

Route code*: 1

1-(3-(tert-butyl)-1-(5-methylthiophen-3-yl)-1H-pyrazol-5-yl)-3-(4-((2-((6-methoxypyrazin-2-yl)amino)pyridin-4-yl)methoxy)naphthalen-1-yl)urea
$R^t$ 2.38 min (Method 1); m/z 635 (M + H)$^+$ (ES$^+$).

Example 114:

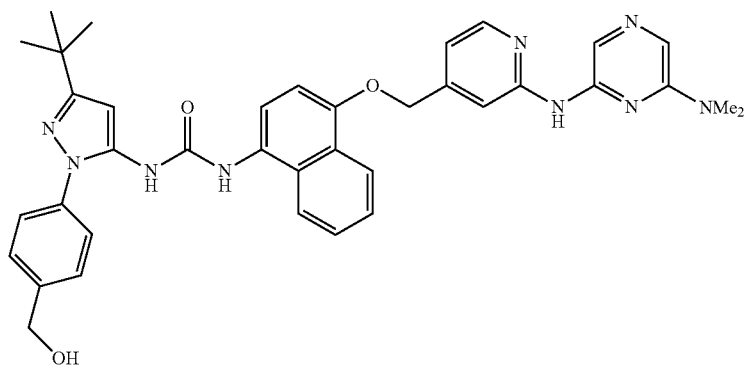

Route code*: 1

1-(3-(tert-butyl)-1-(4-(hydroxymethyl)phenyl)-1H-pyrazol-5-yl)-3-(4-((2-((6-(dimethylamino)pyrazin-2-yl)amino)pyridin-4-yl)methoxy)naphthalen-1-yl)urea
$R^t$ 1.75 min (Method 1); m/z 658 (M + H)$^+$ (ES$^+$).

Example 115:

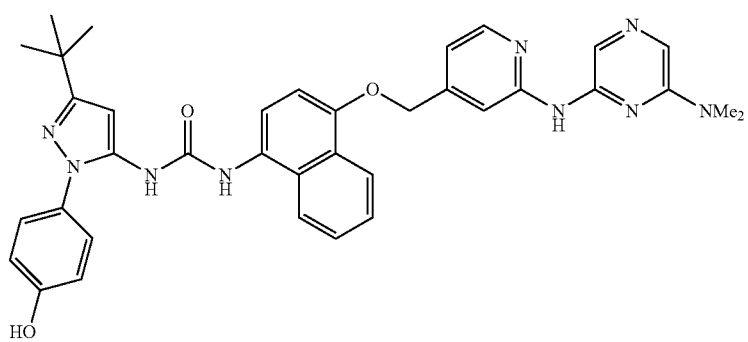

Route code*: 1

1-(3-(tert-butyl)-1-(4-hydroxyphenyl)-1H-pyrazol-5-yl)-3-(4-((2-((6-(dimethylamino)pyrazin-2-yl)amino)pyridin-4-yl)methoxy)naphthalen-1-yl)urea
$R^t$ 1.79 min (Method 1); m/z 644 (M + H)$^+$ (ES$^+$).

Example 116:

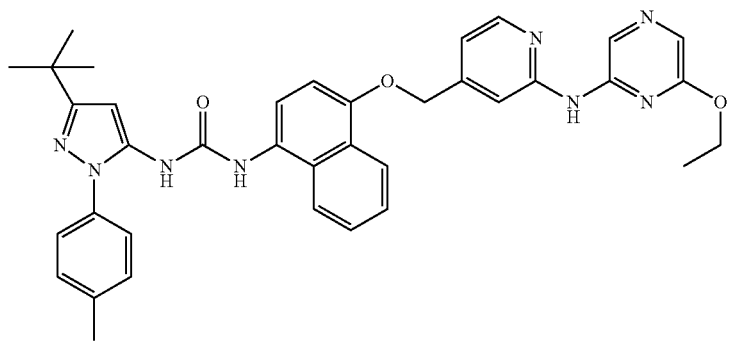

Route code*: 8

1-(3-(tert-butyl)-1-(p-tolyl)-1H-pyrazol-5-yl)-3-(4-((2-((6-ethoxypyrazin-2-yl)amino)pyridin-4-yl)methoxy)naphthalen-1-yl)urea
$R^t$ 2.50 min (Method 1); m/z 643 (M + H)$^+$ (ES$^+$).

Example 117:

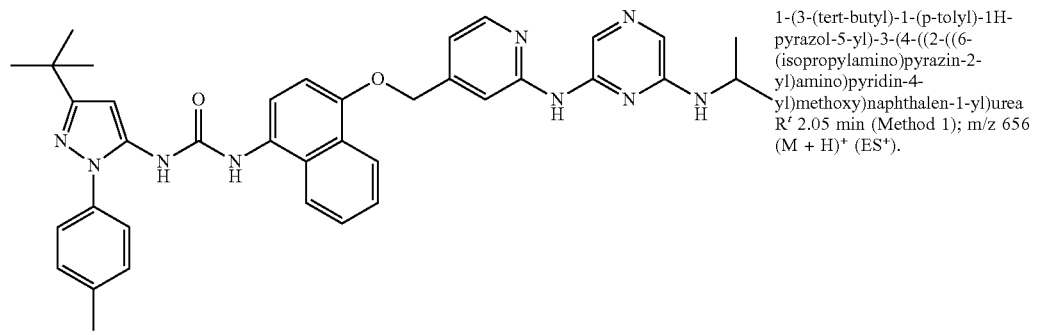

Route code*: 8

1-(3-(tert-butyl)-1-(p-tolyl)-1H-pyrazol-5-yl)-3-(4-((2-((6-(isopropylamino)pyrazin-2-yl)amino)pyridin-4-yl)methoxy)naphthalen-1-yl)urea R$^t$ 2.05 min (Method 1); m/z 656 (M + H)$^+$ (ES$^+$).

Example 118:

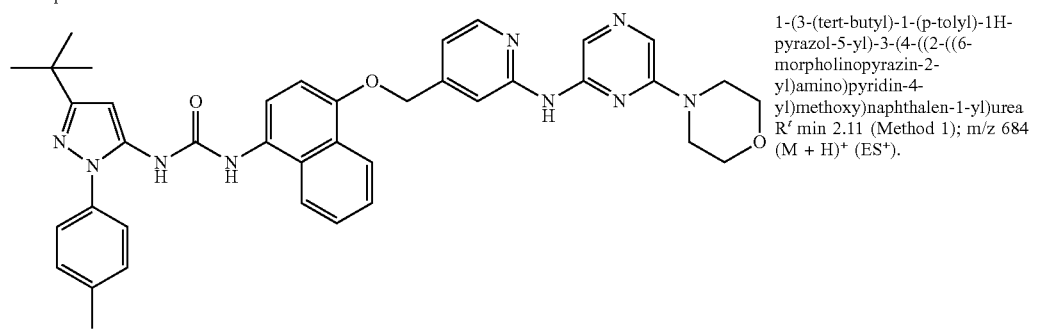

Route code*: 8

1-(3-(tert-butyl)-1-(p-tolyl)-1H-pyrazol-5-yl)-3-(4-((2-((6-morpholinopyrazin-2-yl)amino)pyridin-4-yl)methoxy)naphthalen-1-yl)urea R$^t$ min 2.11 (Method 1); m/z 684 (M + H)$^+$ (ES$^+$).

Example 119:

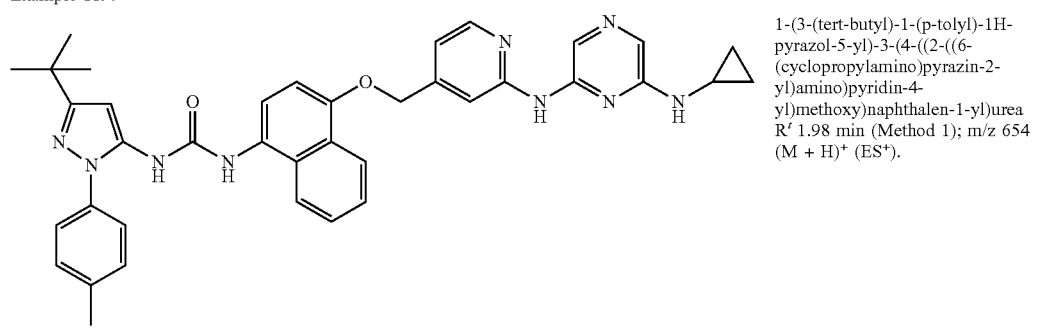

Route code*: 8

1-(3-(tert-butyl)-1-(p-tolyl)-1H-pyrazol-5-yl)-3-(4-((2-((6-(cyclopropylamino)pyrazin-2-yl)amino)pyridin-4-yl)methoxy)naphthalen-1-yl)urea R$^t$ 1.98 min (Method 1); m/z 654 (M + H)$^+$ (ES$^+$).

Example 120:

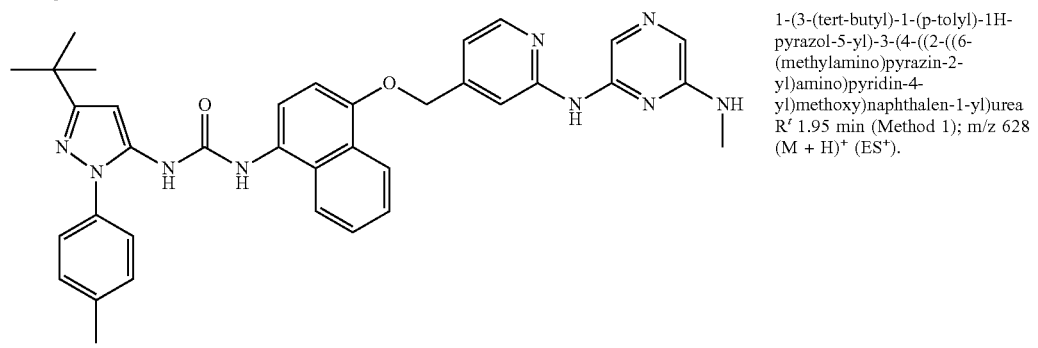

Route code*: 8

1-(3-(tert-butyl)-1-(p-tolyl)-1H-pyrazol-5-yl)-3-(4-((2-((6-(methylamino)pyrazin-2-yl)amino)pyridin-4-yl)methoxy)naphthalen-1-yl)urea R$^t$ 1.95 min (Method 1); m/z 628 (M + H)$^+$ (ES$^+$).

Example 121:

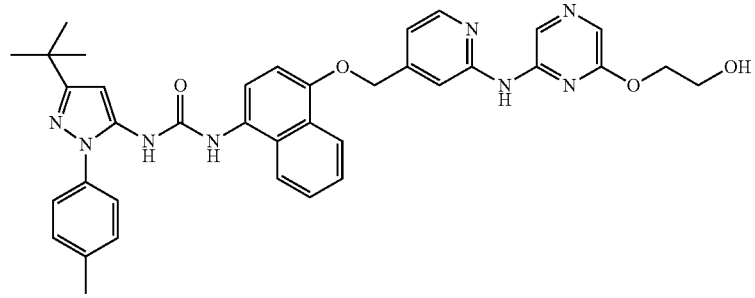

Route code*: 8

1-(3-(tert-butyl)-1-(p-tolyl)-1H-pyrazol-5-yl)-3-(4-((2-((6-(2-hydroxyethoxy)pyrazin-2-yl)amino)pyridin-4-yl)methoxy)naphthalen-1-yl)urea
R$^t$ 2.05 min (Method 1); m/z 659 (M + H)$^+$ (ES$^+$).

Example 122:

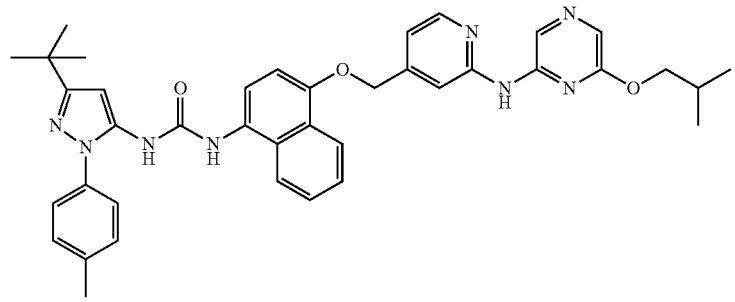

Route code*: 8

1-(3-(tert-butyl)-1-(p-tolyl)-1H-pyrazol-5-yl)-3-(4-((2-((6-isobutoxypyrazin-2-yl)amino)pyridin-4-yl)methoxy)naphthalen-1-yl)urea
R$^t$ 2.78 min (Method 1); m/z 671 (M + H)$^+$ (ES$^+$).

Example 123:

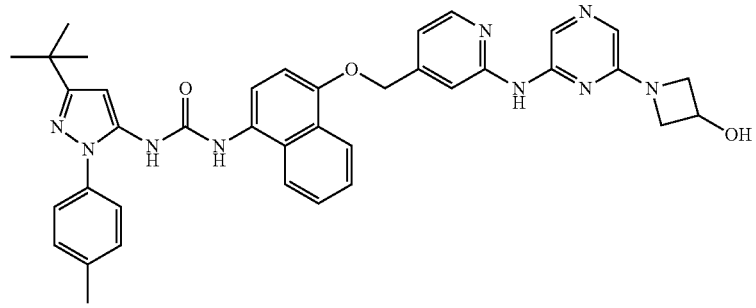

Route code*: 8

1-(3-(tert-butyl)-1-(p-tolyl)-1H-pyrazol-5-yl)-3-(4-((2-((6-(3-hydroxyazetidin-1-yl)pyrazin-2-yl)amino)pyridin-4-yl)methoxy)naphthalen-1-yl)urea
R$^t$ 1.86 min (Method 1); m/z 670 (M + H)$^+$ (ES$^+$).

Example 124:

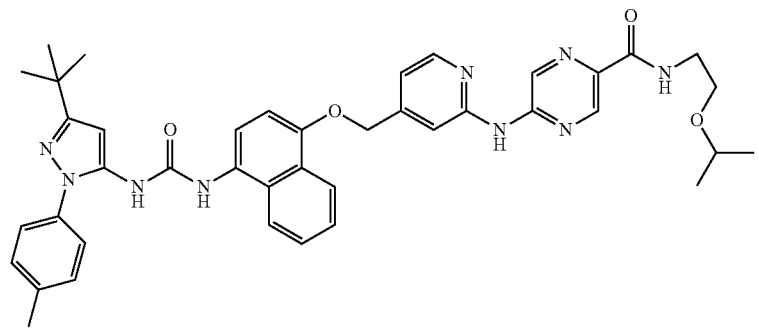

Route code*: 2

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-isopropoxyethyl)pyrazine-2-carboxamide
R$^t$ 2.48 min (Method 1); m/z 728 (M + H)$^+$ (ES$^+$).

Example 125:

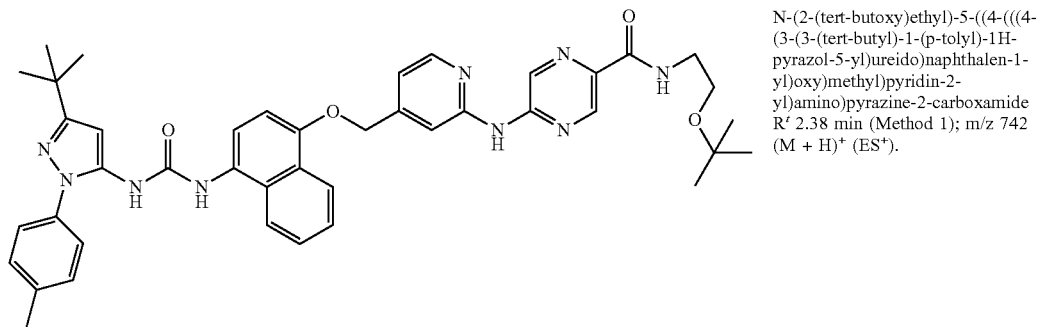

N-(2-(tert-butoxy)ethyl)-5-((4-(((4-(3-(3-(tert-butyl)-1-(p-tolyl)-1H-pyrazol-5-yl)ureido)naphthalen-1-yl)oxy)methyl)pyridin-2-yl)amino)pyrazine-2-carboxamide
$R^t$ 2.38 min (Method 1); m/z 742 (M + H)$^+$ (ES$^+$).

Route code*: 2

Example 126:

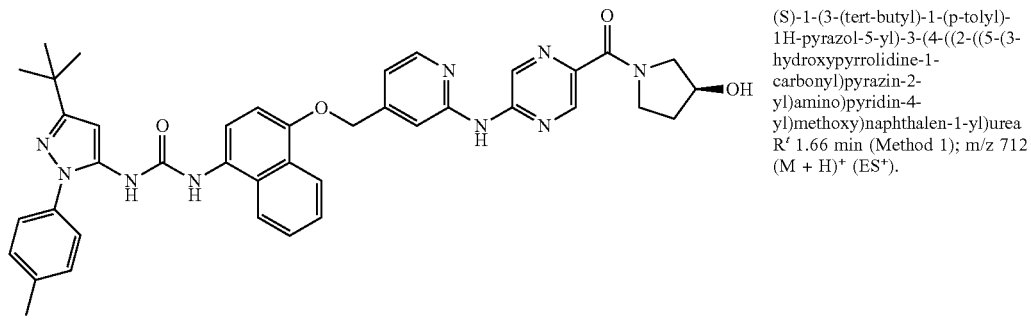

(S)-1-(3-(tert-butyl)-1-(p-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea
$R^t$ 1.66 min (Method 1); m/z 712 (M + H)$^+$ (ES$^+$).

Route code*: 2

Example 127:

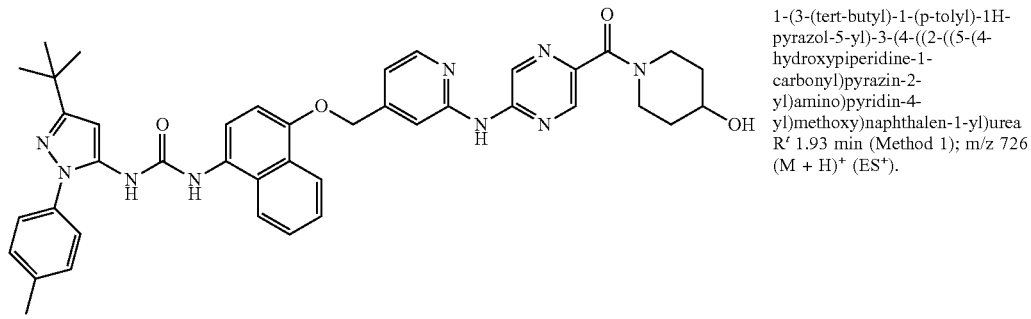

1-(3-(tert-butyl)-1-(p-tolyl)-1H-pyrazol-5-yl)-3-(4-((2-((5-(4-hydroxypiperidine-1-carbonyl)pyrazin-2-yl)amino)pyridin-4-yl)methoxy)naphthalen-1-yl)urea
$R^t$ 1.93 min (Method 1); m/z 726 (M + H)$^+$ (ES$^+$).

Route code*: 2

Example 128:

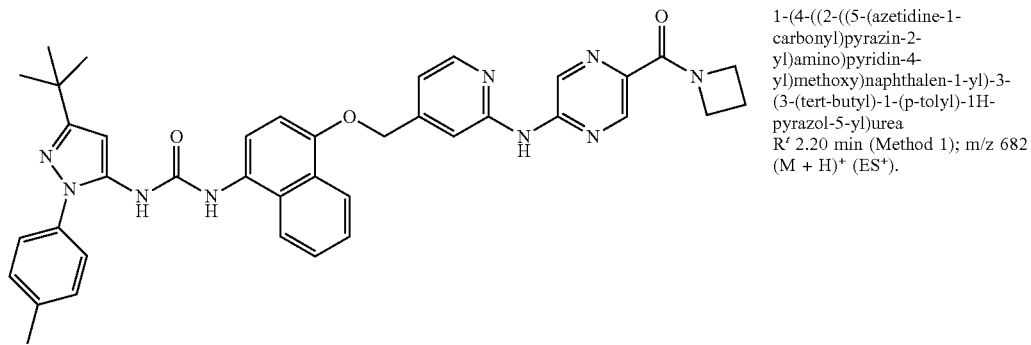

1-(4-((2-((5-(azetidine-1-carbonyl)pyrazin-2-yl)amino)pyridin-4-yl)methoxy)naphthalen-1-yl)-3-(3-(tert-butyl)-1-(p-tolyl)-1H-pyrazol-5-yl)urea
$R^t$ 2.20 min (Method 1); m/z 682 (M + H)$^+$ (ES$^+$).

Route code*: 2

Example 129:

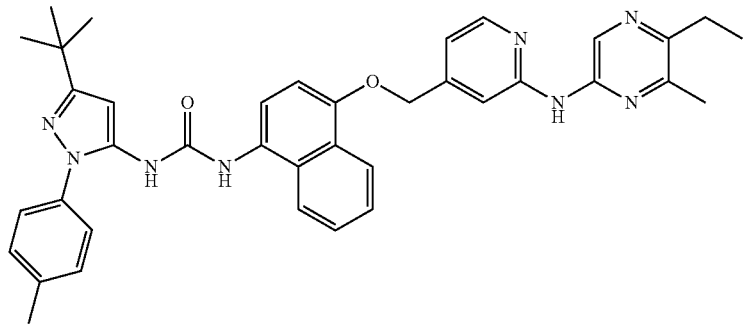

Route code*: 1

1-(3-(tert-butyl)-1-(p-tolyl)-1H-pyrazol-5-yl)-3-(4-((2-((5-ethyl-6-methylpyrazin-2-yl)amino)pyridin-4-yl)methoxy)naphthalen-1-yl)urea
$R^t$ 2.80 min (Method 2); m/z 641 $(M + H)^+$ $(ES^+)$.

Example 130:

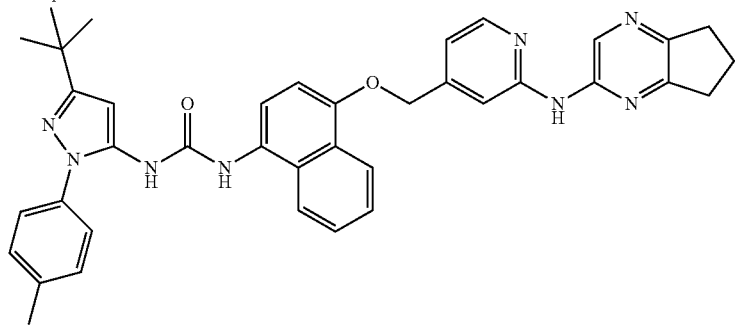

Route code*: 1

1-(3-(tert-butyl)-1-(p-tolyl)-1H-pyrazol-5-yl)-3-(4-((2-((6,7-dihydro-5H-cyclopenta[b]pyrazin-2-yl)amino)pyridin-4-yl)methoxy)naphthalen-1-yl)urea
$R^t$ 2.68 min (Method 2); m/z 639 $(M + H)^+$ $(ES^+)$.

Example 131:

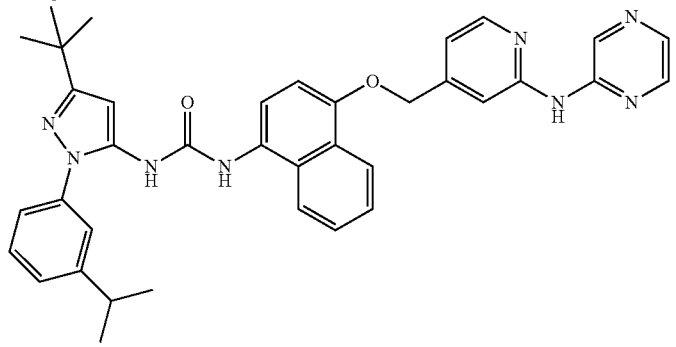

Route code*: 1

1-(3-(tert-butyl)-1-(3-isopropylphenyl)-1H-pyrazol-5-yl)-3-(4-((2-(pyrazin-2-ylamino)pyridin-4-yl)methoxy)naphthalen-1-yl)urea
$R^t$ 2.74 min (Method 2); m/z 627 $(M + H)^+$ $(ES^+)$.

Example 132:

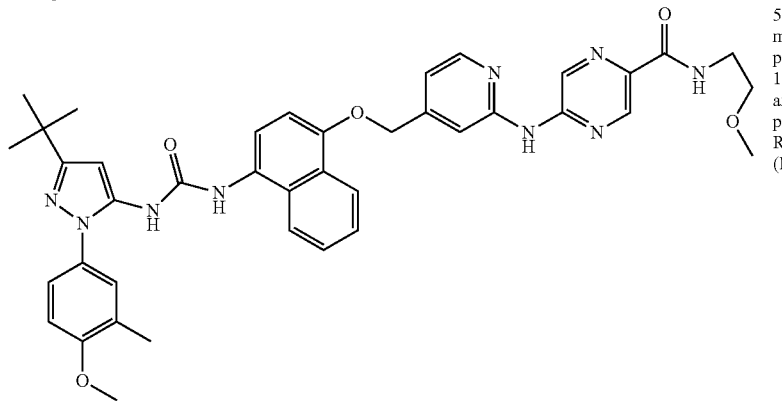

Route code*: 2

5-((4-(((4-(3-(3-(tert-butyl)-1-(4-methoxy-3-methylphenyl)-1H-pyrazol-5-yl)ureido)naphthalen-1-yl)oxy)methyl)pyridin-2-yl)amino)-N-(2-methoxyethyl)pyrazine-2-carboxamide
$R^t$ 2.24 min (Method 1); m/z 365.5 $(M + 2H)^{2+}$ $(ES^+)$.

Example 133:

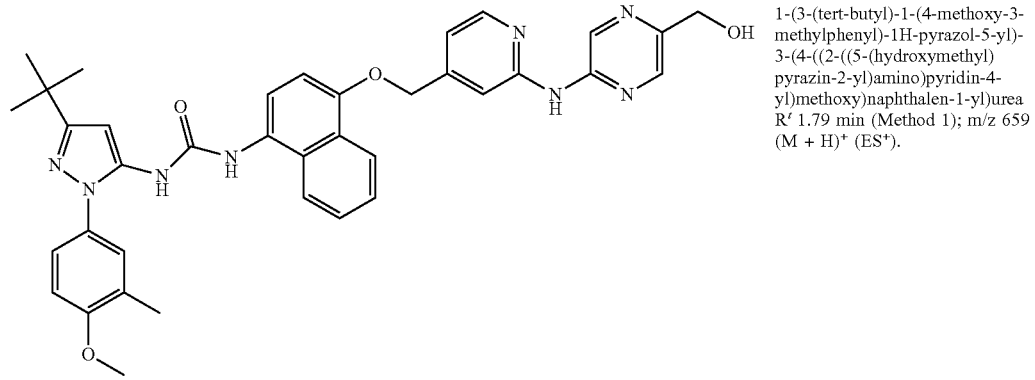

Route code*: 1

1-(3-(tert-butyl)-1-(4-methoxy-3-methylphenyl)-1H-pyrazol-5-yl)-3-(4-((2-((5-(hydroxymethyl)pyrazin-2-yl)amino)pyridin-4-yl)methoxy)naphthalen-1-yl)urea
R$^t$ 1.79 min (Method 1); m/z 659 (M + H)$^+$ (ES$^+$).

Example 134:

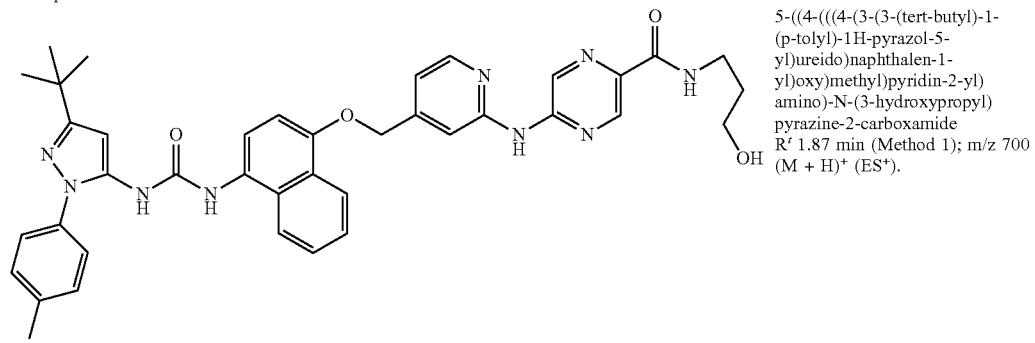

Route code*: 2

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-hydroxypropyl)pyrazine-2-carboxamide
R$^t$ 1.87 min (Method 1); m/z 700 (M + H)$^+$ (ES$^+$).

Example 135:

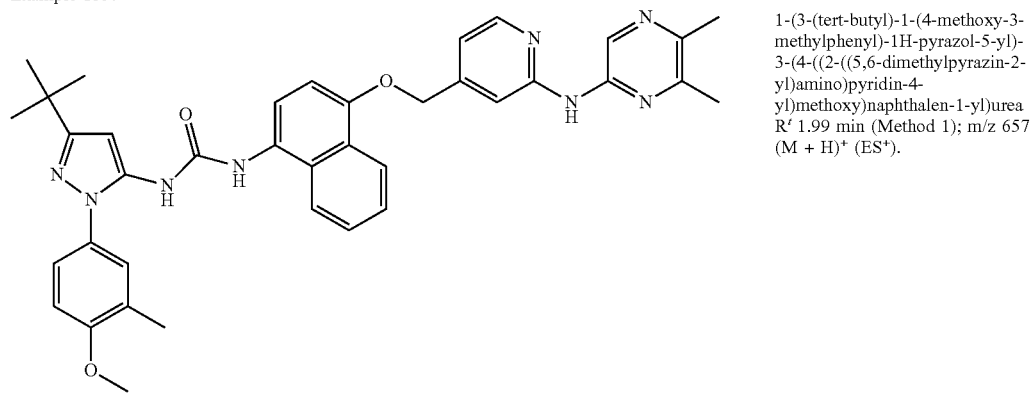

Route code*: 1

1-(3-(tert-butyl)-1-(4-methoxy-3-methylphenyl)-1H-pyrazol-5-yl)-3-(4-((2-((5,6-dimethylpyrazin-2-yl)amino)pyridin-4-yl)methoxy)naphthalen-1-yl)urea
R$^t$ 1.99 min (Method 1); m/z 657 (M + H)$^+$ (ES$^+$).

Example 136:

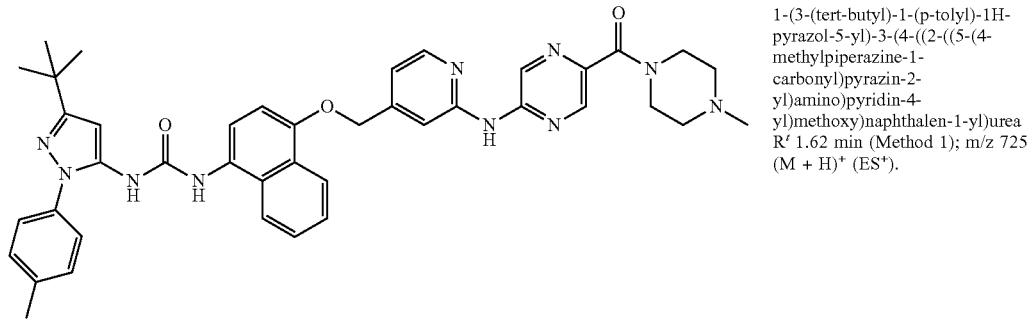

1-(3-(tert-butyl)-1-(p-tolyl)-1H-pyrazol-5-yl)-3-(4-((2-((5-(4-methylpiperazine-1-carbonyl)pyrazin-2-yl)amino)pyridin-4-yl)methoxy)naphthalen-1-yl)urea
R$^t$ 1.62 min (Method 1); m/z 725 (M + H)$^+$ (ES$^+$).

Route code*: 2

Example 137:

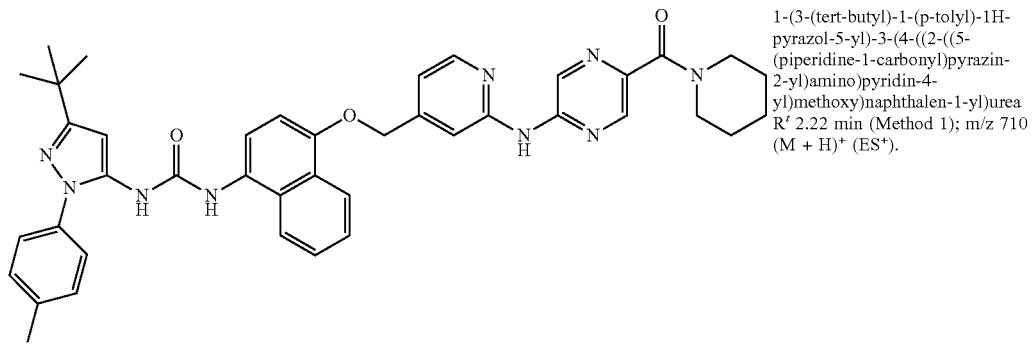

1-(3-(tert-butyl)-1-(p-tolyl)-1H-pyrazol-5-yl)-3-(4-((2-((5-(piperidine-1-carbonyl)pyrazin-2-yl)amino)pyridin-4-yl)methoxy)naphthalen-1-yl)urea
R$^t$ 2.22 min (Method 1); m/z 710 (M + H)$^+$ (ES$^+$).

Route code*: 2

Example 138:

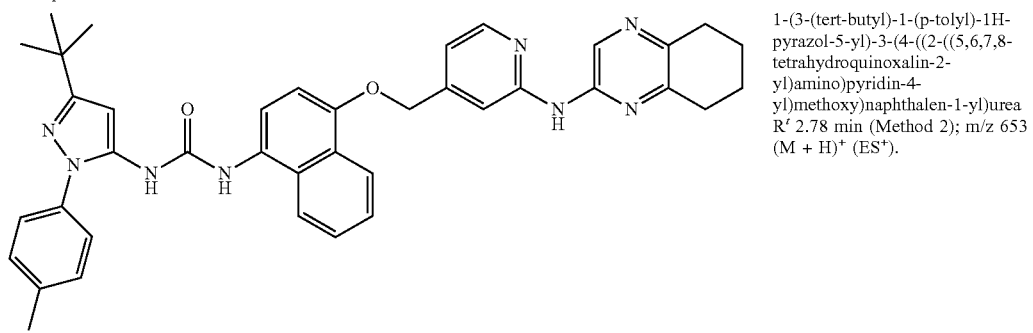

1-(3-(tert-butyl)-1-(p-tolyl)-1H-pyrazol-5-yl)-3-(4-((2-((5,6,7,8-tetrahydroquinoxalin-2-yl)amino)pyridin-4-yl)methoxy)naphthalen-1-yl)urea
R$^t$ 2.78 min (Method 2); m/z 653 (M + H)$^+$ (ES$^+$).

Route code*: 1

Example 139:

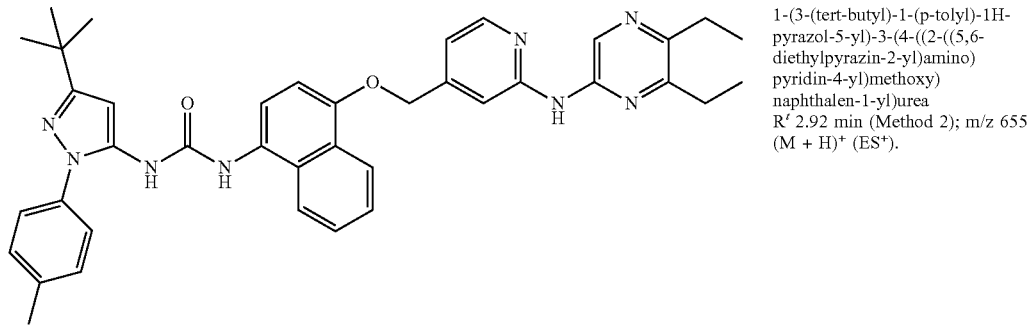

1-(3-(tert-butyl)-1-(p-tolyl)-1H-pyrazol-5-yl)-3-(4-((2-((5,6-diethylpyrazin-2-yl)amino)pyridin-4-yl)methoxy)naphthalen-1-yl)urea
R$^t$ 2.92 min (Method 2); m/z 655 (M + H)$^+$ (ES$^+$).

Route code*: 1

Example 140:

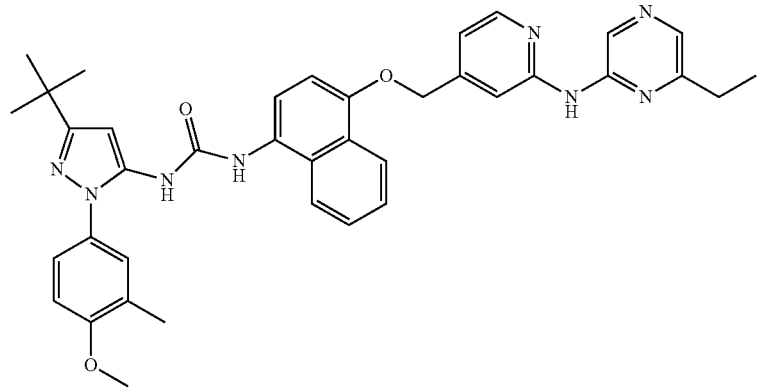

Route code*: 1

1-(3-(tert-butyl)-1-(4-methoxy-3-methylphenyl)-1H-pyrazol-5-yl)-3-(4-((2-((6-ethylpyrazin-2-yl)amino)pyridin-4-yl)methoxy)naphthalen-1-yl)urea
R$^t$ 2.15 min (Method 1); m/z 657 (M + H)$^+$ (ES$^+$).

Example 141:

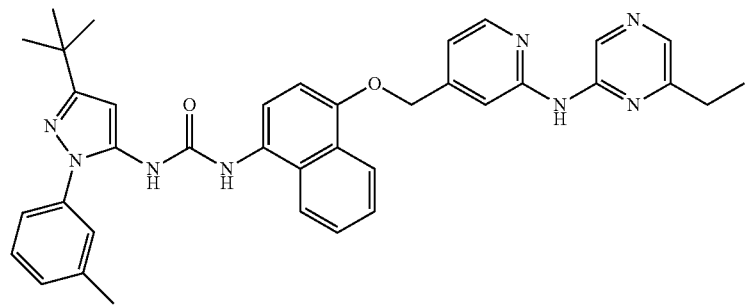

Route code*: 1

1-(3-(tert-butyl)-1-(m-tolyl)-1H-pyrazol-5-yl)-3-(4-((2-((6-ethylpyrazin-2-yl)amino)pyridin-4-yl)methoxy)naphthalen-1-yl)urea
R$^t$ 2.73 min (Method 2); m/z 627 (M + H)$^+$ (ES$^+$).

Example 142:

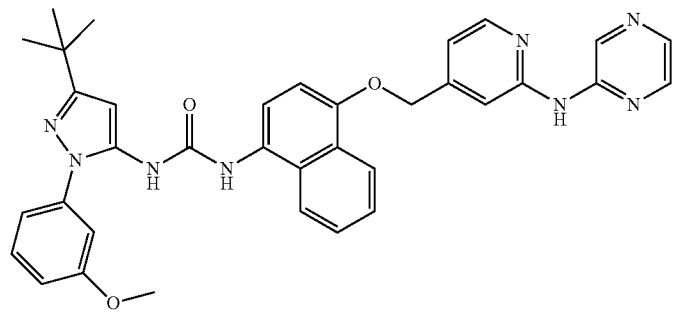

Route code*: 1

1-(3-(tert-butyl)-1-(3-methoxyphenyl)-1H-pyrazol-5-yl)-3-(4-((2-(pyrazin-2-ylamino)pyridin-4-yl)methoxy)naphthalen-1-yl)urea
R$^t$ 2.48 min (Method 2); m/z 615 (M + H)$^+$ (ES$^+$).

Example 143:

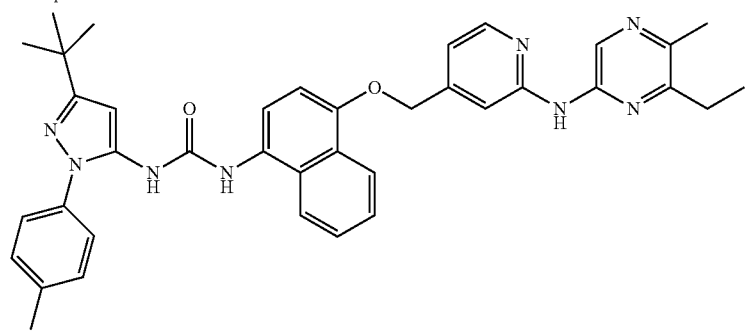

Route code*: 1

1-(3-(tert-butyl)-1-(p-tolyl)-1H-pyrazol-5-yl)-3-(4-((2-((6-ethyl-5-methylpyrazin-2-yl)amino)pyridin-4-yl)methoxy)naphthalen-1-yl)urea
R$^t$ 2.79 min (Method 2); m/z 641 (M + H)$^+$ (ES$^+$).

Example 144:

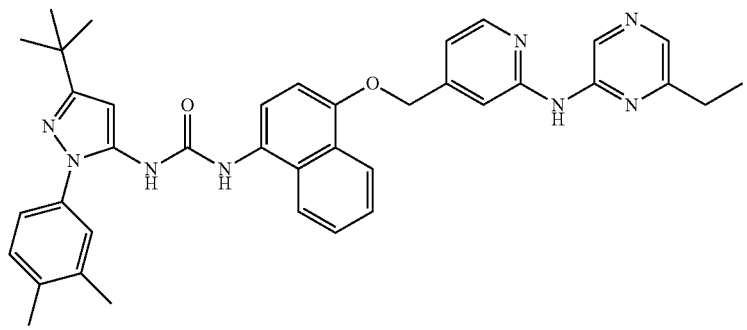

Route code*: 1

1-(3-(tert-butyl)-1-(3,4-dimethylphenyl)-1H-pyrazol-5-yl)-3-(4-((2-((6-ethylpyrazin-2-yl)amino)pyridin-4-yl)methoxy)naphthalen-1-yl)urea
$R^t$ 2.35 min (Method 1); m/z 641 (M + H)$^+$ (ES$^+$).

Example 145:

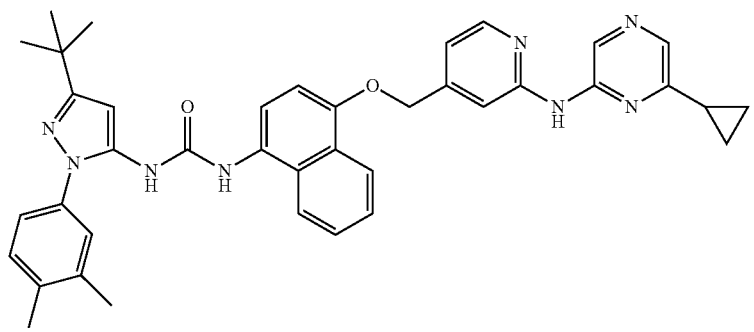

Route code*: 1

1-(3-(tert-butyl)-1-(3,4-dimethylphenyl)-1H-pyrazol-5-yl)-3-(4-((2-((6-cyclopropyl-pyrazin-2-yl)amino)pyridin-4-yl)methoxy)naphthalen-1-yl)urea
$R^t$ 2.53 min (Method 1); m/z 653 (M + H)$^+$ (ES$^+$).

Example 146:

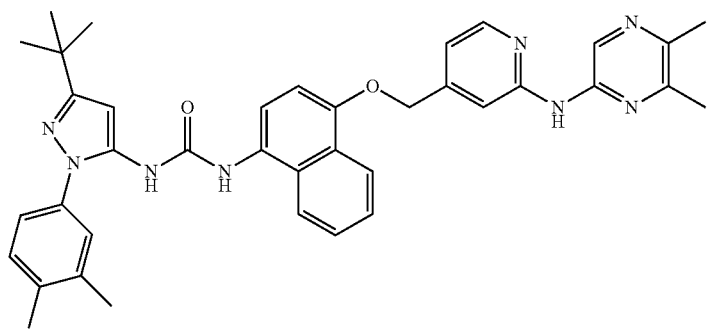

Route code*: 1

1-(3-(tert-butyl)-1-(3,4-dimethylphenyl)-1H-pyrazol-5-yl)-3-(4-((2-((5,6-dimethyl-pyrazin-2-yl)amino)pyridin-4-yl)methoxy)naphthalen-1-yl)urea
$R^t$ 2.18 min (Method 1); m/z 641 (M + H)$^+$ (ES$^+$).

Example 147:

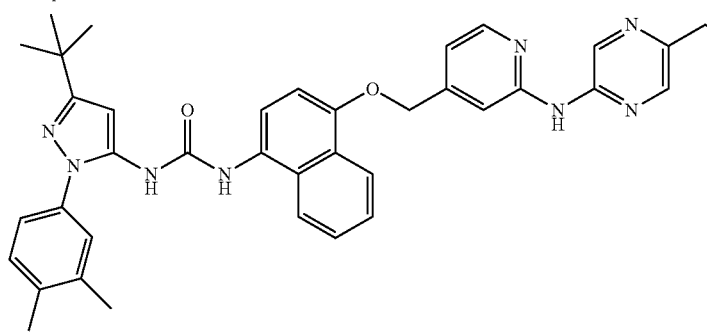

Route code*: 1

1-(3-(tert-butyl)-1-(3,4-dimethylphenyl)-1H-pyrazol-5-yl)-3-(4-((2-((5-(hydroxymethyl)pyrazin-2-yl)amino)pyridin-4-yl)methoxy)naphthalen-1-yl)urea
$R^t$ 1.95 min (Method 1); m/z 643 (M + H)$^+$ (ES$^+$).

Example 148:

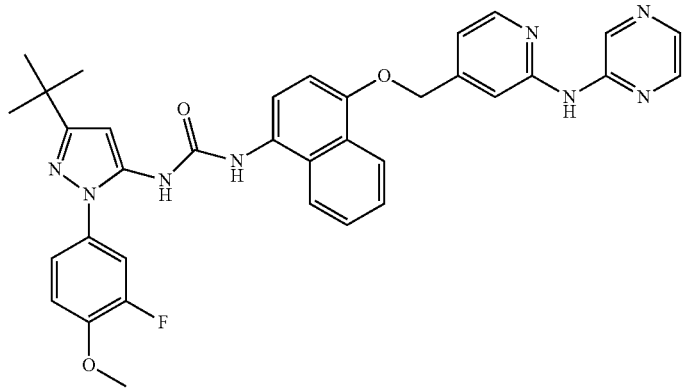

Route code*: 1

1-(3-(tert-butyl)-1-(3-fluoro-4-methoxyphenyl)-1H-pyrazol-5-yl)-3-(4-((2-(pyrazin-2-ylamino)pyridin-4-yl)methoxy)naphthalen-1-yl)urea
$R^t$ 1.87 min (Method 1); m/z 633 $(M + H)^+$ $(ES^+)$.

Example 149:

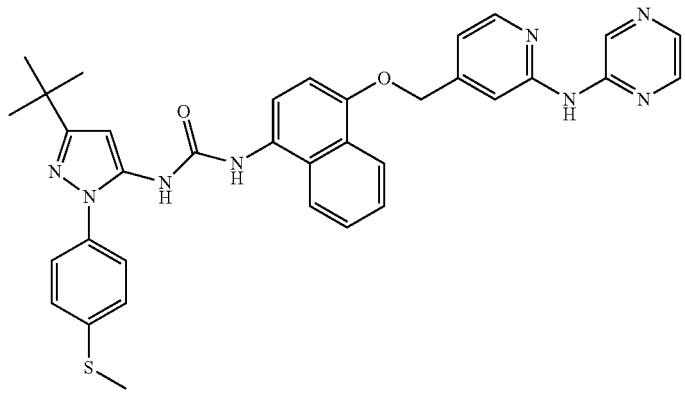

Route code*: 1

1-(3-(tert-butyl)-1-(4-(methylthio)phenyl)-1H-pyrazol-5-yl)-3-(4-((2-(pyrazin-2-ylamino)pyridin-4-yl)methoxy)naphthalen-1-yl)urea
$R^t$ 1.97 min (Method 1); m/z 631 $(M + H)^+$ $(ES^+)$.

Example 150:

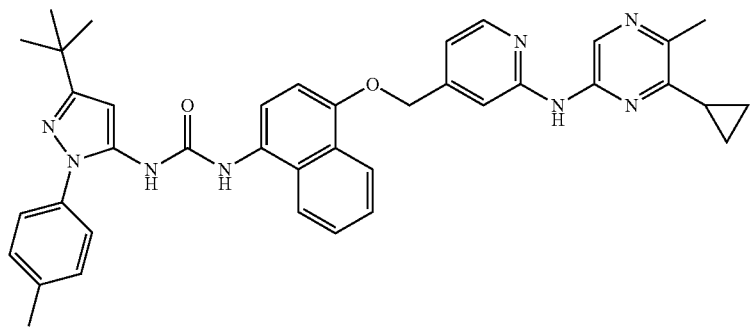

Route code*: 1

1-(3-(tert-butyl)-1-(p-tolyl)-1H-pyrazol-5-yl)-3-(4-((2-((6-cyclopropyl-5-methylpyrazin-2-yl)amino)pyridin-4-yl)methoxy)naphthalen-1-yl)urea
$R^t$ 2.82 min (Method 2); m/z 653 $(M + H)^+$ $(ES^+)$.

-continued

Example 151:

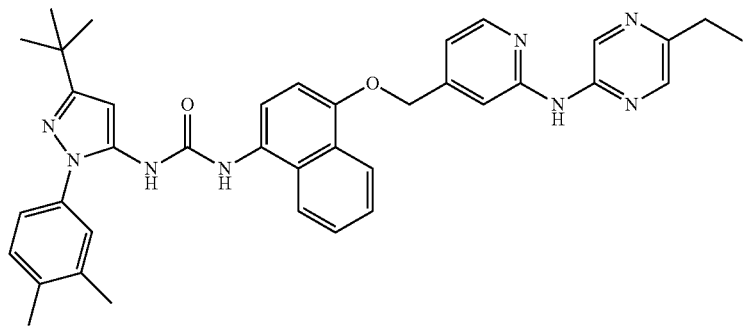

Route code*: 1

1-(3-(tert-butyl)-1-(3,4-dimethylphenyl)-1H-pyrazol-5-yl)-3-(4-((2-((5-ethylpyrazin-2-yl)amino)pyridin-4-yl)methoxy)naphthalen-1-yl)urea
$R^t$ 2.05 min (Method 1); m/z 641 (M + H)$^+$ (ES$^+$).

Example 152:

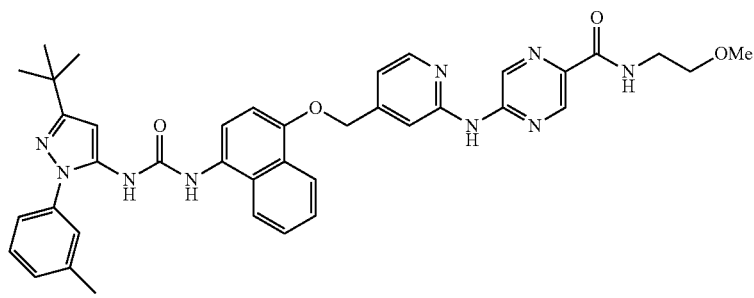

Route code*: 2

5-((4-(((4-(3-(3-(tert-butyl)-1-(m-tolyl)-1H-pyrazol-5-yl)ureido)naphthalen-1-yl)oxy)methyl)pyridin-2-yl)amino)-N-(2-methoxyethyl)pyrazine-2-carboxamide
$R^t$ 2.56 min (Method 2); m/z 700 (M + H)$^+$ (ES$^+$).

Example 153:

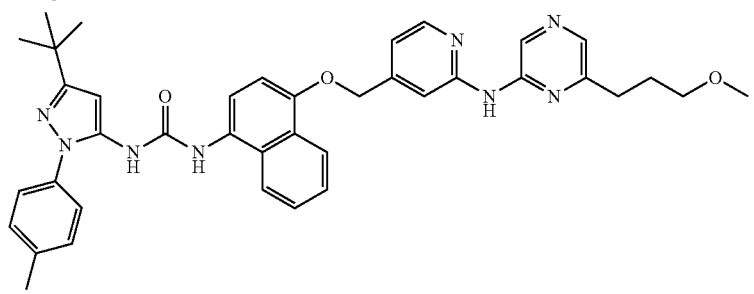

Route code*: 1

1-(3-(tert-butyl)-1-(p-tolyl)-1H-pyrazol-5-yl)-3-(4-((2-((6-(3-methoxypropyl)pyrazin-2-yl)amino)pyridin-4-yl)methoxy)naphthalen-1-yl)urea
$R^t$ 2.09 min (Method 1); m/z 671 (M + H)$^+$ (ES$^+$).

Example 154:

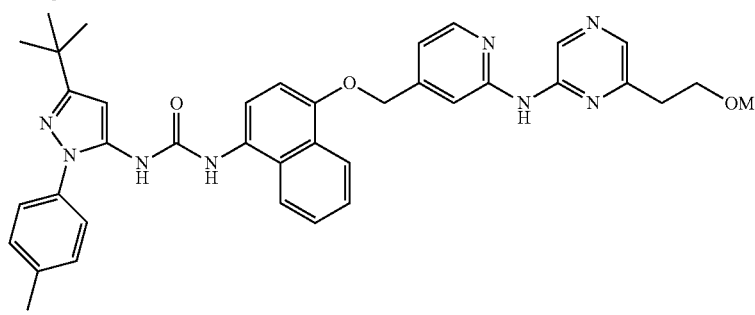

Route code*: 1

1-(3-(tert-butyl)-1-(p-tolyl)-1H-pyrazol-5-yl)-3-(4-((2-((6-(2-methoxyethyl)pyrazin-2-yl)amino)pyridin-4-yl)methoxy)naphthalen-1-yl)urea
$R^t$ 2.06 min (Method 1); m/z 657 (M + H)$^+$ (ES$^+$).

Example 155:

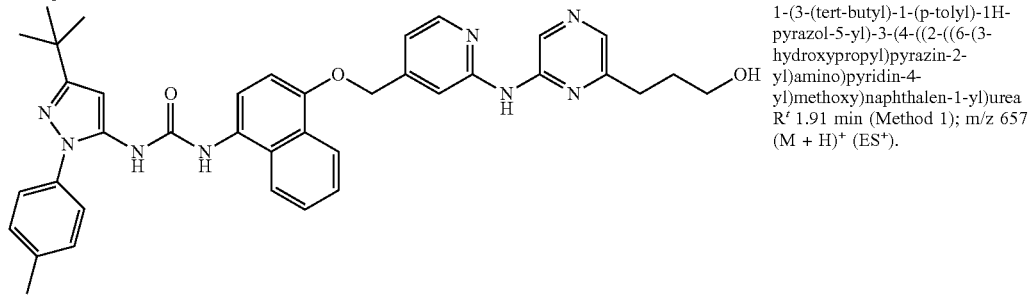

Route code*: 1

1-(3-(tert-butyl)-1-(p-tolyl)-1H-pyrazol-5-yl)-3-(4-((2-((6-(3-hydroxypropyl)pyrazin-2-yl)amino)pyridin-4-yl)methoxy)naphthalen-1-yl)urea
R$^t$ 1.91 min (Method 1); m/z 657 (M + H)$^+$ (ES$^+$).

Example 156:

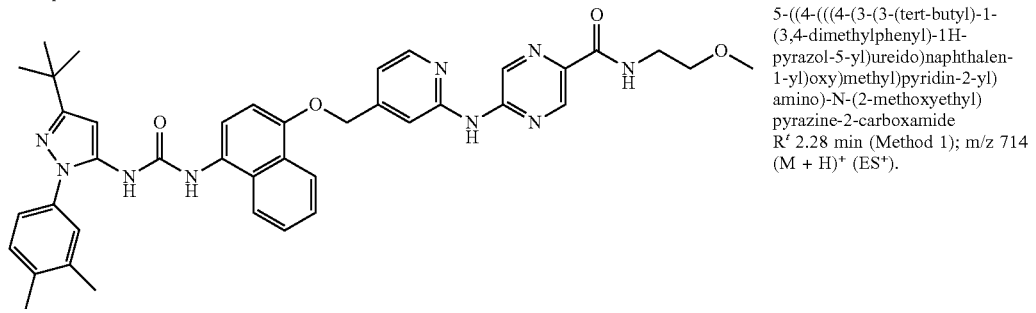

Route code*: 2

5-((4-(((4-(3-(3-(tert-butyl)-1-(3,4-dimethylphenyl)-1H-pyrazol-5-yl)ureido)naphthalen-1-yl)oxy)methyl)pyridin-2-yl)amino)-N-(2-methoxyethyl)pyrazine-2-carboxamide
R$^t$ 2.28 min (Method 1); m/z 714 (M + H)$^+$ (ES$^+$).

Example 157:

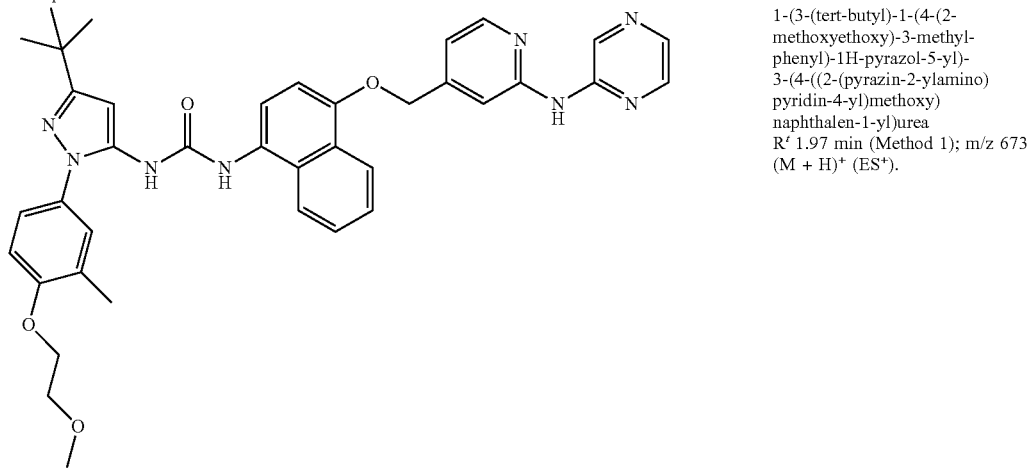

Route code*: 1

1-(3-(tert-butyl)-1-(4-(2-methoxyethoxy)-3-methylphenyl)-1H-pyrazol-5-yl)-3-(4-((2-(pyrazin-2-ylamino)pyridin-4-yl)methoxy)naphthalen-1-yl)urea
R$^t$ 1.97 min (Method 1); m/z 673 (M + H)$^+$ (ES$^+$).

Example 158:

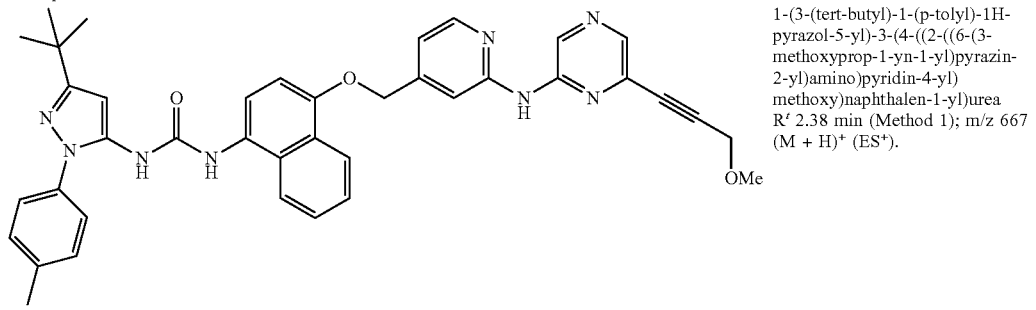

Route code*: 1

1-(3-(tert-butyl)-1-(p-tolyl)-1H-pyrazol-5-yl)-3-(4-((2-((6-(3-methoxyprop-1-yn-1-yl)pyrazin-2-yl)amino)pyridin-4-yl)methoxy)naphthalen-1-yl)urea
R$^t$ 2.38 min (Method 1); m/z 667 (M + H)$^+$ (ES$^+$).

Example 159:

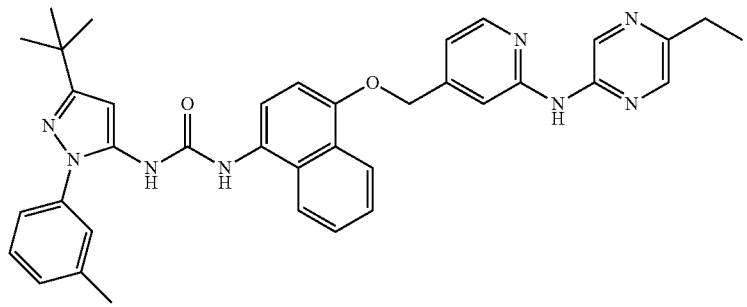

Route code*: 1

1-(3-(tert-butyl)-1-(m-tolyl)-1H-pyrazol-5-yl)-3-(4-((2-((5-ethylpyrazin-2-yl)amino)pyridin-4-yl)methoxy)naphthalen-1-yl)urea R$^t$ 2.73 min (Method 2); m/z 627 (M + H)$^+$ (ES$^+$).

Example 160:

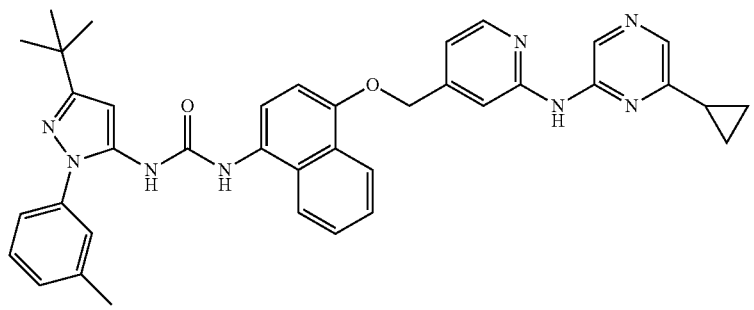

Route code*: 1

1-(3-(tert-butyl)-1-(m-tolyl)-1H-pyrazol-5-yl)-3-(4-((2-((6-cyclopropylpyrazin-2-yl)amino)pyridin-4-yl)methoxy)naphthalen-1-yl)urea R$^t$ 2.75 min (Method 2); m/z 639 (M + H)$^+$ (ES$^+$).

Example 161:

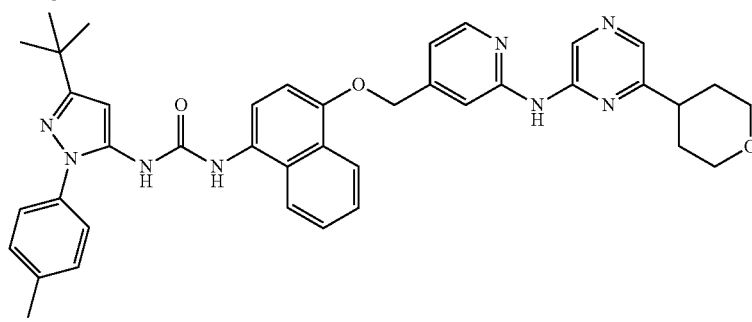

Route code*: 1

1-(3-(tert-butyl)-1-(p-tolyl)-1H-pyrazol-5-yl)-3-(4-((2-((6-(tetrahydro-2H-pyran-4-yl)pyrazin-2-yl)amino)pyridin-4-yl)methoxy)naphthalen-1-yl)urea R$^t$ 2.61 min (Method 2); m/z 683 (M + H)$^+$ (ES$^+$).

Example 162:

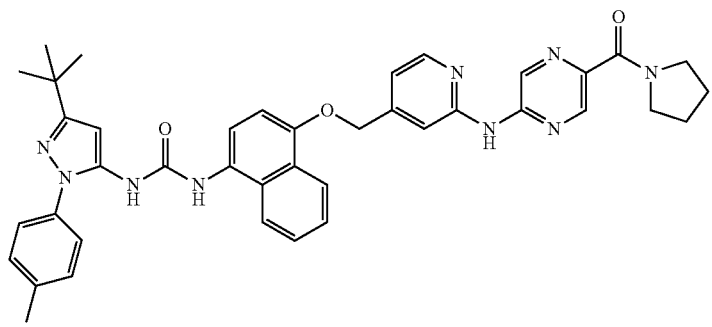

Route code*: 1

(R)-1-(3-(tert-butyl)-1-(p-tolyl)-1H-pyrazol-5-yl)-3-(4-((2-((5-(3-hydroxypyrrolidine-1-carbonyl)pyrazin-2-yl)amino)pyridin-4-yl)methoxy)naphthalen-1-yl)urea R$^t$ 1.94 min (Method 1); m/z 710 (M − H)$^−$ (ES$^−$).

Example 163:

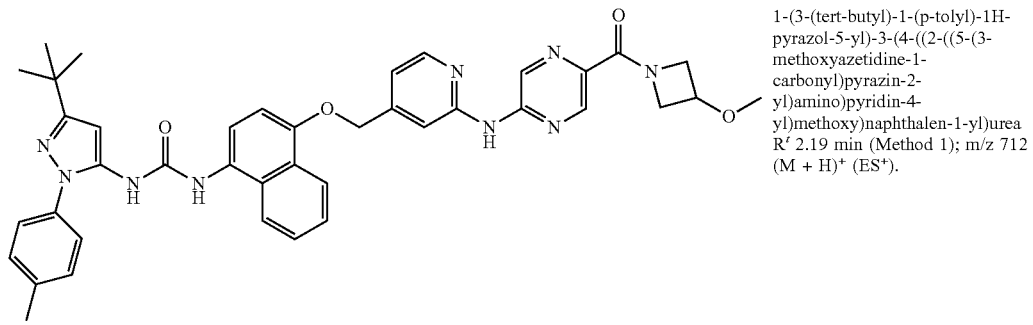

Route code*: 1

1-(3-(tert-butyl)-1-(p-tolyl)-1H-pyrazol-5-yl)-3-(4-((2-((5-(3-methoxyazetidine-1-carbonyl)pyrazin-2-yl)amino)pyridin-4-yl)methoxy)naphthalen-1-yl)urea
$R^t$ 2.19 min (Method 1); m/z 712 (M + H)$^+$ (ES$^+$).

Example 164:

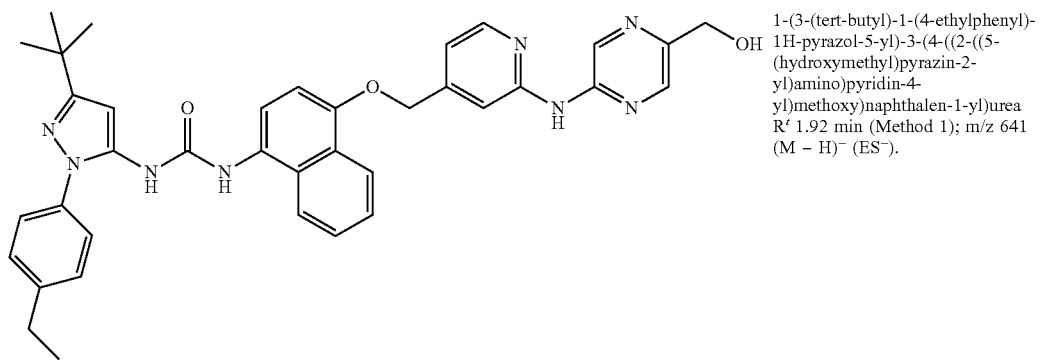

Route code*: 1

1-(3-(tert-butyl)-1-(4-ethylphenyl)-1H-pyrazol-5-yl)-3-(4-((2-((5-(hydroxymethyl)pyrazin-2-yl)amino)pyridin-4-yl)methoxy)naphthalen-1-yl)urea
$R^t$ 1.92 min (Method 1); m/z 641 (M − H)$^−$ (ES$^−$).

Example 165:

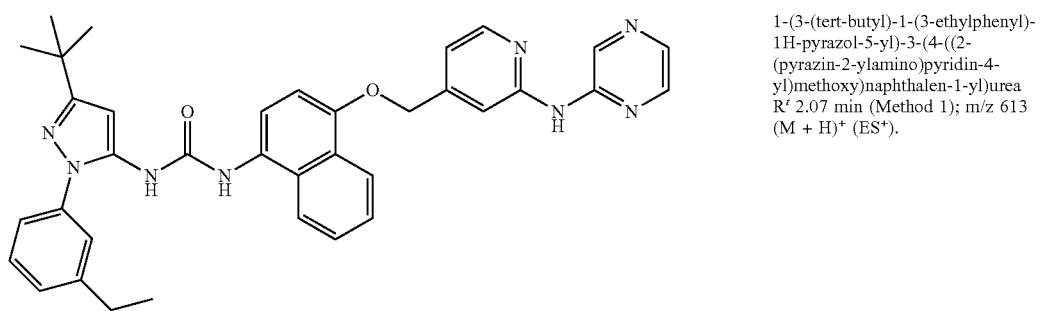

Route code*: 1

1-(3-(tert-butyl)-1-(3-ethylphenyl)-1H-pyrazol-5-yl)-3-(4-((2-(pyrazin-2-ylamino)pyridin-4-yl)methoxy)naphthalen-1-yl)urea
$R^t$ 2.07 min (Method 1); m/z 613 (M + H)$^+$ (ES$^+$).

Example 166:

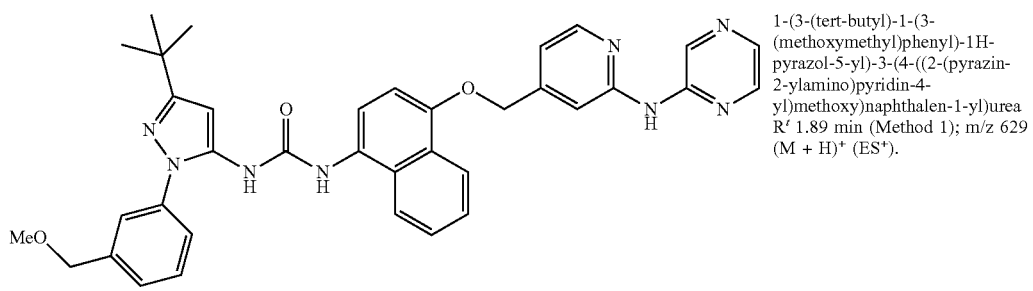

Route code*: 1

1-(3-(tert-butyl)-1-(3-(methoxymethyl)phenyl)-1H-pyrazol-5-yl)-3-(4-((2-(pyrazin-2-ylamino)pyridin-4-yl)methoxy)naphthalen-1-yl)urea
$R^t$ 1.89 min (Method 1); m/z 629 (M + H)$^+$ (ES$^+$).

Example 167:

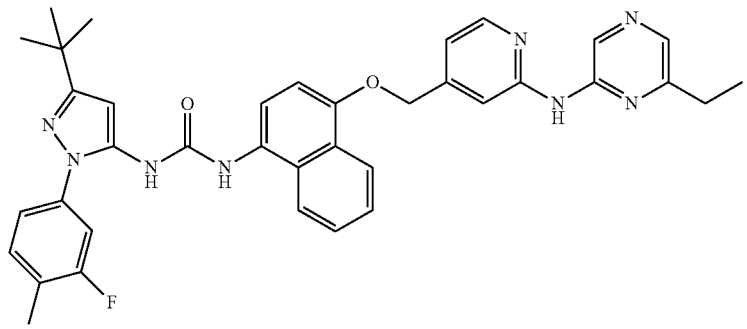

Route code*: 1

1-(3-(tert-butyl)-1-(3-fluoro-4-methylphenyl)-1H-pyrazol-5-yl)-3-(4-((2-((6-ethylpyrazin-2-yl)amino)pyridin-4-yl)methoxy)naphthalen-1-yl)urea
$R^t$ 2.25 min (Method 1); m/z 323 $(M + 2H)^{2+}$ (ES$^+$).

Example 168:

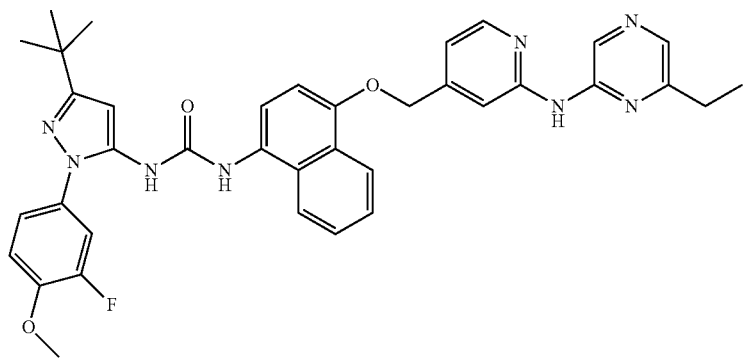 [SMILES: CCc1cncc(Nc2cc(COc3ccc(NC(=O)Nc4cc(C(C)(C)C)nn4-c4ccc(C)c(F)c4)c4ccccc34)ccn2)n1]

Route code*: 1

1-(3-(tert-butyl)-1-(3-fluoro-4-methoxyphenyl)-1H-pyrazol-5-yl)-3-(4-((2-((6-ethylpyrazin-2-yl)amino)pyridin-4-yl)methoxy)naphthalen-1-yl)urea
$R^t$ 2.12 min (Method 1); m/z 331 $(M + 2H)^{2+}$ (ES$^+$).

Example 169:

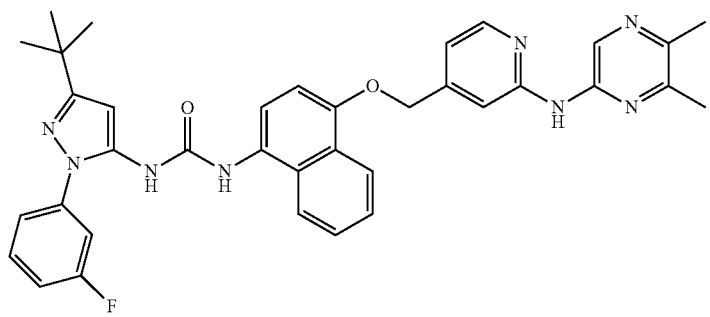

Route code*: 1

1-(3-(tert-butyl)-1-(3-fluorophenyl)-1H-pyrazol-5-yl)-3-(4-((2-((5,6-dimethylpyrazin-2-yl)amino)pyridin-4-yl)methoxy)naphthalen-1-yl)urea
$R^t$ 2.67 min (Method 2); m/z 631 $(M + H)^+$ (ES$^+$).

Example 170:

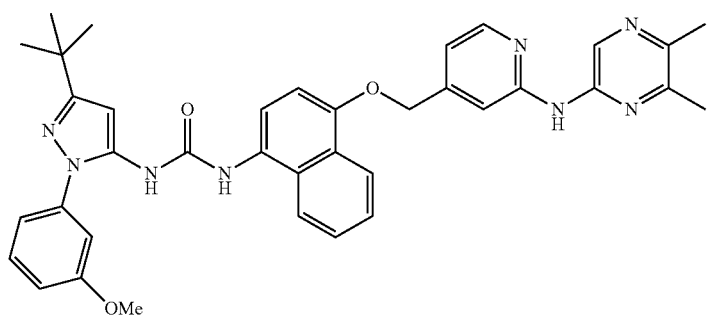

Route code*: 1

1-(3-(tert-butyl)-1-(3-methoxyphenyl)-1H-pyrazol-5-yl)-3-(4-((2-((5,6-dimethylpyrazin-2-yl)amino)pyridin-4-yl)methoxy)naphthalen-1-yl)urea
$R^t$ 2.59 min (Method 2); m/z 643 $(M + H)^+$ (ES$^+$).

-continued

Example 171:

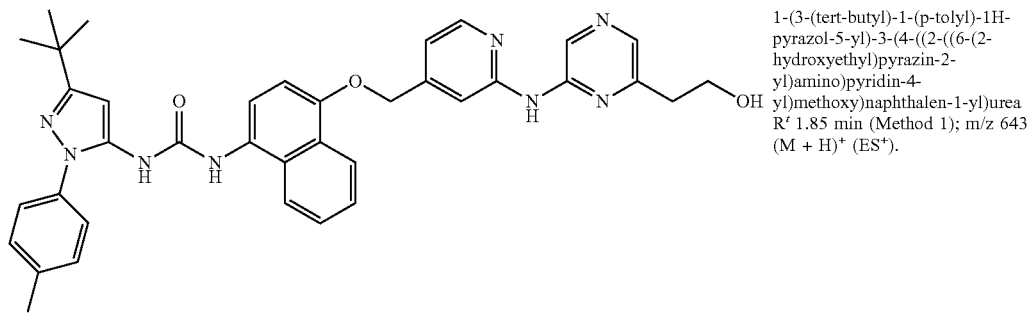

1-(3-(tert-butyl)-1-(p-tolyl)-1H-pyrazol-5-yl)-3-(4-((2-((6-(2-hydroxyethyl)pyrazin-2-yl)amino)pyridin-4-yl)methoxy)naphthalen-1-yl)urea
$R^t$ 1.85 min (Method 1); m/z 643 $(M + H)^+$ $(ES^+)$.

Route code*: 1

Example 172:

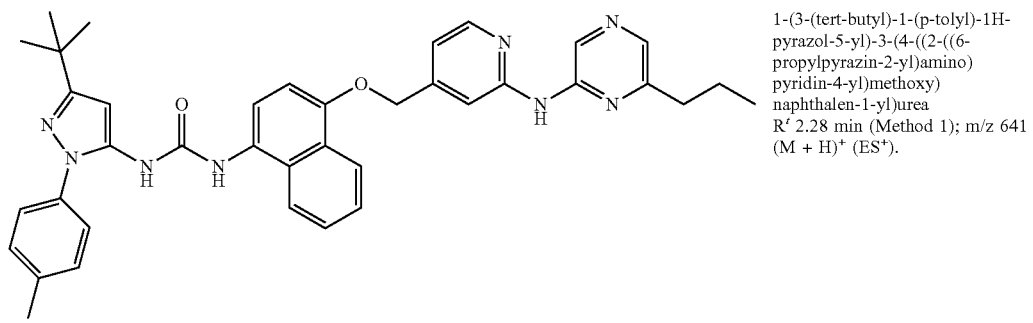

1-(3-(tert-butyl)-1-(p-tolyl)-1H-pyrazol-5-yl)-3-(4-((2-((6-propylpyrazin-2-yl)amino)pyridin-4-yl)methoxy)naphthalen-1-yl)urea
$R^t$ 2.28 min (Method 1); m/z 641 $(M + H)^+$ $(ES^+)$.

Route code*: 1

Example 173:

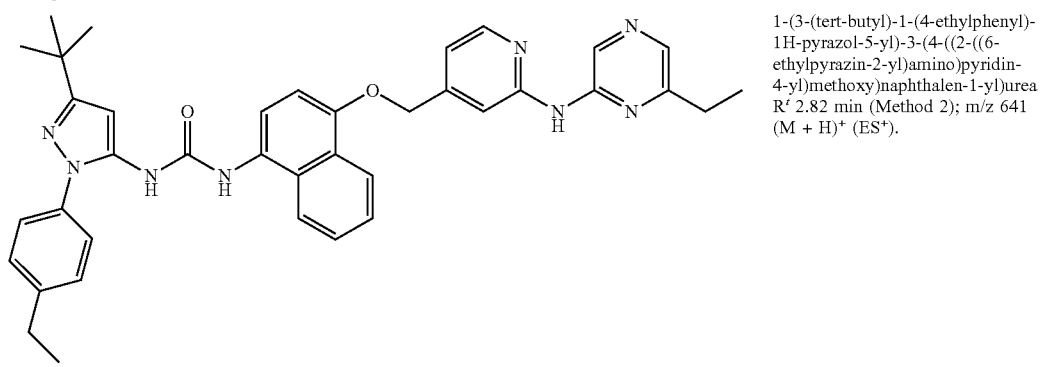

1-(3-(tert-butyl)-1-(4-ethylphenyl)-1H-pyrazol-5-yl)-3-(4-((2-((6-ethylpyrazin-2-yl)amino)pyridin-4-yl)methoxy)naphthalen-1-yl)urea
$R^t$ 2.82 min (Method 2); m/z 641 $(M + H)^+$ $(ES^+)$.

Route code*: 1

Example 174:

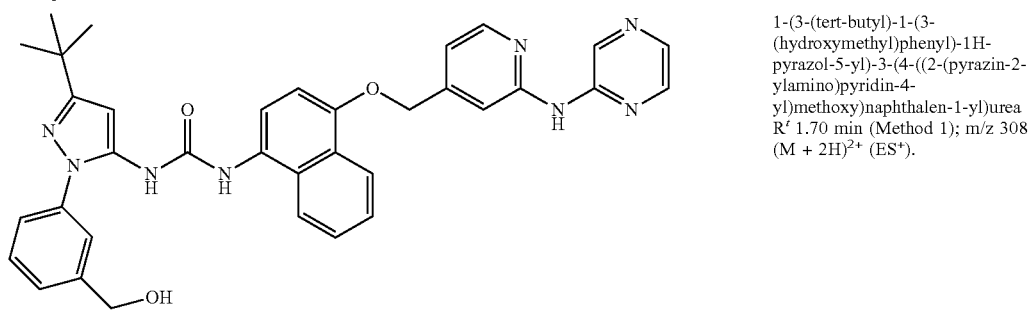

1-(3-(tert-butyl)-1-(3-(hydroxymethyl)phenyl)-1H-pyrazol-5-yl)-3-(4-((2-(pyrazin-2-ylamino)pyridin-4-yl)methoxy)naphthalen-1-yl)urea
$R^t$ 1.70 min (Method 1); m/z 308 $(M + 2H)^{2+}$ $(ES^+)$.

Route code*: 1

Example 175:

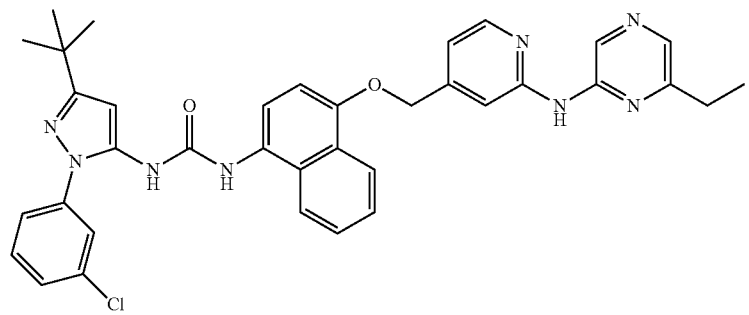

Route code*: 1

1-(3-(tert-butyl)-1-(3-chlorophenyl)-1H-pyrazol-5-yl)-3-(4-((2-((6-ethylpyrazin-2-yl)amino)pyridin-4-yl)methoxy)naphthalen-1-yl)urea
$R^t$ 2.24 min (Method 1); m/z 324 $(M + 2H)^{2+}$ (ES$^+$).

Example 176:

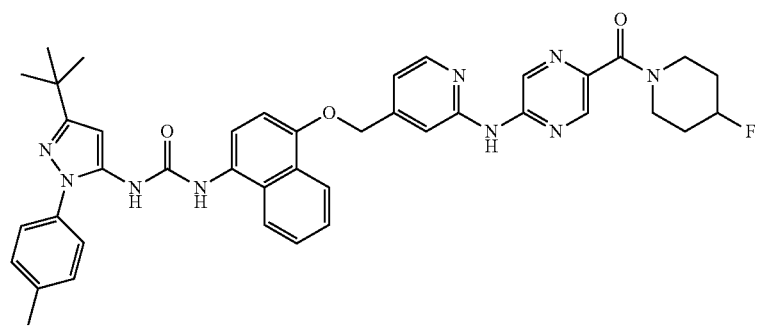

Route code*: 6

1-(3-(tert-butyl)-1-(p-tolyl)-1H-pyrazol-5-yl)-3-(4-((2-((5-(4-fluoropiperidine-1-carbonyl)pyrazin-2-yl)amino)pyridin-4-yl)methoxy)naphthalen-1-yl)urea
$R^t$ 2.23 min (Method 1); m/z 728 $(M + H)^+$ (ES$^+$).

Example 177:

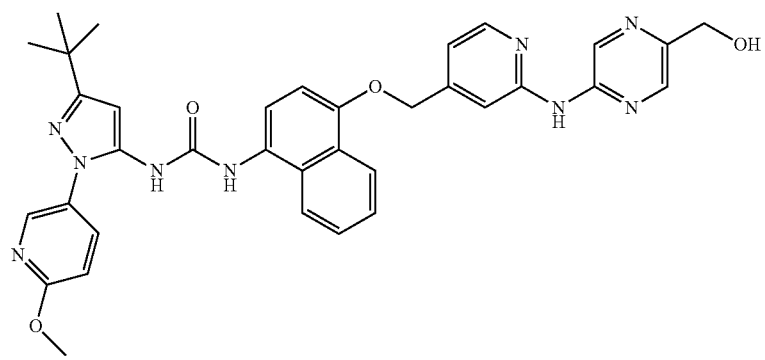

Route code*: 1

1-(3-(tert-butyl)-1-(6-methoxypyridin-3-yl)-1H-pyrazol-5-yl)-3-(4-((2-((5-(hydroxymethyl)pyrazin-2-yl)amino)pyridin-4-yl)methoxy)naphthalen-1-yl)urea.
$R^t$ 1.70 min (Method 1); m/z 646 $(M + H)^+$ (ES$^+$).

Example 178:

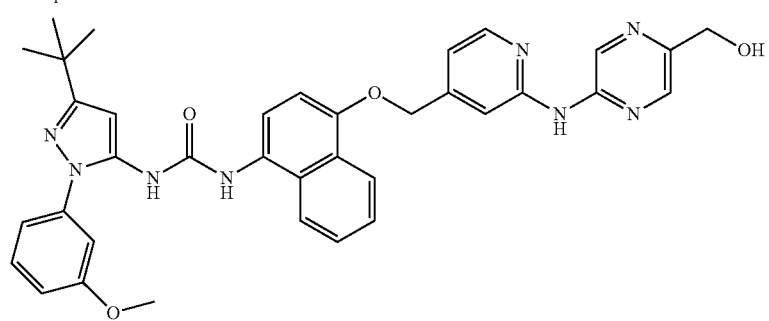

Route code*: 1

1-(3-(tert-butyl)-1-(3-methoxyphenyl)-1H-pyrazol-5-yl)-3-(4-((2-((5-(hydroxymethyl)pyrazin-2-yl)amino)pyridin-4-yl)methoxy)naphthalen-1-yl)urea.
$R^t$ 1.77 min (Method 1); m/z 645 $(M + H)^+$ (ES$^+$).

-continued

Example 179:

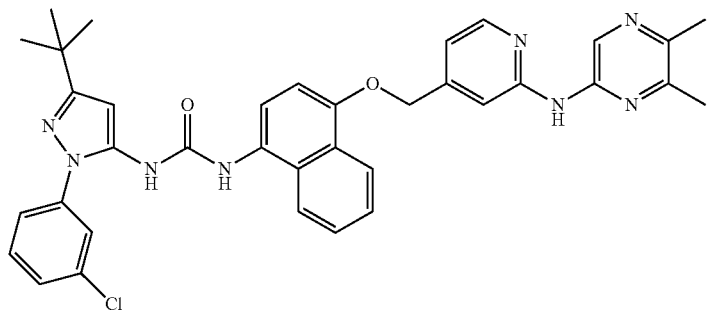

Route code*: 1

1-(3-(tert-butyl)-1-(3-chlorophenyl)-1H-pyrazol-5-yl)-3-(4-((2-((5,6-dimethylpyrazin-2-yl)amino)pyridin-4-yl)methoxy)naphthalen-1-yl)urea
$R^t$ 2.77 min (Method 2); m/z 647 $(M + H)^+$ $(ES^+)$.

Example 180:

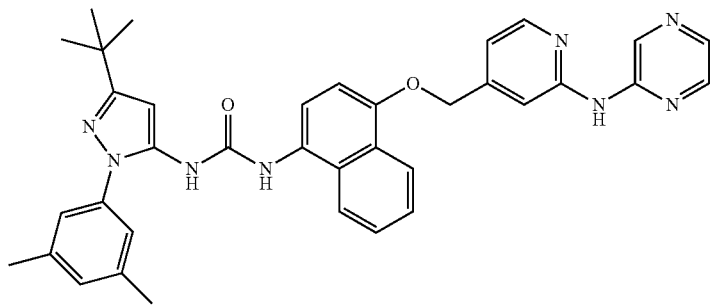

Route code*: 1

1-(3-(tert-butyl)-1-(3,5-dimethylphenyl)-1H-pyrazol-5-yl)-3-(4-((2-(pyrazin-2-ylamino)pyridin-4-yl)methoxy)naphthalen-1-yl)urea
$R^t$ 2.65 min (Method 2); m/z 613 $(M + H)^+$ $(ES^+)$.

Example 181:

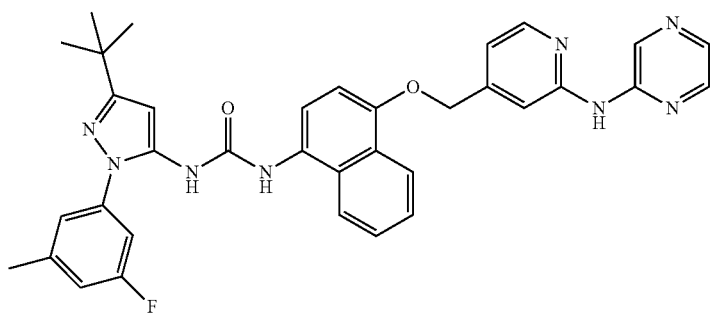

Route code*: 1

1-(3-(tert-butyl)-1-(3-fluoro-5-methylphenyl)-1H-pyrazol-5-yl)-3-(4-((2-(pyrazin-2-ylamino)pyridin-4-yl)methoxy)naphthalen-1-yl)urea
$R^t$ 2.62 min (Method 2); m/z 617 $(M + H)^+$ $(ES^+)$.

Example 182:

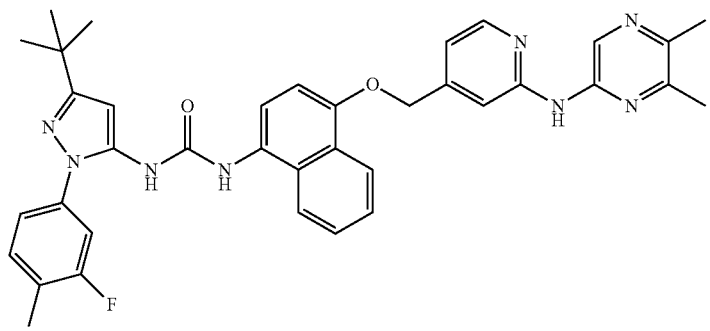

Route code*: 1

1-(3-(tert-butyl)-1-(3-fluoro-4-methylphenyl)-1H-pyrazol-5-yl)-3-(4-((2-((5,6-dimethylpyrazin-2-yl)amino)pyridin-4-yl)methoxy)naphthalen-1-yl)urea
$R^t$ 2.88 min (Method 2); m/z 645 $(M + H)^+$ $(ES^+)$.

Example 183:

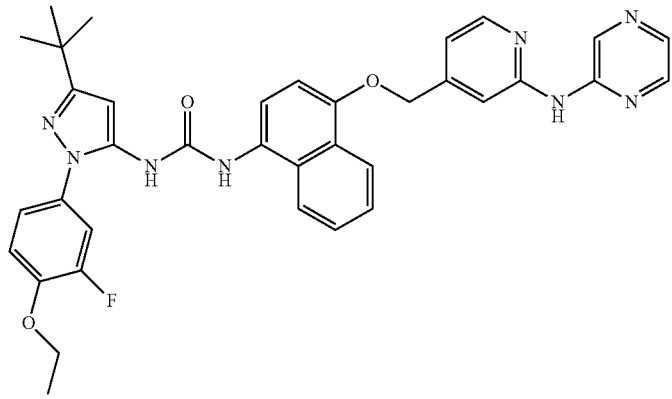

Route code*: 1

1-(3-(tert-butyl)-1-(4-ethoxy-3-fluorophenyl)-1H-pyrazol-5-yl)-3-(4-((2-(pyrazin-2-ylamino)pyridin-4-yl)methoxy)naphthalen-1-yl)urea
$R^t$ 2.03 min (Method 1); m/z 324 $(M + 2H)^{2+}$ (ES$^+$).

Example 184:

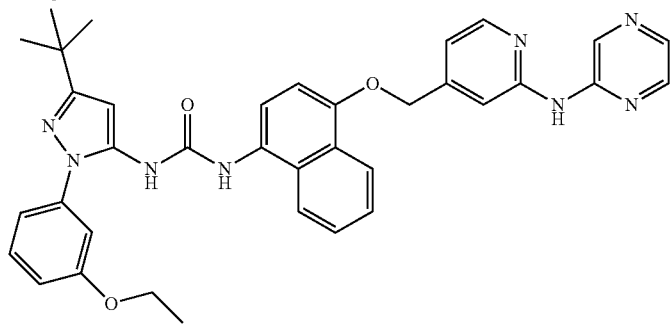

Route code*: 1

1-(3-(tert-butyl)-1-(3-ethoxyphenyl)-1H-pyrazol-5-yl)-3-(4-((2-(pyrazin-2-ylamino)pyridin-4-yl)methoxy)naphthalen-1-yl)urea
$R^t$ 2.01 min (Method 1); m/z 315 $(M + 2H)^{2+}$ (ES$^+$).

Example 185:

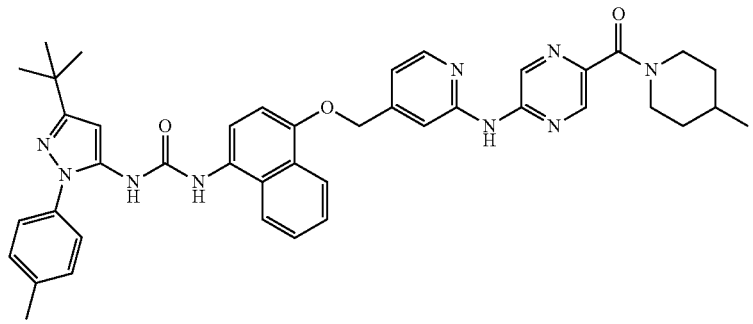

Route code*: 6

1-(3-(tert-butyl)-1-(p-tolyl)-1H-pyrazol-5-yl)-3-(4-((2-((5-(4-methylpiperidine-1-carbonyl)pyrazin-2-yl)amino)pyridin-4-yl)methoxy)naphthalen-1-yl)urea
$R^t$ 2.45 min (Method 1); m/z 724 $(M + H)^+$ (ES$^+$).

Example 186:

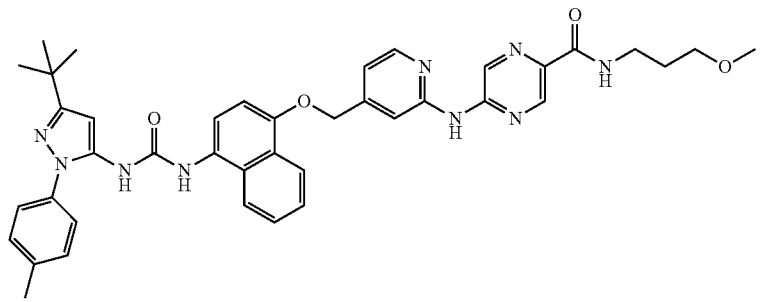

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-methoxypropyl)pyrazine-2-carboxamide
$R^t$ 2.26 min (Method 1); m/z 714 $(M + H)^+$ (ES$^+$).

-continued

Example 187:

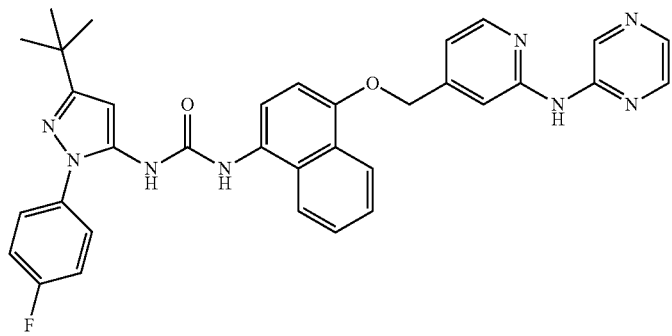

Route code*: 1

1-(3-(tert-butyl)-1-(4-fluorophenyl)-1H-pyrazol-5-yl)-3-(4-((2-(pyrazin-2-ylamino)pyridin-4-yl)methoxy)naphthalen-1-yl)urea
$R^t$ 2.43 min (Method 2); m/z 603 (M + H)$^+$ (ES$^+$).

Example 188:

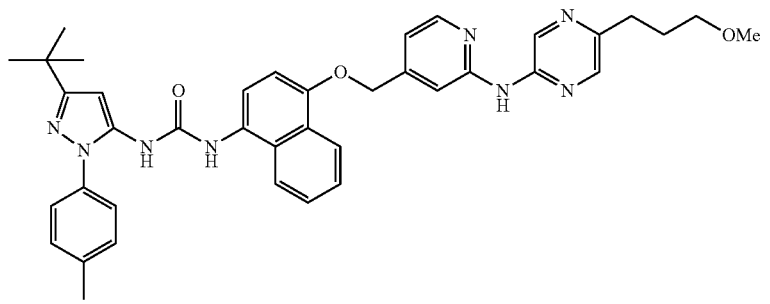

Route code*: 1

1-(3-(tert-butyl)-1-(p-tolyl)-1H-pyrazol-5-yl)-3-(4-((2-((5-(3-methoxypropyl)pyrazin-2-yl)amino)pyridin-4-yl)methoxy)naphthalen-1-yl)urea
$R^t$ 2.07 min (Method 1); m/z 671 (M + H)$^+$ (ES$^+$).

Example 189:

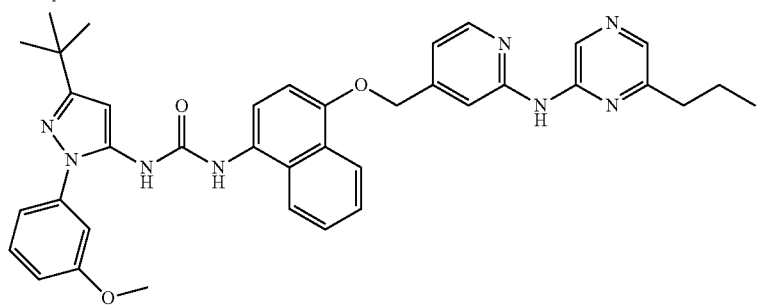

Route code*: 1

1-(3-(tert-butyl)-1-(3-methoxyphenyl)-1H-pyrazol-5-yl)-3-(4-((2-((6-propylpyrazin-2-yl)amino)pyridin-4-yl)methoxy(naphthalen-1-yl)urea
$R^t$ 2.25 min (Method 1); m/z 657 (M + H)$^+$ (ES$^+$).

Example 190:

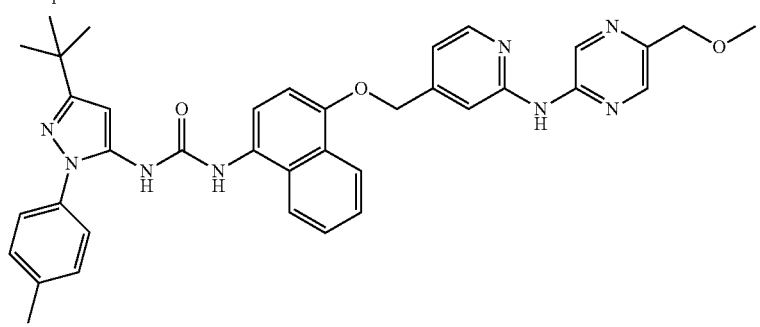

Route code*: 1

1-(3-(tert-butyl)-1-(p-tolyl)-1H-pyrazol-5-yl)-3-(4-((2-((5-(methoxymethyl)pyrazin-2-yl)amino)pyridin-4-yl)methoxy)naphthalen-1-yl)urea
$R^t$ 2.05 min (Method 1); m/z 643 (M + H)$^+$ (ES$^+$).

Example 191:

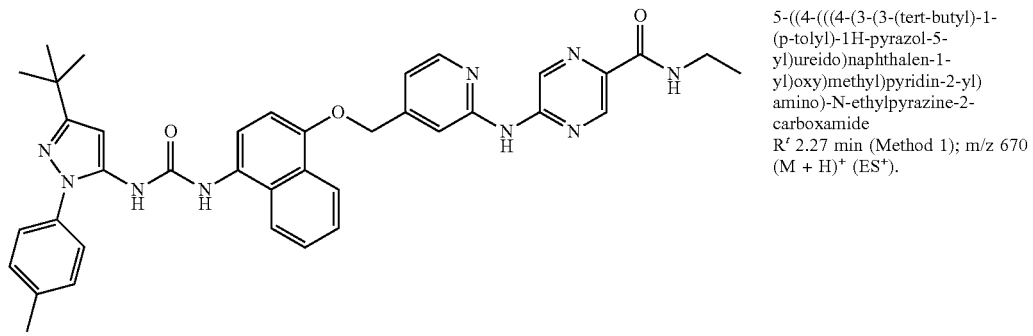

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-ethylpyrazine-2-carboxamide
R$^t$ 2.27 min (Method 1); m/z 670 (M + H)$^+$ (ES$^+$).

Example 192:

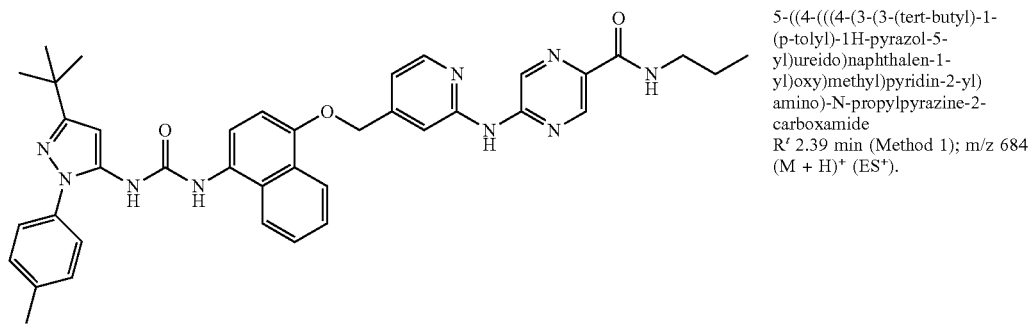

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-propylpyrazine-2-carboxamide
R$^t$ 2.39 min (Method 1); m/z 684 (M + H)$^+$ (ES$^+$).

Example 193:

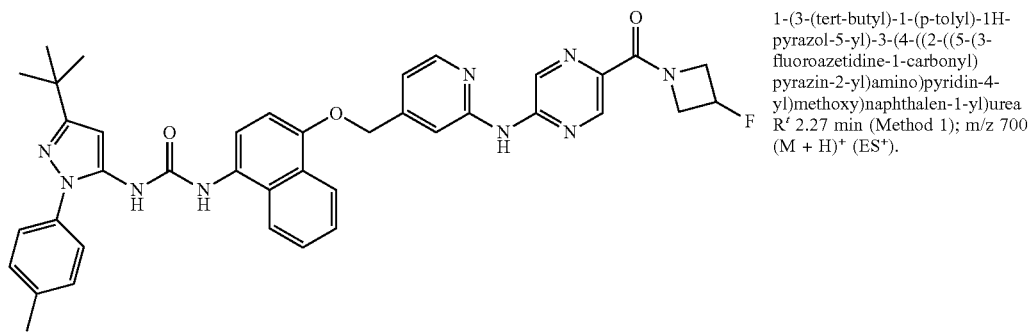

Route code*: 6

1-(3-(tert-butyl)-1-(p-tolyl)-1H-pyrazol-5-yl)-3-(4-((2-((5-(3-fluoroazetidine-1-carbonyl)pyrazin-2-yl)amino)pyridin-4-yl)methoxy)naphthalen-1-yl)urea
R$^t$ 2.27 min (Method 1); m/z 700 (M + H)$^+$ (ES$^+$).

Example 194:

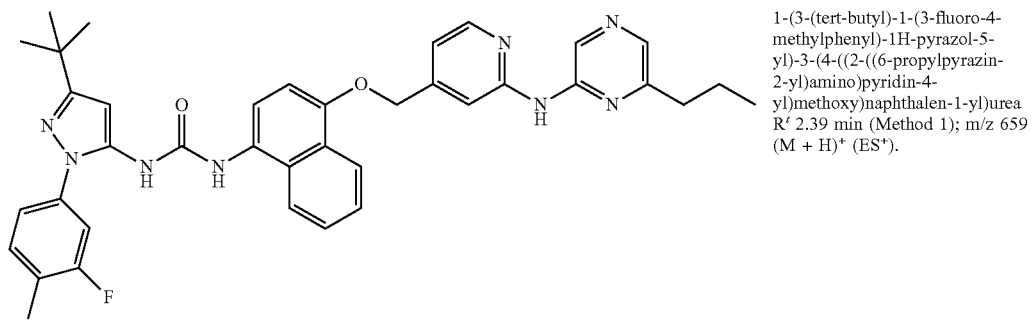

Route code*: 1

1-(3-(tert-butyl)-1-(3-fluoro-4-methylphenyl)-1H-pyrazol-5-yl)-3-(4-((2-((6-propylpyrazin-2-yl)amino)pyridin-4-yl)methoxy)naphthalen-1-yl)urea
R$^t$ 2.39 min (Method 1); m/z 659 (M + H)$^+$ (ES$^+$).

Example 195:

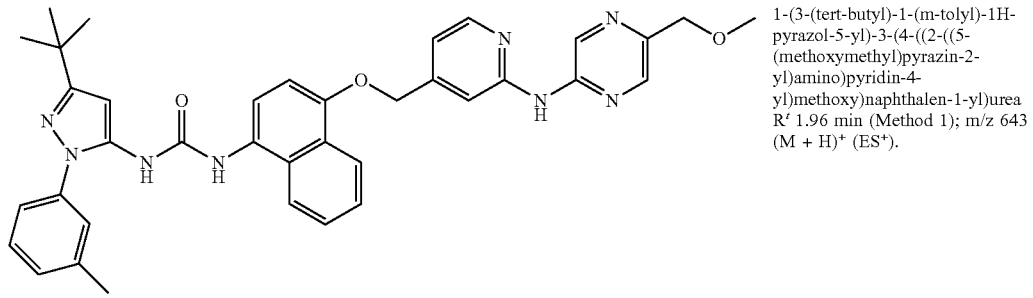

1-(3-(tert-butyl)-1-(m-tolyl)-1H-pyrazol-5-yl)-3-(4-((2-((5-(methoxymethyl)pyrazin-2-yl)amino)pyridin-4-yl)methoxy)naphthalen-1-yl)urea
R$^t$ 1.96 min (Method 1); m/z 643 (M + H)$^+$ (ES$^+$).

Route code*: 1

Example 196:

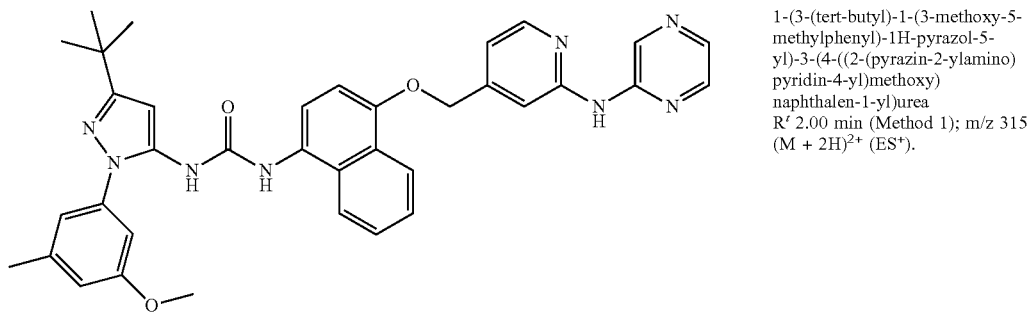

1-(3-(tert-butyl)-1-(3-methoxy-5-methylphenyl)-1H-pyrazol-5-yl)-3-(4-((2-(pyrazin-2-ylamino)pyridin-4-yl)methoxy)naphthalen-1-yl)urea
R$^t$ 2.00 min (Method 1); m/z 315 (M + 2H)$^{2+}$ (ES$^+$).

Route code*: 1

Example 197:

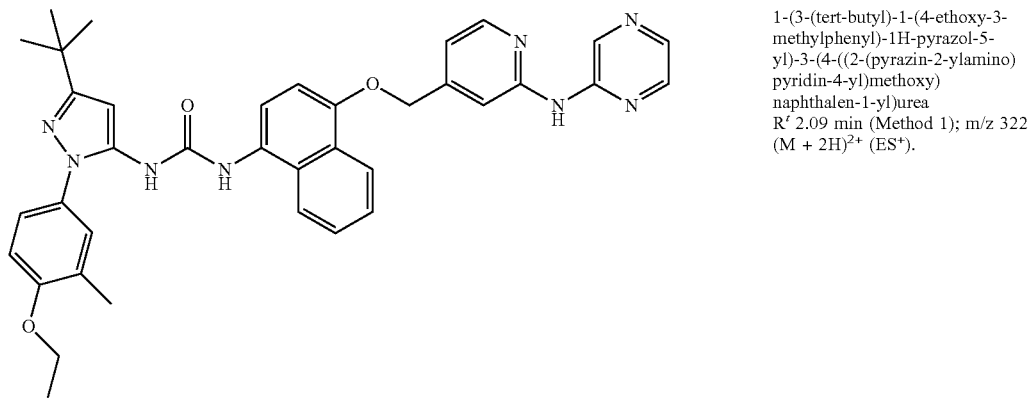

1-(3-(tert-butyl)-1-(4-ethoxy-3-methylphenyl)-1H-pyrazol-5-yl)-3-(4-((2-(pyrazin-2-ylamino)pyridin-4-yl)methoxy)naphthalen-1-yl)urea
R$^t$ 2.09 min (Method 1); m/z 322 (M + 2H)$^{2+}$ (ES$^+$).

Route code*: 1

Example 198:

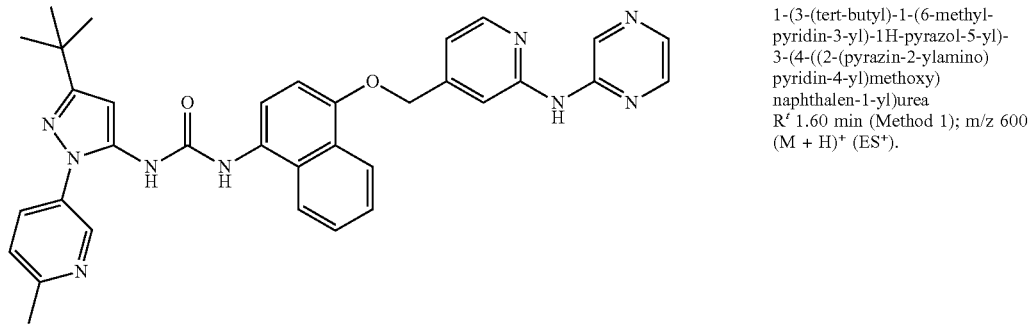

1-(3-(tert-butyl)-1-(6-methyl-pyridin-3-yl)-1H-pyrazol-5-yl)-3-(4-((2-(pyrazin-2-ylamino)pyridin-4-yl)methoxy)naphthalen-1-yl)urea
R$^t$ 1.60 min (Method 1); m/z 600 (M + H)$^+$ (ES$^+$).

Route code*: 1

Example 199:

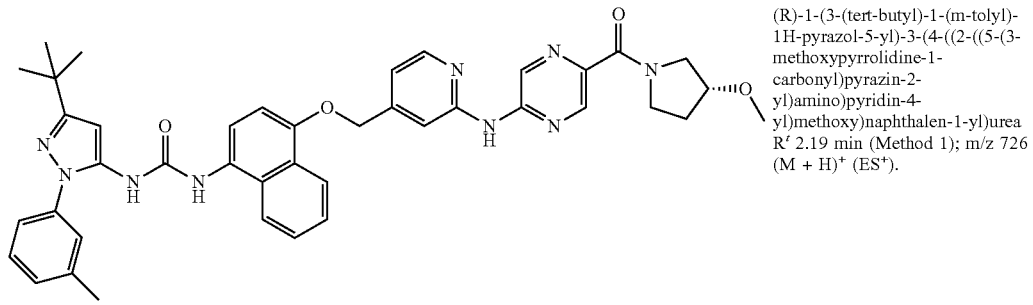

Route code*: 6

(R)-1-(3-(tert-butyl)-1-(m-tolyl)-
1H-pyrazol-5-yl)-3-(4-((2-((5-(3-
methoxypyrrolidine-1-
carbonyl)pyrazin-2-
yl)amino)pyridin-4-
yl)methoxy)naphthalen-1-yl)urea
R$^t$ 2.19 min (Method 1); m/z 726
(M + H)$^+$ (ES$^+$).

Example 200:

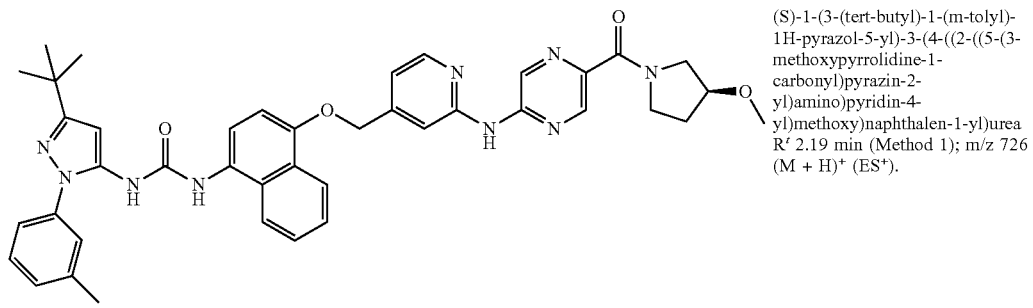

Route code*: 6

(S)-1-(3-(tert-butyl)-1-(m-tolyl)-
1H-pyrazol-5-yl)-3-(4-((2-((5-(3-
methoxypyrrolidine-1-
carbonyl)pyrazin-2-
yl)amino)pyridin-4-
yl)methoxy)naphthalen-1-yl)urea
R$^t$ 2.19 min (Method 1); m/z 726
(M + H)$^+$ (ES$^+$).

Example 201:

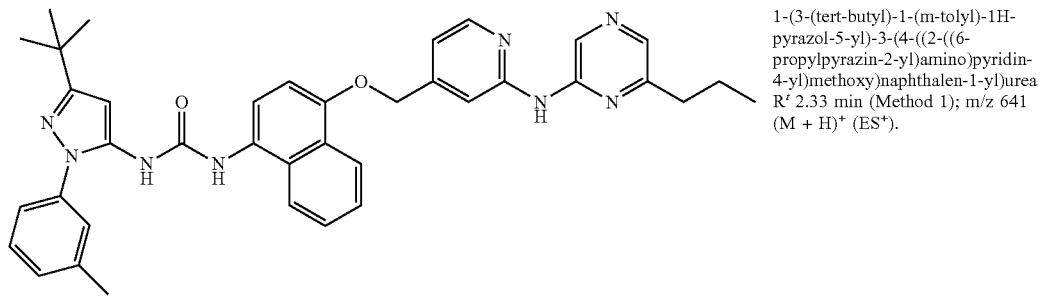

Route code*: 1

1-(3-(tert-butyl)-1-(m-tolyl)-1H-
pyrazol-5-yl)-3-(4-((2-((6-
propylpyrazin-2-yl)amino)pyridin-
4-yl)methoxy)naphthalen-1-yl)urea
R$^t$ 2.33 min (Method 1); m/z 641
(M + H)$^+$ (ES$^+$).

Example 202:

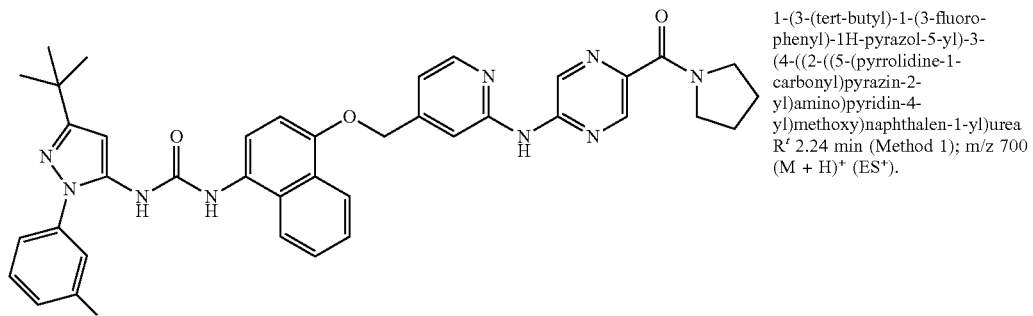

Route code*: 2

1-(3-(tert-butyl)-1-(3-fluoro-
phenyl)-1H-pyrazol-5-yl)-3-
(4-((2-((5-(pyrrolidine-1-
carbonyl)pyrazin-2-
yl)amino)pyridin-4-
yl)methoxy)naphthalen-1-yl)urea
R$^t$ 2.24 min (Method 1); m/z 700
(M + H)$^+$ (ES$^+$).

Example 203:

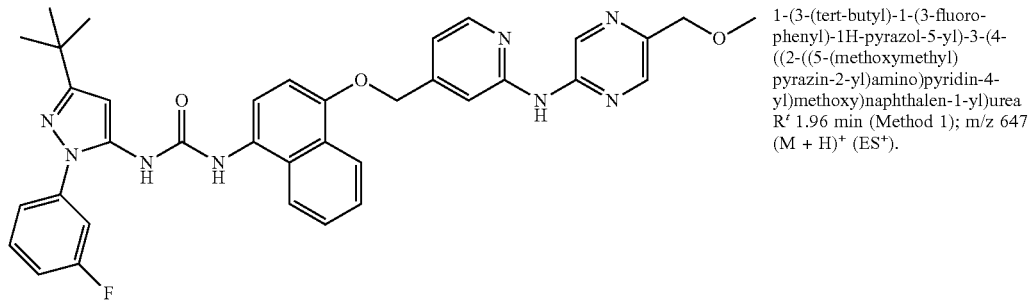

Route code*: 1

1-(3-(tert-butyl)-1-(3-fluoro-phenyl)-1H-pyrazol-5-yl)-3-(4-((2-((5-(methoxymethyl)pyrazin-2-yl)amino)pyridin-4-yl)methoxy)naphthalen-1-yl)urea
$R^t$ 1.96 min (Method 1); m/z 647 (M + H)$^+$ (ES$^+$).

Example 204:

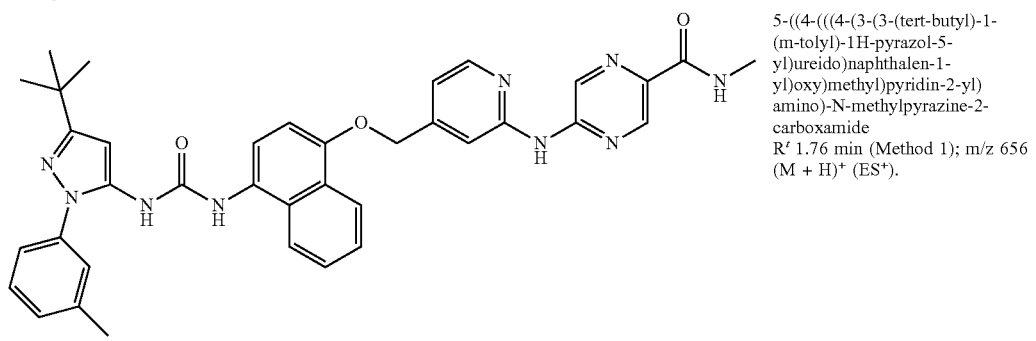

Route code*: 2

5-((4-(((4-(3-(3-(tert-butyl)-1-(m-tolyl)-1H-pyrazol-5-yl)ureido)naphthalen-1-yl)oxy)methyl)pyridin-2-yl)amino)-N-methylpyrazine-2-carboxamide
$R^t$ 1.76 min (Method 1); m/z 656 (M + H)$^+$ (ES$^+$).

Example 205:

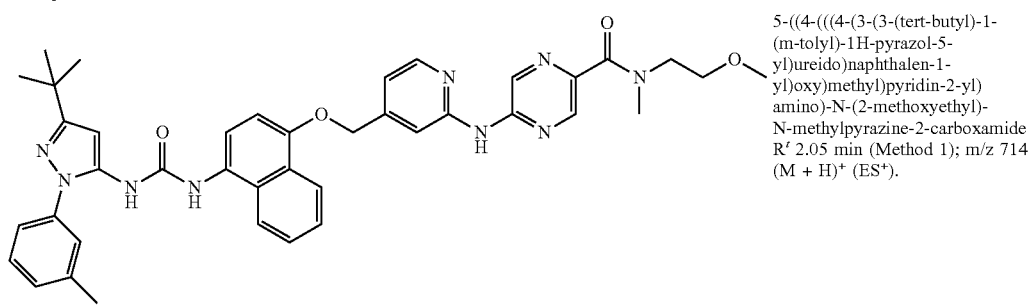

Route code*: 6

5-((4-(((4-(3-(3-(tert-butyl)-1-(m-tolyl)-1H-pyrazol-5-yl)ureido)naphthalen-1-yl)oxy)methyl)pyridin-2-yl)amino)-N-(2-methoxyethyl)-N-methylpyrazine-2-carboxamide
$R^t$ 2.05 min (Method 1); m/z 714 (M + H)$^+$ (ES$^+$).

Example 206:

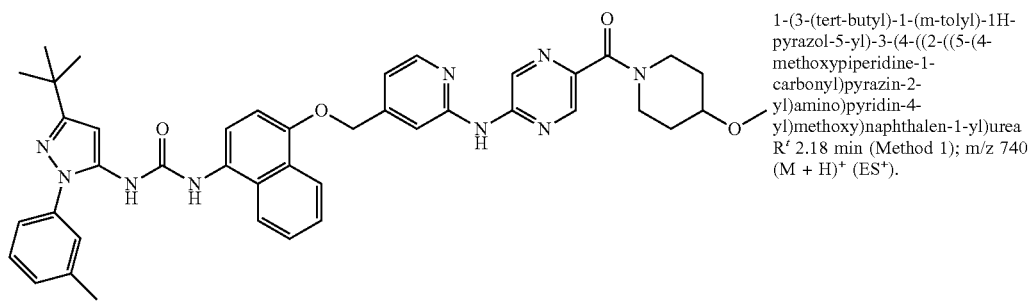

Route code*: 6

1-(3-(tert-butyl)-1-(m-tolyl)-1H-pyrazol-5-yl)-3-(4-((2-((5-(4-methoxypiperidine-1-carbonyl)pyrazin-2-yl)amino)pyridin-4-yl)methoxy)naphthalen-1-yl)urea
$R^t$ 2.18 min (Method 1); m/z 740 (M + H)$^+$ (ES$^+$).

Example 207:

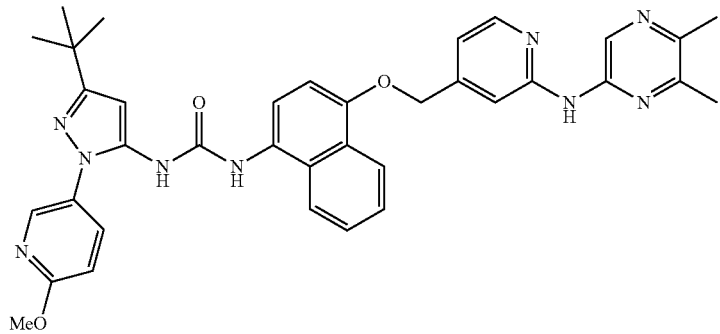

Route code*: 1

1-(3-(tert-butyl)-1-(6-methoxypyridin-3-yl)-1H-pyrazol-5-yl)-3-(4-((2-((5,6-dimethylpyrazin-2-yl)amino)pyridin-4-yl)methoxy)naphthalen-1-yl)urea
$R^t$ 2.50 min (Method 2); m/z 644 $(M + H)^+$ $(ES^+)$.

Example 208:

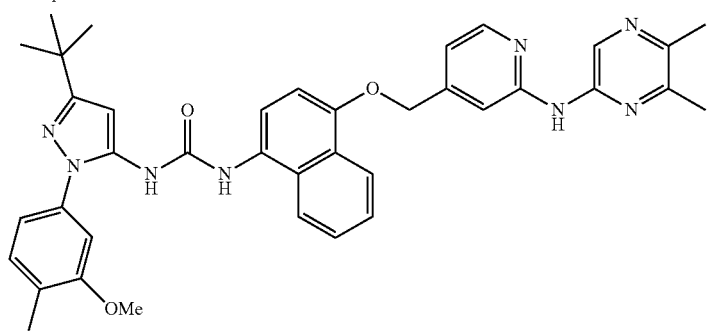

Route code*: 1

1-(3-(tert-butyl)-1-(3-methoxy-4-methylphenyl)-1H-pyrazol-5-yl)-3-(4-((2-((5,6-dimethylpyrazin-2-yl)amino)pyridin-4-yl)methoxy)naphthalen-1-yl)urea
$R^t$ 2.71 min (Method 2); m/z 657 $(M + H)^+$ $(ES^+)$.

Example 209:

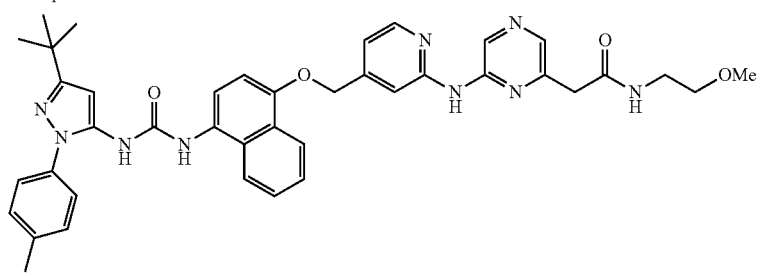

Route code*: 5a 2-(6-((4-(((4-(3-(3-(tert-butyl)-1-(p-tolyl)-1H-pyrazol-5-yl)ureido)naphthalen-1-yl)oxy)methyl)pyridin-2-yl)amino)pyrazin-2-yl)-N-(2-methoxyethyl)acetamide
$R^t$ 1.86 min (Method 1); m/z 714 $(M + H)^+$ $(ES^+)$.

Example 210:

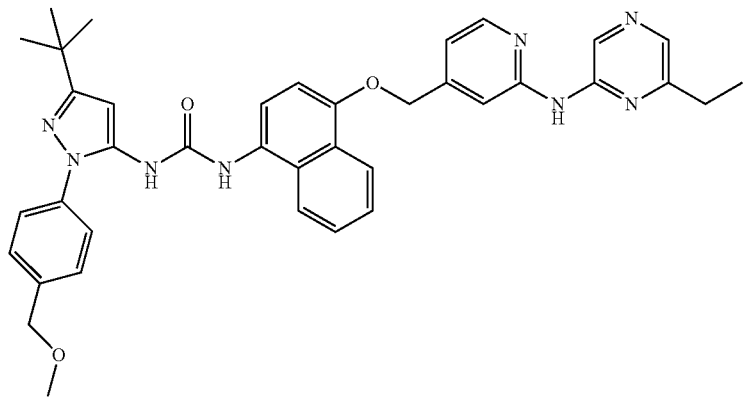

Route code*: 1

1-(3-(tert-butyl)-1-(4-(methoxymethyl)phenyl)-1H-pyrazol-5-yl)-3-(4-((2-((6-ethylpyrazin-2-yl)amino)pyridin-4-yl)methoxy)naphthalen-1-yl)urea
$R^t$ 2.11 min (Method 1); m/z 329 $(M + 2H)^{2+}$ $(ES^+)$.

-continued

Example 211:

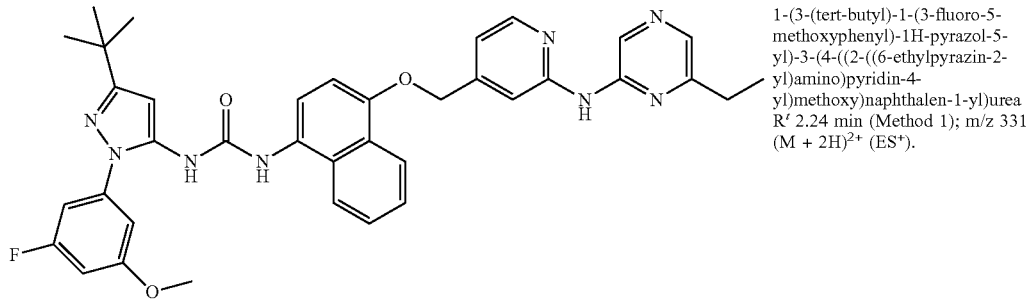

Route code*: 1

1-(3-(tert-butyl)-1-(3-fluoro-5-methoxyphenyl)-1H-pyrazol-5-yl)-3-(4-((2-((6-ethylpyrazin-2-yl)amino)pyridin-4-yl)methoxy)naphthalen-1-yl)urea
R$^t$ 2.24 min (Method 1); m/z 331 (M + 2H)$^{2+}$ (ES$^+$).

Example 212:

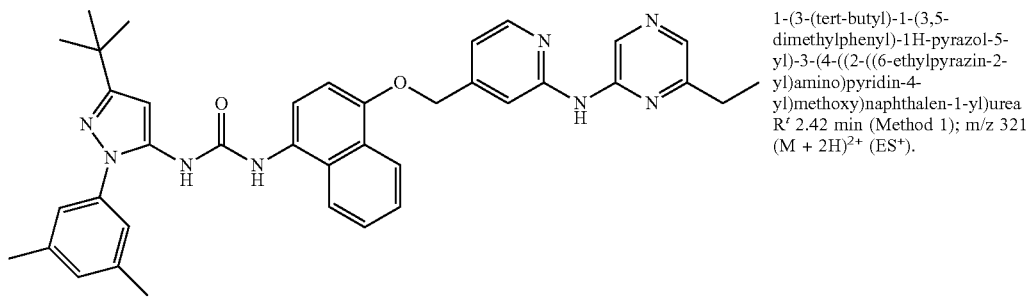

Route code*: 1

1-(3-(tert-butyl)-1-(3,5-dimethylphenyl)-1H-pyrazol-5-yl)-3-(4-((2-((6-ethylpyrazin-2-yl)amino)pyridin-4-yl)methoxy)naphthalen-1-yl)urea
R$^t$ 2.42 min (Method 1); m/z 321 (M + 2H)$^{2+}$ (ES$^+$).

Example 213:

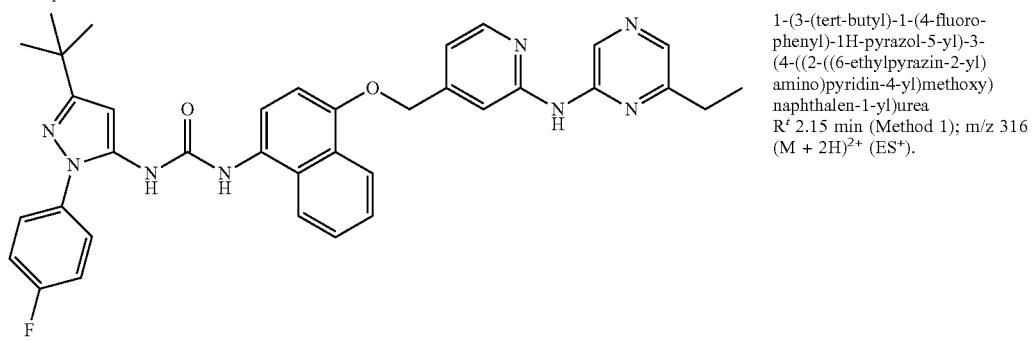

1-(3-(tert-butyl)-1-(4-fluorophenyl)-1H-pyrazol-5-yl)-3-(4-((2-((6-ethylpyrazin-2-yl)amino)pyridin-4-yl)methoxy)naphthalen-1-yl)urea
R$^t$ 2.15 min (Method 1); m/z 316 (M + 2H)$^{2+}$ (ES$^+$).

Route code*: 1

Example 214:

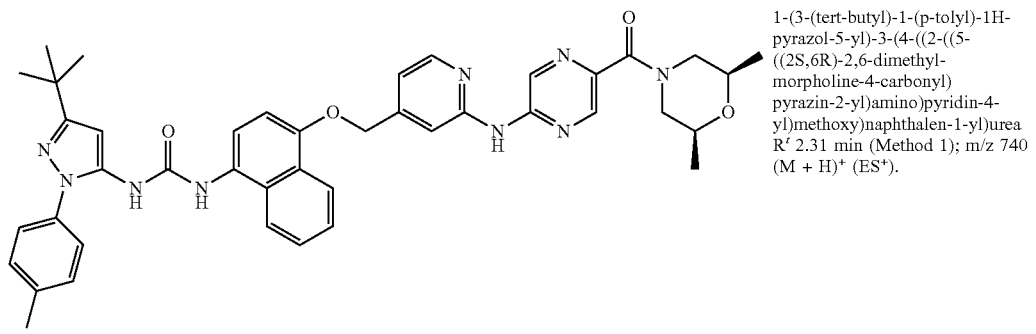

1-(3-(tert-butyl)-1-(p-tolyl)-1H-pyrazol-5-yl)-3-(4-((2-((5-((2S,6R)-2,6-dimethyl-morpholine-4-carbonyl)pyrazin-2-yl)amino)pyridin-4-yl)methoxy)naphthalen-1-yl)urea
R$^t$ 2.31 min (Method 1); m/z 740 (M + H)$^+$ (ES$^+$).

Route code*: 1

-continued

Example 215:

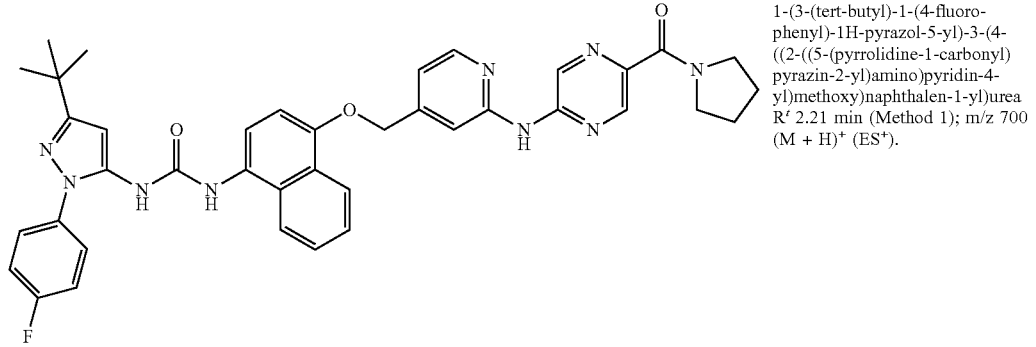

Route code*: 2

1-(3-(tert-butyl)-1-(4-fluoro-phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.21 min (Method 1); m/z 700 (M + H)$^+$ (ES$^+$).

Example 216:

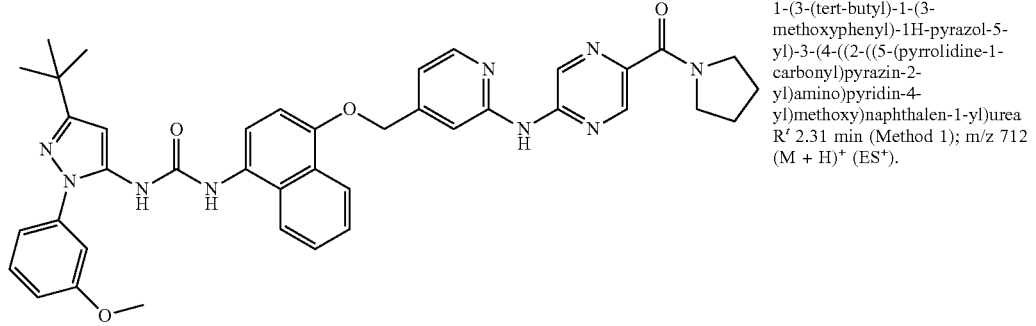

Route code*: 2

1-(3-(tert-butyl)-1-(3-methoxyphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.31 min (Method 1); m/z 712 (M + H)$^+$ (ES$^+$).

Example 217:

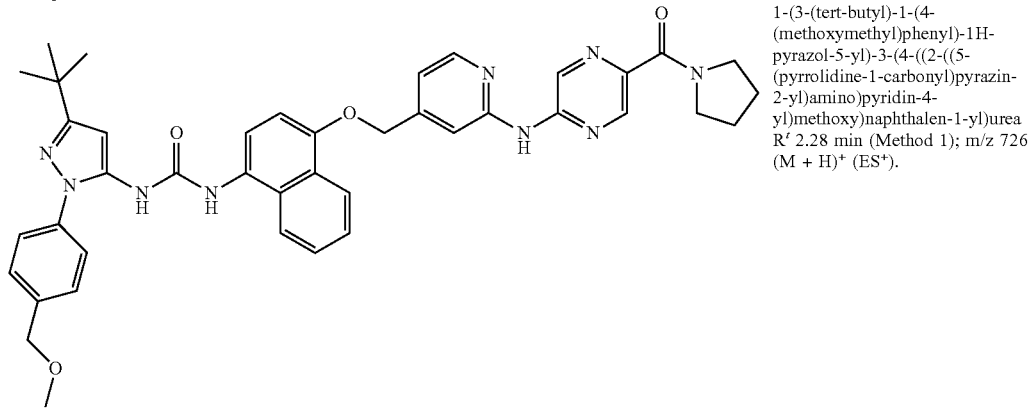

Route code*: 2

1-(3-(tert-butyl)-1-(4-(methoxymethyl)phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.28 min (Method 1); m/z 726 (M + H)$^+$ (ES$^+$).

Example 218:

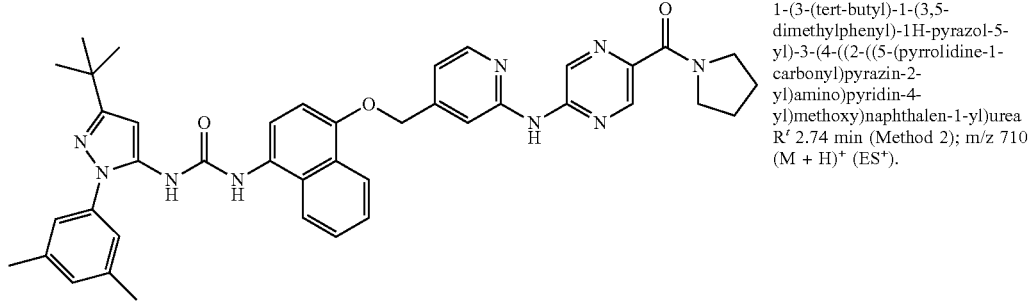

Route code*: 6

1-(3-(tert-butyl)-1-(3,5-dimethylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.74 min (Method 2); m/z 710 (M + H)$^+$ (ES$^+$).

Example 219:

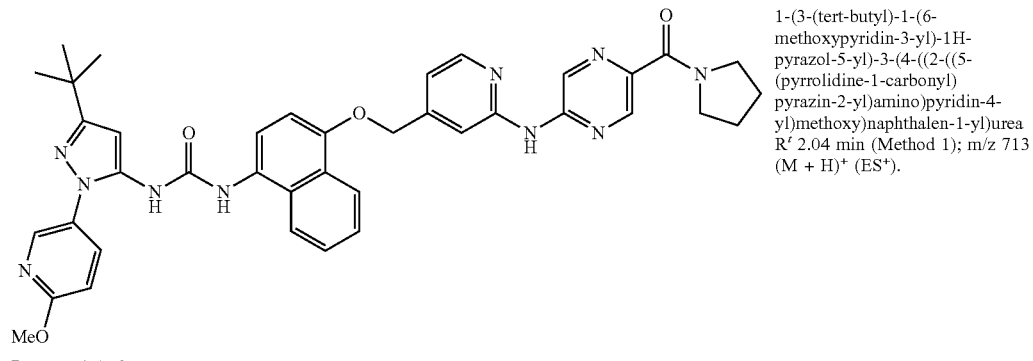

Route code*: 6

1-(3-(tert-butyl)-1-(6-methoxypyridin-3-yl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.04 min (Method 1); m/z 713 $(M + H)^+$ $(ES^+)$.

Example 220:

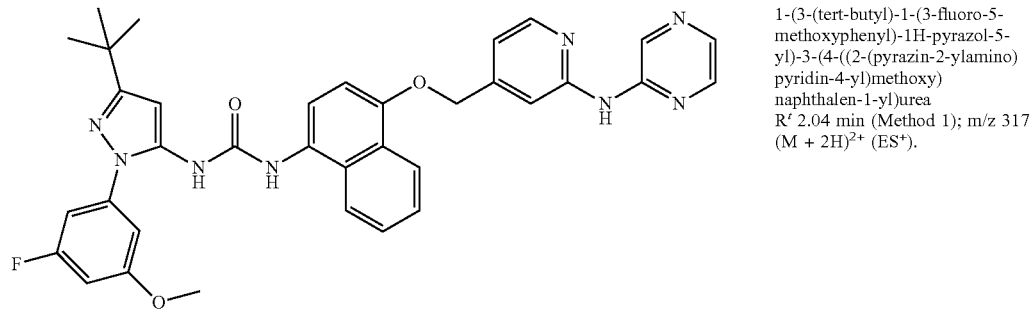

Route code*: 1

1-(3-(tert-butyl)-1-(3-fluoro-5-methoxyphenyl)-1H-pyrazol-5-yl)-3-(4-((2-(pyrazin-2-ylamino)pyridin-4-yl)methoxy)naphthalen-1-yl)urea
$R^t$ 2.04 min (Method 1); m/z 317 $(M + 2H)^{2+}$ $(ES^+)$.

Example 221:

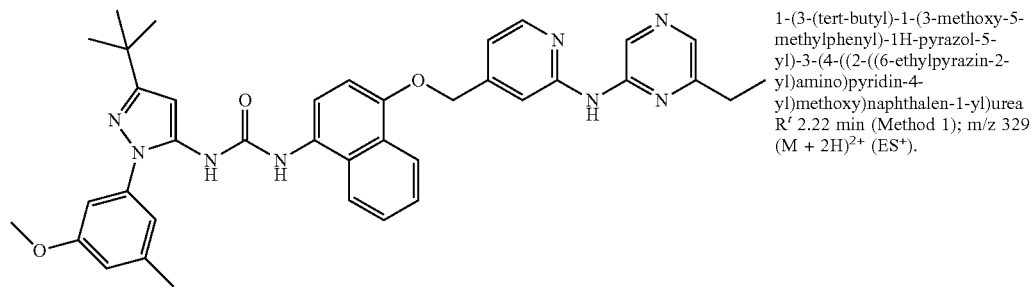

Route code*: 1

1-(3-(tert-butyl)-1-(3-methoxy-5-methylphenyl)-1H-pyrazol-5-yl)-3-(4-((2-((6-ethylpyrazin-2-yl)amino)pyridin-4-yl)methoxy)naphthalen-1-yl)urea
$R^t$ 2.22 min (Method 1); m/z 329 $(M + 2H)^{2+}$ $(ES^+)$.

Example 222:

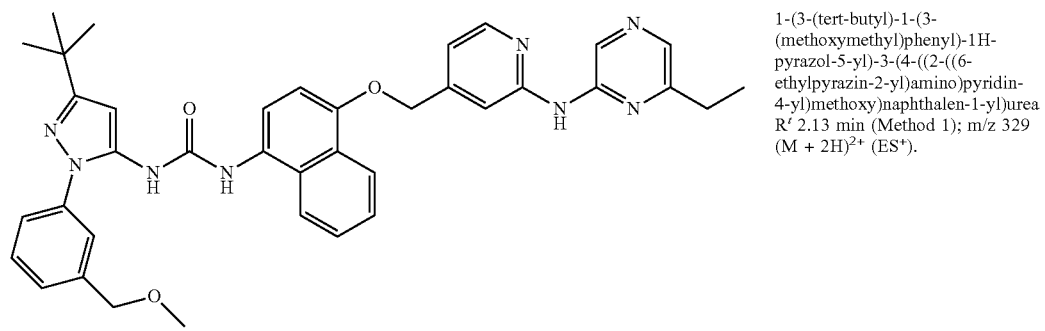

Route code*: 1

1-(3-(tert-butyl)-1-(3-(methoxymethyl)phenyl)-1H-pyrazol-5-yl)-3-(4-((2-((6-ethylpyrazin-2-yl)amino)pyridin-4-yl)methoxy)naphthalen-1-yl)urea
$R^t$ 2.13 min (Method 1); m/z 329 $(M + 2H)^{2+}$ $(ES^+)$.

Example 223:

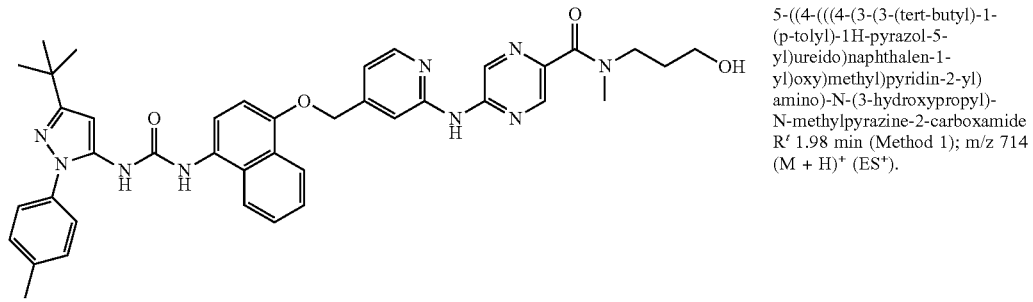

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-hydroxypropyl)-N-methylpyrazine-2-carboxamide
$R^t$ 1.98 min (Method 1); m/z 714 $(M + H)^+$ $(ES^+)$.

Example 224:

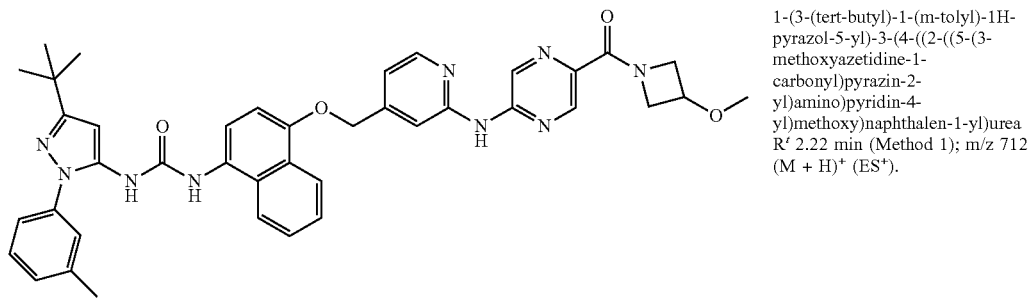

Route code*: 6

1-(3-(tert-butyl)-1-(m-tolyl)-1H-pyrazol-5-yl)-3-(4-((2-((5-(3-methoxyazetidine-1-carbonyl)pyrazin-2-yl)amino)pyridin-4-yl)methoxy)naphthalen-1-yl)urea
$R^t$ 2.22 min (Method 1); m/z 712 $(M + H)^+$ $(ES^+)$.

Example 225:

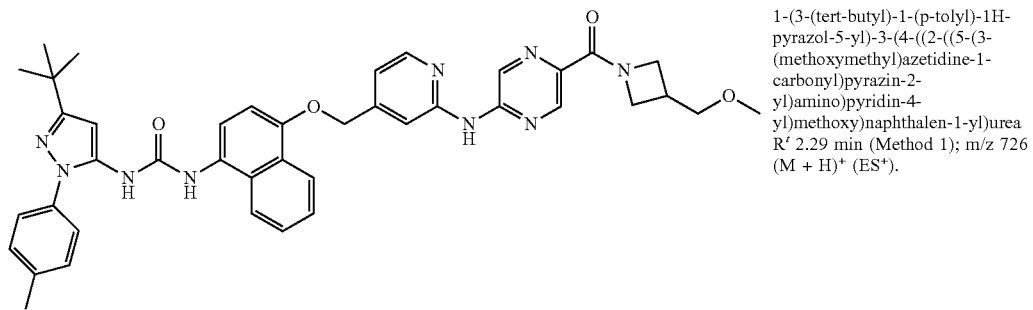

Route code*: 6

1-(3-(tert-butyl)-1-(p-tolyl)-1H-pyrazol-5-yl)-3-(4-((2-((5-(3-(methoxymethyl)azetidine-1-carbonyl)pyrazin-2-yl)amino)pyridin-4-yl)methoxy)naphthalen-1-yl)urea
$R^t$ 2.29 min (Method 1); m/z 726 $(M + H)^+$ $(ES^+)$.

Example 226:

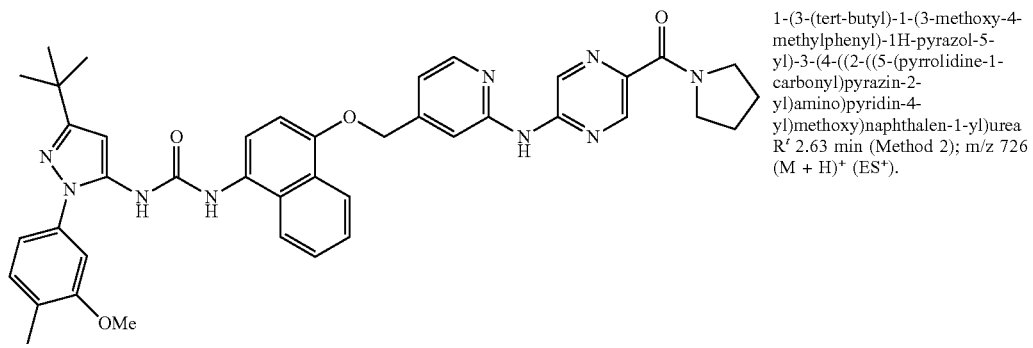

Route code*: 6

1-(3-(tert-butyl)-1-(3-methoxy-4-methylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.63 min (Method 2); m/z 726 $(M + H)^+$ $(ES^+)$.

Example 227:

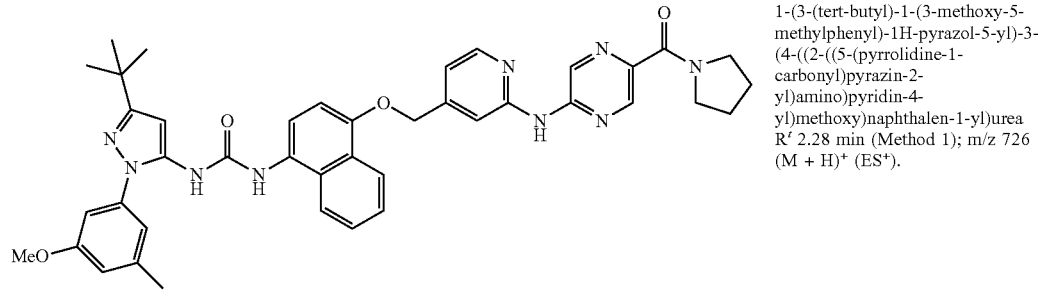

Route code*: 6

1-(3-(tert-butyl)-1-(3-methoxy-5-methylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.28 min (Method 1); m/z 726 (M + H)$^+$ (ES$^+$).

Example 228:

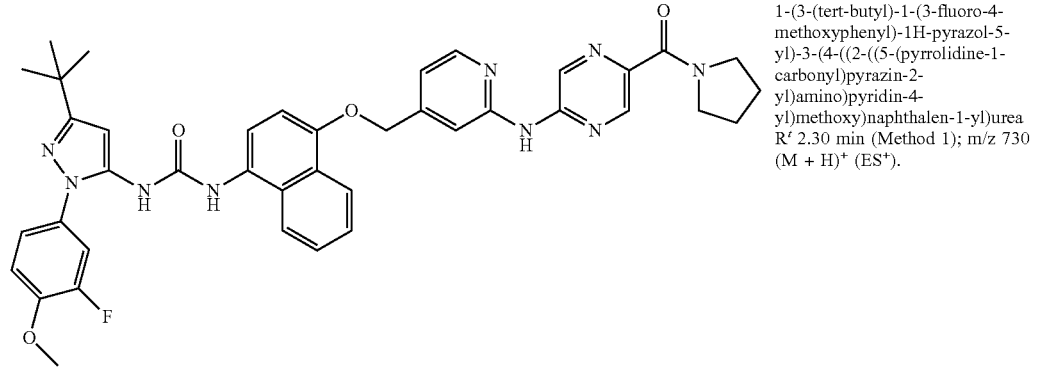

Route code*: 2

1-(3-(tert-butyl)-1-(3-fluoro-4-methoxyphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.30 min (Method 1); m/z 730 (M + H)$^+$ (ES$^+$).

Example 229:

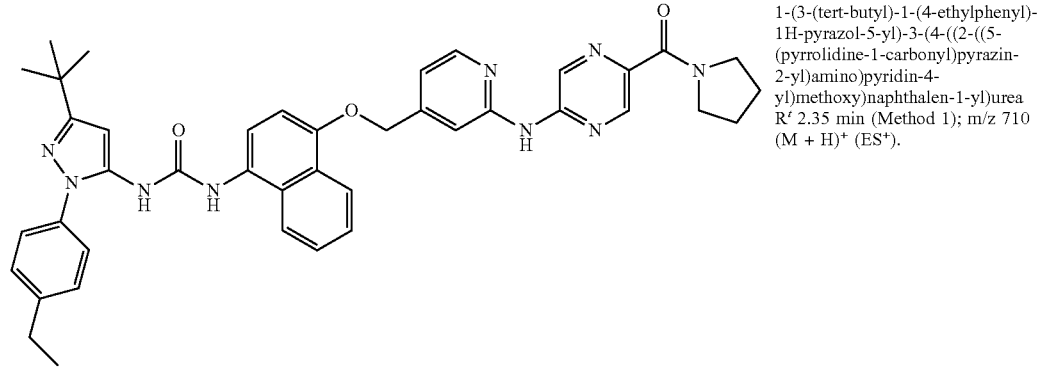

Route code*: 2

1-(3-(tert-butyl)-1-(4-ethylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.35 min (Method 1); m/z 710 (M + H)$^+$ (ES$^+$).

Example 230:

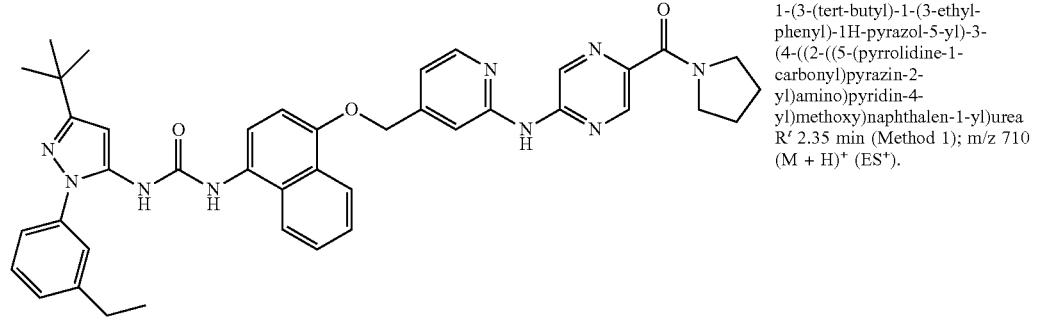

Route code*: 2

1-(3-(tert-butyl)-1-(3-ethyl-phenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.35 min (Method 1); m/z 710 (M + H)$^+$ (ES$^+$).

-continued

Example 231:

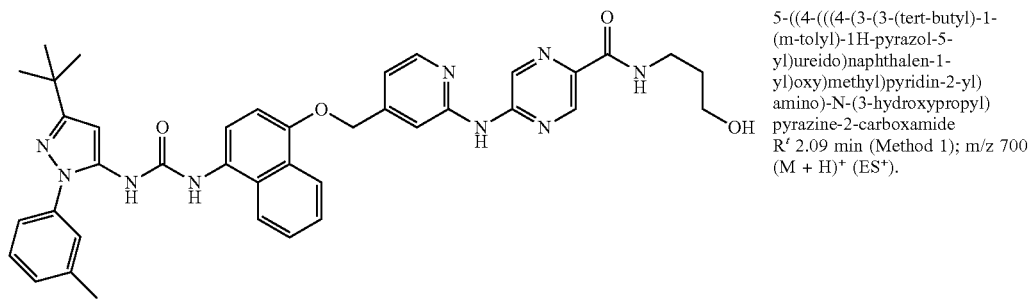

5-((4-(((4-(3-(3-(tert-butyl)-1-(m-tolyl)-1H-pyrazol-5-yl)ureido)naphthalen-1-yl)oxy)methyl)pyridin-2-yl)amino)-N-(3-hydroxypropyl)pyrazine-2-carboxamide
$R^t$ 2.09 min (Method 1); m/z 700 (M + H)$^+$ (ES$^+$).

Route code*: 6

Example 232:

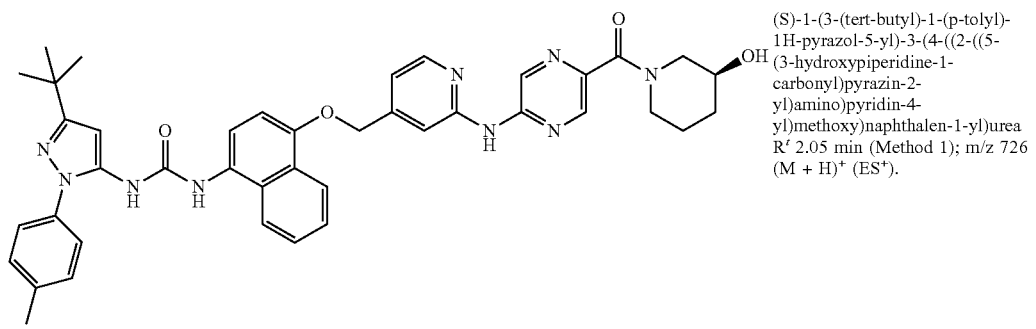

(S)-1-(3-(tert-butyl)-1-(p-tolyl)-1H-pyrazol-5-yl)-3-(4-((2-((5-(3-hydroxypiperidine-1-carbonyl)pyrazin-2-yl)amino)pyridin-4-yl)methoxy)naphthalen-1-yl)urea
$R^t$ 2.05 min (Method 1); m/z 726 (M + H)$^+$ (ES$^+$).

Route code*: 6

Example 233:

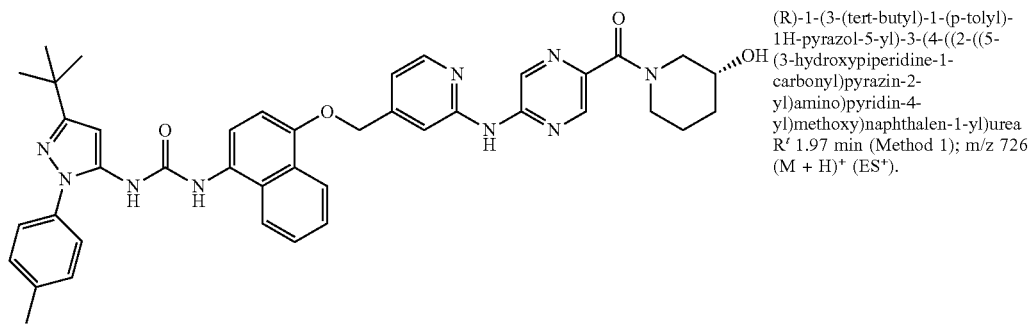

(R)-1-(3-(tert-butyl)-1-(p-tolyl)-1H-pyrazol-5-yl)-3-(4-((2-((5-(3-hydroxypiperidine-1-carbonyl)pyrazin-2-yl)amino)pyridin-4-yl)methoxy)naphthalen-1-yl)urea
$R^t$ 1.97 min (Method 1); m/z 726 (M + H)$^+$ (ES$^+$).

Route code*: 6

Example 234:

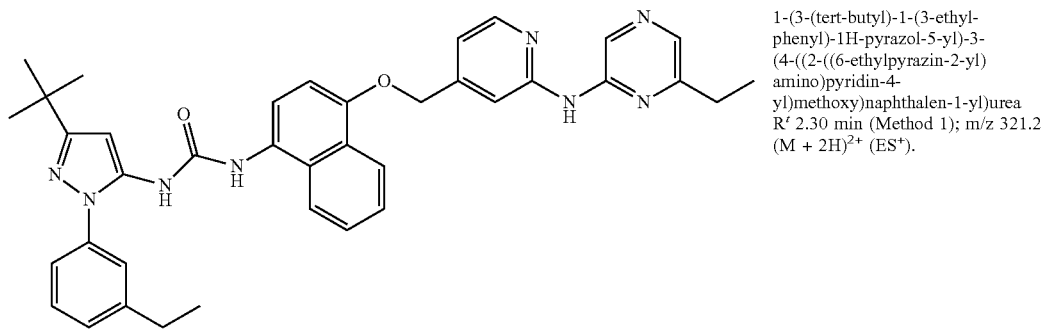

1-(3-(tert-butyl)-1-(3-ethyl-phenyl)-1H-pyrazol-5-yl)-3-(4-((2-((6-ethylpyrazin-2-yl)amino)pyridin-4-yl)methoxy)naphthalen-1-yl)urea
$R^t$ 2.30 min (Method 1); m/z 321.2 (M + 2H)$^{2+}$ (ES$^+$).

Route code*: 1

-continued

Example 235:

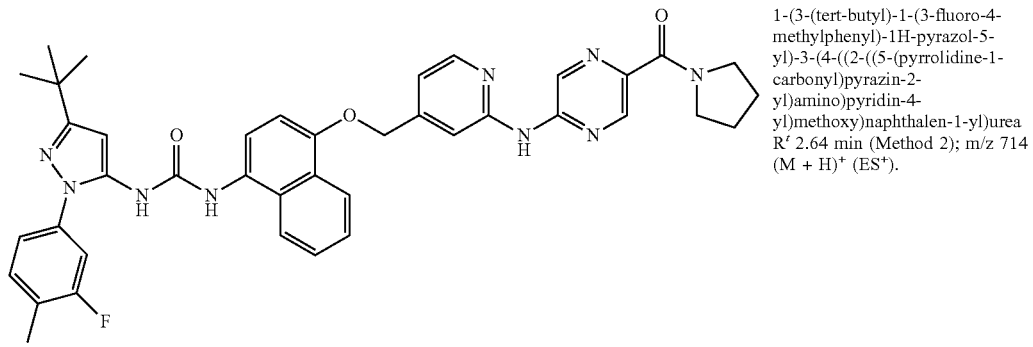

1-(3-(tert-butyl)-1-(3-fluoro-4-methylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.64 min (Method 2); m/z 714 (M + H)$^+$ (ES$^+$).

Route code*: 6

Example 236:

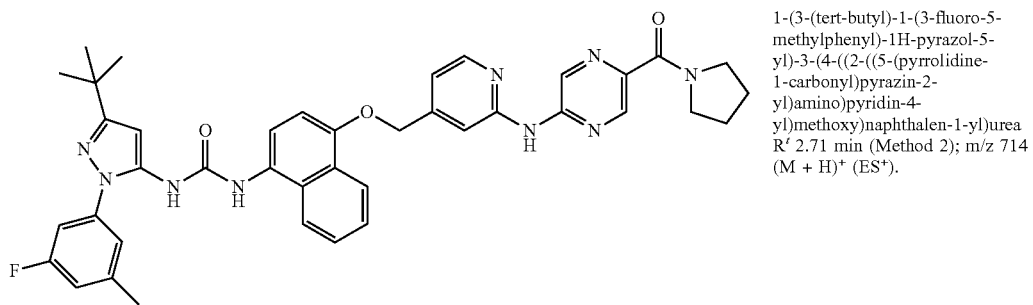

1-(3-(tert-butyl)-1-(3-fluoro-5-methylphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.71 min (Method 2); m/z 714 (M + H)$^+$ (ES$^+$).

Route code*: 6

Example 237:

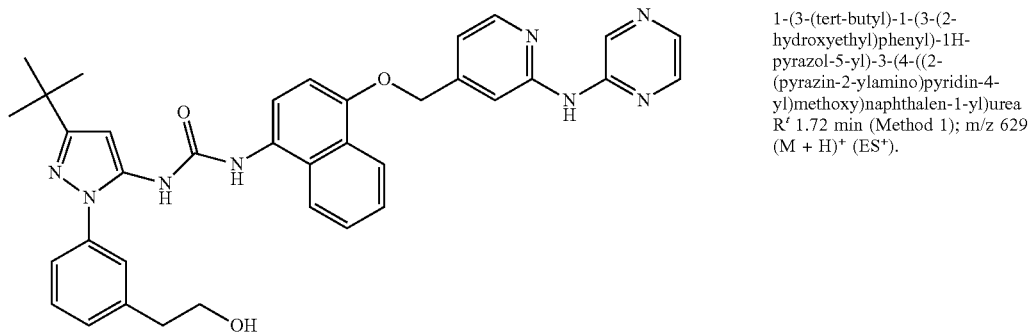

1-(3-(tert-butyl)-1-(3-(2-hydroxyethyl)phenyl)-1H-pyrazol-5-yl)-3-(4-((2-(pyrazin-2-ylamino)pyridin-4-yl)methoxy)naphthalen-1-yl)urea
$R^t$ 1.72 min (Method 1); m/z 629 (M + H)$^+$ (ES$^+$).

Route code*: 1

Example 238:

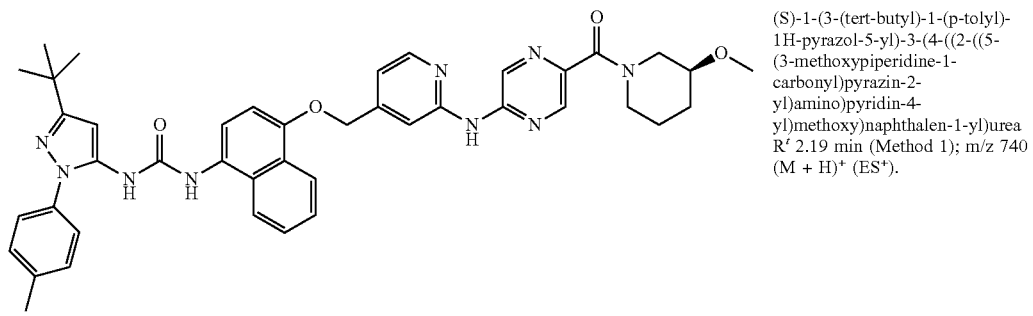

(S)-1-(3-(tert-butyl)-1-(p-tolyl)-1H-pyrazol-5-yl)-3-(4-((2-((5-(3-methoxypiperidine-1-carbonyl)pyrazin-2-yl)amino)pyridin-4-yl)methoxy)naphthalen-1-yl)urea
$R^t$ 2.19 min (Method 1); m/z 740 (M + H)$^+$ (ES$^+$).

Route code*: 6

-continued

Example 239:

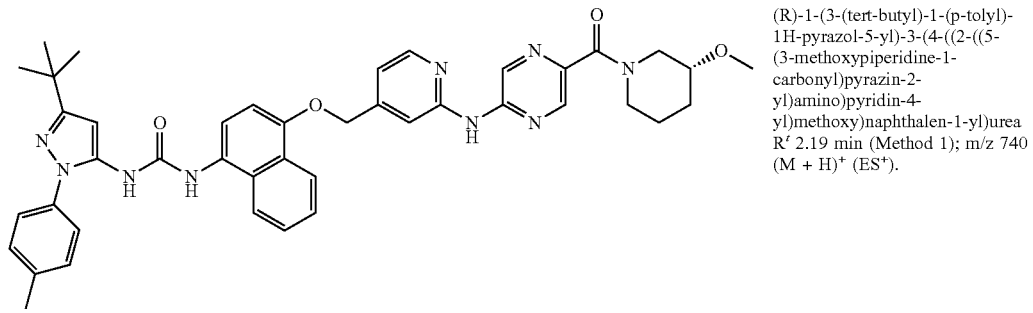

(R)-1-(3-(tert-butyl)-1-(p-tolyl)-1H-pyrazol-5-yl)-3-(4-((2-((5-(3-methoxypiperidine-1-carbonyl)pyrazin-2-yl)amino)pyridin-4-yl)methoxy)naphthalen-1-yl)urea
$R^t$ 2.19 min (Method 1); m/z 740 $(M + H)^+$ $(ES^+)$.

Route code*: 6

Example 240:

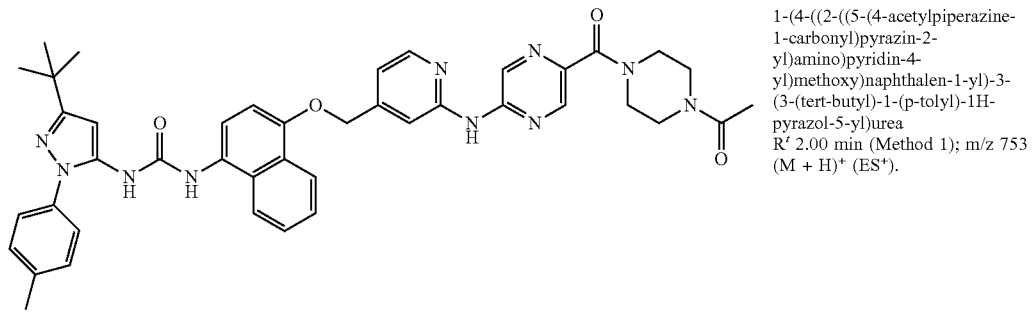

1-(4-((2-((5-(4-acetylpiperazine-1-carbonyl)pyrazin-2-yl)amino)pyridin-4-yl)methoxy)naphthalen-1-yl)-3-(3-(tert-butyl)-1-(p-tolyl)-1H-pyrazol-5-yl)urea
$R^t$ 2.00 min (Method 1); m/z 753 $(M + H)^+$ $(ES^+)$.

Route code*: 6

Example 241:

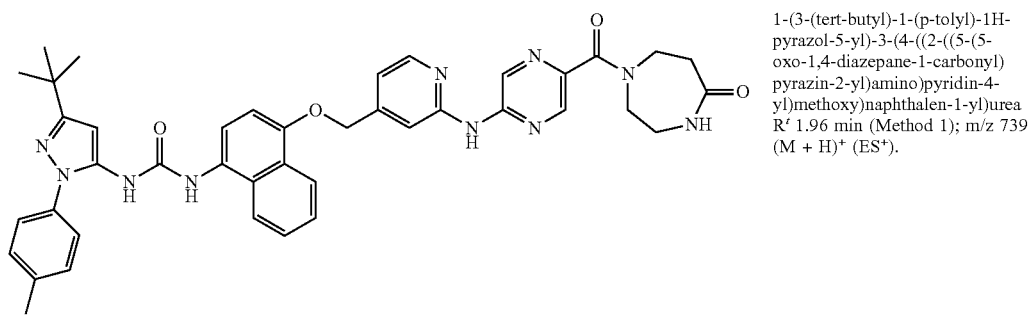

1-(3-(tert-butyl)-1-(p-tolyl)-1H-pyrazol-5-yl)-3-(4-((2-((5-(5-oxo-1,4-diazepane-1-carbonyl)pyrazin-2-yl)amino)pyridin-4-yl)methoxy)naphthalen-1-yl)urea
$R^t$ 1.96 min (Method 1); m/z 739 $(M + H)^+$ $(ES^+)$.

Route code*: 6

Example 242:

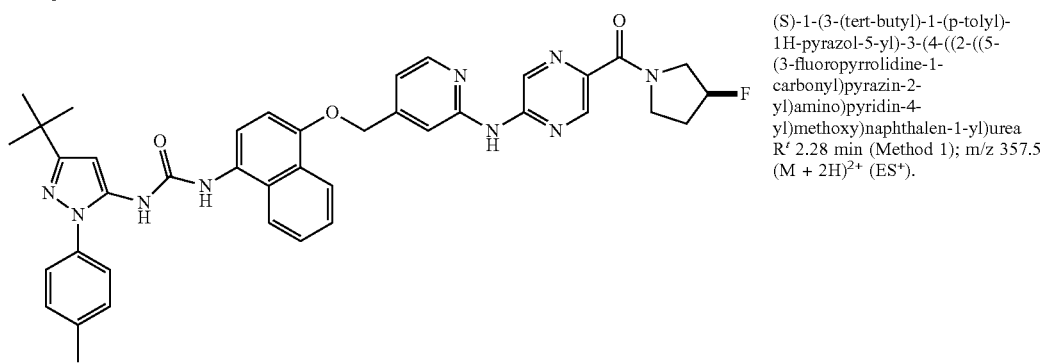

(S)-1-(3-(tert-butyl)-1-(p-tolyl)-1H-pyrazol-5-yl)-3-(4-((2-((5-(3-fluoropyrrolidine-1-carbonyl)pyrazin-2-yl)amino)pyridin-4-yl)methoxy)naphthalen-1-yl)urea
$R^t$ 2.28 min (Method 1); m/z 357.5 $(M + 2H)^{2+}$ $(ES^+)$.

Route code*: 6

Example 243:

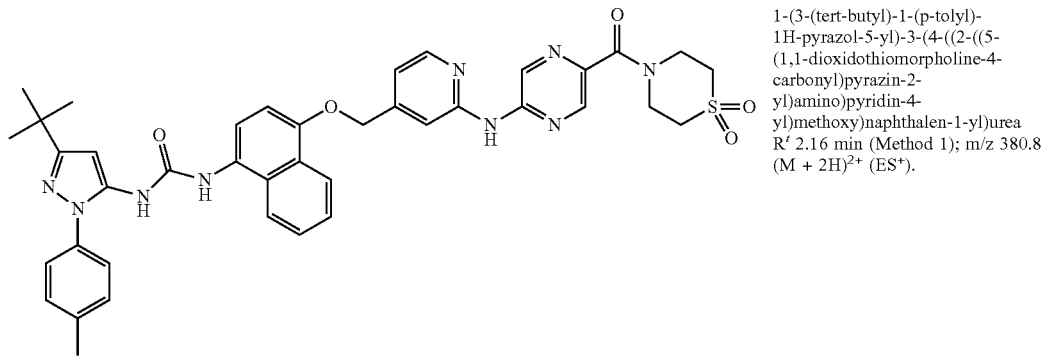

1-(3-(tert-butyl)-1-(p-tolyl)-1H-pyrazol-5-yl)-3-(4-((2-((5-(1,1-dioxidothiomorpholine-4-carbonyl)pyrazin-2-yl)amino)pyridin-4-yl)methoxy)naphthalen-1-yl)urea R$^t$ 2.16 min (Method 1); m/z 380.8 (M + 2H)$^{2+}$ (ES$^+$).

Route code*: 6

Example 244:

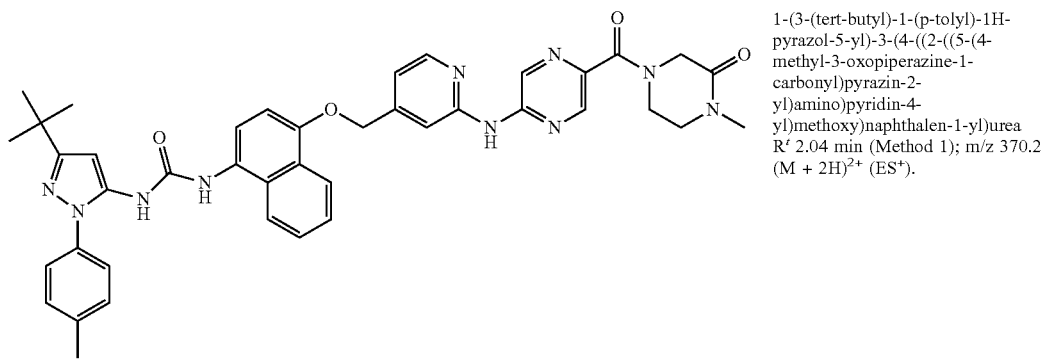

1-(3-(tert-butyl)-1-(p-tolyl)-1H-pyrazol-5-yl)-3-(4-((2-((5-(4-methyl-3-oxopiperazine-1-carbonyl)pyrazin-2-yl)amino)pyridin-4-yl)methoxy)naphthalen-1-yl)urea R$^t$ 2.04 min (Method 1); m/z 370.2 (M + 2H)$^{2+}$ (ES$^+$).

Route code*: 6

Example 245:

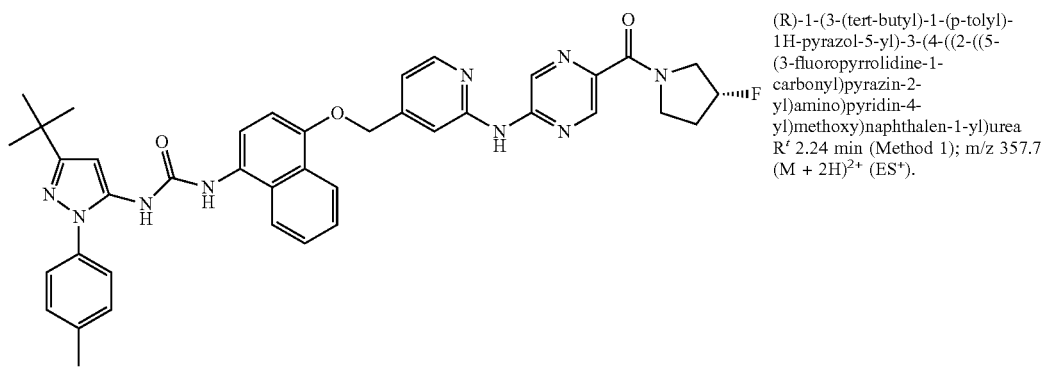

(R)-1-(3-(tert-butyl)-1-(p-tolyl)-1H-pyrazol-5-yl)-3-(4-((2-((5-(3-fluoropyrrolidine-1-carbonyl)pyrazin-2-yl)amino)pyridin-4-yl)methoxy)naphthalen-1-yl)urea R$^t$ 2.24 min (Method 1); m/z 357.7 (M + 2H)$^{2+}$ (ES$^+$).

Route code*: 6

Example 246:

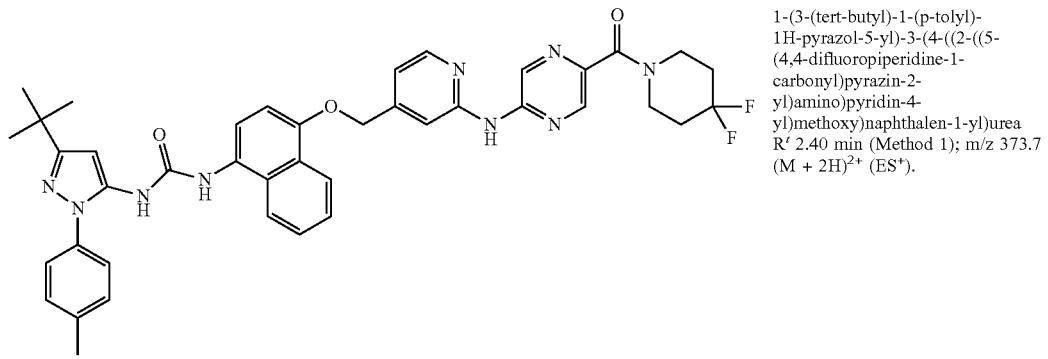

Route code*: 6

1-(3-(tert-butyl)-1-(p-tolyl)-1H-pyrazol-5-yl)-3-(4-((2-((5-(4,4-difluoropiperidine-1-carbonyl)pyrazin-2-yl)amino)pyridin-4-yl)methoxy)naphthalen-1-yl)urea
R$^t$ 2.40 min (Method 1); m/z 373.7 (M + 2H)$^{2+}$ (ES$^+$).

Example 247:

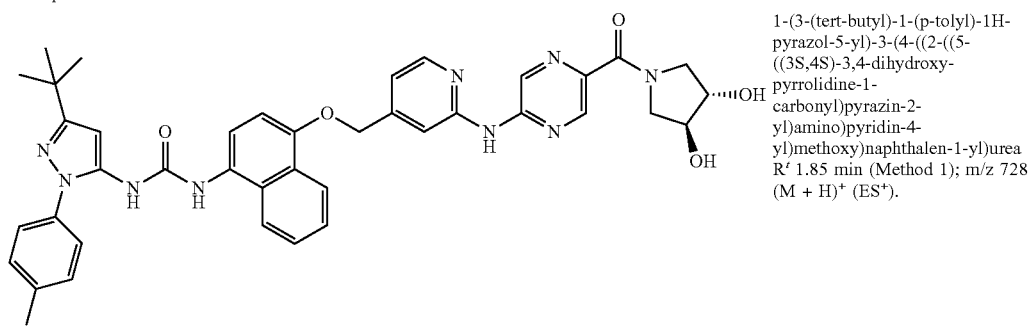

Route code*: 6

1-(3-(tert-butyl)-1-(p-tolyl)-1H-pyrazol-5-yl)-3-(4-((2-((5-((3S,4S)-3,4-dihydroxypyrrolidine-1-carbonyl)pyrazin-2-yl)amino)pyridin-4-yl)methoxy)naphthalen-1-yl)urea
R$^t$ 1.85 min (Method 1); m/z 728 (M + H)$^+$ (ES$^+$).

Example 248:

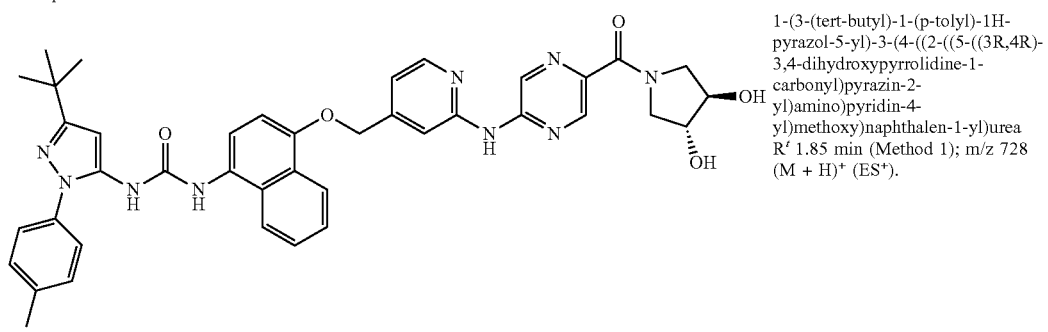

Route code*: 6

1-(3-(tert-butyl)-1-(p-tolyl)-1H-pyrazol-5-yl)-3-(4-((2-((5-((3R,4R)-3,4-dihydroxypyrrolidine-1-carbonyl)pyrazin-2-yl)amino)pyridin-4-yl)methoxy)naphthalen-1-yl)urea
R$^t$ 1.85 min (Method 1); m/z 728 (M + H)$^+$ (ES$^+$).

Example 249:

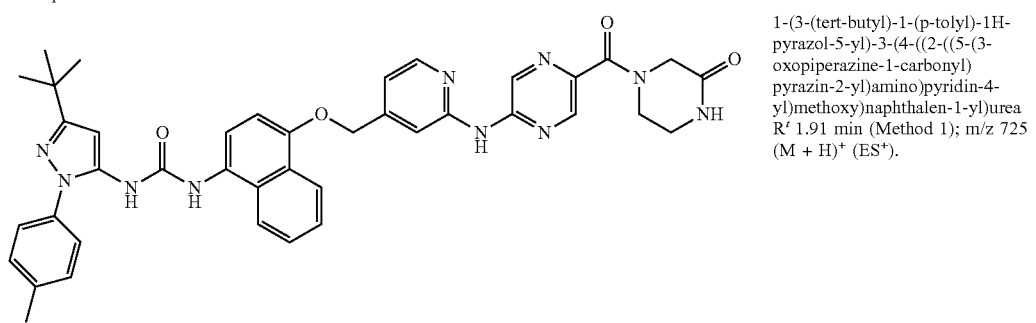

Route code*: 6

1-(3-(tert-butyl)-1-(p-tolyl)-1H-pyrazol-5-yl)-3-(4-((2-((5-(3-oxopiperazine-1-carbonyl)pyrazin-2-yl)amino)pyridin-4-yl)methoxy)naphthalen-1-yl)urea
R$^t$ 1.91 min (Method 1); m/z 725 (M + H)$^+$ (ES$^+$).

-continued

Example 250:

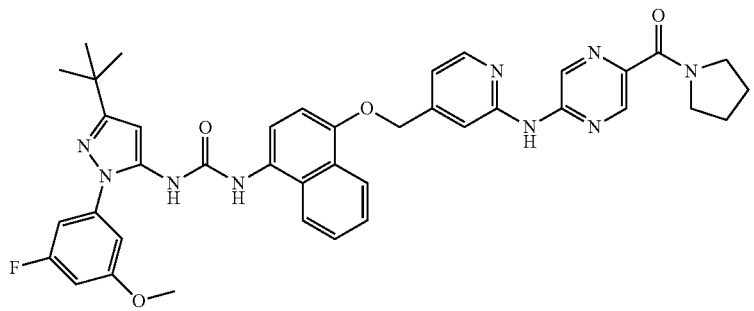

Route code*: 6

1-(3-(tert-butyl)-1-(3-fluoro-5-methoxyphenyl)-1H-pyrazol-5-yl)-3-(4-((2-((5-(pyrrolidine-1-carbonyl)pyrazin-2-yl)amino)pyridin-4-yl)methoxy)naphthalen-1-yl)urea
$R^t$ 2.66 min (Method 2); m/z 730 $(M + H)^+$ $(ES^+)$.

Example 251:

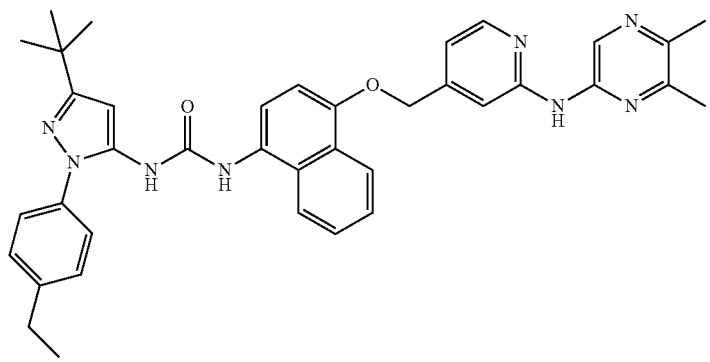 [SMILES: Cc1ccc(-n2nc(C(C)(C)C)cc2NC(=O)Nc2ccc(OCc3ccnc(Nc4cnc(C)c(C)n4)c3)c3ccccc23)cc1F]

Route code*: 1

1-(3-(tert-butyl)-1-(4-ethylphenyl)-1H-pyrazol-5-yl)-3-(4-((2-((5,6-dimethylpyrazin-2-yl)amino)pyridin-4-yl)methoxy)naphthalen-1-yl)urea
$R^t$ 2.73 min (Method 2); m/z 641 $(M + H)^+$ $(ES^+)$.

Example 252:

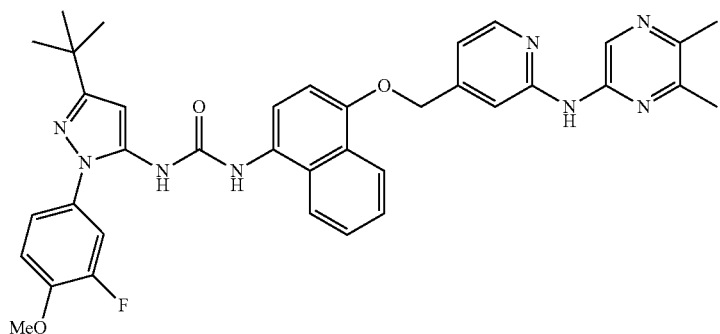

Route code*: 1

1-(3-(tert-butyl)-1-(3-fluoro-4-methoxyphenyl)-1H-pyrazol-5-yl)-3-(4-((2-((5,6-dimethylpyrazin-2-yl)amino)pyridin-4-yl)methoxy)naphthalen-1-yl)urea
$R^t$ 2.59 min (Method 2); m/z 661 $(M + H)^+$ $(ES^+)$.

Example 253:

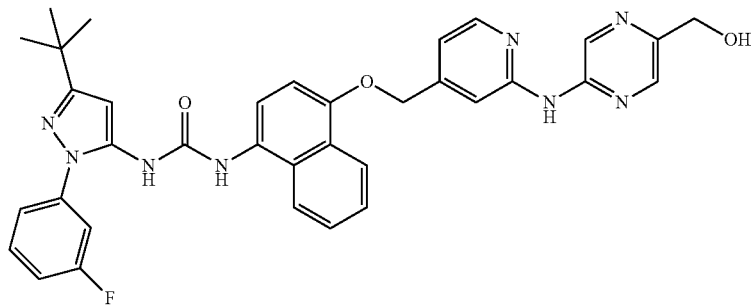

Route code*: 1

1-(3-(tert-butyl)-1-(3-fluorophenyl)-1H-pyrazol-5-yl)-3-(4-((2-((5-(hydroxymethyl)pyrazin-2-yl)amino)pyridin-4-yl)methoxy)naphthalen-1-yl)urea
$R^t$ 1.83 min (Method 1); m/z 633 $(M + H)^+$ $(ES^+)$.

Example 254:

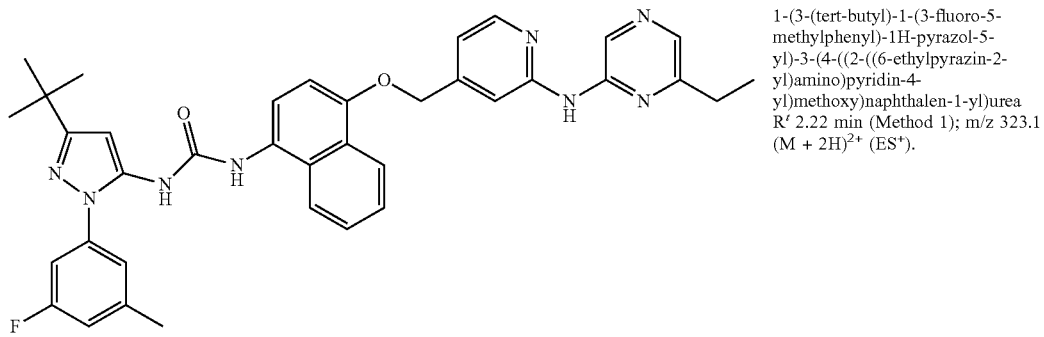

Route code*: 1

1-(3-(tert-butyl)-1-(3-fluoro-5-methylphenyl)-1H-pyrazol-5-yl)-3-(4-((2-((6-ethylpyrazin-2-yl)amino)pyridin-4-yl)methoxy)naphthalen-1-yl)urea
$R^t$ 2.22 min (Method 1); m/z 323.1 $(M + 2H)^{2+}$ (ES$^+$).

Example 255:

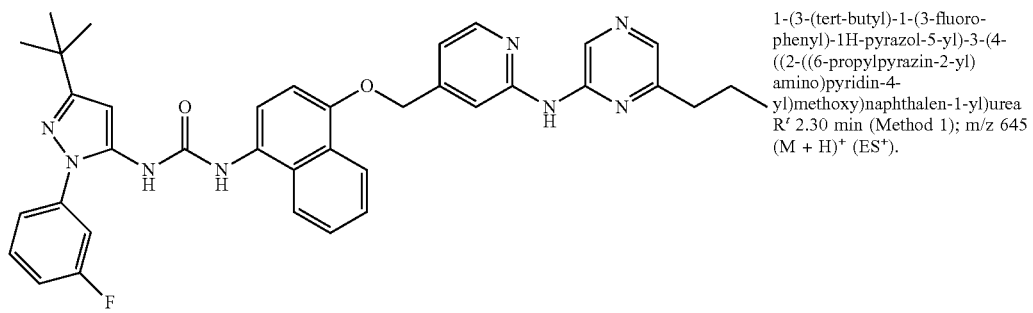

Route code*: 1

1-(3-(tert-butyl)-1-(3-fluorophenyl)-1H-pyrazol-5-yl)-3-(4-((2-((6-propylpyrazin-2-yl)amino)pyridin-4-yl)methoxy)naphthalen-1-yl)urea
$R^t$ 2.30 min (Method 1); m/z 645 $(M + H)^+$ (ES$^+$).

Example 256:

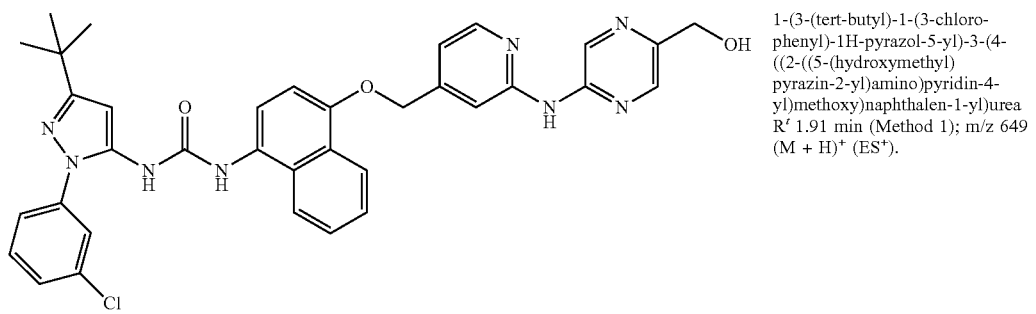

Route code*: 1

1-(3-(tert-butyl)-1-(3-chlorophenyl)-1H-pyrazol-5-yl)-3-(4-((2-((5-(hydroxymethyl)pyrazin-2-yl)amino)pyridin-4-yl)methoxy)naphthalen-1-yl)urea
$R^t$ 1.91 min (Method 1); m/z 649 $(M + H)^+$ (ES$^+$).

Example 257:

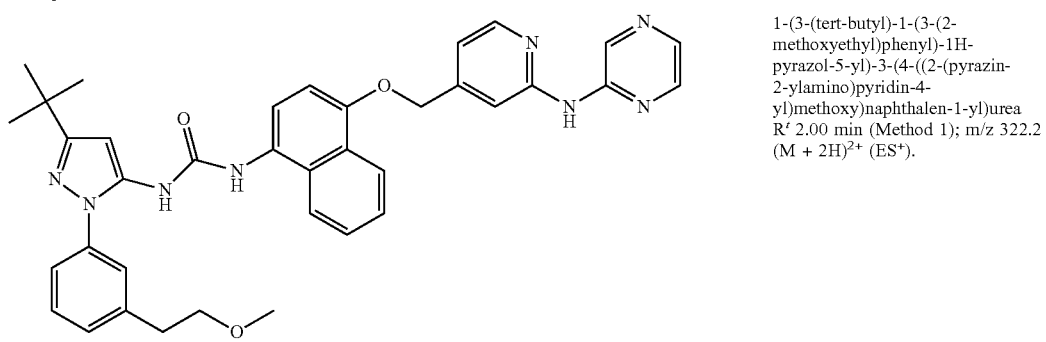

Route code*: 1

1-(3-(tert-butyl)-1-(3-(2-methoxyethyl)phenyl)-1H-pyrazol-5-yl)-3-(4-((2-(pyrazin-2-ylamino)pyridin-4-yl)methoxy)naphthalen-1-yl)urea
$R^t$ 2.00 min (Method 1); m/z 322.2 $(M + 2H)^{2+}$ (ES$^+$).

Example 258:

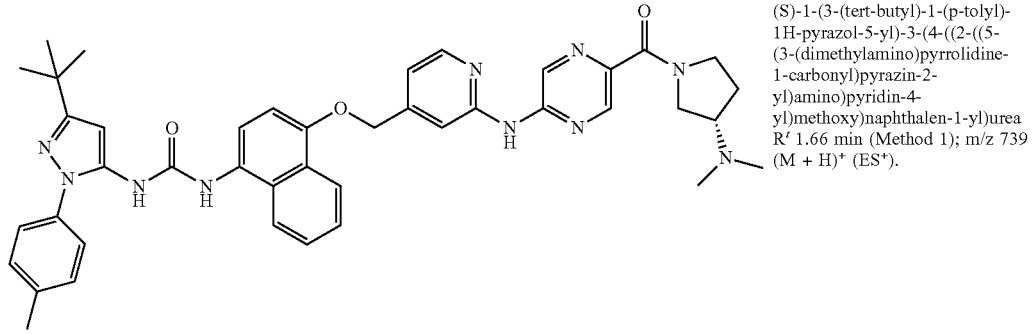

(S)-1-(3-(tert-butyl)-1-(p-tolyl)-1H-pyrazol-5-yl)-3-(4-((2-((5-(3-(dimethylamino)pyrrolidine-1-carbonyl)pyrazin-2-yl)amino)pyridin-4-yl)methoxy)naphthalen-1-yl)urea
$R^t$ 1.66 min (Method 1); m/z 739 (M + H)$^+$ (ES$^+$).

Route code*: 6

Example 259:

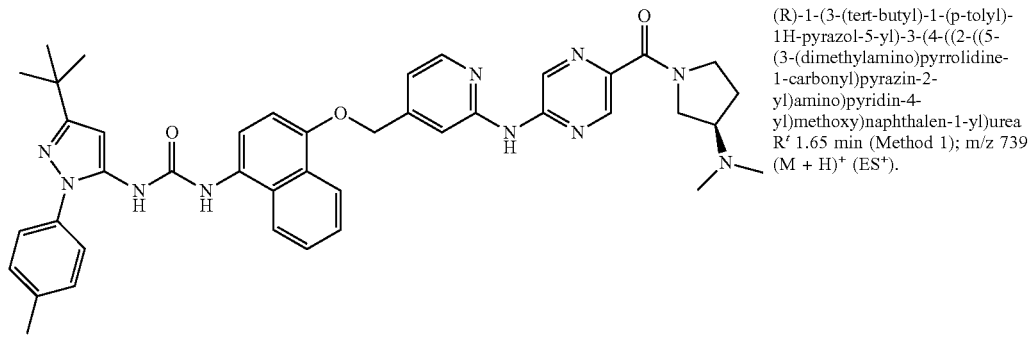

(R)-1-(3-(tert-butyl)-1-(p-tolyl)-1H-pyrazol-5-yl)-3-(4-((2-((5-(3-(dimethylamino)pyrrolidine-1-carbonyl)pyrazin-2-yl)amino)pyridin-4-yl)methoxy)naphthalen-1-yl)urea
$R^t$ 1.65 min (Method 1); m/z 739 (M + H)$^+$ (ES$^+$).

Route code*: 6

Example 260:

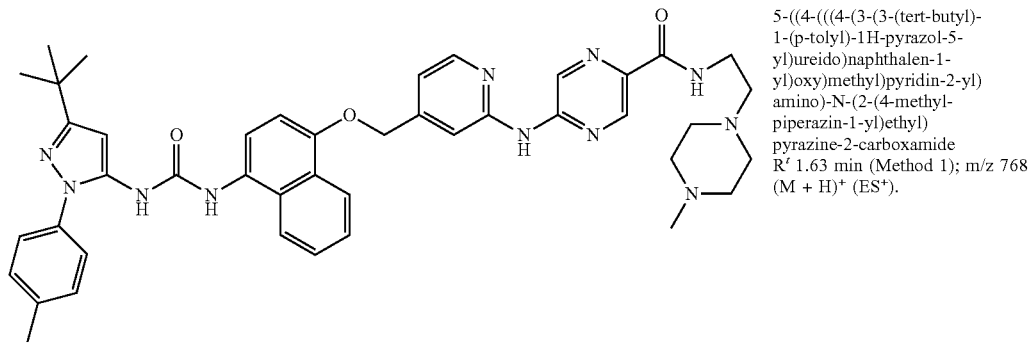

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(4-methyl-piperazin-1-yl)ethyl)pyrazine-2-carboxamide
$R^t$ 1.63 min (Method 1); m/z 768 (M + H)$^+$ (ES$^+$).

Route code*: 6

Example 261:

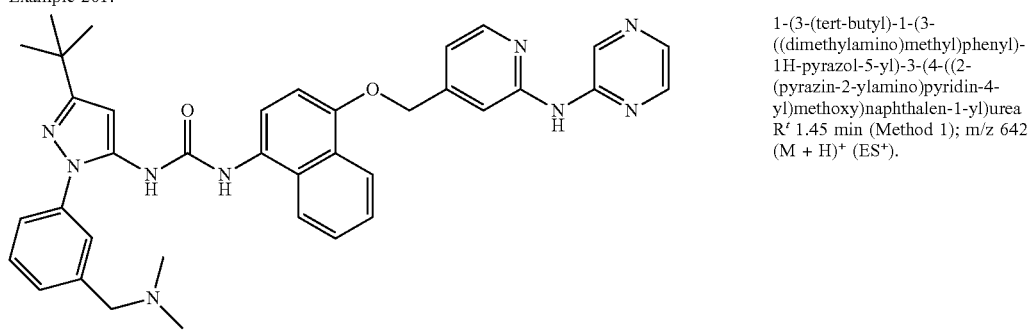

1-(3-(tert-butyl)-1-(3-((dimethylamino)methyl)phenyl)-1H-pyrazol-5-yl)-3-(4-((2-(pyrazin-2-ylamino)pyridin-4-yl)methoxy)naphthalen-1-yl)urea
$R^t$ 1.45 min (Method 1); m/z 642 (M + H)$^+$ (ES$^+$).

Route code*: 1

Example 262:

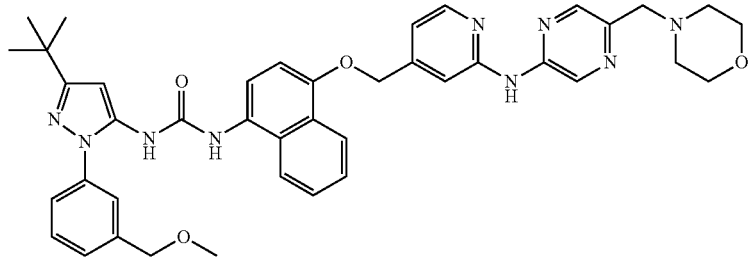

Route code*: 1

1-(3-(tert-butyl)-1-(3-(methoxymethyl)phenyl)-1H-pyrazol-5-yl)-3-(4-((2-((5-(morpholinomethyl)pyrazin-2-yl)amino)pyridin-4-yl)methoxy)naphthalen-1-yl)urea
$R^t$ 1.62 min (Method 1); m/z 364.7 $(M + 2H)^{2+}$ $(ES^+)$.

Example 263:

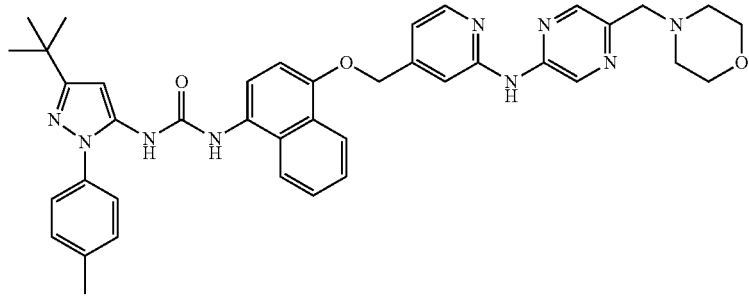

Route code*: 1

1-(3-(tert-butyl)-1-(p-tolyl)-1H-pyrazol-5-yl)-3-(4-((2-((5-(morpholinomethyl)pyrazin-2-yl)amino)pyridin-4-yl)methoxy)naphthalen-1-yl)urea
$R^t$ 1.68 min (Method 1); m/z 349.8 $(M + 2H)^{2+}$ $(ES^+)$.

Example 264:

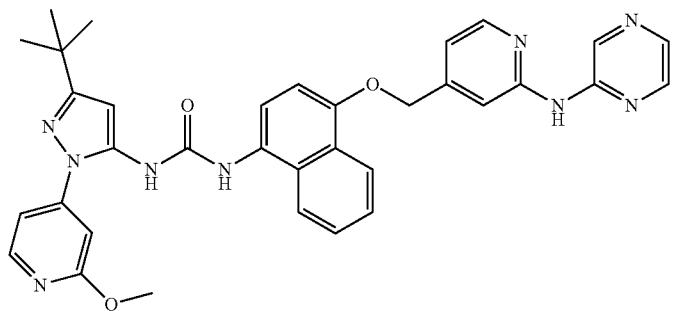

Route code*: 1

1-(3-(tert-butyl)-1-(2-methoxypyridin-4-yl)-1H-pyrazol-5-yl)-3-(4-((2-(pyrazin-2-ylamino)pyridin-4-yl)methoxy)naphthalen-1-yl)urea
$R^t$ 2.41 min (Method 2); m/z 616 $(M + H)^+$ $(ES^+)$.

Example 265:

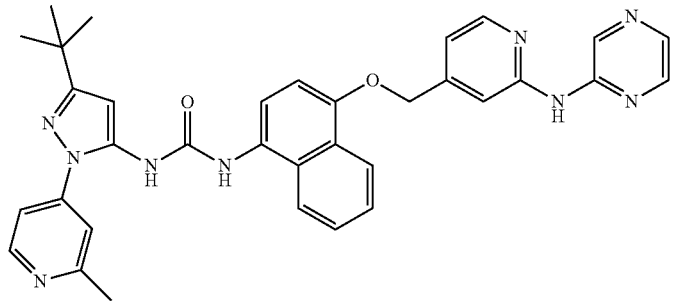

Route code*: 1

1-(3-(tert-butyl)-1-(2-methyl-pyridin-4-yl)-1H-pyrazol-5-yl)-3-(4-((2-(pyrazin-2-ylamino)pyridin-4-yl)methoxy)naphthalen-1-yl)urea
$R^t$ 2.26 min (Method 2); m/z 600 $(M + H)^+$ $(ES^+)$.

-continued

Example 266:

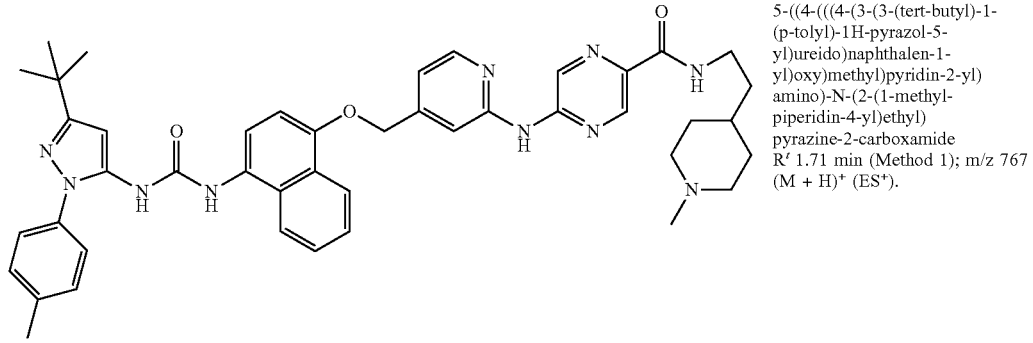

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(1-methyl-piperidin-4-yl)ethyl)pyrazine-2-carboxamide
R$^t$ 1.71 min (Method 1); m/z 767 (M + H)$^+$ (ES$^+$).

Route code*: 6

Example 267:

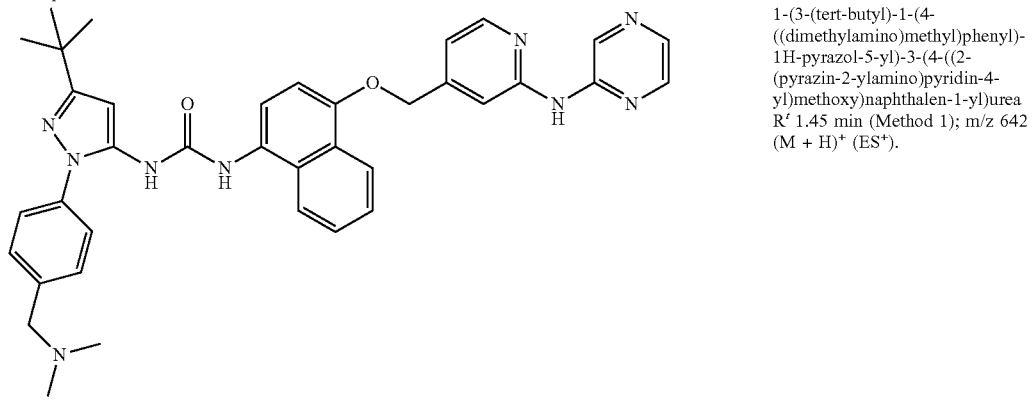

1-(3-(tert-butyl)-1-(4-((dimethylamino)methyl)phenyl)-1H-pyrazol-5-yl)-3-(4-((2-(pyrazin-2-ylamino)pyridin-4-yl)methoxy)naphthalen-1-yl)urea
R$^t$ 1.45 min (Method 1); m/z 642 (M + H)$^+$ (ES$^+$).

Route code*: 1

Example 268:

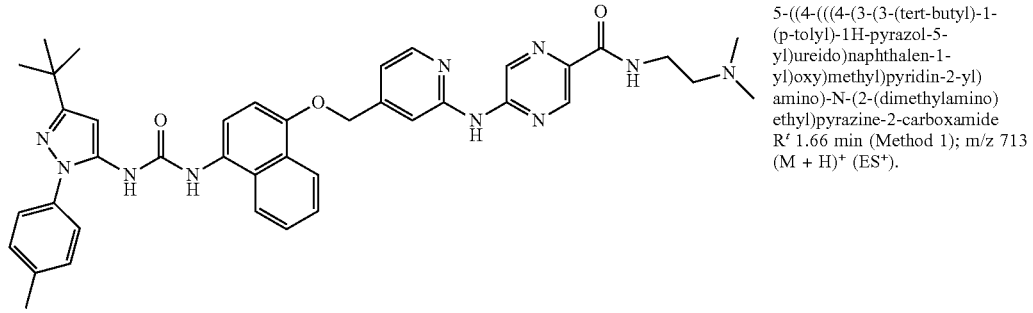

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-(dimethylamino)ethyl)pyrazine-2-carboxamide
R$^t$ 1.66 min (Method 1); m/z 713 (M + H)$^+$ (ES$^+$).

Route code*: 6

Example 269:

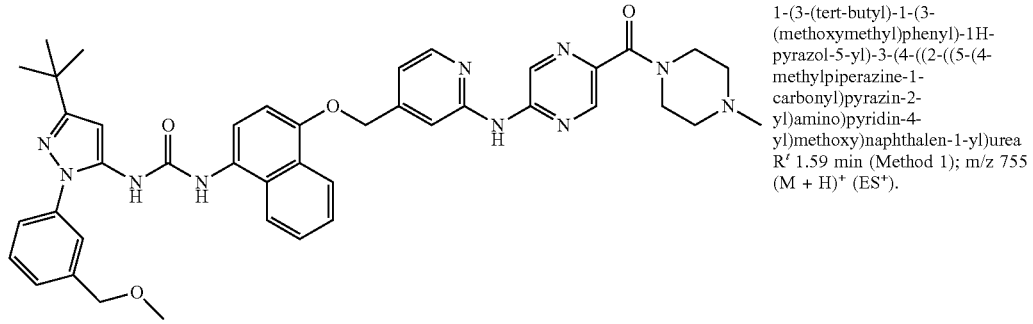

1-(3-(tert-butyl)-1-(3-(methoxymethyl)phenyl)-1H-pyrazol-5-yl)-3-(4-((2-((5-(4-methylpiperazine-1-carbonyl)pyrazin-2-yl)amino)pyridin-4-yl)methoxy)naphthalen-1-yl)urea
R$^t$ 1.59 min (Method 1); m/z 755 (M + H)$^+$ (ES$^+$).

Route code*: 6

-continued

Example 270:

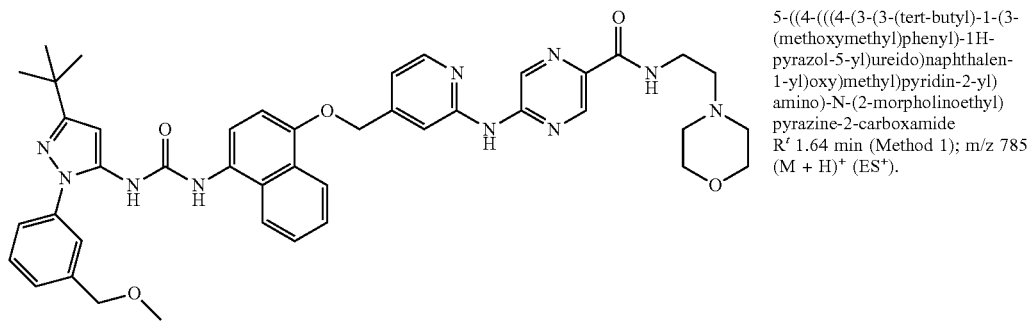

Route code*: 6

5-((4-(((4-(3-(3-(tert-butyl)-1-(3-(methoxymethyl)phenyl)-1H-pyrazol-5-yl)ureido)naphthalen-1-yl)oxy)methyl)pyridin-2-yl)amino)-N-(2-morpholinoethyl)pyrazine-2-carboxamide
R$^t$ 1.64 min (Method 1); m/z 785 (M + H)$^+$ (ES$^+$).

Example 271:

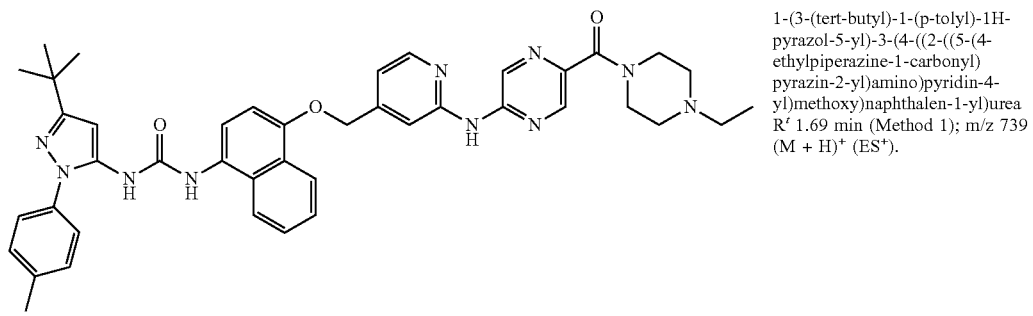

Route code*: 6

1-(3-(tert-butyl)-1-(p-tolyl)-1H-pyrazol-5-yl)-3-(4-((2-((5-(4-ethylpiperazine-1-carbonyl)pyrazin-2-yl)amino)pyridin-4-yl)methoxy)naphthalen-1-yl)urea
R$^t$ 1.69 min (Method 1); m/z 739 (M + H)$^+$ (ES$^+$).

Example 272:

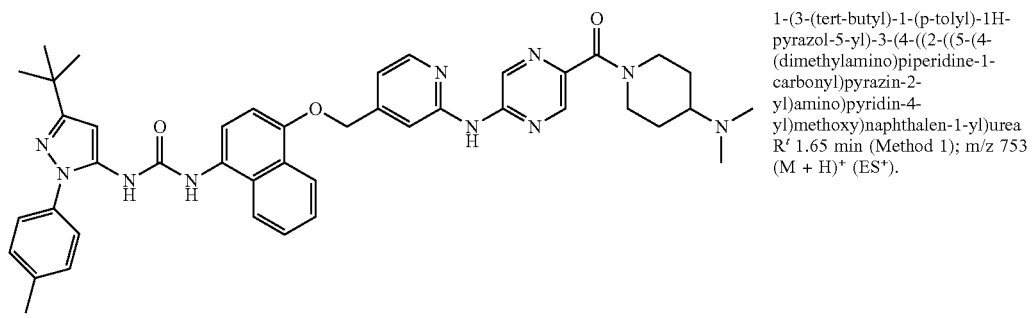

Route code*: 6

1-(3-(tert-butyl)-1-(p-tolyl)-1H-pyrazol-5-yl)-3-(4-((2-((5-(4-(dimethylamino)piperidine-1-carbonyl)pyrazin-2-yl)amino)pyridin-4-yl)methoxy)naphthalen-1-yl)urea
R$^t$ 1.65 min (Method 1); m/z 753 (M + H)$^+$ (ES$^+$).

Example 273:

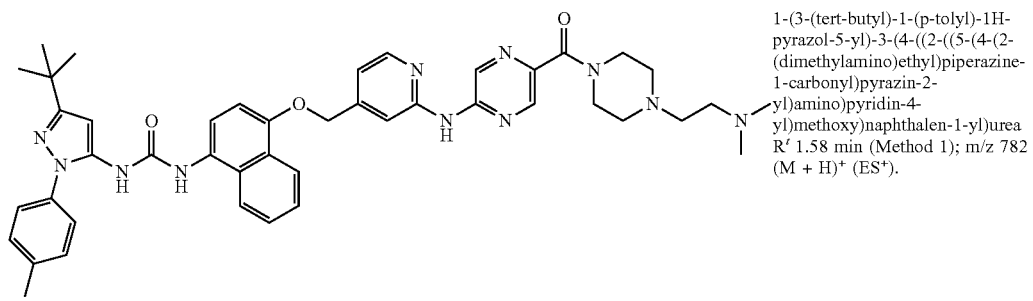

Route code*: 6

1-(3-(tert-butyl)-1-(p-tolyl)-1H-pyrazol-5-yl)-3-(4-((2-((5-(4-(2-(dimethylamino)ethyl)piperazine-1-carbonyl)pyrazin-2-yl)amino)pyridin-4-yl)methoxy)naphthalen-1-yl)urea
R$^t$ 1.58 min (Method 1); m/z 782 (M + H)$^+$ (ES$^+$).

Example 274:

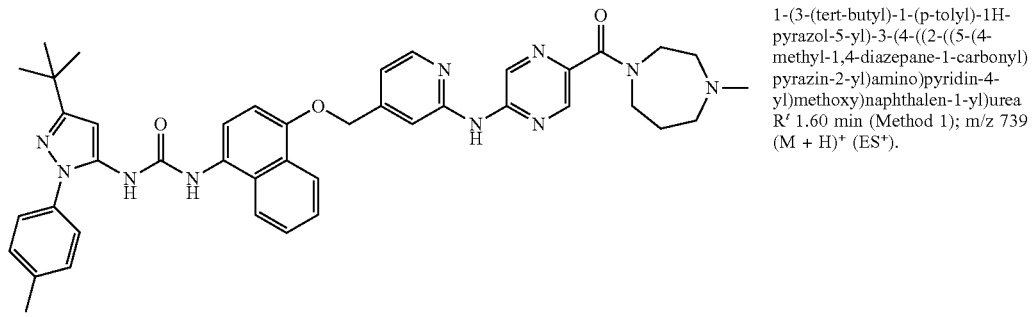

Route code*: 6

1-(3-(tert-butyl)-1-(p-tolyl)-1H-pyrazol-5-yl)-3-(4-((2-((5-(4-methyl-1,4-diazepane-1-carbonyl)pyrazin-2-yl)amino)pyridin-4-yl)methoxy)naphthalen-1-yl)urea R$^t$ 1.60 min (Method 1); m/z 739 (M + H)$^+$ (ES$^+$).

Example 275:

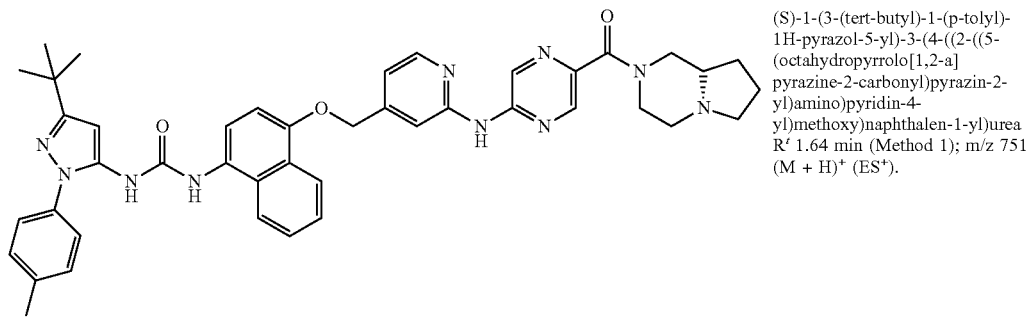

Route code*: 6

(S)-1-(3-(tert-butyl)-1-(p-tolyl)-1H-pyrazol-5-yl)-3-(4-((2-((5-(octahydropyrrolo[1,2-a]pyrazine-2-carbonyl)pyrazin-2-yl)amino)pyridin-4-yl)methoxy)naphthalen-1-yl)urea R$^t$ 1.64 min (Method 1); m/z 751 (M + H)$^+$ (ES$^+$).

Example 276:

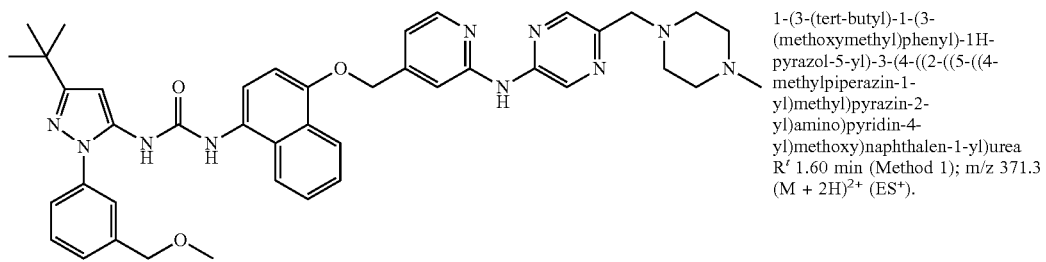

Route code*: 1

1-(3-(tert-butyl)-1-(3-(methoxymethyl)phenyl)-1H-pyrazol-5-yl)-3-(4-((2-((5-((4-methylpiperazin-1-yl)methyl)pyrazin-2-yl)amino)pyridin-4-yl)methoxy)naphthalen-1-yl)urea R$^t$ 1.60 min (Method 1); m/z 371.3 (M + 2H)$^{2+}$ (ES$^+$).

Example 277:

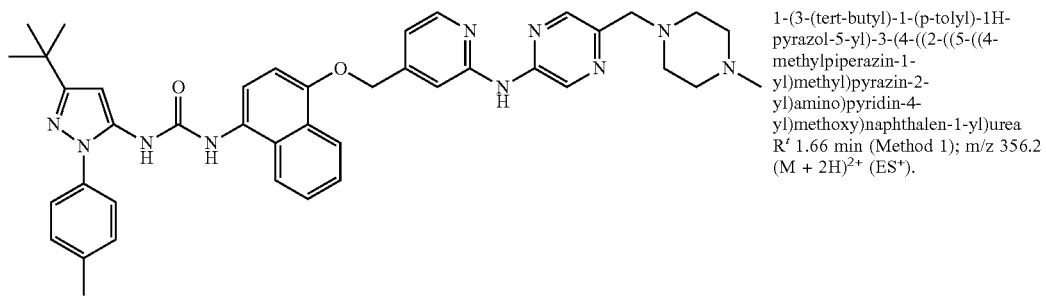

Route code*: 1

1-(3-(tert-butyl)-1-(p-tolyl)-1H-pyrazol-5-yl)-3-(4-((2-((5-((4-methylpiperazin-1-yl)methyl)pyrazin-2-yl)amino)pyridin-4-yl)methoxy)naphthalen-1-yl)urea R$^t$ 1.66 min (Method 1); m/z 356.2 (M + 2H)$^{2+}$ (ES$^+$).

Example 278:

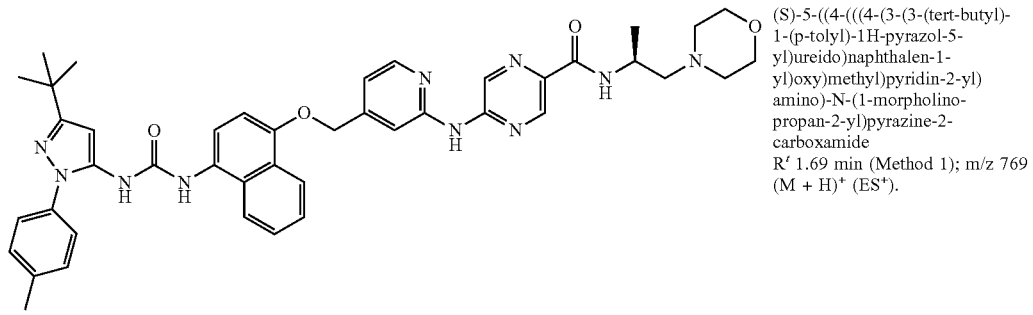

Route code*: 6

(S)-5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-morpholinopropan-2-yl)pyrazine-2-carboxamide
$R^t$ 1.69 min (Method 1); m/z 769 (M + H)$^+$ (ES$^+$).

Example 279:

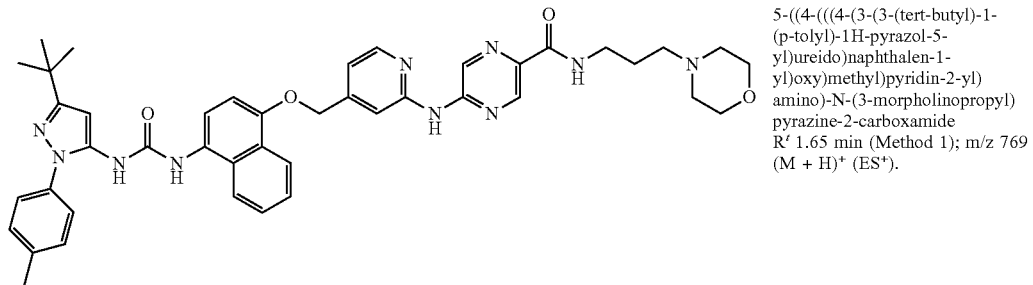

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-morpholinopropyl)pyrazine-2-carboxamide
$R^t$ 1.65 min (Method 1); m/z 769 (M + H)$^+$ (ES$^+$).

Example 280:

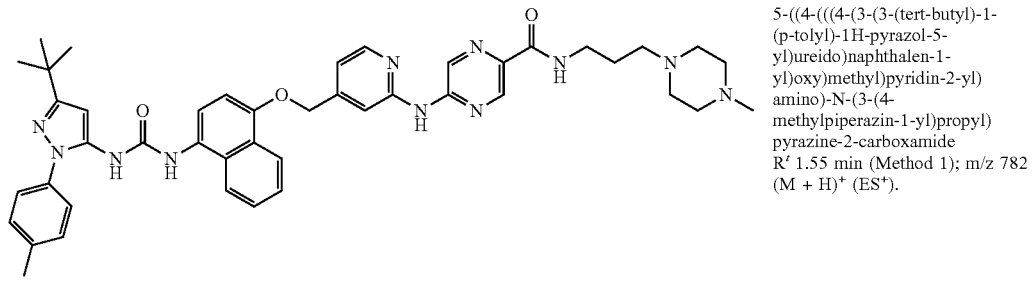

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(3-(4-methylpiperazin-1-yl)propyl)pyrazine-2-carboxamide
$R^t$ 1.55 min (Method 1); m/z 782 (M + H)$^+$ (ES$^+$).

Example 281:

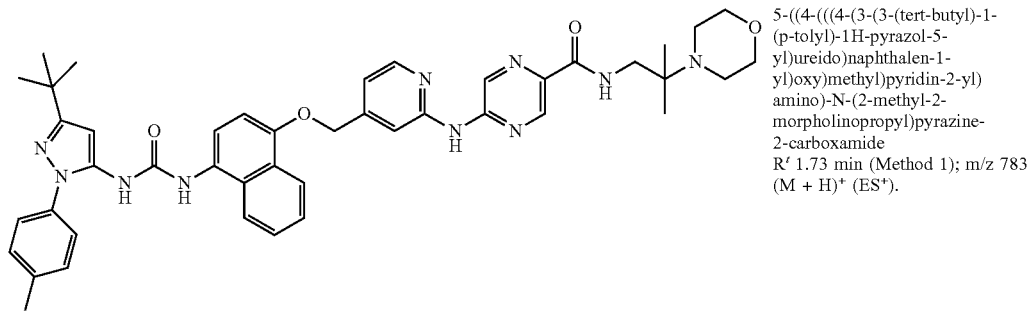

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methyl-2-morpholinopropyl)pyrazine-2-carboxamide
$R^t$ 1.73 min (Method 1); m/z 783 (M + H)$^+$ (ES$^+$).

Example 282:

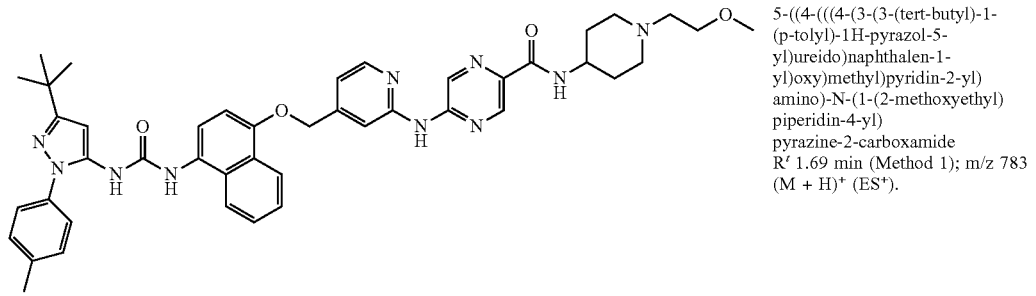

Route code*: 6

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(1-(2-methoxyethyl)piperidin-4-yl)pyrazine-2-carboxamide
R$^t$ 1.69 min (Method 1); m/z 783 (M + H)$^+$ (ES$^+$).

Example 283:

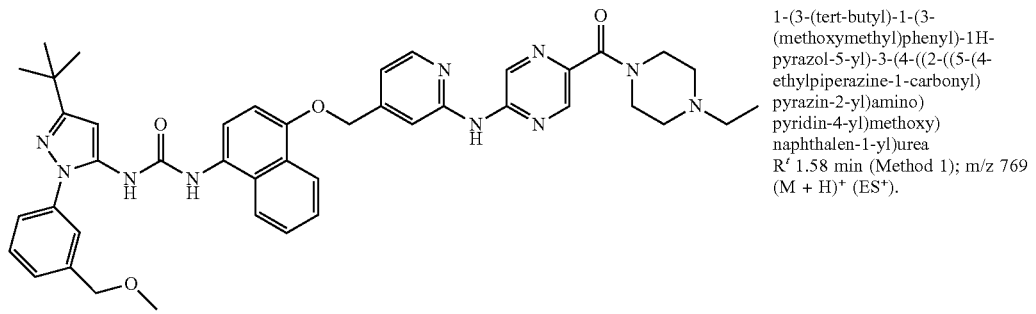

Route code*: 6

1-(3-(tert-butyl)-1-(3-(methoxymethyl)phenyl)-1H-pyrazol-5-yl)-3-(4-((2-((5-(4-ethylpiperazine-1-carbonyl)pyrazin-2-yl)amino)pyridin-4-yl)methoxy)naphthalen-1-yl)urea
R$^t$ 1.58 min (Method 1); m/z 769 (M + H)$^+$ (ES$^+$).

Example 284:

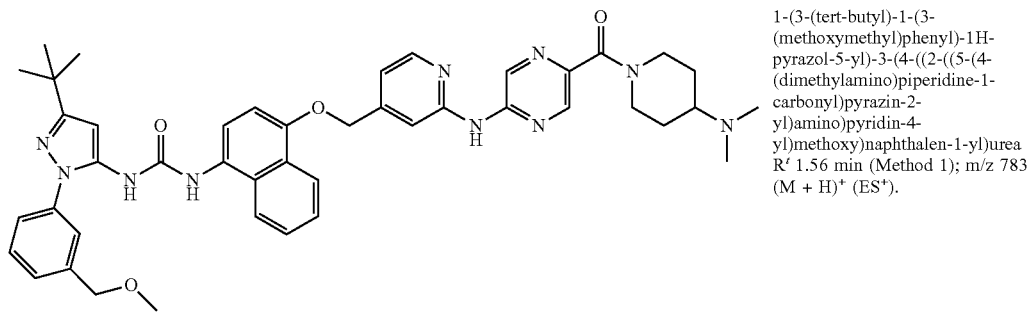

Route code*: 6

1-(3-(tert-butyl)-1-(3-(methoxymethyl)phenyl)-1H-pyrazol-5-yl)-3-(4-((2-((5-(4-(dimethylamino)piperidine-1-carbonyl)pyrazin-2-yl)amino)pyridin-4-yl)methoxy)naphthalen-1-yl)urea
R$^t$ 1.56 min (Method 1); m/z 783 (M + H)$^+$ (ES$^+$).

Example 285:

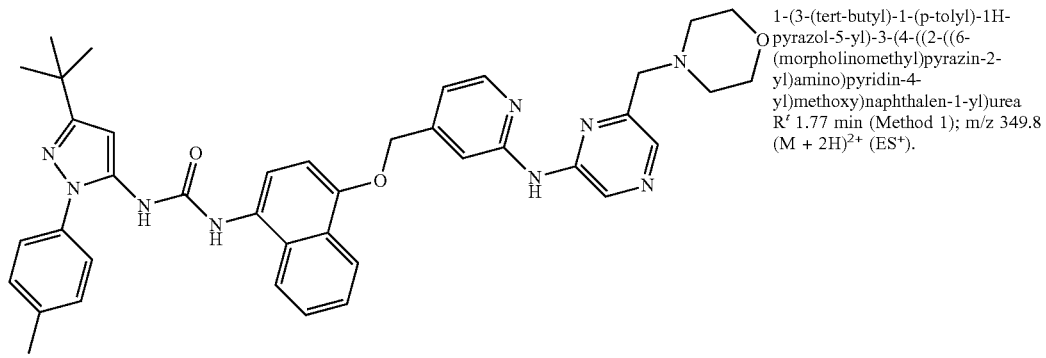

Route code*: 1

1-(3-(tert-butyl)-1-(p-tolyl)-1H-pyrazol-5-yl)-3-(4-((2-((6-(morpholinomethyl)pyrazin-2-yl)amino)pyridin-4-yl)methoxy)naphthalen-1-yl)urea
R$^t$ 1.77 min (Method 1); m/z 349.8 (M + 2H)$^{2+}$ (ES$^+$).

-continued

Example 286:

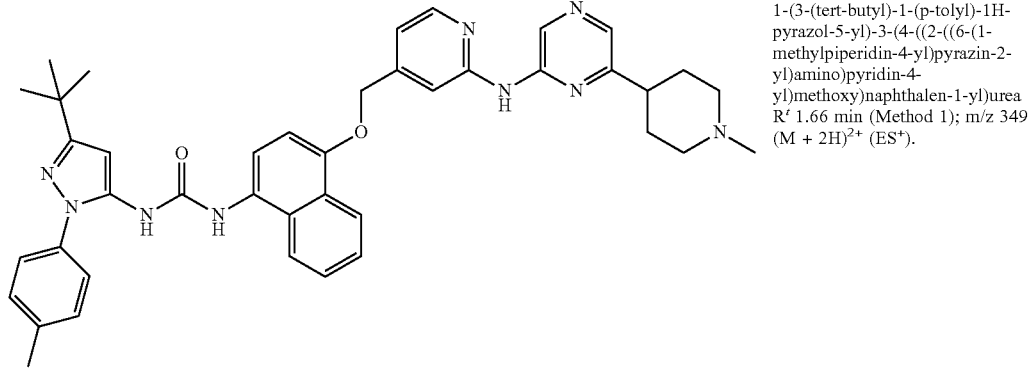

1-(3-(tert-butyl)-1-(p-tolyl)-1H-pyrazol-5-yl)-3-(4-((2-((6-(1-methylpiperidin-4-yl)pyrazin-2-yl)amino)pyridin-4-yl)methoxy)naphthalen-1-yl)urea
$R^t$ 1.66 min (Method 1); m/z 349 $(M + 2H)^{2+}$ (ES$^+$).

Route code*: 1

Example 287:

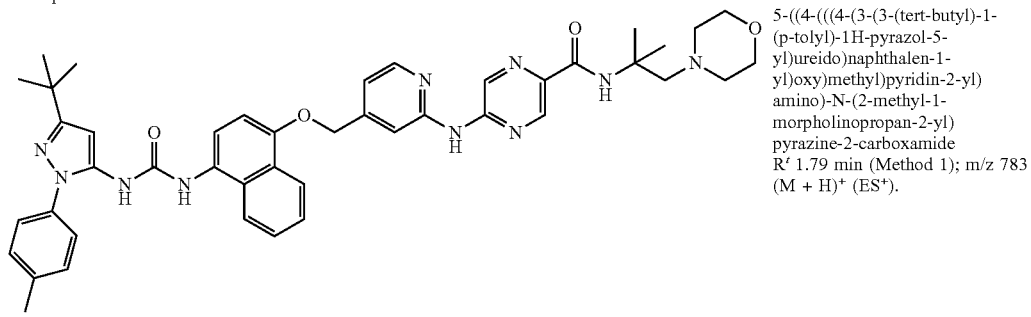

5-((4-(((4-(3-(3-(tert-butyl)-1-(p-tolyl)-1H-pyrazol-5-yl)ureido)naphthalen-1-yl)oxy)methyl)pyridin-2-yl)amino)-N-(2-methyl-1-morpholinopropan-2-yl)pyrazine-2-carboxamide
$R^t$ 1.79 min (Method 1); m/z 783 $(M + H)^+$ (ES$^+$).

Route code*: 6

Example 288:

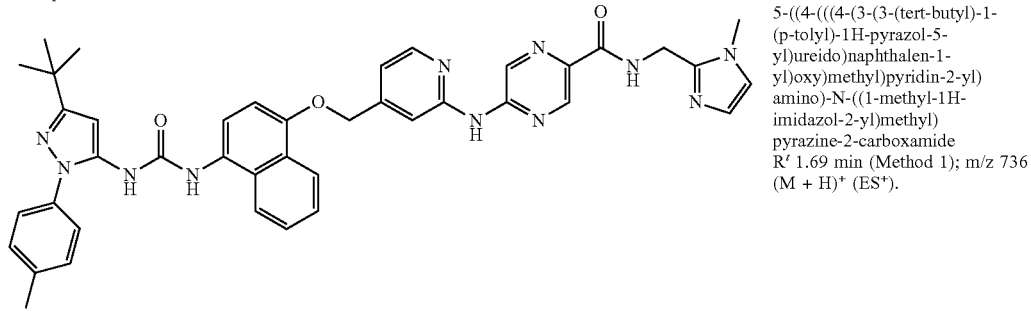

5-((4-(((4-(3-(3-(tert-butyl)-1-(p-tolyl)-1H-pyrazol-5-yl)ureido)naphthalen-1-yl)oxy)methyl)pyridin-2-yl)amino)-N-((1-methyl-1H-imidazol-2-yl)methyl)pyrazine-2-carboxamide
$R^t$ 1.69 min (Method 1); m/z 736 $(M + H)^+$ (ES$^+$).

Route code*: 6

*Route codes:
1-5 are the same as for Examples 10-52

5a: compound (I) prepared by reaction of compound (II) with compound (III); compound (III) prepared by deprotection of compound (IX); compound (IX) prepared from compound (IX"); compound (IX") prepared from the methyl ester derivative of compound (XIVb) by nitro reduction followed by Boc protection and ester hydrolysis; the alkyl ester derivative of compound (XIVb) prepared by reaction of compound (XI) with an analogue of a compound of formula (V) having $R^{2d}$ = CH$_2$COOMe.

6: compound (I) prepared by reaction of compound (II) with compound (III); compound (III) prepared by deprotection of compound (IX); compound (IX) prepared from compound (IX') (carboxylic acid) by amide formation; compound (IX') (carboxylic acid) prepared from compound (IX') (carboxylic acid ester) by hydrolysis; compound (IX') (carboxylic acid ester) prepared by reaction of compound (XVI) with compound (XIII') (carboxylic acid ester). This route is illustrated in the synthesis of Example 53.

7: compound (I) prepared by transformation of another compound of formula (I). This route is illustrated in the synthesis of Example 54.

8: compound (I) prepared by reaction of compound (IV) with compound (V). Compound (IV) prepared by reaction of compound (II) with compound (X). Compound (X) prepared by reduction of compound (XI). This route is illustrated in the synthesis of Example 55

Biological Examples

Experimental Methods for Biological Testing
Enzyme Inhibition Assays

The enzyme inhibitory activities of compounds disclosed herein were determined by FRET using synthetic peptides labelled with both donor and acceptor fluorophores (Z-LYTE, Life Technologies, Paisley, UK).

p38 MAPKα Enzyme Inhibition

The inhibitory activities of compounds of the invention against the p38 MAPKα isoform (MAPK14: Life Technologies), were evaluated indirectly by determining the level of activation/phosphorylation of the target peptide of the p38 MAPKα down-stream molecule, MAPKAP-K2. The enzyme (40 ng/mL, 2.5 μL) was incubated with the test compound (2.5 μL of either 40 μg/mL, 12 μg/mL, 4 μg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptides (8 µM, 2.5 µL) and the p38a inactive target MAPKAP-K2 (Life Technologies, 2000 ng/mL), and appropriate ATP solution (2.5 µL, 40 µM) were then added to the enzyme/compound mixture and incubated for 1 h at RT. Development reagent (protease, 5 µL) was added for 1 h prior to detection in a fluorescence microplate reader (EnVision, Perkin Elmer, Waltham, Mass., USA).

p38 MAPKγ Enzyme Inhibition

The inhibitory activities of compounds of the invention against p38MAPKγ (MAPK12: Life Technologies), were evaluated by determining the level of activation/phosphorylation of the target peptide. The enzyme (800 ng/mL, 2.5 µL) was incubated with the test compound (2.5 µL at either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptides (8 µM, 2.5 µL), and appropriate ATP solution (2.5 µL, 400 µM) were then added to the enzymes/compound mixtures and incubated for 1 h at RT. Development reagent (protease, 5 µL) was added for 1 h prior to detection in a fluorescence microplate reader (EnVision, Perkin Elmer).

Hck, c-Src and Syk Enzyme Inhibition

The inhibitory activities of compounds of the invention against Hck, c-Src and Syk enzymes (Life Technologies) were evaluated in a similar fashion to that described hereinabove. The relevant enzyme (1000 ng/mL, 1400 ng/mL or 2000 ng/mL respectively, 2.5 µL) was incubated with the test compound (either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL, 2.5 µL each) for 2 h at RT. The FRET peptides (8 µM, 2.5 µL), and appropriate ATP solutions (2.5 µL, 800 µM for c-Src, and 60 µM ATP for HCK and Syk) were then added to the enzyme/compound mixtures and incubated for 1 h at RT. Development reagent (protease, 5 µL) was added for 1 h prior to detection in a fluorescence microplate reader (EnVision, Perkin Elmer).

GSK 3α Enzyme Inhibition

The inhibitory activities compounds of the invention against the GSK 3α enzyme isoform (Life Technologies) were evaluated in a similar fashion to that described hereinabove. The GSK3α protein (500 ng/mL, 2.5 µL) was incubated with the test compound (2.5 µL at either 40 µg/mL, 12 µg/mL, 4 µg/mL, 1.2 µg/mL, 0.4 µg/mL, 0.12 µg/mL, 0.04 µg/mL, 0.012 µg/mL, 0.004 µg/mL or 0.0012 µg/mL) for 2 h at RT. The FRET peptide (8 µM, 2.5 µL), which is a phosphorylation target for GSK3α, and ATP (40 µM, 2.5 µL) was then added to the enzyme/compound mixture and the resulting mixture incubated for 1 h at RT. Development reagent (protease, 5 µL) was added for 1 h prior to detection in a fluorescence microplate reader (EnVision, Perkin Elmer).

In all cases, the site-specific protease cleaves non-phosphorylated peptide only and eliminates the FRET signal. Phosphorylation levels of each reaction were calculated using the ratio of coumarin emission (donor) over fluorescein emission (acceptor), for which low ratios indicate high phosphorylation and high ratios indicate low phosphorylation levels. The percentage inhibition of each reaction was calculated relative to non-inhibited control and the 50% inhibitory concentration ($IC_{50}$ value) was then calculated from the concentration-response curve.

Cellular Assays (Employed in the Examples)

The following cellular assays were employed to assess compounds of the present invention and the results are given infra.

LPS-Induced TNFα/IL-8 Release in d-U937 Cells

U937 cells, a human monocytic cell line, were differentiated into macrophage-type cells by incubation with PMA (100-200 ng/mL) for 48 to 72 h. Cells were pre-incubated with final concentrations of test compound for 2 h and were then stimulated with LPS (0.1 µg/mL; from E. Coli: O111: B4, Sigma) for 4 h. The supernatant was collected for determination of TNFα and IL-8 concentrations by sandwich ELISA (Duo-set, R&D systems). The inhibition of TNFα production was calculated as a percentage of that achieved by 10 µg/mL of BIRB-796 at each concentration of test compound by comparison against vehicle control. The relative 50% effective concentration ($REC_{50}$) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

Poly I:C-Induced ICAM-1 Expression in BEAS2B Cells

Poly I:C was used in these studies as a simple, RNA virus mimic. Poly I:C-Oligofectamine mixture (2% Oligofectamine±1 µg/mL Poly I:C, 25 µL; Life Technologies and Invivogen Ltd., San Diego, Calif., respectively) was transfected into BEAS2B cells (human bronchial epithelial cells, ATCC). Cells were pre-incubated with final concentrations of test compounds for 2 h and the level of ICAM-1 expression on the cell surface was determined by cell-based ELISA. At a time point 18 h after poly I:C transfection, cells were fixed with 4% formaldehyde in PBS (100 µL) and then endogenous peroxidase was quenched by the addition of washing buffer (100 µL, 0.05% Tween in PBS: PBS-Tween) containing 0.1% sodium azide and 1% hydrogen peroxide. Cells were washed with wash-buffer (3×200 µL). After blocking the wells with 5% milk in PBS-Tween (100 µL) for 1 h, the cells were incubated with anti-human ICAM-1 antibody (50 µL; Cell Signaling Technology, Danvers, Mass.) in 1% BSA PBS overnight at 4° C.

The cells were washed with PBS-Tween (3×200 µL) and incubated with the secondary antibody (100 µL; HRP-conjugated anti-rabbit IgG, Dako Ltd., Glostrup, Denmark). The cells were then incubated with of substrate (50 µL) for 2-20 min, followed by the addition of stop solution (50 µL, 1N $H_2SO_4$). The ICAM-1 signal was detected by reading the absorbance at 450 nm against a reference wavelength of 655 nm using a spectrophotometer. The cells were then washed with PBS-Tween (3×200 µL) and total cell numbers in each well were determined by reading absorbance at 595 nm after Crystal Violet staining (50 µL of a 2% solution in PBS) and elution by 1% SDS solution (100 µL) in PBS. The measured OD 450-655 readings were corrected for cell number by dividing with the OD595 reading in each well. The inhibition of ICAM-1 expression was calculated at each concentration of test compound by comparison with vehicle control. The 50% inhibitory concentration ($IC_{50}$) was determined from the resultant concentration-response curve.

Cell Mitosis Assay

Peripheral blood mononucleocytes (PBMCs) from healthy subjects were separated from whole blood (Quintiles, London, UK) using a density gradient (Histopaque®-1077, Sigma-Aldrich, Poole, UK). The PBMCs (3 million cells per sample) were subsequently treated with 2% PHA (Sigma-Aldrich, Poole, UK) for 48 h, followed by a 20 h exposure to varying concentrations of test compounds. At 2 h before collection, PBMCs were treated with demecolcine (0.1 µg/mL; Life Technologies, Paisley, UK,) to arrest cells in metaphase. To observe mitotic cells, PBMCs were permeabilised and fixed by adding Intraprep (50 µL; Beckman Coulter, France), and stained with anti-phospho-histone 3 (0.26 ng/L; #9701; Cell Signalling) and propidium iodide (1 mg/mL; Sigma-Aldrich as previously described (Muehlbauer P. A. and Schuler M. J., *Mutation Research*, 2003, 537:117-130). Fluorescence was observed using an ATTUNE flow cytometer (Life Technologies), gating for lymphocytes. The percentage inhibition of mitosis was calculated for each treatment relative to vehicle (0.5% DMSO) treatment.

The Effect of Test Compounds on Cell Viability: MTT Assay

Differentiated U937 cells were pre-incubated with each test compound (final concentration 10 μg/mL in 200 μL media indicated below) under two protocols: the first for 4 h in 5% FCS RPMI1640 media and the second in 10% FCS RPMI1640 media for 24 h. The supernatant was replaced with new media (200 μL) and MTT stock solution (10 μL, 5 mg/mL) was added to each well. After incubation for 1 h the media were removed, DMSO (200 μL) was added to each well and the plates were shaken lightly for 1 h prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

Cytokine Production in LPS-Treated Sputum Macrophages from COPD Patients

Patients with COPD inhaled a nebulised solution of 3% (w/v) hypertonic saline using an ultrasonic nebuliser (Devilbiss, Carthage, Mo.) with tidal breathing for 5 min. This procedure was repeated a maximum of three times until enough sputum was obtained. The sputum samples were homogenized and mixed vigorously using a vortex mixer in 0.02% v/v dithiothreitol (DTT) solution. The samples were re-suspended in PBS (40 mL) followed by centrifugation at 1500 rpm at 4° C. for 10 min to obtain sputum cell pellets. The pellets were washed with PBS (40 mL). The sputum cells were then re-suspended in 4 mL macrophage serum-free medium (macrophage-SFM, Life technologies, containing 20 U/mL penicillin, 0.02 mg/mL streptomycin and 5 μg/mL amphotericin B) and seeded on high bound 96-well plate, followed by incubation for 1 h at 37° C. and at 5% $CO_2$ to allow the macrophages to attach to the bottom of the plate. The cells on the plate were washed with fresh macrophage-SFM (200 μL/well) to remove neutrophils and other contaminated cells. The adherent cells (mainly sputum macrophages) on the plate were used for further analysis. Sputum inductions were conducted in Quintiles Drug Research Unit at Guys Hospital and ethics approval and written informed consent was obtained by Quintiles.

Where appropriate, 1 μL of a solution containing either the test compound or reference article at the stated concentrations (either 0.1 μg/mL, 0.01 μg/mL, or 0.001 μg/mL) or alternatively 1 μL of DMSO as the vehicle control was added to each well (200 μL in media) and the cells were incubated for 2 h. The cells were stimulated with LPS solution (50 μL, final concentration: 1 μg/mL) and incubated for 18 h at 37° C. and 5% $CO_2$. The supernatant was then collected and kept at −80° C. Suitable luminex kits were used to measure the selected analytes. After thawing the supernatant, the magnetic antibody beads were multiplexed and incubated in a 96-well plate with standard, background solution or the appropriate volume of sample overnight with shaking at 4° C. After washing twice with 200 μL of wash buffer provided by the kit per well using a magnetic plate washer, the beads were incubated for 1 h at RT with the biotin conjugated antibody solution provided by the kit with shaking. Streptavidin solution was added for 30 min with shaking at RT. After washing with 200 μL wash buffer per well, the beads were resuspended in sheath fluid (150 μL) and analyzed immediately. The level of each analyte in the supernatant was calculated using XceI Fit software with a 4 or 5-parameter equation using each standard curve. The inhibitions of each cytokine production were calculated at each concentration by comparison with vehicle control.

Rhinovirus-Induced IL-8 Release

Human rhinovirus RV16 is obtained from the American Type Culture Collection (Manassas, Va.). Viral stocks are generated by infecting MRC5 cells with HRV until 80% of the cells were cytopathic.

BEAS2B cells are infected with HRV at an MOI of 1.2 and incubated for 1 h at 33° C. with gentle shaking to promote absorption. The cells are then washed with PBS, fresh media added and the cells are incubated for a further 72 h. The supernatant is collected for assay of IL-8 concentrations using a Duoset ELISA development kit (R&D systems, Minneapolis, Minn.). Compounds are added 2 h before HRV infection and 1 h after infection when non-infected HRV is washed out.

Cellular Assays (not Employed in the Examples)

The following cellular assays could be employed to assess compounds of the present invention:

Rhinovirus-Induced IL-8 Release (Variation on the Above Method) and ICAM-1 Expression Human rhinovirus RV16 is obtained from the American Type Culture Collection (Manassas, Va.). Viral stocks are generated by infecting Hela cells with HRV until 80% of the cells were cytopathic.

BEAS2B cells are infected with HRV at an MOI of 5 and incubated for 1 to 2 h at 33° C. with gentle shaking to promote absorption. The cells are then washed with PBS, fresh media added and the cells are incubated for a further 72 h. The supernatant is collected for assay of IL-8 concentrations using a Duoset ELISA development kit (R&D systems, Minneapolis, Minn.).

The level of cell surface ICAM-1 expression is determined by cell-based ELISA. At 72 h after infection, cells were fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 h, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well were determined by reading absorbance at 595 nm after Crystal Violet staining and elution by 1% SDS solution. The measured $OD_{450-655}$ readings are corrected for cell number by dividing with the $OD_{595}$ reading in each well. Compounds are added 2 h before HRV infection and 1 to 2 h after infection when non-infected HRV is washed out.

LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 h before addition of 1 ng/mL LPS (*Escherichia Coli* 0111:B4 from Sigma Aldrich) for 24 h under normal tissue culture conditions (37° C., 5% $CO_2$). The supernatant is harvested for determination of and TNFα concentrations by sandwich ELISA (Duo-set, R&D systems) and read on the fluorescence microplate reader (Varioskan® Flash, ThermoFisher Scientific). The concentration at 50% inhibition ($IC_{50}$) of IL-8 and TNFα production is calculated from the dose response curve.

IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 µg/mL eBioscience and 3 µg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

IL-1β-Induced IL-8 Release in HT29 Cells

HT29 cells, a human colon adenocarcinoma cell line, are plated in a 96 well plate (24 h) and pre-treated with compounds at the desired concentration for 2 h before addition of 5 ng/mL of IL-1β (Abcam) for 24 h. Supernatants are harvested for IL-8 quantification by Sandwich ELISA (Duo-set, R&D System). The $IC_{50}$ is determined from the dose response curve.

T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2 \times 10^5$ cells per well in 100 µL RPMI/10% FBS on 96 well flat bottomed plate (Corning Costar). 25 µL of test compound are diluted to the appropriate concentration (8× final conc.) in normal medium and added to duplicate wells on the plate to achieve a dose response range of 0.03 ng/mL-250 ng/mL. DMSO is added as a negative control. Plates are allowed to pre-incubate for 2 h before stimulation with 1 µg/mL anti-CD3 (OKT3; eBioscience). After 72 h, the medium in each well is replaced with 150 µL of fresh medium containing 10 µM BrdU (Roche). After 16 h, the supernatant is removed, the plate is dried and the cells fixed by adding 100 µL of fix/denature solution to each well for 20 min as per the manufacturer's instructions (Roche). Plates are washed once with PBS before addition of the anti-BrdU detection antibody and incubated for 90 min at room temperature. Plates are then washed gently 3× with the wash buffer supplied and developed by addition of 100 µL of substrate solution. The reaction is stopped by addition of 50 µL of 1 M $H_2SO_4$, and read for absorbance at 450 nm on a plate reader (Varioskan® Flash, ThermoFisher Scientific). The $IC_{50}$ is determined from the dose response curve.

Human Biopsy Assay

Intestinal mucosa biopsies are obtained from the inflamed regions of the colon of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 h in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows:

The mucosa is removed from the deeper layers of the surgical specimens with a scalpel and cut in fragments 3-4 mm size. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 µm cell strainer, washed twice, resuspended in RPMI-1640 medium (Sigma-Aldrich) containing 10% fetal calf serum, 100 U/mL penicillin and 100 µg/mL streptomycin, and used for cell culture.

Freshly isolated LPMCs ($2 \times 10^5$ cells/well) are stimulated with 1 µg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

Inhibition of Cytokine Release from Myofibroblasts Isolated from IBD Patients

Myofibroblasts from inflamed IBD mucosa are isolated as follows:

The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 µg/mL streptomycin, 50 µg/mL gentamycin, and 1 µg/mL amphotericin (Sigma-Aldrich). Established colonies of myofibroblasts are seeded into 25-cm² culture flasks and cultured in DMEM supplemented with 20% FBS and antibiotics to at least passage 4 to provide a sufficient quantity for use in stimulation experiments.

Subconfluent monolayers of myofibroblasts are then seeded in 12-well plates at $3 \times 10^5$ cells per well are starved in serum-free medium for 24 h at 37 CC, 5% $CO_2$ before being cultured for 24 h in the presence of either DMSO control or appropriate concentrations of compound. After 24 h the supernatant is removed and assayed for the presence of IL-8 and IL-6 by R&D ELISA. Percentage inhibition of cytokine release by the test compounds is calculated relative to the cytokine release determined for the DMSO control (100%).

Human Neutrophil Degranulation

Neutrophils are isolated from human peripheral blood as follows:

Blood is collected by venepuncture and anti-coagulated by addition of 1:1 EDTA: sterile phosphate buffered saline (PBS, no Ca+/Mg+). Dextran (3% w/v) is added (1 part dextran solution to 4 parts blood) and the blood allowed to stand for approximately 20 min at RT. The supernatant is carefully layered on a density gradient (Lymphoprep, Axis-Shield Healthcare) and centrifuged (15 min, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 min, 1200 rpm). Cells are re-suspended in HBSS+(Hank's balanced salt solution (without phenol red) containing cytochalasin B (5 μg/mL) and 1 mM $CaCl_2$) to achieve $5\times10^6$ cells/mL.

$5\times10^4$ cells are added to each well of a V-bottom 96 well plate and incubated (30 min, 37° C.) with the appropriate concentration of test compound (0.3-1000 ng/mL) or vehicle (DMSO, 0.5% final conc). Degranulation is stimulated by addition of fMLP (final conc 1 μM) which after a further incubation (30 min, 37° C.) the cells are removed by centrifugation (5 min, 1500 rpm) and the supernatants transferred to a flat bottom 96 well plate. An equal volume of tetramethylbenzidine (TMB) is added and after 10 min the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

Cell Cytotoxicity Assay $5\times10^4$ TK6 cells (lymphoblastic T cell line) are added to the appropriate number of wells of a 96 well plate in 195 μL of media (RPMI supplemented with 10% foetal bovine serum). 5 μL of DMSO control (final concentration 0.5% v/v) or test compound (final concentration either 5 or 1 μg/mL) is added to the wells and incubated at 37° C., 5% $CO_2$. After 24 h, the plate is centrifuged at 1300 rpm for 3 min and the supernatant discarded. Cells are then resuspended in 7.5 μg/mL propidium iodide (PI) in PBS. After 15 min, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (Employed in the Examples)

The following in vivo screens were employed to assess compounds of the present invention and the results are given infra.

LPS-Induced Neutrophil Accumulation in Mice

Non-fasted Balb/c mice were dosed by the intra tracheal route with either vehicle, or the test substance at the indicated times (within the range 2-8 h) before stimulation of the inflammatory response by application of an LPS challenge. At T=0, mice were placed into an exposure chamber and exposed to LPS (7.0 mL, 0.5 mg/mL solution in PBS for 30 min).

After a further 8 h the animals were anesthetized, their tracheas cannulated and BALF extracted by infusing and then withdrawing from their lungs 1.0 mL of PBS via the tracheal catheter. Total and differential white cell counts in the BALF samples were measured using a Neubaur haemocytometer. Cytospin smears of the BALF samples were prepared by centrifugation at 200 rpm for 5 min at RT and stained using a DiffQuik stain system (Dade Behring). Cells were counted using oil immersion microscopy. Data for neutrophil numbers in BAL are shown as mean±S.E.M. (standard error of the mean). The percentage inhibition of neutrophil accumulation was calculated for each treatment relative to vehicle treatment.

Cigarette Smoke Model

A/J mice (males, 5 weeks old) were exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances were administered intra-nasally (35 μL of solution in 10% DMSO/PBS) once daily for 3 days after the final cigarette smoke exposure. At 12 h after the last dosing, each of the animals was anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil). BALF was centrifuged and the supernatant was collected. The level of keratinocyte chemoattractant (KC; CXCL1) in BALF was quantitated using a Quantikine® mouse KC ELISA kit (R&D systems, Inc., Minneapolis, Minn., USA).

In Vivo Screening: Pharmacodynamics and Anti-Inflammatory Activity (not Employed in the Examples)

The following in vivo screens could be employed to assess compounds of the present invention:

DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with DSS. On Day 0 of the study DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study animals are weighed every day and stool observations are made and recorded as a score, based on stool consistency. At the time of sacrifice on Day +6 the large intestine is removed and the length and weight are recorded. Sections of the colon are taken for either MPO analysis to determine neutrophil infiltration or for histopathology scoring to determine disease severity.

TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1, 5 or 50 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter followed by BID dosing of the vehicle, reference or test compound for 2 or 4 days. During the study animals are weighed every day and stool observations are made and recorded as a score, based on stool consistency. At the time of sacrifice on Day 2 (or Day 4) the large intestine is removed and the length and weight recorded. Sections of the colon are taken for either MPO analysis to determine neutrophil infiltration or for histopathology involving scoring to determine disease severity.

Adoptive Transfer in Mice

On study Day 0, female Balb/C mice are terminated and spleens obtained for $CD45RB^{high}$ cell isolation (Using SCID IBD cell Separation protocol). Approximately $4\times10^5$ cells/mL $CD45RB^{high}$ cells are then injected IP (100 μL/mouse) into female SCID animals. On study Day 14, mice are weighed and randomized into treatment groups based on body weight. On Day 21, compounds are administered BID, via oral gavage, in a peanut oil vehicle at the dose levels outlined below and a dose volume of 5 mL/kg. Treatment continues until study Day 42, at which point the animals are necropsied 4 h after am administration. The colon length and weight is recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between naïve animals and vehicle animals, where higher inhibition implies closer to the non-diseased, naïve, phenotype.

In Vitro and In Vivo Screening Results

In vitro screening results for the examples are set out in Table 2A, Table 2B, Table 3, Table 4, Table 5A, Table 5B, Table 6A and Table 6B below and FIG. 1. In FIG. 1 the compound of the invention is Example 2. Comparison is made with a structurally related Reference Compound N-(4-(4-(3-(3-tert-butyl-1-p-tolyl-1H-pyrazol-5-yl)ureido)naphthalen-1-yloxy)pyridin-2-yl)-2-methoxyacetamide (Example 1 of WO2010/112936), which has been previously described as a potent anti-inflammatory agent with anti-viral effects, as well as with fluticasone propionate which is a well known anti-inflammatory agent.

TABLE 2A p38 MAPKα and γ, HCK, c-Src, Syk and GSK3α Enzyme Profile of Examples

| Example no. | IC$_{50}$ Values for Enzyme Inhibition (nM) | | | | | |
|---|---|---|---|---|---|---|
| | p38 MAPKα | p38 MAPKγ | HCK | c-Src | Syk | GSK3α |
| Reference Compound | 10 | 87 | 7 | 11 | 42 | 18 |
| 1 | 25 | 67 | 29 | 98 | >16703 | >16703 |
| 2 | 26 | 152 | 55 | 199 | >15955 | >15105 |
| 3 | 9 | 222 | 66 | 144 | >14289 | >14289 |
| 4 | 22 | 441 | 111 | 447 | >15955 | >4957 |
| 5 | <0.48 | 16 | <0.48 | <0.48 | >15930 | 2770 |
| 6 | 3 | 37 | 10 | 24 | 7522 | 922 |
| 7 | 15 | 151 | 64 | 358 | >15249 | >15249 |
| 8 | 1 | 43 | 10 | 32 | >14624 | 138 |
| 9 | 134 | 9242 | 1500 | 2514 | >14931 | 3322 |
| 10 | 8 | 31 | 16 | 47 | >15905 | >15905 |
| 11 | 52 | 682 | >8886 | 600 | >16033 | >16033 |
| 12 | 14 | 198 | 39 | 105 | >16242 | >16242 |
| 13 | 9 | 63 | 49 | 129 | >16536 | >14661 |
| 14 | 12 | 237 | 6 | 29 | >15582 | 3367 |
| 15 | 96 | 160 | 15 | 34 | >15655 | 3651 |
| 16 | 87 | >7150 | 355 | 2520 | >15655 | >15655 |
| 17 | 8 | 74 | 17 | 34 | >13247 | 2818 |
| 18 | 13 | 104 | 41 | 196 | >15905 | 9168 |
| 19 | 13 | 229 | 53 | 151 | >16320 | >16320 |
| 20 | 15 | 62 | 52 | 150 | >16320 | 9043 |
| 21 | 5 | 31 | 12 | 33 | >15905 | 1583 |
| 22 | 22 | 377 | 14 | 27 | 6698 | 1711 |
| 23 | 4 | 209 | 13 | 33 | 2153 | 626 |
| 24 | 38 | 334 | 18 | 42 | 8826 | 1129 |
| 25 | 7 | 49 | 5 | 10 | 2220 | 523 |
| 26 | 7 | 74 | 20 | 56 | 1584 | 469 |
| 27 | 17 | 376 | 13 | 42 | 9160 | 1029 |
| 28 | 5 | 106 | 11 | 32 | >14931 | 5169 |
| 29 | 5 | 80 | 10 | 28 | >14624 | 207 |
| 30 | 2 | 29 | 6 | 19 | >15250 | 1488 |
| 31 | 4 | 112 | 59 | 154 | >16536 | 11319 |
| 32 | 3 | 37 | 7 | 25 | >15250 | 1324 |
| 33 | 3 | 53 | 11 | 35 | >14931 | 5963 |
| 34 | 13 | 274 | 7 | 18 | 4262 | 1198 |
| 35 | 9 | 171 | 42 | 51 | >14048 | 3430 |
| 36 | 19 | 1074 | 48 | 61 | >14371 | >13810 |
| 37 | 24 | 569 | 142 | 512 | >15955 | >10010 |
| 38 | 14 | >16268 | 60 | 153 | >16268 | 5994 |
| 39 | 18 | 310 | 31 | 82 | >15905 | >15905 |
| 40 | 11 | 79 | 23 | 85 | >16703 | 8776 |
| 41 | 189 | >15955 | 1428 | 10986 | 6131 | 3572 |
| 42 | 15 | 521 | 89 | 543 | >16320 | 6942 |
| 43 | 12 | 394 | 53 | 73 | >14167 | 7918 |
| 44 | 11 | 454 | 58 | 233 | >14167 | >14167 |
| 45 | 120 | >16152 | 2244 | 7894 | >16152 | 1898 |
| 46 | 85 | 1947 | 68 | 385 | 6703 | 7052 |
| 47 | 87 | 473 | 110 | 402 | 4152 | 2800 |
| 48 | 91 | 1233 | 133 | 459 | >14996 | 4213 |
| 49 | 11 | 129 | 115 | 556 | 9251 | 4478 |
| 50 | 22 | 356 | 113 | 966 | 5816 | 7079 |
| 51 | 14 | 171 | 36 | 160 | >16320 | >16320 |
| 52 | 116 | >14999 | 316 | >14999 | >14999 | >14999 |

TABLE 2B p38 MAPKα and γ Enzyme Profile of Examples

| Example no. | p38 MAPKα | p38 MAPKγ |
|---|---|---|
| Reference Compound | 10 | 87 |
| 53 | 17 | 95 |
| 54 | NT | 150 |
| 55 | 15 | 151 |
| 56 | 21 | 262 |
| 57 | 15 | 229 |
| 58 | 18 | 435 |
| 59 | 18 | 105 |
| 60 | 14 | 144 |
| 61 | 5.6 | 32 |
| 62 | 24 | 560 |
| 63 | 25 | 312 |
| 64 | 9.7 | 39 |
| 65 | 23 | 3116 |
| 66 | 28 | 319 |
| 67 | 39 | 345 |
| 68 | 132 | 624 |
| 69 | 8.0 | 106 |
| 70 | 70 | 372 |
| 71 | 24 | 272 |
| 72 | 11 | 118 |
| 73 | 19 | 259 |
| 74 | 43 | 482 |
| 75 | 17 | 179 |
| 76 | 15 | 148 |
| 77 | NT | 106 |
| 78 | 21 | 422 |
| 79 | <0.40 | 101 |
| 80 | <0.41 | 54 |
| 81 | NT | 16 |
| 82 | NT | 46 |
| 83 | NT | 39 |
| 84 | NT | 67 |
| 85 | NT | 166 |
| 86 | NT | 19 |
| 87 | NT | 63 |
| 88 | NT | 233 |
| 89 | NT | 42 |
| 90 | NT | 83 |
| 91 | NT | 176 |
| 92 | NT | 117 |
| 93 | NT | 103 |
| 94 | NT | 772 |
| 95 | NT | 55 |
| 96 | NT | 269 |
| 97 | NT | 34 |
| 98 | NT | 116 |
| 99 | NT | 11 |
| 100 | NT | 202 |
| 101 | NT | 374 |
| 102 | NT | 46 |
| 103 | NT | 72 |
| 104 | 8.9 | 223 |
| 105 | <1.59 | 4558 |
| 106 | 3.4 | 401 |

TABLE 2B-continued p38 MAPKα and γ Enzyme Profile of Examples

| Example no. | p38 MAPKα Reference Compound 10 | p38 MAPKγ Reference Compound 87 |
|---|---|---|
| 107 | 27 | 5735 |
| 108 | 17 | 15510 |
| 109 | 115 | 1330 |
| 110 | 1.6 | 23 |
| 111 | 33 | 125 |
| 112 | 43 | 277 |
| 113 | 37 | 3203 |
| 114 | 2.0 | 26 |
| 115 | 7.5 | 725 |
| 116 | 23 | 2818 |
| 117 | 16 | 150 |
| 118 | 5.5 | 115 |
| 119 | 13 | 175 |
| 120 | 4.8 | 173 |
| 121 | 38 | 79 |
| 122 | 2779 | 8740 |
| 123 | 60 | 171 |
| 124 | 288 | >13736 |
| 125 | 302 | >13477 |
| 126 | 47 | 187 |
| 127 | 6.8 | 93 |
| 128 | 55 | >14663 |
| 129 | 40 | >15601 |
| 130 | 31 | 2795 |
| 131 | 14 | >15949 |
| 132 | 11 | >13699 |
| 133 | 7.3 | 10245 |
| 134 | 3.8 | 35 |
| 135 | 52 | >15244 |
| 136 | <0.41 | 41 |
| 137 | 6.0 | >14085 |
| 138 | 29 | >15337 |
| 139 | 53 | 1108 |
| 140 | 29 | >15244 |
| 141 | 18 | 438 |
| 142 | 5.7 | 78 |
| 143 | 19 | 211 |
| 144 | 63 | 518 |
| 145 | 43 | 260 |
| 146 | 69 | 1550 |
| 147 | 4.1 | 119 |
| 148 | 13 | 247 |
| 149 | 13 | >15873 |
| 150 | 25 | 229 |
| 151 | 35 | 439 |
| 152 | 14 | 240 |
| 153 | 20 | 77 |
| 154 | 10 | 49 |
| 155 | 8.9 | 31 |
| 156 | 21 | 495 |
| 157 | 23 | >14881 |
| 158 | 435 | >14993 |
| 159 | 36 | 427 |
| 160 | 34 | 510 |
| 161 | 10 | 74 |
| 162 | 4.7 | 37 |
| 163 | 19 | 389 |
| 164 | 6.8 | 2344 |
| 165 | 12 | 128 |
| 166 | 6.2 | 52 |
| 167 | 25 | 259 |
| 168 | 34 | 1200 |
| 169 | 26 | 449 |
| 170 | 35 | 329 |
| 171 | 12 | 49 |
| 172 | 31 | 169 |
| 173 | 54 | 571 |
| 174 | 7.7 | 56 |
| 175 | 38 | >15456 |
| 176 | 36 | 458 |
| 177 | 5.2 | 81 |
| 178 | 5.8 | 36 |
| 179 | 46 | >15456 |
| 180 | 19 | 112 |
| 181 | 15 | 64 |
| 182 | 44 | 1137 |
| 183 | 38 | >15480 |
| 184 | 19 | >15898 |
| 185 | 110 | 2507 |
| 186 | 25 | >14006 |
| 187 | 16 | 180 |
| 188 | 32 | 442 |
| 189 | 72 | 579 |
| 190 | 23 | 232 |
| 191 | 47 | 460 |
| 192 | 46 | >14620 |
| 193 | 89 | >14286 |
| 194 | 207 | 8407 |
| 195 | 15 | 245 |
| 196 | 29 | 219 |
| 197 | 37 | >15576 |
| 198 | 10 | 111 |
| 199 | 11 | >13774 |
| 200 | 13 | 1243 |
| 201 | 112 | 7901 |
| 202 | 19 | 1127 |
| 203 | 17 | 250 |
| 204 | 16 | 330 |
| 205 | 13 | 263 |
| 206 | 22 | 517 |
| 207 | 30 | 2389 |
| 208 | 50 | >15244 |
| 209 | 6.5 | 54 |
| 210 | 28 | 509 |
| 211 | 60 | 582 |
| 212 | 89 | >15625 |
| 213 | 36 | 735 |
| 214 | 31 | 1931 |
| 215 | 15 | >14306 |
| 216 | 15 | 401 |
| 217 | 17 | 424 |
| 218 | 28 | >14085 |
| 219 | 18 | >14025 |
| 220 | 31 | 164 |
| 221 | 81 | 1267 |
| 222 | 23 | 175 |
| 223 | 11 | 103 |
| 224 | 54 | >14045 |
| 225 | 14 | 342 |
| 226 | 35 | >13774 |
| 227 | 43 | >13774 |
| 228 | 35 | >13717 |
| 229 | 27 | >14104 |
| 230 | 43 | >14104 |
| 231 | 15 | 95 |
| 232 | 18 | 117 |
| 233 | 9.4 | 98 |
| 234 | 64 | >15625 |
| 235 | 65 | >14006 |
| 236 | 42 | >14006 |
| 237 | 8.4 | 29 |
| 238 | 19 | 151 |
| 239 | 14 | 130 |
| 240 | 12 | 80 |
| 241 | 3.4 | 48 |
| 242 | 19 | >14025 |
| 243 | 8.5 | 96 |
| 244 | 3.0 | 46 |
| 245 | 18 | 1704 |
| 246 | 58 | 3729 |
| 247 | 7.0 | 61 |
| 248 | 4.7 | 51 |

TABLE 2B-continued p38 MAPKα and γ Enzyme Profile of Examples

| Example no. | p38 MAPKα Reference Compound 10 | p38 MAPKγ Reference Compound 87 |
|---|---|---|
| 249 | 3.6 | 46 |
| 250 | 11 | >13699 |
| 251 | 81 | >15625 |
| 252 | NT | >15129 |
| 253 | NT | 75 |
| 254 | NT | 1935 |
| 255 | NT | >15504 |
| 256 | NT | >15408 |
| 257 | 12 | 68 |
| 258 | 2.4 | 77 |
| 259 | 1.2 | 146 |
| 260 | <0.39 | 47 |
| 261 | <0.47 | 146 |
| 262 | 11 | 174 |
| 263 | 21 | 218 |
| 264 | 23 | 109 |
| 265 | 11 | 57 |
| 266 | <0.39 | 51 |
| 267 | <0.47 | 2036 |
| 268 | <0.42 | 74 |
| 269 | <0.40 | 138 |
| 270 | 4.5 | 66 |
| 271 | NT | 108 |
| 272 | NT | 4.0 |
| 273 | NT | 4.7 |
| 274 | NT | 13 |
| 275 | NT | 129 |
| 276 | NT | 8.4 |
| 277 | NT | 31 |
| 278 | NT | 197 |
| 279 | NT | 116 |
| 280 | NT | 31 |
| 281 | NT | 289 |
| 282 | NT | 62 |
| 283 | NT | 35 |
| 284 | NT | 1.7 |
| 285 | NT | 83 |
| 286 | NT | 5.8 |
| 287 | NT | >12771 |
| 288 | NT | >13587 |

NT = not tested

TABLE 3

Inhibition of LPS Induced TNFα and IL-8 Release and PolyIC Induced ICAM-Expression for Examples

| Example no. | IL-8 IC$_{50}$ (dU937) | TNFα REC$_{50}$ (dU937) | PolyIC/ICAM1 (nM) IC$_{50}$ (BEAS2B) |
|---|---|---|---|
| Reference Compound | 1.2 | 0.7 | 3.8 |
| 1 | 13.0 | 1.6 | 81.8 |
| 2 | 11.4 | 5.5 | 61.1 |
| 3 | 8.8 | 5.5 | 460.3 |
| 4 | 25.4 | 25.6 | >1596 |
| 5 | 2.4 | 2.8 | 473.5 |
| 6 | 90.7 | 8.5 | 52.4 |
| 7 | 16.7 | 10.7 | >1525 |
| 8 | 10.3 | 3.9 | 31.5 |
| 9 | 8.8 | 1.3 | 72.5 |
| 10 | 15.3 | 2.8 | 32.5 |
| 11 | 12.5 | 2.3 | >1603 |
| 12 | 9.3 | 16.8 | 241.9 |
| 13 | 7.8 | 18.2 | 556.1 |
| 14 | 5.5 | 2.9 | 64.3 |
| 15 | 1.9 | 2.1 | 15.7 |
| 16 | 89.6 | 144.0 | >1565 |
| 17 | 16.5 | 12.7 | 433.2 |
| 18 | 2.1 | 2.6 | 97.8 |
| 19 | 1.4 | 13.2 | 339.5 |
| 20 | 1.3 | 1.3 | 151.9 |
| 21 | 7.9 | 0.6 | 76.5 |
| 22 | 1.6 | 2.1 | 19.6 |
| 23 | 6.2 | 3.1 | 33.5 |
| 24 | 4.5 | 3.1 | 55.1 |
| 25 | 5.8 | 1.4 | 13.1 |
| 26 | 14.6 | 4.5 | 972.9 |
| 27 | 4.0 | 4.3 | 71.2 |
| 28 | 29.9 | 2.7 | 75.5 |
| 29 | 8.5 | 4.2 | 43.0 |
| 30 | 6.9 | 5.2 | 114.7 |
| 31 | 33.4 | 1.0 | 874.3 |
| 32 | 15.0 | 13.0 | 65.6 |
| 33 | 42.4 | 2.6 | 150.4 |
| 34 | 8.3 | 5.4 | 41.1 |
| 35 | 102.2 | 12.1 | 113.4 |
| 36 | 2.8 | 1.6 | 187.8 |
| 37 | 19.3 | 14.3 | 611.2 |
| 38 | 9.6 | 2.7 | 75.5 |
| 39 | 12.8 | 3.4 | 46.6 |
| 40 | 11.7 | 3.0 | 636.8 |
| 41 | 43.8 | 3.0 | >1596 |
| 42 | 18.3 | 4.3 | 197.3 |
| 43 | 41.4 | 16.8 | >1417 |
| 44 | 52.2 | 88.2 | 1154.5 |
| 45 | 17.1 | 3.5 | 1437.1 |
| 46 | 268.2 | 0.7 | 211.7 |
| 47 | 15.6 | 5.8 | 151.3 |
| 48 | 16.7 | 0.3 | 92.5 |
| 49 | 24.3 | 2.3 | 474.5 |
| 50 | 30.3 | 7.1 | >1615 |
| 51 | 25.7 | 2.2 | 280.6 |
| 52 | >1500 | 18.7 | >1500 |

NT = not tested

TABLE 4

Effect of examples on Cell Viability

| Example no. | MTT Assay[1] Cell viability at time point indicated in d-U937 Cells 4 h | 24 h |
|---|---|---|
| Reference Compound | − | + |
| 1 | − | − |
| 2 | − | − |
| 3 | − | − |
| 4 | − | − |
| 5 | − | + |
| 6 | − | − |
| 7 | + | + |
| 8 | − | + |
| 9 | − | − |
| 10 | − | − |
| 11 | − | − |
| 12 | − | − |
| 13 | − | − |

TABLE 4-continued

Effect of examples on Cell Viability

| | MTT Assay[1] Cell viability at time point indicated in d-U937 Cells | |
|---|---|---|
| Example no. | 4 h | 24 h |
| 14 | − | − |
| 15 | − | − |
| 16 | − | − |
| 17 | − | − |
| 18 | − | + |
| 19 | − | − |
| 20 | − | − |
| 21 | − | − |
| 22 | − | − |
| 23 | − | + |
| 24 | − | − |
| 25 | − | + |
| 26 | − | + |
| 27 | − | + |
| 28 | − | + |
| 29 | − | + |
| 30 | − | − |
| 31 | − | − |
| 32 | − | − |
| 33 | − | − |
| 34 | − | − |
| 35 | − | − |
| 36 | − | − |
| 37 | − | − |
| 38 | − | − |
| 39 | − | − |
| 40 | − | − |
| 41 | − | − |
| 42 | − | − |
| 43 | − | − |
| 44 | − | + |
| 45 | − | − |
| 46 | − | − |
| 47 | − | − |
| 48 | − | − |
| 49 | − | − |
| 50 | − | − |
| 51 | − | − |
| 52 | − | − |

[1]Cell viability screen: −ve and +ve indicate the value is below and above, respectively, the no significant effect threshold defined as 30% inhibition at 10 μg/mL at the time point indicated.

TABLE 5A

Effect of Example 1 on Cell Division

| Test Substance | Mitosis Assay % Inhibition at 5 μg/mL in PBMC Cells |
|---|---|
| Example 1 | 29.9 |
| Reference Compound | 87.9 |

TABLE 5B

Effect of Example 2 on Cell Division

| Test Substance | Mitosis Assay % Inhibition at 5 μg/mL in PBMC Cells[1] |
|---|---|
| Example 2 | 18 ± 7 |
| Reference Compound | 93 ± 5 |

[1]Mean ± SEM

TABLE 6A

Effect of Example 1 and fluticasone propionate on cytokine production in LPS-treated sputum macrophages from COPD patients

| | | IC$_{50}$ values (nM) and/or E max (% in parentheses)[1] for Test Substance Indicated | |
|---|---|---|---|
| Cells Type | Cytokine | Example 1 | Fluticasone Propionate |
| Sputum Macrophage | IL-6 | 28 (60%) | ND (42%) |

[1]E-max values (maximum inhibition) were calculated as the % inhibition obtained at 0.1 μg/mL. ND = not determined (single dose tested)

TABLE 6B

Effect of Example 2 and fluticasone propionate on cytokine production in LPS- treated sputum macrophages from COPD patients

| Test Compound | Percent Inhibition at 0.1 μg/mL[1] IL-6 |
|---|---|
| Fluticasone propionate | 29 ± 21 |
| Example 2 | 48 ± 9 |

[1]Mean ± SEM

Further In Vivo Studies on Example 1

Additional in vivo studies were performed on Example 1, as shown in Tables 7-9 below:

TABLE 7

The Effects of Treatment with Example 1 on LPS-Induced Airway Neutrophilia in Mice.

| Example 1 | Neutrophil numbers in BALF (×10$^5$/mL) at pre-dose time indicated (% inhibition)[1] | |
|---|---|---|
| (mg/mL) | 2 hr | 8 hr |
| Vehicle | 15.28 | |
| 0.2 | 4.92 (67.8%) | 7.59 (50.3%) |

[1]N = 8 per group

TABLE 8

The Effects of Treatment with Example 1 on Tobacco Smoke in Mice.

| Treatment | Cell numbers in BALF × 10$^4$/mL (% inhibition) | |
|---|---|---|
| Example 1 (μg/mouse) | Macrophage | Neutrophil |
| Vehicle + Air | 4.25 | 1.81 |
| Vehicle + Tobacco Smoke | 18.76 | 10.63 |
| 7 | 11.34 (51.1%) | 6.04 (52.0%) |
| 0.7 | 14.92 (26.5%) | 7.66 (33.7%) |
| 0.07 | 17.27 (10.2%) | 9.42 (13.7%) |

The data for cell numbers are shown as the mean ± SEM, N = 5-6

TABLE 9

The Effects of Treatment with Example 1 on CXCL1 (KC) release in BALF on Tobacco Smoke in Mice.

| Treatment Example 1 (μg/mouse) | CXCL1 in BALF pg/mL (% inhibition) |
|---|---|
| Vehicle + Air | 6.14 |
| Vehicle + Tobacco Smoke | 15.89 |
| 7 | 9.03 (70.3%) |
| 0.7 | 12.49 (34.9%) |
| 0.07 | 14.47 (14.6%) |

The data for CXCL1 level are shown as the mean ± SEM, N = 5-6

Summary of In Vitro and In Vivo Screening Results

The examples of the invention demonstrate a profile in in vitro and in vivo assays consistent with good anti-inflammatory activity. In most cases they have very weak activity at Syk and GSK3α kinases and low toxicity in a cell viability assay (Tables 2A, 2B, 3 and 4).

Examples 1 and 2 demonstrated a similar inhibitory profile to the Reference Compound in the range of kinase enzyme assays with the marked exception of the inhibitory activities against the enzymes Syk and GSK3α kinases which are very much weaker than the Reference Compound (Table 2A). Examples 1 and 2 demonstrated a similar profile to the Reference Compound in cellular assays that reveal anti-inflammatory properties against endotoxin mediated release of both TNFα and IL-8 (Table 3).

In general the examples showed markedly less activity in an assay system that measures their impact on cell viability indicating that they are likely to possess a superior therapeutic index over the Reference Compound (Table 4).

Examples 1 and 2 showed markedly less activity in an assay systems that measures its impact on cell division (mitosis) further indicating that the compound is likely to possess a superior therapeutic index over the Reference Compound (Table 5A and 5B) Examples 1 and 2 demonstrated higher efficacy in inhibition of pro-inflammatory cytokine production in sputum macrophage than fluticasone propionate, a corticosteroid (Tables 6A and 6B).

Treatment of mice with Example 1 was found to produce inhibition on LPS-induced neutrophil accumulation and a time course experiment revealed that the drug substance had a long duration of action (Table 7).

Treatment of mice with Example 1 was found to produce a dose-dependent inhibition on both macrophage and neutrophil accumulation in BALF induced by cigarette smoke (Table 8). The cigarette smoke model used for this study is reported to be a corticosteroid refractory system, (Medicherla S. et al., *J. Pharmacol. Exp. Ther.*, 2008, 324(3):921-9) and it was confirmed that fluticasone propionate did not inhibit either neutrophil or macrophage accumulation into airways at 1.75 μg/mouse (35 μL, bid, i.n.), the same dose that produced >80% inhibition of LPS-induced neutrophil accumulation.

Treatment of mice with Example 1 also inhibited tobacco smoke induced CXCL1 (KC) production in BALF in a dose-dependent manner (Table 9).

Example 2 shows dose-dependent inhibition of HRV-induced IL-8 (FIG. 1).

In summary, these results suggest that the compounds of the invention, exemplified by Examples 1 and 2 and other examples, have similar anti-inflammatory properties to the Reference Compound disclosed above and, advantageously, are associated with a superior therapeutic index.

The invention claimed is:
1. A dry powder pharmaceutical formulation comprising a compound of formula (I)

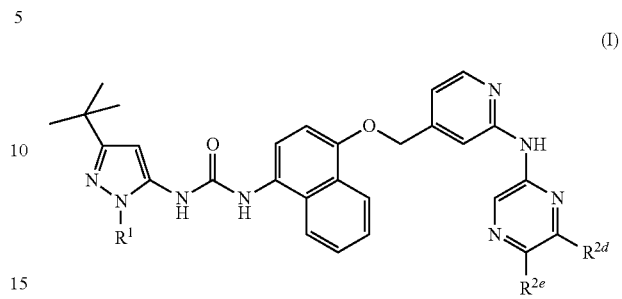

(I)

wherein:
$R^1$ represents

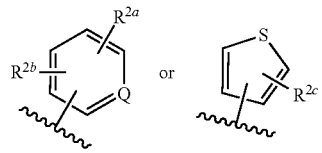

Q represents N or CH;
$R^{2a}$, $R^{2b}$ and $R^{2c}$ are independently selected from hydrogen, hydroxyl, halogen, —$C_{1-6}$alkyl, —$C_{1-6}$haloalkyl, $C_{3-5}$cycloalkyl; —$C_{1-3}$alkylene-OH, —$OC_{2-3}$alkylene-OH, —$C_{1-6}$alkoxy, —$C_{1-3}$alkylene-N—$(C_{1-3}$alkyl$)_2$, —N($C_{1-3}$alkyl$)_2$, —S$C_{1-3}$alkyl and —$C_{1-3}$alkylene-S—$C_{1-3}$alkyl;
$R^{2d}$ and $R^{2e}$ are defined as follows: either
(i) $R^{2d}$ represents hydrogen, —$C_{1-8}$ alkyl in which 1 to 3 carbon atoms are optionally substituted by halogen, —$C_{0-2}$alkylene-Cyc, —$C_{0-2}$alkylene-Het, —$CH_2$-J, —C≡C—$CH_2$-J, —$NR^3R^4$, —$OR^5$ or —CN; and $R^{2e}$ represents hydrogen or —$C_{1-6}$ alkyl; or
(ii) $R^{2e}$ represents —$C_{0-2}$alkylene-Cyc, —$C_{0-2}$alkylene-Het, —CO—K-Cyc, —CO—K'-Het, —CO—K'-HetAr, —$CH_2$-J, —CO-J', or —$C_{1-8}$ alkyl in which 1 to 3 carbon atoms are optionally substituted by halogen; and $R^{2d}$ represents hydrogen or —$C_{1-6}$ alkyl; or
(iii) $R^{2d}$ and $R^{2e}$ are joined and together represent a $C_{3-5}$alkylene chain in which one carbon atom of said alkylene chain, not being in a position adjacent to the pyrazine ring, is optionally replaced by O or $NR^{2f}$ wherein $R^{2f}$ represents H or $C_{1-3}$alkyl and wherein a carbon atom of said alkylene chain is optionally substituted by one or more groups selected from halogen, oxo and methyl;
J and J' independently represent a $C_{1-10}$ alkyl moiety in which 1, 2 or 3 carbon atoms are replaced by a heteroatom selected from O and N provided that any two heteroatoms if present are separated by at least two carbon atoms and wherein 1 or 2 carbon atoms are optionally substituted by oxo and which moiety is optionally substituted by 1 to 3 halogen groups provided that J' does not represent OH;
K and K' independently represent a bond or a $C_{1-10}$ alkylene chain in which 1, 2 or 3 carbon atoms are optionally replaced by a heteroatom selected from O and N provided that any two heteroatoms if present are separated by at least two carbon atoms and provided that neither K nor K' represents O;

$R^3$ and $R^4$ independently represent H or $—C_{1-8}$alkyl optionally substituted by 1 to 3 groups selected from hydroxyl, $C_{1-3}$alkoxy, hydroxy$C_{1-3}$alkyl and halogen and wherein 1 or 2 carbon atoms of said alkyl are optionally substituted by oxo; or $R^3$ and $R^4$ are joined such that $—NR^3R^4$ together represents a 4-7 membered heterocyclic ring optionally substituted by one to three groups selected from $C_{1-3}$alkyl, hydroxyl, $C_{1-3}$alkoxy, hydroxy$C_{1-3}$alkyl and halogen in which a carbon atom separated by at least two carbon atoms from the nitrogen atom is optionally replaced by a heteroatom selected from O and N; and wherein a methylene group is optionally substituted by oxo; or $R^3$ represents $C_{3-6}$cycloalkyl and $R^4$ represents hydrogen;

$R^5$ represents $—C_{1-8}$alkyl optionally substituted by 1 to 3 groups selected from hydroxyl, $C_{1-3}$alkoxy, hydroxy$C_{1-3}$alkyl and halogen and wherein 1 to 3 carbon atoms are optionally substituted by halogen;

Het represents a 4 to 7 membered non-aromatic heterocyclic ring containing 1 or 2 heteroatoms selected from O, S and N or an 8 to 10 membered non-aromatic bicyclic heterocyclic ring containing 1, 2 or 3 heteroatoms selected from O, S and N in either case optionally substituted by one to three groups selected from $C_{1-3}$alkyl, hydroxyl, $C_{1-3}$alkoxy, hydroxy$C_{1-3}$alkyl-, $C_{1-3}$haloalkyl, halogen, oxo, $—N(C_{1-3}alkyl)_2$, $—C(═O)C_{1-3}$alkyl, $—C(═O)OC_{1-3}$ alkyl, $—C_{1-3}$ alkylene-N—$(C_{1-3}alkyl)_2$, $—C_{1-3}$ alkylene-O—$C_{1-3}$ alkyl, $C_{3-6}$cycloalkyl and a 4-6 membered non-aromatic heterocyclic ring containing 1 or 2 heteroatoms selected from O, S and N optionally substituted by methyl, provided that Het is not directly attached to the pyrazine ring via a heteroatom and wherein a methylene group is optionally substituted by oxo;

Cyc represents a 3 to 7 membered non-aromatic carbocyclic ring optionally substituted by 1 to 3 groups selected from $C_{1-3}$alkyl, hydroxyl, $C_{1-3}$alkoxy, hydroxy$C_{1-3}$alkyl and halogen and wherein a methylene group is optionally substituted by oxo; and HetAr represents a 5- or 6 membered heteroaromatic ring containing 1 to 3 heteroatoms selected from O, N and S and optionally substituted by one to three groups selected from $C_{1-3}$alkyl, hydroxyl, $C_{1-3}$alkoxy, hydroxy$C_{1-4}$alkyl-, halogen and $C_{1-3}$haloalkyl;

or a pharmaceutically acceptable salt thereof, including all stereoisomers, tautomers and isotopic derivatives thereof; and optionally, lactose.

2. The dry powder pharmaceutical formulation according to claim 1, wherein the compound of formula (I) has a mass median diameter (MMAD) of 1-10 μm.

3. The dry powder pharmaceutical formulation according to claim 1, wherein the compound of formula (I) is micronized.

4. The dry powder pharmaceutical formulation according to claim 1, wherein the formulation further comprises magnesium stearate.

5. The dry powder pharmaceutical formulation according to claim 1, wherein the compound of formula (I) is in the form of its maleate salt.

6. The dry powder pharmaceutical formulation according to claim 2, wherein the compound of formula (I) is in the form of its maleate salt.

7. The dry powder pharmaceutical formulation according to claim 3, wherein the compound of formula (I) is in the form of its maleate salt.

8. The dry powder pharmaceutical formulation according to claim 4, wherein the compound of formula (I) is in the form of its maleate salt.

9. The dry powder pharmaceutical formulation according to claim 1, wherein the compound of formula (I) is in the form of its free base.

10. The dry powder pharmaceutical formulation according to claim 5, wherein the compound of formula (I) is in the form of its Form 2 crystalline polymorph.

11. The dry powder pharmaceutical formulation according to claim 6, wherein the compound of formula (I) is in the form of its Form 2 crystalline polymorph.

12. The dry powder pharmaceutical formulation according to claim 7, wherein the compound of formula (I) is in the form of its Form 2 crystalline polymorph.

13. The dry powder pharmaceutical formulation according to claim 8, wherein the compound of formula (I) is in the form of its Form 2 crystalline polymorph.

* * * * *